United States Patent [19]

Mitsuhashi et al.

[11] Patent Number: 5,639,612

[45] Date of Patent: Jun. 17, 1997

[54] METHOD FOR DETECTING POLYNUCLEOTIDES WITH IMMOBILIZED POLYNUCLEOTIDE PROBES IDENTIFIED BASED ON $T_M$

[75] Inventors: Masato Mitsuhashi, Irvine, Calif.; Allan Cooper, Bellview, Wash.

[73] Assignee: Hitachi Chemical Company, Ltd., Tokyo, Japan

[21] Appl. No.: 379,078

[22] Filed: Jan. 26, 1995

Related U.S. Application Data

[63] Continuation of Ser. No. 974,406, Nov. 12, 1992, abandoned, which is a continuation-in-part of Ser. No. 922,522, Jul. 28, 1992, abandoned.

[51] Int. Cl.$^6$ .............................. C12Q 1/68; C07H 21/04
[52] U.S. Cl. ...................... 435/6; 536/24.3; 536/24.31; 536/24.32
[58] Field of Search ............................ 435/6, 5, 810; 536/24.3, 24.31, 24.32; 935/78

[56] References Cited

U.S. PATENT DOCUMENTS

| | | |
|---|---|---|
| 4,729,950 | 3/1988 | Kricka et al. . |
| 4,734,363 | 3/1988 | Dattagupta et al. ................ 435/91 |
| 4,751,177 | 6/1988 | Stabinsky . |
| 4,797,355 | 1/1989 | Stabinsky . |
| 4,851,330 | 7/1989 | Kohne ................................ 435/6 |
| 4,894,325 | 1/1990 | Englehardt et al. . |
| 5,081,584 | 1/1992 | Omichinski et al. ............... 364/497 |
| 5,082,935 | 1/1992 | Cruickshank ....................... 536/27 |
| 5,084,565 | 1/1992 | Parodos et al. .................... 536/27 |

FOREIGN PATENT DOCUMENTS

| | | |
|---|---|---|
| 0130515 | 6/1984 | European Pat. Off. . |
| 0152886 | 8/1985 | European Pat. Off. . |
| 0327390 | 2/1989 | European Pat. Off. . |
| 0335633 | 3/1989 | European Pat. Off. . |
| 0329822 | 8/1989 | European Pat. Off. . |
| 0369775 | 11/1989 | European Pat. Off. . |
| 0370694 | 11/1989 | European Pat. Off. . |
| 0397269 | 5/1990 | European Pat. Off. . |
| 9006042 | 6/1990 | European Pat. Off. . |
| 0422872 | 10/1990 | European Pat. Off. . |
| 0469610 | 8/1991 | European Pat. Off. . |
| 2187283 | 9/1987 | United Kingdom . |
| 8603782 | 7/1986 | WIPO . |
| 8801302 | 2/1988 | WIPO . |
| 8803957 | 6/1988 | WIPO . |
| 9006044 | 6/1990 | WIPO . |
| 9006045 | 6/1990 | WIPO . |
| 9102092 | 2/1991 | WIPO . |

OTHER PUBLICATIONS

Meinkoth et al., *Analyt. Bioch.* 138, 267–284 (1984).

L. J. Emorine et al., "Structure of the gene for human $\beta_2$–adrenergic receptor: Expression and promoter characterization", Proceedings of the National Academy of Science, USA, vol. 84, Oct. 1987, pp. 6995–6999.

C. B. Harley, "Hybridization of Oligo(dT) to RNA on Nitrocellulose", Gene Analysis Techniques, vol. 4, 1987, pp. 17–22.

A. R. Dunn et al., "Mapping Viral mRNAs by Sandwich Hybridization", Methods in Enzymology, vol. 65, pt. 1, 1980, pp. 468–478.

A. Palva et al., "Laboratory Methods: Quantification of α–Amylase mRNA in *Bacillus subtilis* by Nucleic Acid Sandwich Hybridization", DNA, vol. 7, No. 2, 1988, pp. 135–142.

R. Nussinov, "Efficient algorithms for searching for exact repetition of nucleotid sequences.", Journal of Molecular Evolution, vol. 19, Nos. 3–4, pp. 283–285.

W. W. Ralph et al., "A modified Chou and Fasman protein structure algorithm", Computer Application in the Biosciences, vol. 8, No. 3, Sep. 1987, pp. 211–216.

C. Hough et al., "Differential down–regulation of $\beta_1$–and $\beta_2$–adrenergic receptor mRNA in $C_6$ glioma cells", Biochemical and Biophysical Research Communications, vol. 170, No. 1, 1990, pp. 46–52.

A. Ballagi–Pordany et al., "Quantitative determination of mRNA phenotypes by the polymerase chain reaction", Analytical Biochemistry, vol. 196, 1991, pp. 89–94.

B. Feve et al., "Differential regulation of $\beta_1$–and $\beta_2$–adrenergic receptor protein and mRNA levels by glucocorticoids during 3T3–F442A adipose differentiation", Journal of Biological Chemistry, vol. 265, No. 27, Sep. 25, 1990, pp. 16343–16349.

P. Muzzin et al., "An adipose tissue–specific β–adrenergic receptor", Journal of Biological Chemistry, vol. 266 No. 35, Dec. 15, 1991, pp. 24053–24058.

C. Albretsen et al., "Optimal conditions for hybridization with oligonucleotides: a study with *myc* –oncogene DNA probes", Analytical Biochemistry, vol. 170, 1988, pp. 193–202.

M. S. Waterman et al., "Phase transitions in sequence matches and nucleic acid structure", Proceedings of the National Academy of Science USA, vol. 84, Mar. 1987, pp. 1239–1243.

M. S. Waterman et al., "A new algorithm for best subsequence alignments with application to tRNA–rRNA comparisons", Journal of Molecular Biology, vol. 197, 1987, pp. 723–728.

R. J. Cano et al., "DNA hybridization assay using ATTOPHOS™, a fluorescent substrate for alkaline phosphatase", Biotechniques, vol. 12, No. 2, Feb. 1992, pp. 264–269.

(List continued on next page.)

*Primary Examiner*—Kenneth R. Horlick
*Attorney, Agent, or Firm*—Knobbe, Martens, Olson & Bear

[57] ABSTRACT

A method for detecting the presence of a particular organism, infectious agent, or biological component of a cell or organism in a sample, based on sandwich hybridization in which first and second probes are used, and the specificity of the first probe is determined based on its melting temperature ($T_m$) with the target polynucleotide at a selected sodium and formamide concentration.

37 Claims, 63 Drawing Sheets

OTHER PUBLICATIONS

N. P. Gerard, "Human substance P Receptor (NK-1): Organization of the gene, chromosome localization, and functional expression of cDNA clones", Biochemistry, vol. 30, 1991, pp. 10640–10646.

S. -I. Hirai et al., "Characterization of junD: a new member of the jun protooncogene family", The EMBO Journal, vol. 8, No. 5, 1989, pp. 1433–1439.

D. T. Jones et al., "Molecular cloning of five GTP–binding protein cDNA species from rat olfactory neuroepithelium", Journal of Biological Chemistry, vol. 262, No. 29, Oct. 15, 1987, pp. 14241–14249.

L. Li et al., "Different members of the jun protooncogene family exhibit distinct patterns of expression in response ot type β transforming growth factor", Journal of Biological Chemistry, vol. 265, No. 3, Jan. 25, 1990, pp. 1556–1562.

Y. Yokota et al., "Molecular characterization of a functional cDNA for rat substance P receptor", Journal of Biological Chemistry, vol. 264, No. 30, Oct. 25, 1989, pp. 17649–17652.

J. Codina et al., "$\alpha_i 3$ cDNA encodes the $\alpha$ subunit of $G_k$, the stimulatory G protein of receptor–regulated $K^+$ channels", Journal of Biological Chemistry, vol. 263, No. 14, May 15, 1988, pp. 6746–6750.

H. Itoh et al., "Presence of three distinct molecular species of $G_i$ protein $\alpha$ subunit", Journal of Biological Chemistry, vol. 263, No. 14, May 15, 1988, pp. 6656–6664.

K. Hattori et al., "Structure and chromosomal localization of the functional intronless human JUN protooncogene", Proceedings of the National Academy of Science USA, vol. 85, Dec. 1988, pp. 9148–9152.

P. Bray et al., "Human cDNA clones for an $\alpha$ subunit of $G_i$ signal–transduction proteins", Proceedings of the National Academy of Science USA, vol. 84, Aug. 1987, pp. 5115–5119.

C. R. Beals et al., "A small multigene family encodes $G_i$ signal–transduction proteins", Proceeding of the National Academy of Science USA, vol. 84, Nov. 1987, pp. 7886–7890.

B. A. Harris, "Complete cDNA sequence of a human stimulatory GTP–binding protein alpha subunit", Nucleic Acids Research, vol. 16, No. 8, 1988, p. 3585.

R. Mattera et al., "Identification by molecular cloning of two forms of the $\alpha$–subunit of the human liver stimulatory ($G_s$) regulatory component of adenylyl cyclase", FEBS Letters, vol. 206, No. 1, Sep. 1986, pp. 36–42.

J. R. Didsbury et al., "Molecular cloning of a new human G protein", FEBS Letters, vol. 219, No. 1, Jul. 1987, pp. 259–263.

A. Swaroop et al., "Differential expression of novel $G_{s\alpha}$ signal transduction protein cDNA species", Nucleic Acids Research, vol. 19, No. 17, 1991, pp. 4725–4729.

Polsky–Cynkin et al., "Use of DNA Immobilized on Plastic and Agarose Supports to Detect DNA by Sandwich Hybridization", Clinical Chemistry, vol. 31, No. 9, 1985, pp. 1438–1443.

Hayashi et al., "A Novel Diagnostic Method of Pneymocystis carinii", Laboratory Investigation, vol. 63, No. 4, 1990, pp. 575–580.

Giovannoni et al., "Phylogenic Group–Specific Oligodeoxynucleotide Probes for Identification of Single Microbial Cells", Journal of Bacteriology, vol. 170, No. 2, Feb. 1988, pp. 720–726.

Kitabayashi et al., "Nucleotide Sequence of Rat c–jun Protooncogene", Nucleic Acids Research, vol. 18, No. 11, 1990, EMBL Accession No. X17215.

Hershey et al., "Molecular Characterization of a Functional cDNA Encoding the Rat Substance P Receptor", Science, vol. 247, Feb. 23, 1990, pp. 958–961.

Chung et al., "Cloning and Sequence Analysis of the Human Brain B–adrenergic Receptor", FEBS Letters, vol. 211, No. 2, pp. 200–206.

Saiki et al., "Primer–Directed Enzymatic Amplification of DNA with a Thermostable DNA Polymerase", Science, vol. 239, Jan. 29, 1988, pp. 487–491.

I. Raineri et al., "Improved Efficiency for Single–Sided PCR by Creating a Reusable Pool of First–Strand cDNA coupled to a Solid Phase", Nucleic Acids Research, vol. 19, No. 14, 1991, p. 4010.

S. Inouye et al., "Microplate Hybridization of Amplified Viral DNA Segment", Journal of Clinical Microbiology, vol. 28, No. 6, Jun. 1990, pp. 1469–1472.

M. J. Palazzolo et al., "A Family of Lambda Phage cDNA Cloning Vectors, λSWAJ, Allowing the Amplification of RNA Sequences", Gene, vol. 52, 1987, pp. 197–206.

R. Bischoff et al., "Introduction of 5'–Terminal Functional Groups into Synthetic Oligonucleotides for Selective Immobilization", Analytical Biochemistry, vol. 164, No. 2, Aug. 1, 1987, pp. 336–344.

I. Martin et al., "Characterization of the levanase gene of Bacillus subtilis which shows homology to yeast invertase", Mol. Gen. Genet., vol. 208, 1987, pp. 177–184.

D. Betzl et al., "Identification of Lactococci and Enterococci by Colony Hybridization with 23S rRNA–Targeted Oligonucleotide Probes", Applied and Environmental Microbiology, vol. 56, No. 9, 1990, pp. 2927–2929.

E. Baldwin et al., "Generation of a Catalytic Antibody by Site–Directed Mutagenesis", Science, vol. 245, 1989, pp. 1104–1107.

J. Rey–Campos et al., "Synthesis of Thymosin $\alpha_1$ Precursor cDNA and Purification of Active mRNA by Affinity Chromatography", International Journal of Biochemistry, vol. 15, 1983, pp. 155–157.

T. Atkinson et al., "A convenient procedure for the synthesis of oligodeoxyribonucleotide affinity columns for the isolation of mRNA", Nucleic Acids Research, vol. 16, No. 13, 1988, p. 6232.

J. A. Arias et al., "Promoter–dependent Transcription by RNA Polymerase II Using Immobilized Enzyme Complexes", Journal of Biological Chemistry, vol. 264, No. 6, 1989, pp. 3223–3229.

Y. Masu et al., "cDNA cloning of bovine substance–K receptor through oocyte expression system", Nature, vol. 329, No.29, 1987, pp. 836–838.

C. R. Thrash et al., "Synthesis of RNA from Cellulose-–bound Complementary DNA", Journal of Biological Chemistry, vol. 252, No. 16, 1977, pp. 5615–5618.

S. L. Griffiths et al., "Diabetes–induced changes in guanine-–nucleotide–regulatory–protein mRNA detected using synthetic oligonucleotide probes", European Journal of Biochemistry, vol. 193, No. 2, 1990, pp. 367–374.

Y. Wataya et al., "Kagaku Ryoho no Ryoiki", vol. 8, No. 3, 1992, pp. 487–496.

M. S. Urdea et al., "A comparison of non–radiosotopic hybridization assay methods using fluorescent chemiluminescent and enzyme labeled synthetic oligodeoxyribonucleotide probes", Nucleic Acids Research, vol. 16, No. 11, 1988, pp. 4937–1956.

B. H. Bowman et al., "Designing a PCR/Probe Detection System for Pathogenic Fungi", Clinical Immunology Newsletter, vol. 12, pp. 65–80.

Bethesda Research Laboratories Life Technologies, Inc. Product: Vanadyl Ribonucleotide Complex.

Biofeedback; "A Procedure for Productive Coupling of Synthetic Oligonucleotides to Polystyrene Microtier Wells for Hybridization Capture"; Biotechniques; vol. 8, pp. 278–279, 1990.

Pal Venetianer, et al., Pro Nat. Acad. Sci. USA, vol. 71, No. 10, pp. 3892–3895, Oct. 1974; "Enzymatic Synthesis of Solid Phase–Bound DNA Sequences Corresponding to Specific Mammalian Gene".

P. T. Gilham, Journal of the American Chemical Society, vol. 86, pp. 4982–4985; "The Synthesis of Polynucleotide–Celluloses and Their use in the Fractionation of Polynucleotides".

M. R. Ven Murthy, et al., Nucleic Acids Research, vol. 14, No. 17, Jul. 24, 1986; "Preparation and Biochemical Manipulation of mRNAs and CDNAs on small Oligo(dt)–cellulose discs".

Jane A. Matthews, et al., Analytical Biochemistry 169, pp. 1–25 (1988); "Analytical Strategies for the Use of DNA Probes".

Stefan Stamm, et al., Nucleic Acids Research, vol. 19, No. 16, p. 1350; "Sanchored PCR: PCR with cDNA Coupled to a Solid Phase".

R. Julian S. Duncan, et al., Analytical Biochemistry 132, pp. 68–73 (1983); "A New Regent Which May Be Used to Introduce Sulfhydryl Groups into Proteins, and Its Us in the Preparation of Conjugates for Immunoassay".

Seiichi Hashida, et al., Journal of Applied Biochemistry 6, pp. 56–63 (1984); "More Useful Maleimide Compounds for the Conjugation of Fab' to Horseradish Peroxidase through Thiol Groups in the Hinge".

Hidenori Yamada, et al., Biochemistry 1981, 20 pp. 4836–4842; "Selective Modification of Aspartic Acid–101 in Lysozyme by Carbodiimide Reaction".

James V. Staros, et al., Analytical Biochemistry 156, pp. 220–222 (1986); "Enhancement by N–Hydroxsulfosuccinimide of Water–Soluble Carbodiimide–Mediated Coupling reactions".

Norman Arnheim, et al., C&EN, Oct. 1, 1990, pp. 36–46; "Polymerase Chain Reaction".

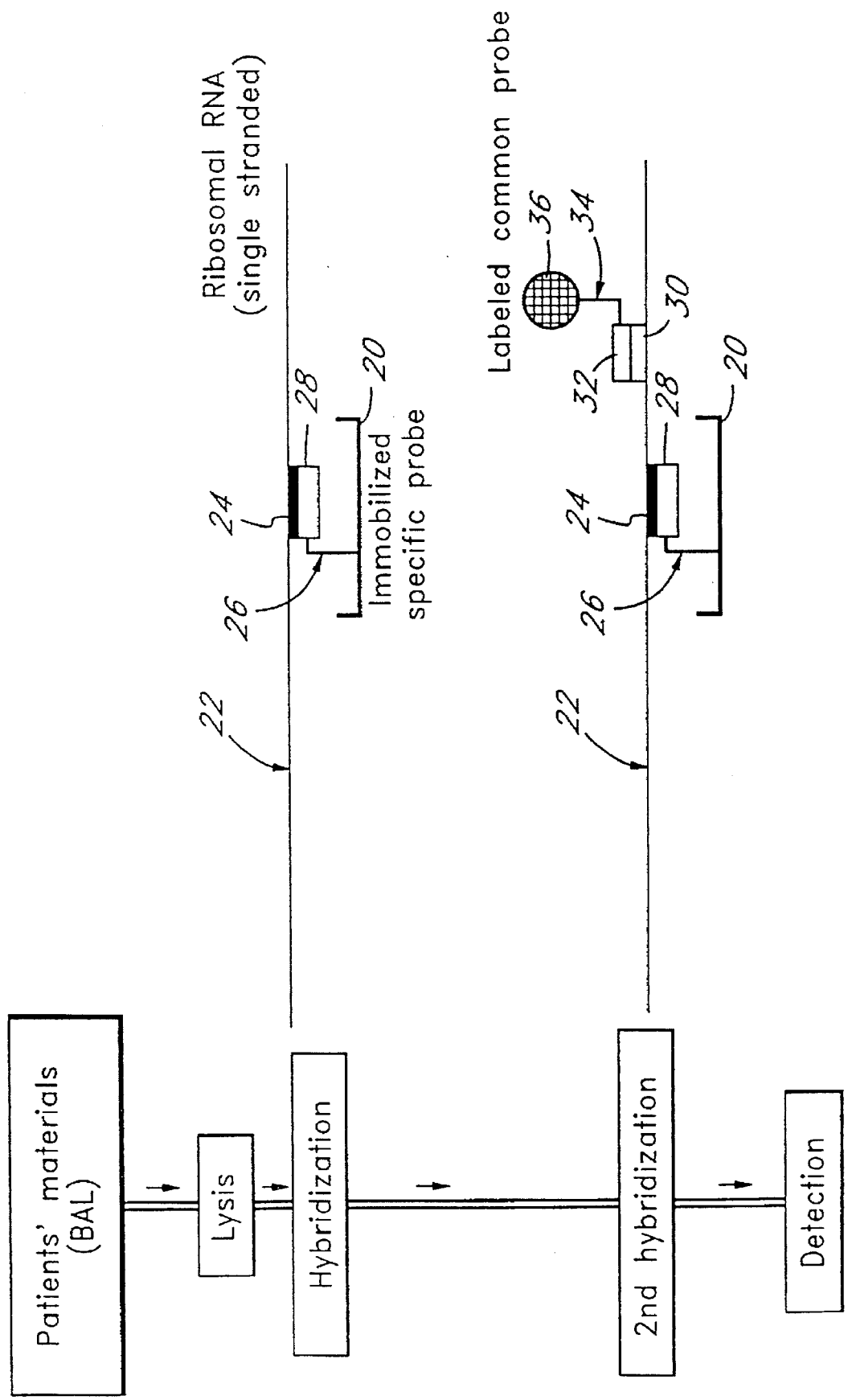

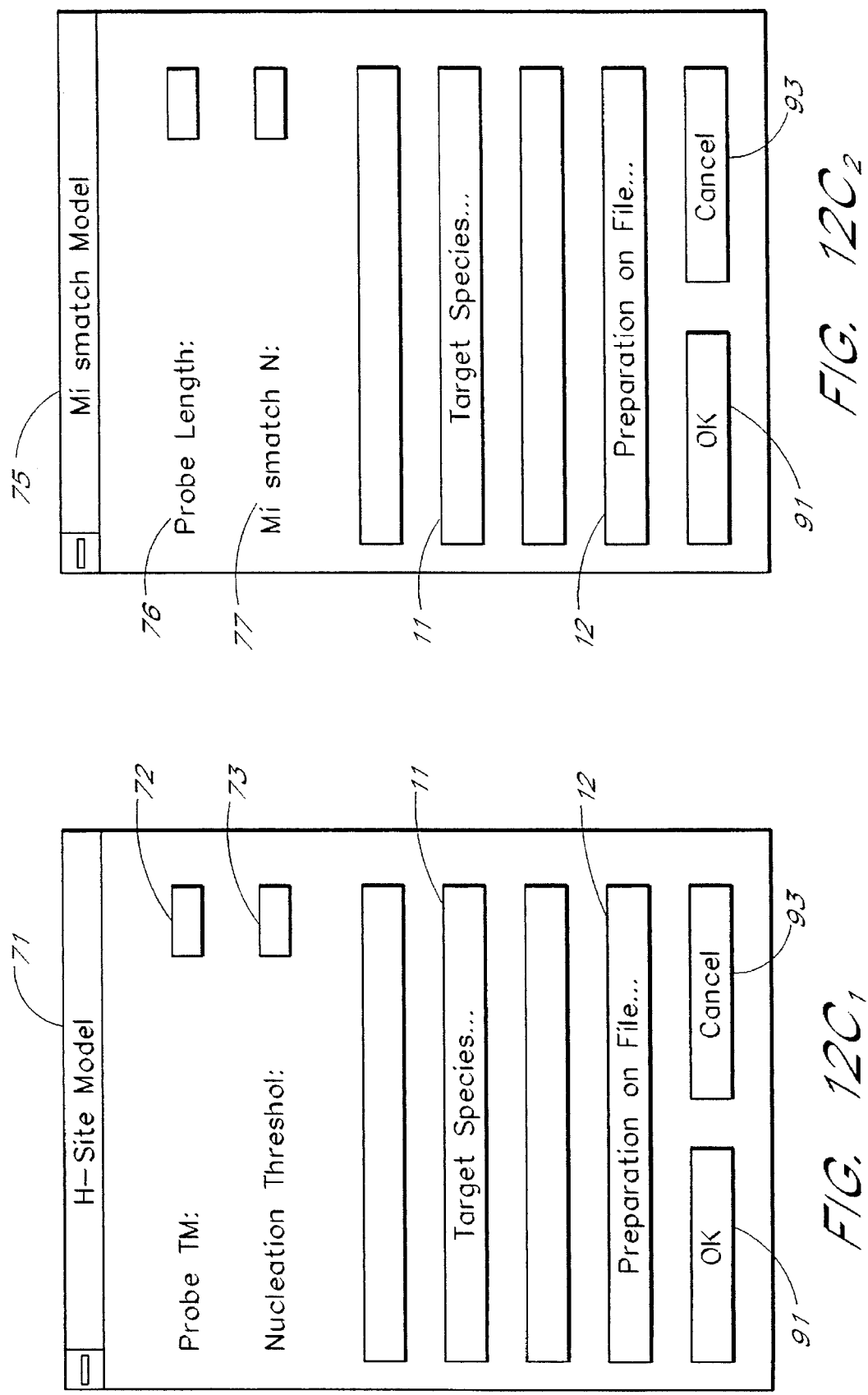

```
┌─────────────────────────────────────────────────┐
│ ▭  Probes Selected — JUNMIX.prb                 │── 156
│   File                                          │
│ ┌───────────────────────────────────────────┬─┐ │
│ │                                           │▲│ │
│ │ PROBE:        C:\HITACHI\JUNMIX.PRP       │ │ │
│ │ HYBRIDIZATION:  C:\HITACHI\HUMBJU         │ │ │
│ │ Length = 374    Hairpin = 3 5             │ │ │
│ │ Locus      Pos      Tm                    │ │ │
│ │ humbjunx   374    61.47    ------------   │ │ │
│ │ musbjunx   365    61.47    ------------   │ │ │
│ │ humdjunx    41    34.82    t--------g-g-  │ │ │
│ │ humbjunx   182    31.12    a--------gtgg  │ │ │
│ │ humdjunx   602    31.12    c--------xc-gg │ │ │
│ │ PROBE:        C:\HITACHI\JUNMIX.PRP       │ │ │
│ │ HYBRIDIZATION:  C:\HITACHI\HUMBJU         │ │ │
│ │ Length = 467    Hairpin = 2 13            │ │ │
│ │ Locus      Pos      Tm                    │ │ │
│ │ humbjunx   467    61.7     ------------   │ │ │
│ │ musbjunx   458    51.6     -----------c-  │ │ │
│ │ humdjunx    32    29.35    tgagcgg------  │ │ │
│ │ humdjunx    32    29.35    tgagcgg------  │ │ │
│ │                                           │▼│ │
│ ├─┬───────────────────────────────────────┬─┼─┤ │
│ │←│                                       │→│ │ │
│ └─┴───────────────────────────────────────┴─┴─┘ │
└─────────────────────────────────────────────────┘
```

```
PROBE: C:\HITACHI\JUNMIX.PRP
HYBRIDIZATION: C:\HITACHI\HUMBJUNX.CDS
Length = 374  Hairpin = 3 5
Locus      Pos   Tm
humbjunx   374   61.47   ------------------
musbjunx   365   61.47   ------------------
humdjunx   41    34.82   t---------g-g--agt
humbjunx   182   31.12   a---------gtgg--gc
humdjunx   602   31.12   c---------c-ggg-gc
humdjunx   602   31.12   c---------c-ggg-gc PROBE: C:\HITACHI\JUNMIX.PRP
HYBRIDIZATION: C:\HITACHI\HUMBJUNX.CDS
Length = 377  Hairpin = 2 14
Locus      Pos   Tm
humbjunx   377   61.55   ------------------
musbjunx   368   61.55   ------------------
humdjunx   383   28.12   tg-cg-c--g--------
musdjunx   383   28.12   tg-ca-c--g--------
musdjunx   383   28.12   tg-ca-c--g-------

PROBE: C:\HITACHI\JUNMIX.PRP
HYBRIDIZATION: C:\HITACHI\HUMBJUNX.CDS
Length = 389  Hairpin = 3 3
Locus      Pos   Tm
humbjunx   389   61.7    ------------------
muscjunx   314   56.65   -c----------------
musbjunx   380   50.85   ---------------t--g
humcjunx   314   49.35   -5-----------g------
humdjunx   395   33.85   -----------tt-gc--ag
musdjunx   395   33.85   -----------tt-gc--ag
humcjunx   326   32.35   g-ttcgcc-----------tg
humdjunx   404   32.35   --ttcgcc-----------t-
muscjunx   326   32.35   gctcgcc-----------tg
musdjunx   253   30.85   gacg-gct-ct---------
humbjunx   953   30.65   g--------t---c-cagct-
musdjunx   83    27.3    cc-gcggt-gt--------g PROBE: C:\HITACHI\JUNMIX.PRP
HYBRIDIZATION: C:\HITACHI\HUMBJUNX.CDS
Length = 397  Hairpin = 4 1
Locus      Pos   Tm
humbjunx   397   61.55   ------------------
muscjunx   322   53.44   --------------g---
humcjunx   322   45.33   -----g--------g---
musbjunx   388   41.38   --------t--g-----t
humdjunx   214   36.83   cccccctgc---------
humdjunx   99    36.16   cg----gc-c--------
musdjunx   261   34.55   -ct---------gatct
humdjunx   400   33.27   c---ag--------g---
musdjunx   400   33.27   c---ag--------a---
humcjunx   334   32.28   ----------tgcg--c-
humdjunx   412   32.28   ----------t-a-g-c-
muscjunx   334   32.28   ----------tgcg--c-
humbjunx   658   30.17   cc-cc--------gt---
humdjunx   241   28.95   -c--cacc-c--------
humdjunx   342   28.95   c-cca-ca--------ag
musbjunx   606   28.95   ---ct-a-ac--------
musdjunx   229   28.95   -c-ctgcg-c--------
musdjunx   91    26.67   -gt--------gcc-ccg
```

16A₂

```
PROBE: C:\HITACHI\JUNMIX.PRP
HYBRIDIZATION: C:\HITACHI\HUMBJUNX.CDS
Length = 417  Hairpin = 2 15
Locus      Pos  Tm
humbjunx   417  60.08  ----------------------
musbjunx   408  55.52  ------------------c----
humdjunx   420  37.3   c-----g--------g---t-a-
musbjunx   61   29.0   g---gg---------ca-cctgt-
muscjunx   672  26.27  gc-gc---------a-g--aga--

PROBE: C:\HITACHI\JUNMIX.PRP
HYBRIDIZATION: C:\HITACHI\HUMBJUNX.CDS
Length = 461  Hairpin = 4 9
Locus      Pos  Tm
humbjunx   461  61.63  -------------------
musbjunx   452  61.63  -------------------
musbjunx   452  61.63  -------------------

PROBE: C:\HITACHI\JUNMIX.PRP
HYBRIDIZATION: C:\HITACHI\HUMBJUNX.CDS
Length = 467  Hairpin = 2 13
Locus      Pos  Tm
humbjunx   467  61.7   --------------------
musbjunx   458  51.6   ----------------c-g-
humdjunx   32   29.35  tgagcgg--------gcgg-
humdjunx   32   29.35  tgagcgg--------gcgg- PROBE: C:\HITACHI\JUNMIX.PRP
HYBRIDIZATION: C:\HITACHI\HUMBJUNX.CDS
Length = 477  Hairpin = 2 4
Locus      Pos  Tm
humbjunx   477  61.37  -----------------
humdjunx   489  34.93  c-c---cg---------
humdjunx   489  34.93  c-c---cg---------

PROBE: C:\HITACHI\JUNMIX.PRP
HYBRIDIZATION: C:\HITACHI\HUMBJUNX.CDS
Length = 487  Hairpin = 3 3
Locus      Pos  Tm
humbjunx   487  61.14  --------------
musdjunx   74   51.0   ct------------
humdjunx   499  45.64  ---------t---g
humdjunx   527  30.72  cc-c-c--------
musdjunx   97   30.72  ttc-c--------g
musdjunx   580  30.72  -cc--------t-g
musdjunx   637  30.72  cc-cc--------g
musdjunx   637  30.72  cc-cc--------g PROBE: C:\HITACHI\JUNMIX.PRP
HYBRIDIATION: C:\HITACHI\HUMBJUNX.CDS
Length = 498  Hairpin = 3 2
Locus      Pos  Tm
humbjunx   498  61.26  ---------------
humbjunx   498  61.26  ---------------

PROBE: C:\HITACHI\JUNMIX.PRP
HYBRIDIATION: C:\HITACHI\HUMBJUNX.CDS
Length = 504  Hairpin = 3 2
Locus      Pos  Tm
humbjunx   504  61.47  -----------------
musbjunx   495  40.35  c--a----------t--
humdjunx   609  35.29  cg---------cgggg-
humdjunx   609  35.29  cg---------cgggg-
```

FIG. 30

OligoProbe DesignStation

Probes:   C:\HITACHI\HUMBJUNX.CDS
Database: C:\HATACHI\JUNMIX.SEQ

Mismatch Model, l = 21, k = 4

| Position | | Mismatches | | | | | | | | screensN | |
|---|---|---|---|---|---|---|---|---|---|---|---|
| | length | 0 | 1 | 2 | 3 | 4 | 5 | 6 | 7 | 8 | Probe |
| 1 | 21 | 1 | 1 | 1 | 1 | 1 | | | | | ATGTGCACTAAAATGGAACAG |
| 2 | 21 | 1 | 1 | 1 | 1 | 1 | | | | | TGTGCACTAAAATGGAACAGC |
| 3 | 21 | 1 | 1 | 1 | 1 | 1 | | | | | GTGCACTAAAATGGAACAGCC |
| 4 | 21 | 1 | 1 | 1 | 1 | 1 | | | | | TGCACTAAAATGGAACAGCCC |
| 5 | 21 | 1 | 1 | 1 | 1 | 1 | | | | | GCACTAAAATGGAACAGCCCT |
| 6 | 21 | 1 | 1 | 1 | 1 | 1 | | | | | CACTAAAATGGAACAGCCCTT |
| 7 | 21 | 1 | 1 | 1 | 1 | 1 | | | | | ACTAAAATGGAACAGCCCTTC |
| 8 | 21 | 1 | 1 | 1 | 1 | 1 | | | | | CTAAAATGGAACAGCCCTTCT |
| 9 | 21 | 1 | 1 | 1 | 1 | 1 | | | | | TAAAATGGAACAGCCCTTCTA |
| 10 | 21 | 1 | 1 | 1 | 1 | 1 | | | | | AAAATGGAACAGCCCTTCTAC |
| 11 | 21 | 1 | 1 | 1 | 1 | 1 | | | | | AAATGGAACAGCCCTTCTACC |
| 12 | 21 | 1 | 1 | 1 | 1 | 1 | | | | | AATGGAACAGCCCTTCTACCA |
| 13 | 21 | 1 | 1 | 1 | 1 | 1 | | | | | ATGGAACAGCCCTTCTACCAC |
| 14 | 21 | 1 | 1 | 1 | 1 | 1 | | | | | TGGAACAGCCCTTCTACCACG |
| 15 | 21 | 1 | 1 | 1 | 1 | 1 | | | | | GGAACAGCCCTTCTACCACGA |
| 16 | 21 | 1 | 1 | 1 | 1 | 1 | | | | | GAACAGCCCTTCTACCACGAC |
| 17 | 21 | 1 | 1 | 1 | 1 | 1 | | | | | AACAGCCCTTCTACCACGACG |
| 18 | 21 | 1 | 1 | 1 | 1 | 1 | | | | | ACAGCCCTTCTACCACGACGA |
| 19 | 21 | 1 | 1 | 1 | 1 | 1 | | | | | CAGCCCTTCTACCACGACGAC |
| 20 | 21 | 1 | 1 | 1 | 1 | 1 | | | | | AGCCCTTCTACCACGACGACT |
| 21 | 21 | 1 | 1 | 1 | 1 | 1 | | | | | GCCCTTCTACCACGACGACTC |
| 22 | 21 | 1 | 1 | 1 | 1 | 1 | | | | | CCCTTCTACCACGACGACTCA |
| 23 | 21 | 1 | 1 | 1 | 1 | 1 | | | | | CCTTCTACCACGACGACTCAT |
| 24 | 21 | 1 | 1 | 1 | 1 | 1 | | | | | CTTCTACCACGACGACTCATA |
| 25 | 21 | 1 | 1 | 1 | 1 | 1 | | | | | TTCTACCACGACGACTCATAC |
| 26 | 21 | 1 | 1 | 1 | 1 | 1 | | | | | TCTACCACGACGACTCATACA |
| 27 | 21 | 1 | 1 | 1 | 1 | 1 | | | | | CTACCACGACGACTCATACAC |
| 28 | 21 | 1 | 1 | 1 | 1 | 1 | | | | | TACCACGACGACTCATACACA |
| 29 | 21 | 1 | 1 | 1 | 1 | 1 | | | | | ACCACGACGACTCATACACAG |
| 30 | 21 | 1 | 1 | 1 | 1 | 1 | | | | | CCACGACGACTCATACACAGC |
| 31 | 21 | 1 | 1 | 1 | 1 | 1 | | | | | CACGACGACTCATACACAGCT |
| 32 | 21 | 1 | 1 | 1 | 1 | 1 | | | | | ACGACGACTCATACACAGCTA |
| 33 | 21 | 1 | 1 | 1 | 1 | 1 | | | | | CGACGACTCATACACAGCTAC |
| 34 | 21 | 1 | 1 | 1 | 1 | 1 | | | | | GACGACTCATACACAGCTACG |
| 35 | 21 | 1 | 1 | 1 | 1 | 1 | | | | | ACGACTCATACACAGCTACGG |
| 36 | 21 | 1 | 1 | 1 | 1 | 1 | | | | | CGACTCATACACAGCTACGGG |
| 37 | 21 | 1 | 1 | 1 | 1 | 1 | | | | | GACTCATACACAGCTACGGGA |
| 38 | 21 | 1 | 1 | 1 | 1 | 1 | | | | | ACTCATACACAGCTACGGGAT |
| 39 | 21 | 1 | 1 | 1 | 1 | 1 | | | | | CTCATACACAGCTACGGGATA |
| 40 | 21 | 1 | 1 | 1 | 1 | 1 | | | | | TCATACACAGCTACGGGATAC |
| 41 | 21 | 1 | 1 | 1 | 1 | 1 | | | | | CATACACAGCTACGGGATACG |
| 42 | 21 | 1 | 1 | 1 | 1 | 1 | | | | | ATACACAGCTACGGGATACGG |
| 43 | 21 | 1 | 1 | 1 | 1 | 1 | | | | | TACACAGCTACGGGATACGGC |
| 44 | 21 | 1 | 1 | 1 | 1 | 1 | | | | | ACACAGCTACGGGATACGGCC |
| 45 | 21 | 1 | 1 | 1 | 1 | 1 | | | | | CACAGCTACGGGATACGGCCG |
| 46 | 21 | 1 | 1 | 1 | 1 | 1 | | | | | ACAGCTACGGGATACGGCCGG |
| 47 | 21 | 1 | 1 | 1 | 1 | 1 | | | | | CAGCTACGGGATACGGCCGGG |
| 48 | 21 | 1 | 1 | 1 | 1 | 1 | | | | | AGCTACGGGATACGGCCGGGC |
| 49 | 21 | 1 | 1 | 1 | 1 | 1 | | | | | GCTACGGGATACGGCCGGGCC |
| 50 | 21 | 1 | 1 | 1 | 1 | 1 | | | | | CTACGGGATACGGCCGGGCCC |
| 51 | 21 | 1 | 1 | 1 | 1 | 1 | | | | | TACGGGATACGGCCGGGCCCC |
| 52 | 21 | 1 | 1 | 1 | 1 | 1 | | | | | ACGGGATACGGCCGGGCCCCT |
| 53 | 21 | 1 | 1 | 1 | 1 | 1 | | | | | CGGGATACGGCCGGGCCCCTG |

FIG. 34A

OligoProbe DesignStation
Probes:   C:\HITACHI\HUMBJUNX.CDS
Database: C:\HATACHI\JUNMIX.SEQ Mismatch Model, l = 21, k = 4

| Position | | Mismatches | | | | | | | | screensN | |
| length | 0 | 1 | 2 | 3 | 4 | 5 | 6 | 7 | 8 | Probe |
|---|---|---|---|---|---|---|---|---|---|---|
| 1  | 21 | 0 | 0 | 0 | 0 | 0 | ATGTGCACTAAAATGGAACAG |
| 2  | 21 | 0 | 0 | 0 | 0 | 0 | TGTGCACTAAAATGGAACAGC |
| 3  | 21 | 0 | 0 | 0 | 0 | 0 | GTGCACTAAAATGGAACAGCC |
| 4  | 21 | 0 | 0 | 0 | 0 | 0 | TGCACTAAAATGGAACAGCCC |
| 5  | 21 | 0 | 0 | 0 | 0 | 0 | GCACTAAAATGGAACAGCCCT |
| 6  | 21 | 0 | 0 | 0 | 0 | 0 | CACTAAAATGGAACAGCCCTT |
| 7  | 21 | 0 | 0 | 0 | 0 | 0 | ACTAAAATGGAACAGCCCTTC |
| 8  | 21 | 0 | 0 | 0 | 0 | 0 | CTAAAATGGAACAGCCCTTCT |
| 9  | 21 | 0 | 0 | 0 | 0 | 0 | TAAAATGGAACAGCCCTTCTA |
| 10 | 21 | 0 | 0 | 0 | 0 | 0 | AAAATGGAACAGCCCTTCTAC |
| 11 | 21 | 0 | 0 | 0 | 0 | 0 | AAATGGAACAGCCCTTCTACC |
| 12 | 21 | 0 | 0 | 0 | 0 | 0 | AATGGAACAGCCCTTCTACCA |
| 13 | 21 | 0 | 0 | 0 | 0 | 0 | ATGGAACAGCCCTTCTACCAC |
| 14 | 21 | 0 | 0 | 0 | 0 | 0 | TGGAACAGCCCTTCTACCACG |
| 15 | 21 | 0 | 0 | 0 | 0 | 0 | GGAACAGCCCTTCTACCACGA |
| 16 | 21 | 0 | 0 | 0 | 0 | 0 | GAACAGCCCTTCTACCACGAC |
| 17 | 21 | 0 | 0 | 0 | 0 | 0 | AACAGCCCTTCTACCACGACG |
| 18 | 21 | 0 | 0 | 0 | 0 | 0 | ACAGCCCTTCTACCACGACGA |
| 19 | 21 | 0 | 0 | 0 | 0 | 0 | CAGCCCTTCTACCACGACGAC |
| 20 | 21 | 0 | 0 | 0 | 0 | 0 | AGCCCTTCTACCACGACGACT |
| 21 | 21 | 0 | 0 | 0 | 0 | 0 | GCCCTTCTACCACGACGACTC |
| 22 | 21 | 0 | 0 | 0 | 0 | 0 | CCCTTCTACCACGACGACTCA |
| 23 | 21 | 0 | 0 | 0 | 0 | 0 | CCTTCTACCACGACGACTCAT |
| 24 | 21 | 0 | 0 | 0 | 0 | 0 | CTTCTACCACGACGACTCATA |
| 25 | 21 | 0 | 0 | 0 | 0 | 0 | TTCTACCACGACGACTCATAC |
| 26 | 21 | 0 | 0 | 0 | 0 | 0 | TCTACCACGACGACTCATACA |
| 27 | 21 | 0 | 0 | 0 | 0 | 0 | CTACCACGACGACTCATACAC |
| 28 | 21 | 0 | 0 | 0 | 0 | 0 | TACCACGACGACTCATACACA |
| 29 | 21 | 0 | 0 | 0 | 0 | 0 | ACCACGACGACTCATACACAG |
| 30 | 21 | 0 | 0 | 0 | 0 | 0 | CCACGACGACTCATACACAGC |
| 31 | 21 | 0 | 0 | 0 | 0 | 0 | CACGACGACTCATACACAGCT |
| 32 | 21 | 0 | 0 | 0 | 0 | 0 | ACGACGACTCATACACAGCTA |
| 33 | 21 | 0 | 0 | 0 | 0 | 0 | CGACGACTCATACACAGCTAC |
| 34 | 21 | 0 | 0 | 0 | 0 | 0 | GACGACTCATACACAGCTACG |
| 35 | 21 | 0 | 0 | 0 | 0 | 0 | ACGACTCATACACAGCTACGG |
| 36 | 21 | 0 | 0 | 0 | 0 | 0 | CGACTCATACACAGCTACGGG |
| 37 | 21 | 0 | 0 | 0 | 0 | 0 | GACTCATACACAGCTACGGGA |
| 38 | 21 | 0 | 0 | 0 | 0 | 0 | ACTCATACACAGCTACGGGAT |
| 39 | 21 | 0 | 0 | 0 | 0 | 0 | CTCATACACAGCTACGGGATA |
| 40 | 21 | 0 | 0 | 0 | 0 | 0 | TCATACACAGCTACGGGATAC |
| 41 | 21 | 0 | 0 | 0 | 0 | 0 | CATACACAGCTACGGGATACG |
| 42 | 21 | 0 | 0 | 0 | 0 | 0 | ATACACAGCTACGGGATACGG |
| 43 | 21 | 0 | 0 | 0 | 0 | 0 | TACACAGCTACGGGATACGGC |
| 44 | 21 | 0 | 0 | 0 | 0 | 0 | ACACAGCTACGGGATACGGCC |
| 45 | 21 | 0 | 0 | 0 | 0 | 0 | CACAGCTACGGGATACGGCCG |
| 46 | 21 | 0 | 0 | 0 | 0 | 0 | ACAGCTACGGGATACGGCCGG |
| 47 | 21 | 0 | 0 | 0 | 0 | 0 | CAGCTACGGGATACGGCCGGG |
| 48 | 21 | 0 | 0 | 0 | 0 | 0 | AGCTACGGGATACGGCCGGGC |
| 49 | 21 | 0 | 0 | 0 | 0 | 0 | GCTACGGGATACGGCCGGGCC |
| 50 | 21 | 0 | 0 | 0 | 0 | 0 | CTACGGGATACGGCCGGGCCC |
| 51 | 21 | 0 | 0 | 0 | 0 | 0 | TACGGGATACGGCCGGGCCCC |
| 52 | 21 | 0 | 0 | 0 | 0 | 0 | ACGGGATACGGCCGGGCCCCT |
| 53 | 21 | 0 | 0 | 0 | 0 | 0 | CGGGATACGGCCGGGCCCCTG |

FIG. 34B (Partial File — 10 pages of 190 pages)

OligoProbe DesignStation

Probes:       C:\HITACHI\HUMBJUNX.CDS
Preparation:  C:\HITACHI\JUNMIX.PRP

```
       Locus pos    Tm         Locu pos    Tm              Locus pos   Tm atgtgcactaaaatggaacagcccttctac
      1  30      1      1      1      2      2      2      2      2      3      4
         humbjunx  1       60.76
         musbjunx  1       50.03
         muscjunx  1       30.07
         musdjunx  721     27.84 tgtgcactaaaatggaacagcccttctac
      2  29      1      1      1      2      2      2      2      2      3      4
         humbjunx  65533   60.68
         musbjunx  65533   49.58
         muscjunx  1       29.97
         musdjunx  721     27.66 gtgcactaaaatggaacagcccttctac
      3  28      1      1      1      2      2      2      2      2      3      4
         humbjunx  65533   60.60
         musbjunx  65533   49.10
         muscjunx  1       29.86
         musdjunx  721     27.47 tgcactaaaatggaacagcccttctacc
      4  28      1      1      1      1      2      2      2      2      3      4
         humbjunx  65533   60.60
         musbjunx  65533   46.57
         muscjunx  1       29.86
         musdjunx  729     27.47 gcactaaaatggaacagcccttctacc
      5  27      1      1      1      1      2      2      2      2      3      4
         humbjunx  5       60.51
         musbjunx  5       45.96
         muscjunx  1       29.75
         musdjunx  729     27.26
```

FIG. 37

```
LOCUS       HUMBJUNX      1044 bp    DNA                        19-DEC-1991
BASE COUNT      195 A     368 C    340 G      141 T
ORIGIN
        1 ATGTGCACTA AAATGGAACA GCCCTTCTAC CACGACGACT CATACACAGC TACGGGATAC
       61 GGCCGGGCCC CTGGTGGCCT CTCTCTACAC GACTACAAAC TCCTGAAACC GAGCCTGGCG
      121 GTCAACCTGG CCGACCCCTA CCGGAGTCTC AAAGCGCCTG GGGCTCGCGG ACCCGGCCCA
      181 GAGGGCGGCG GTGGCGGCAG CTACTTTTCT GGTCAGGGCT CGGACACCGG CGCGTCTCTC
      241 AAGCTCGCCT CTTCGGAGCT GGAACGCCTG ATTGTCCCCA ACAGCAACGG CGTGATCACG
      301 ACGACGCCTA CACCCCCGGG ACAGTACTTT TACCCCCGCG GGGGTGGCAG CGGTGGAGGT
      361 GCAGGGGGCG CAGGGGGCGG CGTCACCGAG GAGCAGGAGG GCTTCGCCGA CGGCTTTGTC
      421 AAAGCCCTGG ACGATCTGCA CAAGATGAAC CACGTGACAC CCCCAACGT GTCCCTGGGC
      481 GCTACCGGGG GGCCCCCGGC TGGGCCCGGG GGCGTCTACG CCGGCCCGGA GCCACCTCCC
      541 GTTTACACCA ACCTCAGCAG CTACTCCCCA GCCTCTGCGT CCTCGGGAGG CGCCGGGGCT
      601 GCCGTCGGGA CCGGGAGCTC GTACCCGACG ACCACCATCA GCTACCTCCC ACACGCGCCG
      661 CCCTTCGCCG GTGGCCACCC GGCGCAGCTG GGCTTGGGCC GCGGCGCCTC CACCTTCAAG
      721 GAGGAACCGC AGACCGTGCC GGAGGCGCGC AGCCGGGACG CCACGCCGCC GGTGTCCCCC
      781 ATCAACATGG AAGACCAAGA GCGCATCAAA GTGGAGCGCA AGCGGCTGCG GAACCGGCTG
      841 GCGGCCACCA AGTGCCGGAA GCGGAAGCTG GAGCGCATCG CGCGCCTGGA GGACAAGGTG
      901 AAGACGCTCA AGGCCGAGAA CGCGGGGCTG TCGAGTACCG CCGGCCTCCT CCGGGAGCAG
      961 GTGGCCCAGC TCAAACAGAA GGTCATGACC CACGTCAGCA ACGGCTGTCA GCTGCTGCTT
     1021 GGGGTCAAGG GACACGCCTT CTGA
//
```

FIG. 38A₁

```
LOCUS       HUMBJUNX       1044 bp    DNA                    19-DEC-1991
BASE COUNT      195 A      368 C      340 G      141 T
ORIGIN
        1 ATGTGCACTA AAATGGAACA GCCCTTCTAC CACGACGACT CATACACAGC TACGGGATAC
       61 GGCCGGGCCC CTGGTGGCCT CTCTCTACAC GACTACAAAC TCCTGAAACC GAGCCTGGCG
      121 GTCAACCTGG CCGACCCCTA CCGGAGTCTC AAAGCGCCTG GGGCTCGCGG ACCCGGCCCA
      181 GAGGGCGGCG GTGGCGGCAG CTACTTTTCT GGTCAGGGCT CGGACACCGG CGCGTCTCTC
      241 AAGCTCGCCT CTTCGGAGCT GGAACGCCTG ATTGTCCCCA ACAGCAACGG CGTGATCACG
      301 ACGACGCCTA CACCCCCGGG ACAGTACTTT TACCCCCGCG GGGGTGGCAG CGGTGGAGGT
      361 GCAGGGGCG CAGGGGGCGG CGTCACCGAG GAGCAGGAGG GCTTCGCCGA CGGCTTTGTC
      421 AAAGCCCTGG ACGATCTGCA CAAGATGAAC CACGTGACAC CCCCCAACGT GTCCCTGGGC
      481 GCTACCGGGG GGCCCCCGGC TGGGCCCGGG GGCGTCTACG CCGGCCCGGA GCCACCTCCC
      541 GTTTACACCA ACCTCAGCAG CTACTCCCCA GCCTCTGCGT CCTCGGGAGG CGCCGGGGCT
      601 GCCGTCGGGA CCGGGAGCTC GTACCCGACG ACCACCATCA GCTACCTCCC ACACGCGCCG
      661 CCCTTCGCCG GTGGCCACCC GGCGCAGCTG GGCTTGGGCC GCGGCGCCTC CACCTTCAAG
      721 GAGGAACCGC AGACCGTGCC GGAGGCGCGC AGCCGGGACG CCACGCCGCC GGTGTCCCCC
      781 ATCAACATGG AAGACCAAGA GCGCATCAAA GTGGAGCGCA AGCGGCTGCG GAACCGGCTG
      841 GCGGCCACCA AGTGCCGGAA GCGGAAGCTG GAGCGCATCG CGCGCCTGGA GGACAAGGTG
      901 AAGACGCTCA AGGCCGAGAA CGCGGGCTG TCGAGTACCG CCGGCCTCCT CCGGGAGCAG
      961 GTGGCCCAGC TCAAACAGAA GGTCATGACC CACGTCAGCA ACGGCTGTCA GCTGCTGCTT
     1021 GGGGTCAAGG GACACGCCTT CTGA
//

LOCUS       HUMCJUNX       996 bp     DNA                    19-DEC-1991
BASE COUNT      226 A      342 C      299 G      129 T
ORIGIN
        1 ATGACTGCAA AGATGGAAAC GACCTTCTAT GACGATGCCC TCAACGCCTC GTTCCTCCCG
       61 TCCGAGAGCG GACCTTATGG CTACAGTAAC CCCAAGATCC TGAAACAGAG CATGACCCTG
      121 AACCTGGCCG ACCCAGTGGG GAGCCTGAAG CCGCACCTCC GCGCCAAGAA CTCGGACCTC
      181 CTCACCTCGC CCGACGTGGG GCTGCTCAAG CTGGCGTCGC CCGAGCTGGA GCGCCTGATA
      241 ATCCAGTCCA GCAACGGGCA CATCACCACC ACGCCGACCC CCACCCAGTT CCTGTGCCCC
      301 AAGAACGTGA CAGATGAGCA GGAGGGGTTC GCCGAGGGCT TCGTGCGCGC CCTGGCCGAA
      361 CTGCACAGCC AGAACACGCT GCCCAGCGTC ACGTCGGCGG CGCAGCCGGT CAACGGGGCA
      421 GGCATGGTGG CTCCCGCGGT AGCCTCGGTG GCAGGGGCA GCGGCAGCGG CGGCTTCAGC
      481 GCCAGCCTGC ACAGCGAGCC GCCGGTCTAC GCAAACCTCA GCAACTTCAA CCCAGGCGCG
      541 CTGAGCAGCG GCGGCGGGGC GCCCTCCTAC GGCGCGGCCG GCCTGGCCTT TCCCGCGCAA
      601 CCCCAGCAGC AGCAGCAGCC GCCGCACCAC CTGCCCCAGC AGATGCCCGT GCAGCACCCG
      661 CGGCTGCAGG CCCTGAAGGA GGAGCCTCAG ACAGTGCCCG AGATGCCCGG CGAGACACCG
      721 CCCCTGTCCC CCATCGACAT GGAGTCCCAG GAGCGGATCA AGGCGGAGAG GAAGCGCATG
      781 AGGAACCGCA TCGCTGCCTC CAAGTGCCGA AAAAGGAAGC TGGAGAGAAT CGCCCGGCTG
      841 GAGGAAAAAG TGAAAACCTT GAAAGCTCAG AACTCGGAGC TGGCGTCCAC GGCCAACATG
      901 CTCAGGGAAC AGGTGGCACA GCTTAAACAG AAAGTCATGA ACCACGTTAA CAGTGGGTGC
      961 CAACTCATGC TAACGCAGCA GTTGCAAACA TTTTGA
//
```

FIG. 38A₂

```
LOCUS       HUMDJUNX      1044 bp ss-mRNA        PRI        24-MAY-1991
DEFINITION  Human junD mRNA
ACCESSION   X56681
KEYWORDS    jun-D gene; oncogene.
SOURCE      Homo sapiens RNA.
  ORGANISM  Homo sapiens
            Eukaryota; Animalia; Metazoa; Chordata; Vertebrata; Mammalia;
            Theria; Eutheria; Primates; Haplorhini; Catarrhini; Hominidae.
REFERENCE   1  (bases 1 to 1891)
  AUTHORS   Shaul,Y.
  JOURNAL   Unpublished (1990)
  STANDARD  full automatic
REFERENCE   2  (sites)
```

FIG. 38B₁

```
AUTHORS    Berger,I. and Shaul,Y.
TITLE      Structure and function of human jun-D
JOURNAL    Unpublished (1990)
STANDARD   full staff_review
COMMENT    From EMBL 26     entry HSJUNDR;    dated 18-MAR-1991.
FEATURES           Location/Qualifiers
    mRNA           1..1891
                   /gene="junD"
                   /evidence=EXPERIMENTAL
    CDS            175..1218
                   /product="judD protein"
                   /gene="junD"
                   /codon_start=1
    polyA_site     1891..1891

BASE COUNT       162 A     405 C     360 G     117 T
ORIGIN
       1 ATGGAAACAC CCTTCTACGG CGATGAGGCG CTGAGCGGCC TGGGCGGCGG CGCCAGTGGC
      61 AGCGGCGGCA CGTTCGCGTC CCCGGGCCGC TTGTTCCCCG GGCGCCCCC  GACGGCCGCG
     121 GCCGGCAGCA TGATGAAGAA GGACGCGCTG ACGCTGAGCC TGAGTGAGCA GGTGGCGGCA
     181 GCGCTCAAGC CTGCGCCCGC GCCCGCCTCC TACCCCCCTG CCGCCGACGG CGCCCCCAGC
     241 GCGGCACCCC CCGACGGCCT GCTCGCCTCT CCCGACCTGG GGCTGCTGAA GCTGGCCTCC
     301 CCCGAGCTCG AGCGCCTCAT CATCCAGTCC AACGGGCTGG TCACCACCAC GCCGACGAGC
     361 TCACAGTTCC TCTACCCCAA GGTGGCGGCC AGCGAGGAGC AGGAGTTCGC CGAGGGCTTC
     421 GTCAAGGCCC TGGAGGATTT ACACAAGCAG AACCAGCTCG CGCGGGCCG  GGCCGCTGCC
     481 GCCGCCGCCG CCGCCGCCGG GGGGCCCTCG GGCACGGCCA CGGGCTCCGC GCCCCCCCGC
     541 GAGCTGGCCC CGGCGGCGGC CGCGCCCGAA GCGCCTGTCT ACGCGAACCT GAGCAGCTAC
     601 GCGGGCGGCG CCGGGGGCGC GGGGGGCGCC GCGACGGTCG CCTTCGCTGC CGAACCTGTG
     661 CCCTTCCCGC CGCCGCCACC CCCAGGCGCG TTGGGGCCGC CGCGCCTGGC TGCGCTCAAG
     721 GACGAGCCAC AGACGGTGCC CGACGTGCCG AGCTTCGGCG AGAGCCCGCC GTTGTCGCCC
     781 ATCGACATGG AGTGCCGCAA GCGCATCAAG GCGGAGCGCA AGCGGCTGCG CAACCGCATC
     841 GCCGCCTCCA AGAGTCAGAA GCGCAAGCTG GAGCGCATCT CGCGCCTGGA AGAGAAAGTG
     901 AAGACCCTCA TCAAGCAGAA CACGGAGCTG GCGTCCACGG CGAGCCTGCT GCGCGAGCAG
     961 GTGGCGCAGC TCCCGGCGTA AGTCCTCAGC CACGTCAACA GCGGCTGCCA GCTGCTGCCC
    1021 CAGCACCAGG            CTGA
//
```

FIG. 38B₂

```
LOCUS        MUSBJUNX       1035 bp   DNA                           19-DEC-1991
BASE COUNT        210 A       333 C      333 G       159 T
ORIGIN
     1 ATGTGCACGA AAATGGAACA GCCTTTCTAT CACGACGACT CTTACGCAGC GGCGGGATAC
    61 GGTCGGAGCC CTGGCAGCCT GTCTCTACAC GACTACAAAC TCCTGAAACC CACCTTGGCG
   121 CTCAACCTGG CGGATCCCTA TCGGGGTCTC AAGGGTCCTG GGGCGCGGGG TCCAGGCCCG
   181 GAGGGCAGTG GGGCAGGCAG CTACTTTTCG GGTCAGGGAT CAGACACAGG CGCATCTCTG
   241 AAGCTAGCCT CCACGGAACT GGAGCGCTTG ATCGTCCCCA ACAGCAACGG CGTGATCACG
   301 ACGACGCCCA CGCCTCCGGG ACAGTACTTT TACCCCCGTG GGGGTGGCAG CGGTGGAGGT
   361 ACAGGGGGCG GCGTCACCGA GGAGCAGGAG GGCTTTGCGG ACGGTTTTGT CAAAGCCCTG
   421 GACGACCTGC ACAAGATGAA CCACGTGACG CCCCCCAACG TGTCCCTGGG CGCCAGCGGG
   481 GGTCCCCAGG CCGGCCCAGG GGGCGTCTAT GCTGGTCCGG AGCCGCCTCC CGTCTACACC
   541 AACCTCAGCA GTTACTCTCC AGCCTCTGCA CCCTCTGGAG GCTCCGGGAC CGCCGTCGGG
   601 ACTGGGAGCT CATACCCGAC GGCCACCATC AGCTACCTCC CACATGCACC ACCCTTTGCG
   661 GGCGGCCACC CGGCACAGCT GGGTTTGAGT CGTGGCGCTT CCGCCTTTAA AGAGGAACCG
   721 CAGACCGTAC CGGAGGCACG CAGCCGCGAC GCCACGCCGC CTGTGTCCCC CATCAACATG
   781 GAAGACCAGG AGCGCATCAA AGTGGAGCGA AAGCGGCTGC GGAACAGGCT GGCGGCCACC
   841 AAGTGCCGGA AGCGGAAGCT GGAGCGCATC GCGCGCCTGG AGGACAAGGT GAAGACACTC
   901 AAGGCTGAGA ACGCGGGGCT GTCGAGTGCT GCCGGTCTCC TAAGGGAGCA AGTGGCGCAG
   961 CTCAAGCAGA AGGTCATGAC CCATGTCAGC AACGGCTGCC AGTTGCTGCT AGGGGTCAAG
  1021 GGACACGCCT TCTGA
//
```

FIG. 38C

```
LOCUS       MUSCJUNX        1005 bp    DNA              19-DEC-1991
BASE COUNT       223 A      334 C     300 G     148 T
ORIGIN
        1 ATGACTGCAA AGATGGAAAC GACCTTCTAC GACGATGCCC TCAACGCCTC GTTCCTCCAG
       61 TCCGAGAGCG GTGCCTACGG CTACAGTAAC CCTAAGATCC TAAAACAGAG CATGACCTTG
      121 AACCTGGCCG ACCCGGTGGG CAGTCTGAAG CCGCACCTCC GCGCCAAGAA CTCGGACCTT
      181 CTCACGTCGC CCGACGTCGG GCTGCTCAAG CTGGCGTCGC CGGAGCTGGA GCGCCTGATC
      241 ATCCAGTCCA GCAATGGGCA CATCACCACT ACACCGACCC CCACCCAGTT CTTGTGCCCC
      301 AAGAACGTGA CCGACGAGCA GGAGGGCTTC GCCGAGGGCT TCGTGCGCGC CCTGGCTGAA
      361 CTGCATAGCC AGAACACGCT TCCCAGTGTC ACCTCCGCGG CACAGCCGGT CAGCGGGCG
      421 GGCATGGTGG CTCCCGCGGT GGCCTCAGTA GCAGGCGCTG GCGGCGGTGG TGGCTACAGC
      481 GCCAGCCTGC ACAGTGAGCC TCCGGTCTAC GCCAACCTCA GCAACTTCAA CCCGGGTGCG
      541 CTGAGCAGCG GCGGTGGGGC GCCCTCCTAT GGCGCGGCCG GCTGGCCTT TCCCTCGCAG
      601 CCGCAGCAGC AGCAGCAGCC GCCTCAGCCG CCGCACCACT TGCCCCAACA GATCCCGGTG
      661 CAGCACCCGC GGCTGCAAGC CCTGAAGGAA GAGCCGCAGA CCGTGCCGGA GATGCCGGGA
      721 GAGACGCCGC CCCTGTCCCC TATCGACATG GAGTCTCAGG AGCGGATCAA GGCAGAGAGG
      781 AAGCGCATGA GGAACCGCAT TGCCGCCTCC AAGTGCCGGA AAAGGAAGCT GGAGCGGATC
      841 GCTCGGCTAG AGGAAAAAGT GAAAACCTTG AAAGCGCAAA ACTCCGAGCT GGCATCCACG
      901 GCCAACATGC TCAGGGAACA GGTGGCACAG CTTAAGCAGA AAGTCATGAA CCACGTTAAC
      961 AGTGGGTGCC AACTCATGCT AACGCAGCAG TTGCAAACGT TTTGA
//
LOCUS       MUSDJUNX        1026 bp    DNA              19-DEC-1991
BASE COUNT       172 A      382 C     343 G     129 T
ORIGIN
        1 ATGGAAACGC CCTTCTATGG CGAGGAGGCG CTGAGCGGCC TGGCTGCGGG TGCGTCGAGC
       61 GTCGCTGGTG CTACTGGGGC CCCCGGCGGT GGTGGCTTCG CGCCCCCGGG CCGCGCTTTC
      121 CCCGGGGCGC CCCCGACGAG CAGCATGCTG AAGAAAGACG CGCTGACGCT CAGCCTGGCG
      181 GAGCAGGGAG CGGCGGGATT GAAACCAGGG TCGGCCACTG CACCTTCTGC GCTGCGCCCC
      241 GACGGCGCCC CCGACGGGCT GCTGGCTTCG CCGGATCTTG GCTGCTCAA ACTCGCGTCG
      301 CCGGAGCTGG AGAGGCTGAT CATCCAGTCC AACGGGCTGG TGACCACTAC CCCGACCAGT
      361 ACGCAGTTCC TCTACCCGAA GGTGGCAGCC AGCGAGGAGC AGGAGTTCGC CGAAGGCTTC
      421 GTCAAGGCGC TGGAGGACCT GCACAAGCAA AGCCAGCTGG GTGCGGCCAC CGCGGCCACC
      481 TCAGGGCTC CCGCGCCTCC CGCGCCCGCC GACCTGGCCG CCACCCCCGG GGCCACGGAG
      541 ACCCCGGTCT ACGCCAACCT GAGCAGTTTC GCGGGTGGCG CCGGGCCCCC TGGGGCGCG
      601 GCCACCGTGG CTTTCGCCGC GGAGCCAGTG CCCTTCCCGC CGCCCCCGGG CGCGCTGGGG
      661 CCGCCGCCAC CTCCGCATCC ACCGCGCCTG GCCGCGCTCA AGGACGAGCC GCAGACCGTG
      721 CCGGACGTGC CGAGCTTCGG CGACAGCCCT CCGCTGTCGC CCATCGACAT GGACACGCAA
      781 GAACGCATCA AGGCGGAGCG CAAGAGGCTG CGCAACCGCA TCGCCGCCTC CAAATGCCGC
      841 AAGCGCAAGC TGGAGCGTAT CTCGCGCCTG GAGGAGAAAG TCAAGACCCT CAAAAGCCAG
      901 AACACCGAGC TGGCGTCCAC CGCCAGCCTG CTGCGCGAGC AGGTGGCGCA GCTCAAACAG
      961 AAAGTCCTCA GCCACGTCAA CAGCGGCTGC CAGCTGCTGC CCCAGCACCA GGTCCCGGCG
     1021 TACTGA
//
```

METHOD FOR DETECTING POLYNUCLEOTIDES WITH IMMOBILIZED POLYNUCLEOTIDE PROBES IDENTIFIED BASED ON $T_M$

The present application is a continuation of application Ser. No. 07/974,406, filed on Nov. 12, 1992, abandoned, which is a continuation-in-part of application Ser. No. 07/922,522, filed Jul. 28, 1992, now abandoned. The disclosure of this previous application is hereby incorporated herein in its entirety by this reference thereto, including all sequences listed therein.

FIELD OF THE INVENTION

The present invention relates to methods for detecting the presence of an organism or a member of a group of organisms in a biological sample by probing the sample for polynucleotides indicative of the presence of such organisms. The present invention also relates to methods for detecting the presence of other infectious agents or biological components in a biological sample which comprises polynucleotides.

BACKGROUND OF THE INVENTION

At the present time, the identity of an organism or infectious agent suspected of infecting a subject is normally determined by culturing a sample of biological material from the subject. For example, if it is suspected that a subject is suffering from an infection of the lung caused by the fungus *Candida albicans*, a sputum sample can be cultured. After a period of time, the culture is visually observed, and if a fungus grows in the culture in numbers sufficient to indicate a fungal infection, that fungus is identified by observing its morphological characteristics.

This method of confirming a diagnosis, however, has serious drawbacks. For example, it requires that the biological sample be cultured for a long enough period of time to allow a detectable amount of the organism to grow. This method also requires that the cultured sample be inspected by a technician trained in identifying different varieties of organisms. There is therefore a great need for an assay which can quickly and specifically identify an organism or infectious agent or a group of organisms or infectious agents. An assay which does not require a great deal of training to perform and interpret would also be advantageous.

There is also a need for an improved method for identifying other biological components present in a biological sample, where such components comprise polynucleotides or where the presence of such components is indicated by the presence of a polynucleotide. Present methods for detecting polynucleotides in a cell or tissue sample, such as the Norther blot method, require a relatively large amount of starting material. The Norther blot method is a widely accepted method of detecting specific genes (Sambrook J. et al., Molecular Cloning: A Laboratory Manual, 2nd ed., pp. 7.39–7.52) (hereinafter "Molecular Cloning"), and has been adapted for detecting cellular components such as jun oncogenes (Sherman, et al., Proc. Natl. Acac. Sci. USA, 87:5663–5666 (1990); Oursler M. J. et al., Proc. Natl. Acad. Sci. USA, 88:6613–6617 (1991)). In this method, mRNA is first purified from a tissue or cell culture, such as through electrophoresis on an agarose gel. Following electrophoresis, the mRNA is transferred onto membranes and hybridized with radioactive probes to identify positive band(s) through autoradiography. However, this method is not sensitive enough to identify signals corresponding to specific genes or gene products if the cells from which the mRNA is extracted have only a small quantity of genetic material.

Alternatively, reverse PCR (discussed in Molecular Cloning) can also be used to detect a wide variety of genes from different tissues and cells. In this method, mRNA is first converted to cDNA by reverse transcriptase, and specific gene fragments are then amplified by PCR using a set of primers (sense and anti-sense primers). The amplified gene can then be seen through agarose gel electrophoresis.

SUMMARY

The present invention provides an improved method of detecting the presence of an organism, an infectious agent, or a biological component of a cell or organism in a biological sample. In this method, a polynucleotide probe is hybridized to an analyte polynucleotide in the biological sample which belongs to the organism, infectious agent, or biological component or which is indicative of the presence of the organism, infectious agent or biological component. When only small amounts of such an analyte polynucleotide are available, an alternative method can be used which employs the Polymerase Chain Reaction (PCR). In addition, the present invention embodies polynucleotide probes and primers for use in the present methods, as well as kits which incorporate such probes and primers.

In one embodiment, the present invention includes a method of detecting the presence of a particular organism, infectious agent, or biological component of a cell or organism in a biological sample that contains polynucleotides. This method involves detecting an analyte polynucleotide in the sample that is indicative of the presence of the organism, infectious agent, or biological component and comprises the steps of:

(a) identifying a first polynucleotide probe, wherein the nucleotide sequence of the first polynucleotide probe is sufficiently complementary to a first nucleotide sequence contained in the analyte polynucleotide that the first polynucleotide probe can hybridize to the first nucleotide sequence of the analyte polynucleotide, the first nucleotide sequence of the analyte polynucleotide being specific to the particular organism, infectious agent, or biological component;

(b) immobilizing the first polynucleotide probe to a solid support;

(c) hybridizing the analyte polynucleotide in the sample with the first polynucleotide probe;

(d) identifying a second polynucleotide probe, wherein the nucleotide sequence of the second polynucleotide probe is sufficiently complementary to a second nucleotide sequence contained in the analyte polynucleotide that the second polynucleotide probe can hybridize to the second nucleotide sequence, the second nucleotide sequence being common to a plurality of organisms, infectious agents, or biological components including the particular organism, infectious agent, or biological component;

(e) hybridizing the second polynucleotide probe with the analyte polynucleotide which is hybridized to the first polynucleotide probe; and (f) determining the presence of the particular organism, infectious agent, or biological component in the sample by detecting the presence of the second polynucleotide probe on the solid support.

In another embodiment, the present method for detecting the presence of an organism, infectious agent, or biological component of a cell or organism in a biological sample comprises the steps of:

(a) immobilizing a first polynucleotide probe to a solid support, wherein the nucleotide sequence of the first polynucleotide probe is sufficiently complementary to a first nucleotide sequence contained in an analyte polynucleotide in the organism, infectious agent, or biological component that the first polynucleotide probe can hybridize to the first nucleotide sequence of the analyte polynucleotide of the organism, infectious agent, or biological component;

(b) contacting the polynucleotides present in the sample with the first polynucleotide probe;

(c) hybridizing the analyte polynucleotide in the sample to the first polynucleotide probe, if the analyte polynucleotide is present in the sample;

(d) contacting a second polynucleotide probe with the analyte polynucleotide hybridized to the first polynucleotide probe, if the analyte polynucleotide from the sample has hybridized to the first polynucleotide probe, wherein the nucleotide sequence of the second polynucleotide probe is sufficiently complementary to a second nucleotide sequence contained in the analyte polynucleotide of the organism, infectious agent, or biological component that the second polynucleotide probe can hybridize to the second nucleotide sequence;

(e) hybridizing the second polynucleotide probe to the analyte polynucleotide hybridized to the first polynucleotide probe, if the analyte polynucleotide has hybridized to the first polynucleotide probe; and (f) determining the presence of the organism, infectious agent, or biological component in the sample by detecting the presence of the second polynucleotide probe hybridized to the analyte polynucleotide which has hybridized to the first polynucleotide probe.

In this method, the second polynucleotide probe can preferably have the same or lower $T_m$ as the first polynucleotide probe. Preferably, the first polynucleotide probe also has a $T_m$ within the range of from approximately 48° C. to approximately 60° C. The first nucleotide sequence of the analyte polynucleotide can also in one embodiment be common to a plurality of organisms, infectious agents, or biological components of a cell or organism. Alternatively, the first nucleotide sequence of the analyte polynucleotide can be specific to a particular organism, infectious agent, or biological component of a cell or organism.

The second nucleotide sequence of the analyte polynucleotide can have a sequence common to a plurality of organisms, infectious agents, or biological components of a cell or organism in this embodiment of the present method. In an alternative embodiment, the second nucleotide sequence of the analyte polynucleotide can have a sequence that is specific for a particular organism, infectious agent, or biological component of a cell or organism. Additionally, a label can advantageously be attached to the second polynucleotide probe. Any of a number of polynucleotide labels known to the art can be used, including a radionuclide, an enzyme, an enzyme substrate, a specific binding moiety, an binding partner for a specific binding moiety, biotin, avidin, a nucleic acid stain, or a fluorescent material. If a nucleic acid stain is used as the label, the stain can consist of either ethidium bromide, yoyo-1, or toto-1. When the label is a light-emitting substance, the label can advantageously be detected by measuring the amount of light emitted therefrom. When measuring the amount of light emitted by the label, light can be recorded on film, after which the amount of exposure of the film is measured using a densitometer. In an even more preferable embodiment, the label comprises alkaline phosphatase and the label is detected by adding ATTOPHOS to the solution containing the labeled probe and then measuring the fluorescence emitted using a fluorimeter.

A solid support such as a microtiter plate having a plurality of wells can be used to perform the present method. Preferably, each of the wells has a specific polynucleotide probe immobilized thereon. The first polynucleotide probe, which can be immobilized on the microtiter plate, advantageously comprises DNA, and more advantageously both the first and second polynucleotide probes comprise DNA.

A further preferable step of the method of the present invention involves washing the solid support after hybridizing the analyte polynucleotide in the sample to the first polynucleotide probe. In this way, substantially all of the biological sample not annealed to the first polynucleotide probe is removed from the solid support. Yet another step of the method includes the step of washing the solid support after hybridizing the second polynucleotide probe with the analyte polynucleotide, which is itself hybridized to the first polynucleotide probe. After such washing, substantially all of the second polynucleotide probe not hybridized with the analyte polynucleotide is removed from the solid support. The analyte polynucleotide in this method can be selected from the group consisting of mRNA, rRNA, and genomic DNA.

Another embodiment of the present invention is a method of detecting the presence of an organism, infectious agent, or biological component of a cell or organism in a biological sample containing polynucleotides, comprising the steps of:

(a) identifying a first polynucleotide probe and a second polynucleotide probe, wherein the nucleotide sequence of the first polynucleotide probe is sufficiently complementary to a first nucleotide sequence contained in an analyte polynucleotide of the organism, infectious agent, or biological component that the first polynucleotide probe can hybridize to the first nucleotide sequence of the analyte polynucleotide of the organism, infectious agent, or biological component, and wherein the nucleotide sequence of the second polynucleotide probe is sufficiently complementary to a second nucleotide sequence contained in the analyte polynucleotide of the organism, infectious agent, or biological component that the second polynucleotide probe can hybridize to the second nucleotide sequence, the second nucleotide sequence being common to a plurality of organisms, infectious agents, or biological components;

(b) immobilizing the first polynucleotide probe to a solid support;

(c) contacting the polynucleotides present in the sample with the first polynucleotide probe;

(d) hybridizing an analyte polynucleotide in the sample to the first polynucleotide probe, if the analyte polynucleotide is present in the sample;

(e) contacting the second polynucleotide probe with the analyte polynucleotide hybridized to the first polynucleotide probe, if the analyte polynucleotide from the sample has hybridized to the first polynucleotide probe;

(f) hybridizing the second polynucleotide probe to the analyte polynucleotide hybridized to the first polynucleotide probe, if the analyte polynucleotide has hybridized to the first polynucleotide probe; and (g) determining the presence of the organism, infectious agent, or biological component in the sample by detecting the presence of the second polynucleotide probe hybridized to the analyte polynucleotide which has hybridized to the first polynucleotide probe.

In this embodiment, the identifying step can advantageously comprise the use of a computer, preferably one which uses an H-site model to identify the first polynucleotide probe. Using the H-site model to identify the first polynucleotide probe involves the steps of:

specifying a minimum melting temperature for the first nucleotide probe and the nucleotide sequence specific to the organism;

specifying a nucleation threshold that places a minimum value on the number of base pairs at any nucleation site;

determining the melting temperatures (Tm) of the first nucleotide probe and the sequence specific to the organism at every possible hybridization point; and selecting the nucleotide probe having the highest Tm value.

When using the H-site model, the melting temperature is preferably determined by the formula;

(a) $Tm = 81.5 - 16.6(\log[Na]) - 0.63\%(\text{formamide}) + 0.41(\%(G+C)) - 600/N$, wherein Log[Na] is the log function of the sodium concentration, 0.063% (formamide) is the concentration of formamide, %(G+C) is the percentage of matched GC base pairs, and N is the probe length.

In this method the second polynucleotide probe can also be identified using a computer which makes use of the H-site model. Identifying the second polynucleotide probe with the H-site model is preferably accomplished by following the steps of:

specifying a minimum melting temperature for the second nucleotide probe and the nucleotide sequence specific to the organism;

specifying a nucleation threshold that places a minimum value on the number of base pairs at any nucleation site;

determining the melting temperatures (Tm) of the first nucleotide probe and the sequence specific to the organism at every possible hybridization point; and selecting the nucleotide probe of the proper length having the lowest Tm value.

The melting temperature of the second polynucleotide probe can likewise be determined by the formula;

$Tm = 81.5 - 16.6(\log[Na]) - 0.63\%(\text{formamide}) + 0.41(\%(G+C)) - 600/N$, wherein Log[Na] is the log function of the sodium concentration, 0.63% (formamide) is the concentration of formamide, %(G+C) is the percentage of matched GC base pairs, and N is the probe length.

In this method, the second polynucleotide probe can advantageously have the same or lower $T_m$ as the first polynucleotide probe. The first polynucleotide probe also preferably has a $T_m$ within the range of from approximately 48° C. to approximately 60° C. The first nucleotide sequence of the analyte polynucleotide can also in one embodiment be common to a plurality of organisms, infectious agents, or biological components of a cell or organism. Alternatively, the first nucleotide sequence of the analyte polynucleotide can be specific to a particular organism, infectious agent, or biological component of a cell or organism.

The second nucleotide sequence of the analyte polynucleotide can have a sequence common to a plurality of organisms, infectious agents, or biological components of a cell or organism in this embodiment of the present method. In an alternative embodiment, the second nucleotide sequence of the analyte polynucleotide can have a sequence that is specific for a particular organism, infectious agent, or biological component of a cell or organism. Additionally, a label can advantageously be attached to the second polynucleotide probe. Any of a number of polynucleotide labels known to the art can be used, including a radionuclide, an enzyme, an enzyme substrate, a specific binding moiety, an binding partner for a specific binding moiety, biotin, avidin, a nucleic acid stain, or a fluorescent material. If a nucleic acid stain is used as the label, the stain can consist of either ethidium bromide, yoyo-1, or toto-1. When the label is a light-emitting substance, the label can advantageously be detected by measuring the amount of light emitted therefrom. When measuring the amount of light emitted by the label, light can be recorded on film, after which the amount of exposure of the film is measured using a densitometer. In an even more preferable embodiment, the label comprises alkaline phosphatase and the label is detected by adding ATTOPHOS to the solution containing the labeled probe and then measuring the fluorescence emitted using a fluorimeter.

A solid support such as a microtiter plate having a plurality of wells can be used to perform the present method. Preferably, each of the wells has a specific polynucleotide probe immobilized thereon. The first polynucleotide probe, which can be immobilized on the microtiter plate, advantageously comprises DNA, and more advantageously both the first and second polynucleotide probes comprise DNA.

A further preferable step of the method of the present invention involves washing the solid support after hybridizing the analyte polynucleotide in the sample to the first polynucleotide probe. In this way, substantially all of the biological sample not annealed to the first polynucleotide probe is removed from the solid support. Yet another step of the method includes the step of washing the solid support after hybridizing the second polynucleotide probe with the analyte polynucleotide, which is itself hybridized to the first polynucleotide probe. After such washing, substantially all of the second polynucleotide probe not hybridized with the analyte polynucleotide is removed from the solid support. The analyte polynucleotide in this method can be selected from the group consisting of mRNA, rRNA, and genomic DNA.

Another embodiment of the present invention comprises a solid support-polynucleotide structure for identifying the presence of an organism, infectious agent, or biological component of a cell or organism in a biological sample containing polynucleotides. This structure comprises a solid support having immobilized thereto a first polynucleotide probe, the first polynucleotide probe having a sequence complementary to a first nucleotide sequence specific to the organism, infectious agent, or biological component. The structure also includes an analyte polynucleotide from the cell, organism, or infectious agent which contains the first nucleotide sequence, the analyte polynucleotide being hybridized to the first polynucleotide probe at the first nucleotide sequence. The structure includes as well a second polynucleotide probe, preferably having a label, which is complementary to a second nucleotide sequence present on the analyte polynucleotide from the cell, organism, or infectious agent which is hybridized to the first polynucleotide probe, the second polynucleotide probe being hybridized to the analyte polynucleotide at the second nucleotide sequence.

The label of the above method is preferably selected from the group consisting of a radionuclide, an enzyme, an enzyme substrate, a specific binding moiety, an binding partner for a specific binding moiety, biotin, avidin, a nucleic acid stain, and a fluorescent material. Additionally, the solid support-polynucleotide structure can even more advantageously have a second polynucleotide probe that is common to polynucleotides contained in a plurality of organisms, infectious agents, or biological components of a cell or organism. In still another preferred embodiment of this method, the first and second polynucleotide probes are determined through the use of a computer system for designing oligonucleotide probes for use with a gene sequence data source. This the computer system can comprise an input means for retrieving the gene sequence data, a processor, and instructions directing the processor to determine the first oligonucleotide probe. Yet still more preferably, the solid support-polynucleotide structure of the above method has a polynucleotide selected from the group consisting of mRNA, rRNA, and genomic DNA.

Another embodiment of the present invention is a kit for identifying the presence of an organism, infectious agent, or biological component of a cell or organism in a biological sample which contains:

a specific polynucleotide probe, the specific polynucleotide probe being complementary to or homologous to a first nucleotide sequence in an analyte polynucleotide specific to a particular organism, infectious agent, or biological component to be detected; and a common polynucleotide probe complementary to or homologous to a second nucleotide sequence in the analyte polynucleotide of the organism, infectious agent, or biological component, the common polynucleotide probe being complementary to polynucleotides contained in a plurality of organisms, infectious agents, or biological components.

In addition, the above kit can advantageously have a solid support to which a polynucleotide can be immobilized. Even more preferably, the kit has a specific polynucleotide probe immobilized to the solid support. Still more advantageously, the above kit has a solid support with a plurality of specific polynucleotide probes immobilized thereto, each of the probes specific to a different organism, infectious agent, or biological component. Most preferably, the solid support of the kit has a plurality of wells, each of the specific polynucleotide probes being immobilized to a different well, and a buffer appropriate for the hybridization of the probes and polynucleotides, with the polynucleotides being selected from the group consisting of mRNA, rRNA, and genomic DNA.

Similarly, the second polynucleotide probe of the above kit can advantageously bear a label, with the label being selected from the group consisting of a radionuclide, an enzyme, an enzyme substrate, a specific binding moiety, an binding partner for a specific binding moiety, biotin, avidin, a nucleic acid stain, and a fluorescent material. Further, the above kit can have a specific polynucleotide probe comprising a first specific primer which is complementary or homologous to a sequence specific to a particular organism, infectious agent, or biological component, the kit additionally comprising a second specific polynucleotide primer which is complementary or homologous to a different sequence specific to the organism, infectious agent, or biological component.

When the above kit is designed to be used with PCR, it should have one or more of the following: dNTP's, a reverse transcriptase, a polymerase, and a buffer appropriate for the addition of dNTP's to a primer using a reverse transcriptase or polymerase. Additionally, the kit can include a DNA polymerase that has significant polymerase activity at temperatures above 50° C.

In yet another embodiment, the present method comprises a means of detecting the presence of one or more organisms, infectious agents, or biological components in a biological sample containing polynucleotides, wherein at least one of the polynucleotides is indicative of the presence of the one or more organisms, infectious agents or biological components and is present in minute quantities. This method makes use of PCR and employs the steps of:

(a) obtaining a biological sample containing polynucleotides;

(b) contacting the sample with a first polynucleotide primer, the first primer having a nucleotide sequence complementary to a nucleotide sequence common to a plurality of organisms, infectious agents, or biological components;

(c) hybridizing the first primer to an analyte polynucleotide present in the sample that is complementary to the first primer, if such an analyte polynucleotide is present;

(d) extending the first primer, thereby producing a double-stranded polynucleotide including a complementary nucleotide strand comprising the first primer and having a nucleotide sequence complementary to the analyte polynucleotide;

(e) contacting the sample with a second polynucleotide primer, the second primer being complementary to a sequence contained in the complementary nucleotide strand;

(f) hybridizing the second primer to the complementary nucleotide strand;

(g) extending the second primer to form a nucleotide strand homologous to the analyte polynucleotide;

(h) contacting the sample with a third and a fourth polynucleotide primer, the third and fourth primers having sequences complementary to the homologous nucleotide strand and the complementary nucleotide strand, respectively, wherein the third primer has a nucleotide sequence complementary to a sequence common to a plurality of organisms, infectious agents, or biological components whose presence is to be determined and wherein the sequence of the third primer is different from that of the first primer;

(i) hybridizing the third and fourth primers to the complementary nucleotide strand and the homologous nucleotide strand;

(j) extending the third and fourth primers, thereby producing double-stranded polynucleotides; and (k) determining the presence of the one or more organisms, infectious agents, or biological components in the sample by detecting the extension of at least one of the first, second, third, or fourth primers.

In this method, the second primer can have a nucleotide sequence that is common to a plurality of the organisms, infectious agents, or biological components whose presence is being determined. This method is preferably practiced such that the extending and hybridizing steps are repeated a plurality of times. In this method, the extension step can be accomplished with a reverse transcriptase when the primer is bound to RNA, while this step is accomplished with a DNA polymerase when the bound polynucleotide is DNA. If a DNA polymerase is used, it preferably has significant polymerase activity at temperatures above 50° C. In the present method the nucleotide sequences of the first and second primers can be determined by a computer-assisted method, and preferably by a computer-assisted method which determines the sequences of the first and second nucleotide probes using an H-Site model.

Yet another method of detecting the presence of one or more organisms, infectious agents, or biological components in a biological sample containing polynucleotides, wherein at least one of the polynucleotides is indicative of the presence of the one or more organisms, infectious agents or biological components and is present in minute quantities, comprises the steps of:

obtaining a biological sample containing polynucleotides;

contacting the sample with a first polynucleotide primer, the first primer having a nucleotide sequence complementary to a nucleotide sequence common to a plurality of organisms, infectious agents, or biological components;

hybridizing the first primer to an analyte polynucleotide present in the sample that is complementary to the first primer, if such an analyte polynucleotide is present;

extending the first primer, thereby producing a double-stranded polynucleotide including a complementary nucleotide strand comprising the first primer and having a nucleotide sequence complementary to the analyte polynucleotide;

contacting the sample with a second polynucleotide primer, the second primer being complementary to a sequence contained in the complementary nucleotide strand;

hybridizing the second primer to the complementary nucleotide strand;

extending the second primer to form a nucleotide strand homologous to the analyte polynucleotide;

contacting the sample with a third polynucleotide primer, the third primer having a sequence complementary to the homologous nucleotide strand, wherein the third primer has a nucleotide sequence complementary to a sequence that is specific to a particular organism, infectious agent, or biological component whose presence is to be determined;

hybridizing the third primer to the homologous nucleotide strand;

extending the third primer, thereby producing a double-stranded polynucleotide; and determining the presence of the particular organism, infectious agent, or biological component in the sample by detecting the extension of at least one of the third primer.

This method is preferably practiced such that the extending and hybridizing steps are repeated a plurality of times. The extension step in particular can be accomplished with a reverse transcriptase when the primer is bound to RNA, while a DNA polymerase is used when the bound polynucleotide is DNA. Such a DNA polymerase preferably has significant polymerase activity at temperatures above 50° C.

In the present method the nucleotide sequences of the first and second primers can be determined by a computer-assisted method, and preferably by a computer-assisted method which determines the sequences of the first and second nucleotide probes using an H-Site model. In this method, the second primer can have a nucleotide sequence that is common to a plurality of the organisms, infectious agents, or biological components whose presence is being determined. The third primer also preferably includes a label, so that the detecting step comprises the extension of this labeled primer. The label used can be selected from the group consisting of a radionuclide, an enzyme, an enzyme substrate, a specific binding moiety, a binding partner for a specific binding moiety, biotin, avidin, a nucleic acid stain, and a fluorescent material.

Yet another method of detecting the presence of a particular organism, infectious agent, or biological component in a biological sample containing polynucleotides, wherein at least one of the polynucleotides is indicative of the presence of the organism, infectious agent, or biological component and is present in minute quantities, comprises the steps of:

(a) obtaining a biological sample containing polynucleotides;

(b) contacting the sample with a first polynucleotide primer, the first primer having a nucleotide sequence complementary to a nucleotide sequence that is specific to the particular organism, infectious agent, or biological component, wherein the nucleotide sequence of the first primer is determined by means of a computer-assisted method;

(c) hybridizing the first primer to a sample polynucleotide present in the sample that is complementary to the first primer, if such a sample polynucleotide is present;

(d) extending the first primer, thereby producing a double-stranded polynucleotide including a complementary nucleotide strand comprising the first primer and having a nucleotide sequence complementary to the sample polynucleotide;

(e) contacting the sample with a second polynucleotide primer, the second primer being complementary to a sequence contained in the complementary nucleotide strand;

(f) hybridizing the second primer to the complementary nucleotide strand;

(g) extending the second primer to form a nucleotide strand homologous to the sample polynucleotide; and (h) determining the presence of the particular organism, infectious agent, or biological component in the sample by detecting the extension of at least one of the first or second primers.

We have also discovered a number of useful probes and primers for use in the foregoing methods, including primers for detecting jun oncogenes, G proteins, β receptors, and Substance P receptors, such as those identified with a sequence identifier herein. Among the sequences we have discovered for use as probes and primers in the present method are SEQ ID NO:473, SEQ ID NO:600, SEQ ID NO:615, SEQ ID NO:622, SEQ ID NO:622, SEQ ID NO:730, SEQ ID NO:747, SEQ ID NO:748, SEQ ID NO:488, SEQ ID NO:513, SEQ ID NO:630, SEQ ID NO:639, SEQ ID NO:728, SEQ ID NO:729, SEQ ID NO:733, SEQ ID NO:734, SEQ ID NO:739, SEQ ID NO:740, SEQ ID NO:741, SEQ ID NO:742, SEQ ID NO:743, SEQ ID NO:744, SEQ ID NO:759, SEQ ID NO:758, SEQ ID NO:751, SEQ ID NO:553, SEQ ID NO:670, SEQ ID NO:752, SEQ ID NO:753, SEQ ID NO:565, SEQ ID NO:678, SEQ ID NO:686, SEQ ID NO:754, SEQ ID NO:577, SEQ ID NO:697, SEQ ID NO:704, SEQ ID NO:755, SEQ ID NO:756, SEQ ID NO:732, SEQ ID NO:642, SEQ ID NO:652, SEQ ID NO:757, SEQ ID NO:593, SEQ ID NO:710, SEQ ID NO:721, SEQ ID NO:528, SEQ ID NO:731, SEQ ID NO:749, and SEQ ID NO:750

BRIEF DESCRIPTION OF THE FIGURES

FIG. 2 is a schematic representation of the common and specific sequences identified in various species of fungi.

FIG. 8 shows a gel of samples containing varying amounts of each of five different G protein oligonucleotides (as indicated by number of "+" symbols) amplified with the $G_2$ and $G_4$ PCR primers and also provides Southern blots using each of the five G protein sequences as a probe.

FIGS. 12A–12C2 show display screen representations of the main oligoprobe design station dialog windows of this invention;

FIG. 16 is a display screen representation of the probesedit window;

FIGS. 16A1–16A2 are printouts of the probesedit output file;

FIG. 30 is the first page of a printout of a sample file containing the output of the Mismatch Model program of this invention;

FIG. 34A is the first page of a printout of a sample file containing output of Mismatch Model program;

FIG. 34B is the first page of a printout of a sample file containing output of H-Site Model program;

FIG. 37 is a printout of a sample target species file;

FIGS. 38A1–38C are printouts of a sample preparation file.

DETAILED DESCRIPTION OF THE INVENTION

Figure 1:
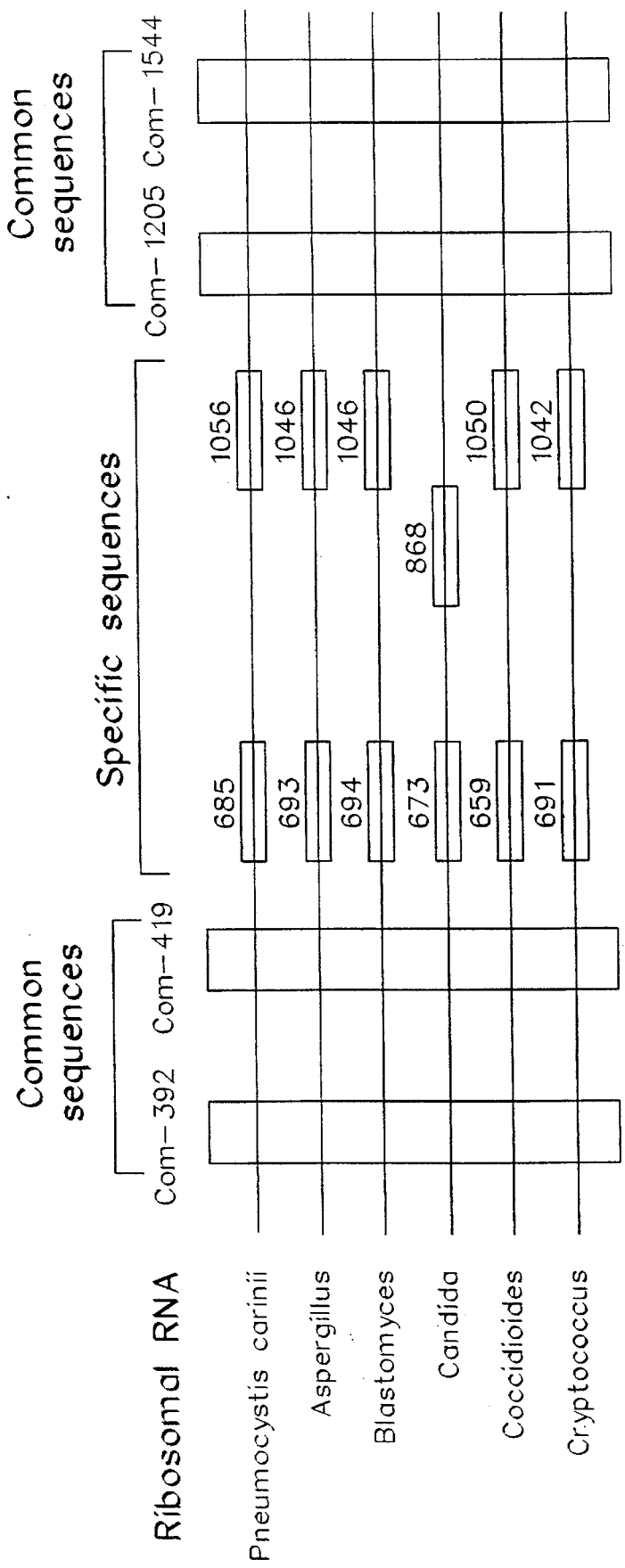
FIG. 1 is a schematic representation of one embodiment of the method of the present invention.

The present method of detecting organisms, infectious agents, or other biological components in a biological sample which contains polynucleotides represents an advance over prior art diagnostic tests in its speed, ease of use, and accuracy. For example, the time necessary to make an accurate identification of an organism in a biological sample using prior art methods required enough time to culture such an organism, which could take from hours to days. Such methods also required that a technician trained to differentiate between different disease-causing organisms examine cultures of a biological sample. The present method, on the other hand, can be accomplished by someone without such specialized training. The present method can also be performed so as to identify either a specific organism or a group of organisms, such as a genus of fungus or bacteria, without the possibility of error due to the misidentification of an organism by a technician examining a culture of a biological sample. Infectious agents such as viruses can also be detected.

The present method also includes an improved way of detecting other biological components which comprise polynucleotides or whose presence is indicated by a polynucleotide. A biological sample can thus be probed with oligonucleotides specific to a biological component, such as a jun oncogene or G protein mRNA. In the present application, "biological component" means a component of a cell or organism which comprises a polynucleotide, such as mRNA, rRNA, and genomic DNA. A component which does not contain a polynucleotide but whose presence is indicated by presence of a polynucleotide in the cell or organism is also included where the detection of a polynucleotide is an indication of the presence of the component. Other probes which can be specific to the biological component or which can be common to the biological component and other biological components can then be used to detect the binding of the specific probe to the biological component. Alternatively, a biological sample can be probed with oligonucleotides capable of binding to a number of polynucleotides with related gene sequences in order to increase the sensitivity of the assay. These and other aspects of the present invention will be described in greater detail below.

I. Common and Specific Sequences

We have discovered a number of specific sequences that are unique to the rRNA of a single fungal species or genus which can be used in the present method. These sequences are SEQ ID NO:81, SEQ ID NO:104, SEQ ID NO:131 through SEQ ID NO:133, SEQ ID NO:154 through SEQ ID NO:156, SEQ ID NO:176, SEQ ID NO:199, SEQ ID NO:267, SEQ ID NO:290, SEQ ID NO:312, SEQ ID NO:335, SEQ ID NO:364 through SEQ ID NO:376, and SEQ ID NO:391 through SEQ ID NO:392. Reference can be made to Tables V through XVI for a comparison of these specific sequences to corresponding sequences in other species or genera.

SEQ ID NO:227 and SEQ ID NO:250 are sequences that are specific to the rRNA of certain strains of C. albicans. However, reported sequences in other strains of the same species have slight changes in these sequences in their rRNA, as seen in SEQ ID NO:226 and SEQ ID NO:249, respectively. Accordingly, these particular sequences are less preferred for use as specific sequences within the context of the present invention. However, these sequences can be useful for identifying the particular strain of C. albicans in a sample.

We have also discovered a number of common sequences that are common to the rRNA of several fungal species and genera. These sequences are SEQ ID NO:1 through SEQ ID NO:80. Reference can be made to Tables 1 through 4 to see that these sequences are common to all species shown.

In a further discovery, we have discovered sequences common to a number of rat and human G protein sequences, as well as sequences that are specific to particular G protein subtypes. Oligonucleotides containing such sequences can be useful as probes or primers for identifying the presence of such sequences in a sample in which such sequences are present in only small quantities. As will be discussed infra in more detail, oligonucleotides containing the inventive sequences can be used as primers in the Polymerase Chain Reaction (PCR) to detect G protein sequences in a biological sample.

Sequences have as well been identified which are common to the different jun oncogenes which have been identified in humans and in mice. Such sequences can also be used in PCR primers to identify the presence of jun gene sequences in a biological sample. In addition, sequences specific to particular subtypes of jun oncogenes have also been discovered. Other sequences useful in the present method are described below.

Advantageously, all of these probes, both common and specific, have been designed to have approximately, the same melting temperature ($T_m$)) when annealed to a complementary sequence. Thus, various procedures requiring annealing of these sequences can all be performed under the same conditions. Those of skill in the art will recognize that longer or shorter sequences, with a correspondingly higher or lower $T_m$, respectively, can also be obtained upon reference to the full-length sequences available from GenBank. When the term "$T_m$" is used herein in connection with a single-stranded polynucleotide, this term refers to the melting temperature of that single-stranded polynucleotide when it is annealed to a complementary strand.

As is known to those of skill in the art, the $T_m$ of a polynucleotide strand can be determined using the following formulas:

$$T_m = 69.3 + 0.41 \, (G+C)\% - 650/L \tag{a}$$

(where G is the number of guanine residues in the strand, C is the number of cytosine residues, and L is the total length, in bases, of the polynucleotide);

$$(T_m) \, u_2 - (T_m) \, u_1 = 18.5 \, \log_{10} u_2/u_1 \tag{b}$$

(where $u_1$ and $u_2$ are the ionic strengths of two solutions); and (c) The Tm of duplex DNA decreases 1° C. with every increase of 1% in the number of mismatched base pairs.

In a preferred embodiment of the present invention, a plurality of probes that have the same $T_m$ are immobilized to one or more solid supports. When probes having the same $T_m$ are used, such probes can be hybridized together under the temperatures. Preferably, the specific probes in this same conditions because they require the same reaction embodiment have a $T_m$ between approximately 48° C. and 60° C. Other probes that have the same $T_m$ and are within this range can be determined by using the formulas above and by performing routine experimentation.

Unless otherwise specified, in the present application the term "specific sequence" denotes a sequence of nucleic acids which is present only in a specific organism or infectious agent, or which is present in a biological sample only as a result of the presence of a specific organism or infectious agent. A "specific sequence" can also be one present in a particular kind of biological component, such as the mRNA of a subtype of jun oncogene. Of course, the sequence complementary to a specific sequence can also be said to be specific. The term "complementary" is used herein to describe a polynucleotide sequence in which adenine is replaced by thymine or a nucleotide that reacts in an equivalent way to thymine such as uracil, and in which thymine (or uracil) is replaced by adenine or a nucleotide that reacts in a similar way to adenine. In such a complementary molecule the guanine residues would also be replaced by cytosines or equivalent nucleotide molecules, and the cytosine residues would be replaced by guanine or equivalent nucleotides.

In the present application, the term "homologous" is used to describe a polynucleotide having a sequence which contains the same nucleotides or equivalent nucleotides, in the same order, as another polynucleotide. For example, a second polynucleotide having the same sequence of nucleotides as a first polynucleotide but in which uracil residues have been substituted for the thymine residues is homologous to the first polynucleotide. Other equivalent nucleotide substitutions known to the art are also included.

Sequences useful in the methods of the present invention can be determined in any way known to the art. Preferably, such sequences are identified with a computer program, as will be detailed infra. Therefore, the sequences discussed herein are only examples of sequences which will work in the present invention and are not the only sequences which can be used.

II. Fungus Assay

One example of the method of the present invention involves the detection of a particular species of fungus in a biological sample. We have discovered that the presence of a particular species of fungus can be determined by probing the ribosomal RNA of a sample for sequences specific to the ribosomal RNA of a particular species of fungus. Probes which carry sequences complementary to sequences found in a group of fungi which include the specific fungus probed for can then be used to detect the specific species of fungus. Those of skill in the art will recognize that other organisms, infectious agents, and biological components present in a biological sample can also be detected using the present method. Those of skill in the art will similarly recognize that other kinds of nucleic acids present in a biological sample can also be probed, including mRNA and genomic DNA.

In the present example, it has been found that each one of a plurality of fungal species carries ribosomal RNA sequences specific to only one species of fungus. The presence of a particular species of fungus in a biological sample can thus be detected by probing that sample for a sequence of ribosomal RNA found only in the ribosomal RNA of that species of fungus. The specific ribosomal RNA sequences found in a number of species of fungus appear to occur in regions that pick up mutations at a relatively high rate. Thus, many species of fungi are likely to have different nucleotide sequences in those regions. Although ribosomal RNA is not expressed, such regions would be analogous to unexpressed regions of genomic DNA, which pick up mutations at a relatively faster rate than expressed regions.

It has been further discovered that a number of species of fungi share sequences of ribosomal RNA common to all of those species. Thus, the presence of any of those fungal species in a biological sample can be determined by probing the sample for polynucleotides having such common sequences. If a fungus contains both specific and common sequences, probing for such common sequences can be used to detect the presence of a variety of that species of fungus which contains one or more mutations in its specific ribosomal RNA sequences. The existence of common sequences can also be exploited by annealing labeled probes to those sequences in order to facilitate the detection of polynucleotides which carry such common sequences.

In one group of pathogenic fungal species, two separate ribosomal RNA sequences have been identified in each of the species which are specific to the individual species carrying such sequences. This group comprises the following fungal species: *Pneumocystis carinii, Aspergillus fumagatus, Aspergillus fumigatus, Cryptococcus neoformans, Coccidiodes immitis, Blastomyces dermatitidis*, and a number of species in the Candida group, including *Candida abicans* and *Candida tropicalis*. The Genbank accession numbers of the ribosomal RNA of the fungal species of this group are shown in Table A below:

TABLE 1

| Fungal Species | Accession No. |
|---|---|
| *Aspergillus fumagatus* | M55626 |
| *Aspergillus fumagatus* | M60300 |
| *Aspergillus fumagatus* | M60301 |
| *Blastomyces dermatitidis* | M55624 |
| *Candida albicans* | M60302 |
| *Candida albicans* | X53497 |
| *Candida guilliermondii* | M60304 |
| *Candida glabrata* | X51831 |
| *Candida kefyr* | M60303 |
| *Candida krusei* | M55528 |
| *Candida krusei* | M60305 |
| *Candida lusitaniae* | M55526 |
| *Candida lusitaniae* | M60306 |
| *Candida parapsilosis* | M60307 |
| *Candida tropicalis* | M55527 |
| *Candida tropicalis* | M60308 |
| *Candida viswanathii* | M60309 |
| *Pneumocystis carinii* | X12708 |
| *Coccidiodes immitis* | M55627 |
| *Cryptococcus neoformans* | M55625 |

In the embodiment of the present invention comprising a fungal assay, the term "specific sequence" is used to indicated a sequence of ribosomal RNA specific to one species of fungus. Such a sequence is specific to that fungus species and thus is not found in the ribosomal RNA of any other fungal species. The sequence is also different from other RNA sequences found in the cells being tested. A probe which has a sequence complementary to one of these specific sequences will therefore anneal only to the ribosomal RNA of a particular species of fungus, or to a polynucleotide homologous to such ribosomal RNA.

In the group of pathogenic fungi containing specific sequences referred to above, four common sequences of ribosomal RNA have also been identified. "Common sequences" are those common to a group of organisms, such as those common to a particular genus or family of organisms. The term "common" can also denote sequences shared by a group of infectious agents or biological components, such as sequences shared by different subtypes of jun oncogene. As shown in FIG. 1, two such common sequences for the group of fungi listed above in Table 1 occur 5' of the specific sequences identified in such fungi, while two other common sequences are located 3' of these specific sequences.

Thus, in one embodiment of the present invention, primers complementary to the common sequences located 3' of the specific sequences in the ribosomal RNA of a fungal species of this group are used to create a polynucleotide, preferably a strand of cDNA, complementary to the portion of the ribosomal RNA of the species that contains the specific sequences. A probe homologous to one of the common sequences located 5' of the specific sequences can also be annealed to a strand complementary to the ribosomal RNA of a species of fungus and then extended in order to create a polynucleotide strand homologous to the strand of fungal ribosomal RNA that contains at least one of the sequences specific to a particular fungus. Further aspects of the method of detecting fungi of the present invention are detailed in the examples below.

III. Obtaining a Biological Sample

In order to obtain a biological sample containing an organism, an infectious agent, or a biological component of a cell or organism to be detected according to the method of the present invention, an organism or tissue suspected of harboring such an infectious agent, organism, or biological component can be identified. The identification can be made in any way known to the art. Preferably, the organism suspected of carrying an infectious agent or other organism is a human, and the identification is made by a physician who observes symptoms indicative of the presence of such an organism or agent in such a human. For example, a patient diagnosed as having AIDS who comes down with pneumonia and who does not respond to anti-bacterial agents is identified by a physician as possibly harboring the fungus *Pneumocystis carinii*.

Alternatively, a biological sample taken from a host with no overt signs of having a medical condition or harboring an organism or agent can be tested. For example, a food sample or tissue from an AIDS patient without signs of a fungal growth can be tested for the presence of a fungus. In this embodiment, any biological sample can be tested, even though overt signs of the presence of a fungus are lacking in that sample. Appropriate action may thereby be taken if a fungus is in fact found in such a biological sample.

The biological sample to be tested can be obtained by any means known to the art. For example, if an AIDS patient is suspected of suffering from interstitial plasma pneumonia caused by the fungus *Pneumocystis carinii*, a sputum sample can be taken from the lungs of that patient. The sputum can be obtained by having the patient cough up phlegm from the lungs and deposit it into a cup. Alternatively, a sputum sample can be obtained by scraping the bronchial passage with a sterile swab, or by any other means known to the art. Any other biological sample which could possibly carry a fungus is likewise obtained in an appropriate fashion.

IV. Preparing the Biological Sample

The biological sample is next prepared so that the RNA and/or DNA present in the biological sample can be probed. When a fungus is being probed for, ribosomal RNA of any fungi present in the sample can be probed in accordance with the methods of the present invention. In order to probe the ribosomal RNA of any fungal cells present, these cells should first be lysed. Lysis of fungal cells or of other cells containing RNA or DNA of interest can be accomplished by any of a number of methods known to the art, including those set out in Molecular Cloning.

In one embodiment, the cells are lysed before they come into contact with the solid support. This embodiment might be used, for example, when the solid support is one which is not designed to hold a sample of lysed cells, such as a nitrocellulose filter. In this embodiment, the cells are contacted with the solid support after they have been lysed.

A variety of techniques can be used for cell lysis. When the ribosomal RNA of fungi is being probed, for example, techniques that separate the ribsomal RNA from the ribosomal proteins are preferred. Example 1 is provided to show one technique believed to be useful in obtaining ribosomal RNA. However, techniques for obtaining ribosomal RNA are well known. Techniques for obtaining DNA and other kinds of RNA are also well known to those of skill in the art. Thus, the technique of Example 1 is not necessarily a preferred method of obtaining ribosomal RNA-containing samples. Example 1, like all of the examples provided herein, are provided merely to illustrate certain aspects of the present invention. As such, they are not intended to limit the invention in any way.

EXAMPLE 1

Lysing Cells in a Biological Sample

Cells present in a biological sample can be lysed by treatment with a solution of 10 mM ethylenediaminetetraacetic acid (EDTA) (pH 8.0), 0.2M NaCl, 0.5% of sodium dodecyl sulfate (SDS), 500 Unit/ml of RNase inhibitor, 10 mM of Vanadyl Ribonucleosyl Complex and 200 µg/l of Proteinase K (hereafter called Lysis Buffer). After lysis of the cells, the NaCl concentration of the resulting cell lysate in solution is adjusted to 0.5M.

V. Solid Support

In a preferred embodiment, the solid support is capable of containing a biological sample and is resistant to the reagents used to lyse cells in the biological sample. The sample can thus be lysed in the solid support. However, the use of such a solid support is not necessary if the sample can be obtained without lysis or is lysed in a separate container. An example of a solid support that is resistant to a large number of treatments is a microtiter well or a plate made from a resistant plastic material.

The solid support can also be any of a variety of other solid supports known to the art, such as a membrane filter, a bead, or any other solid, insoluble support to which polynucleotides can be attached. The solid support is preferably made of a material which can immobilize a polynucleotide probe. Immobilization can be through covalent bonds or through any of a variety of interactions that are known to those having skill in the art. Plastic materials containing carboxyl or amino groups on their surfaces, such as polystyrene, are preferred for the solid support of the present invention because polynucleotide probes can be immobilized on their surfaces, because they are inexpensive and easy to make, and because they are resistant to the reagents used to lyse the cells of the biological samples used in the present invention. For example, the Sumilon microtiter plate MS-3796F made by Sumitomo Bakelite, which has a carboxyl group on its surface, can be used in such a preferred embodiment. A plastic plate having an amino group on its surface, such as the Sumilon microtiter plate MS-3696, can also be used.

VI. Contacting the Sample and First Polynucleotide Probe

After the cells in the biological sample have been lysed, the RNA and/or DNA contained in such cells is substantially released into solution or otherwise made available to being probed. If the biological sample was not lysed in the solid support, the cell lysate is next brought into contact with the solid support. Immobilized to the solid support is a first polynucleotide probe which preferably contains a sequence complementary to a specific sequence in the RNA and/or DNA of a particular organism, infectious agent, or biological component of a cell or organism in the biological sample. In an alternate embodiment, the first polynucleotide probe can also contain a sequence common to a plurality of organisms, infectious agents, or biological components when any of a group of such organisms, infectious agents, or biological components is sought to be identified. When the RNA and/or DNA present in the cell lysate contacts the solid support, therefore, it also comes into contact with the first polynucleotide probe.

Preferably, the first polynucleotide probe is an oligodeoxyribonucleotide (DNA) rather than an oligoribonucleotide (RNA), since DNA is more stable than RNA. The number of nucleotides in the polynucleotide probe is not restricted. However, if an oligodeoxynucleotide is used as the specific polynucleotide probe, a preferred length for the oligodeoxynucleotide is from 15 to 100 nucleotides. Lengths longer than 100 nucleotides are usable within the scope of the present invention. However, lengths of 100 nucleotides or less are preferable because many automated polynucleotide synthesizers have a limit of 100 nucleotides. Longer sequences can be obtained by ligating two sequences of less than 100 nucleotides.

In one embodiment, the first polynucleotide probe is an oligonucleotide complementary to one of the following sequences: SEQ ID NO:81, SEQ ID NO:104, SEQ ID NO:131 through SEQ ID NO:133, SEQ ID NO:154 through SEQ ID NO:156, SEQ ID NO:176, SEQ ID NO:199, SEQ ID NO:267, SEQ ID NO:290, SEQ ID NO:312, SEQ ID NO:335, SEQ ID NO:364 through SEQ ID NO:376, or SEQ ID NO:391 through SEQ ID NO:392. These sequences are specific to the ribosomal RNA of various pathogenic species of fungi, as listed in the sequence listing, and Tables V through XII.

Example 2 is provided to show one particular probe that is useful for determining the presence of Pneumocystis carinii in a biological sample.

EXAMPLE 2

Preparing the First Polynucleotide Probe

A first polynucleotide probe that is specific to a sequence of ribosomal RNA in Pneumocystis carinii prepared. The probe is produced with a DNA synthesizer such as a DNA synthesizer made by Applied Biosystems of Menlo Park, Calif. The probe is complementary to a polynucleotide having the following sequence where A, T, G, and C stand for adenine, thymine, guanine and cytosine, respectively: 5'-GCGCAACTGATCCTTCCC-3' (SEQ ID NO:81).

VII. Immobilizing the First Polynucleotide Probe

Various methods of immobilizing polynucleotides to a solid support are known to the art, including covalent binding, ionic binding, and the physical absorbance method. In certain embodiments of the present invention, the polynucleotides, such as the first polynucleotide probe, are immobilized to microtiter wells which exhibit functional groups such as carboxyl residues, amine residues, or hydroxyl residues on the surfaces thereof. Thus, in one procedure for the immobilization of the first polynucleotide probe to a solid support, the solid support exhibits a functional group and the 5'-terminal end of the polynucleotide is covalently linked to the functional group. Any of a variety of methods for the covalent binding of polynucleotides to these functional groups can be used. Examples of preferred, well-known methods include the maleimide method and the carbodiimide method.

The maleimide method involves a reaction between a substance containing a maleimide group and another material containing a sulfhydryl residue (SH). The 5' end of the specific polynucleotide probe is immobilized on a solid support in this method by reacting the 5' end of the polynucleotide with a maleimide compound. A suitable maleimide compound is sulfosuccinimidyl-4-(N-maleimidomethyl) cyclohexane-1-carboxylate (sulfo-SMCC).

The SH residue is provided on the support by a reaction between a support having an amino group and succinimidyl-S-acetylthioacetate (SATA), followed by deacetylation using hydroxylamine (NH$_2$OH). Sulfo-SMCC and SATA are readily available from a variety of commercial sources, including the Pierce Company. The resulting SH group on the support is reacted with the maleimide group on the 5' end of the first polynucleotide probe when these groups are brought into contact under the appropriate conditions, thereby immobilizing the first polynucleotide probe to a solid support.

One problem we have experienced in the use of the maleimide method is that the SH group on the support can react not only with an amino group at the 5' end of the first polynucleotide probe, but also with primary amino groups on the purine bases, adenine and guanine. In order to assure that the polynucleotides are immobilized at their 5' ends, so that the sequences complementary to the ribosomal RNA sequences specific to a particular species of fungus are available for hybridization, the amino groups on the purine bases can be protected by pairing the specific polynucleotide probe to a complementary polynucleotide prior to immobilization. After immobilization, the complementary polynucleotide can be removed through denaturation, such as through heating, leaving the single-stranded probe immobilized to the solid support.

Another method of immobilizing a polynucleotide to a solid support is the carbodiimide method. This method involves a reaction between an amino group and a material containing a carboxyl residue using a carbodiimide compound. An example of a carbodiimide compound is 1-ethyl-3-(3-dimethylaminopropyl) carbodiimide hydrochloride (hereafter called EDC). This reaction can be enhanced with N-hydroxysulfosuccinimide (hereafter called Sulfo-NHS). Both EDC and Sulfo-NHS are available from well known commercial sources, including the Pierce Company.

In the practice of a preferred carbodiimide method for attaching polynucleotides to a solid support, a support having a carboxyl residue attached is used. Before contacting EDC with the support, the EDC is activated by reacting it with Sulfo-NHS. This activated EDC is then reacted with the solid support containing surface-bound carboxyl residues. The support, after being so treated, can be reacted with strands of the first polynucleotide probe, which have an amino group at their 5'-terminal ends, thereby immobilizing the specific polynucleotide probe to the support.

In order to assure that the first polynucleotide probe is immobilized at its 5' end, the primary amino groups on the probe (the adenyl, guanyl and cytosyl groups) can be protected by hybridizing the nucleotide to a complementary polynucleotide prior to immobilization. After immobilization, the complementary polynucleotide can then be removed through denaturation, such as through heating, leaving the single-stranded probe immobilized to the solid support. In order to further prevent the non-specific binding of activated amino or carboxyl residues on solid supports, the solid supports to which the specific polynucleotide probes are immobilized can be treated with a primary amine compound, preferably glycine.

Example 3 is provided as an indication to those of skill in the art of but a single method of immobilizing a probe to a solid support. Those of skill in the art will recognize that any of a variety of methods of so immobilizing the probe can be used, including those described above.

EXAMPLE 3

Immobilizing the First Polynucleotide Probe onto a Solid Support with the Carbodiimide Method Both EDC and sulfo-NHS (Pierce, Ill.) are dissolved in DEPC-treated water at concentrations of 20 mM and 10 mM, respectively. EDC/Sulfo-NHS solution is then prepared by mixing equal volumes of both EDC and sulfo-NHS. The specific nucleotide probe is dissolved in DEPC-treated water at a concentration of 1 µg/µl and then mixed with the EDC/Sulfo-NHS solution in the ration 1:25 (Vol:Vol).

50 µl of this probe solution is added to each well of a microtiter plate (MS-3796F, Sumitomo Bakelite, JAPAN), which is known to have carboxyl groups on the surface of the plate. After incubation at room temperature overnight, the reaction solution is removed by aspiration.

VIII. Hybridizing the First Polynucleotide Probe

In a preferred embodiment, the cell lysate or other sample containing polynucleotides is next hybridized to a first, specific polynucleotide probe immobilized to the solid support. The first polynucleotide probe can, however, also be a common probe, depending on the purpose of a particular assay performed according to the present invention. Hybridization can be accomplished by incubating the cell lysate and the first polynucleotide probe at a temperature dependent on a variety of factors, as is well known to those with ordinary skill in the art. These factors include the length of complementary nucleotide sequences, the ratio of guanine and cytosine bases to the entire base content in the complementary nucleotide sequences (the GC content), the NaCl concentration in the buffer solution, the number of bases which mismatch in the complementary nucleotide sequence, and the type of nucleotide. In a preferred form of this invention, the following equation can be used to calculate the preferred incubation temperature ($T_{inc}$):

$$T_{inc} = 16.6 \times \log(M) + 0.41(GC) + 81.5 - 675/n - 15\ (°C).$$

In the equation shown above, M is the NaCl concentration in solution, GC represents the GC content (the percentage of guanine and cytosine residues in the sequence), and n represents the length of the nucleotide sequences (the number of hybridizing nucleotides). The incubation temperature can also be determined according to methods described in Molecular Cloning.

The time for incubation is preferably from 1 hour to overnight, and the sample is preferably gently rocked during incubation. Incubation is preferably performed in an appropriate buffer solution. The same buffer used to hybridize RNA and DNA in the Northern Blot or the Dot Blot methods, as described in the Maniatis treatise, can be used. The buffer is preferably prepared in a way so as not to contaminate it with RNase. If any RNase contamination is present, the activation of RNase should be controlled so as to be as low as possible.

Example 4 illustrates one method of hybridizing ribosomal RNA in a sample to an immobilized probe.

EXAMPLE 4

Hybridizing the First Polynucleotide Probe to Ribosomal RNA

RNase is removed from a microtiter well to which a first polynucleotide probe having a sequence complementary to SEQ ID NO:81 has been bound by adding 250 μl of Lysis Buffer containing 0.5M NaCl and incubating the well at 45° C. for one hour. The buffer is removed from individual wells by aspiration, and 50 μl of Lysis Buffer containing the biological sample is added to each well. These solutions are incubated at 39° C. for one hour ($T_m=54°$) to allow hybridization and then slowly cooled over the course of 20–30 minutes.

In the methods of the present invention that involve probing samples containing RNA, or in any procedure in which it is desired to prevent the degradation of RNA, it is advantageous to inhibit the activity of any ribonucleases (RNases) which may be present. One RNase inhibitor which can be used is Vanadyl Ribonucleoside Complex (VRC) (Bethesda Research Laboratories, Gaithersburg, Md.). VRC has been reported to be useful during cell fractionation and in the preparation of RNA, and has been shown not to interfere with the phenol extraction or ethanol precipitation of RNA. In addition, VRC does not affect other cytoplasmic components of cells. Therefore, VRC is an ideal inhibitor of RNase in many experimental procedures.

However, prior art procedures for inhibiting RNases with VRC taught that VRC should not be used in buffer systems containing EDTA or SDS, which are commonly used in the field of molecular biology. The reason for this prohibition was that it was believed that the Complex would dissociate in the presence of these buffers, leading to a loss of RNase inhibiting activity. In fact, the BRL insert accompanying the VRC product recommends that a five- to ten-fold molar excess of EDTA be added to an RNA solution containing VRC in order "destroy" the VRC prior to ethanol extraction of the RNA from the solution. The apparent inability to use VRC together with common buffers that include EDTA and SDS thus presented a major impediment to the exploitation of VRC as an RNase inhibitor.

We have discovered, however, that VRC is in fact an effective RNase inhibitor even in the presence of SDS and/or EDTA. Thus, VRC can be used in assays which use buffers including SDS or EDTA, where heretofore it was believed that VRC would not be effective in such systems. VRC is an effective RNase inhibitor at the concentrations of EDTA and SDS that are normally used when manipulating RNA or when performing a variety of other molecular biology techniques. For example, we have found that VRC effectively inhibits RNase in a buffer solution comprising approximately 1 mM EDTA. We also found VRC to be effective in 0.5% SDS solutions, and is believed to be effective in solutions ranging up to 2% SDS, more preferably up to 1% SDS. VRC can, of course, also be used in other solutions including EDTA and SDS.

Figure 1A:
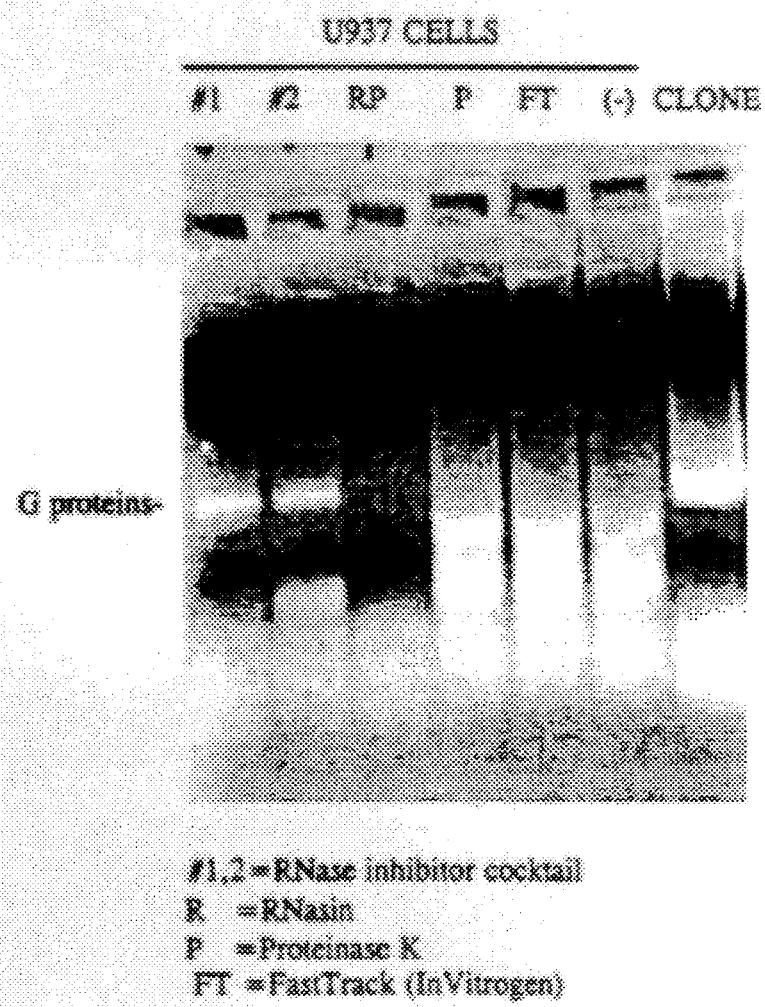
FIG. 1A is a picture of a gel showing the effect of various RNase inhibitors on mRNA preparations containing SDS and EDTA.

We have found that VRC is a particularly potent inhibitor of RNases when used in combination with Proteinase K. Proteinase K is also available from BRL. As shown in the gel in FIG. 1a, mRNA prepared from U937 cells (human macrophage cell line) was protected from RNase degradation by a combination of VRC and Proteinase K. Lane 1 of the gel shows the mRNA from a cell preparation which included VRC, Proteinase K, and RNasin, while lane 2 represents the mRNA from a cell preparation that included VRC and Proteinase K. RNasin is available from Promega of Madison, Wis.. The distinct band 10 in lanes 1 and 2 matches the band seen in lane 7, which contains pure clonal cDNA from an RNase-free preparation of U937 cells, thus showing that the mRNA in the preparations of lanes 1 and 2 did not experience substantial mRNA degradation.

A comparison of lanes 1 and 2 with lanes 3–6 shows that VRC in combination with Proteinase K inhibits RNase activity in the above-mentioned mRNA preparation from U937 cells to a far greater extent than either Protein K alone (lane 4), Proteinase K in combination with RNasin (lane 3), or a commercial RNase-inhibiting preparation sold under the name "FastTrack" (available from In Vitrogen of San Diego, Calif.) (lane 5). None of lanes 3–5 exhibit the distinct band 10 representing undegraded mRNA. On the contrary, lane 4 (Proteinase K alone) and lane 5 (FastTrack) have the same smear of degraded mRNA as band 20 in lane 6 (no inhibitors). The gel shown in FIG. 1a also shows the effectiveness of VRC in a buffer solution of 1 mM EDTA and 0.5% SDS, which is the buffer used in the U937 cell preparations tested, since lane 2 (VRC and Proteinase K) shows less mRNA degradation than lane 4 (Proteinase K alone) or lane 3 (Proteinase K and RNasin).

In order to eliminate RNase activity from water used in the methods of this invention, the water is preferably treated with diethylpyrocarbonate (DEPC). The preferred DEPC treatment involves addition of 0.1% DEPC to the water, followed by storage overnight at 37° C. and sterilization in an autoclave. The DEPC is deactivated by such autoclaving so that it does not interfere with the enzymatic processes of the methods of the present invention. Alternatively, if the water is sterilized in some other manner, the DEPC in the water can be deactivated by other means known to the art.

IX. Washing the Solid Support

Following hybridization, the non-hybridized portions of the biological sample are preferably separated from the solid support, so that substantially all of the biological sample not annealed to the first polynucleotide probe is removed from the solid support. If the solid support is a microtiter well, for example, and the first polynucleotide probe is immobilized to the walls or bottom of the well, the non-hybridized cell lysate can be removed by pouring the lysate out of the well or by aspirating the cell lysate. The well itself can then be "washed" or rinsed with a washing solution such as the Lysis Buffer by applying the washing solution to the walls of the well and then removing the washing solution through aspiration. Any washing solution known to the art can be used, provided that the salt content and other parameters of the solution are controlled so that the washing solution does not remove any polynucleotide hybridized to the polynucleotide probe.

X. Contacting and Hybridizing the Second Polynucleotide Probe

When the solid support has been washed, a second polynucleotide probe is then contacted with and hybridized to the polynucleotide strand of RNA or DNA which is hybridized to the immobilized first polynucleotide probe, if such a polynucleotide was present in the cell lysate. The contacting and hybridization steps are performed as with the first polynucleotide probe, above, or by any other methods known to the art.

In a preferred embodiment, the second polynucleotide probe contains a polynucleotide sequence complementary to a sequence which is common to the RNA and/or DNA of a group of organisms, infectious agents, or biological components. For example, if a particular organism is being probed for and that organism is a fungus, the second probe can contain a sequence common to a plurality of species of fungus including the species being probed for. If an infectious agent such as a virus is being assayed for, the second probe can contain a sequence common to a number of related viruses. In this way, the same second polynucleotide probe can be hybridized to the RNA and/or DNA of any of a group of organisms, infectious agents, or biological components. In an even more preferred embodiment, the second, common probe has the same or lower $T_m$ as the first, specific probe so that the hybridization of the second probe can be performed under the same conditions as the conditions used to hybridize the first probe.

This embodiment of the present invention is preferred when a plurality of specific probes are used to assay for the presence of a plurality of organisms, infectious agents, or biological components, because then the same second probe can be annealed to the RNA and/or DNA of the plurality of such organisms, agents, or biological components. The common polynucleotide probe of this embodiment can also advantageously be included in a kit in which a plurality of specific probes are used to detect the presence of a plurality of organisms or agents.

The second polynucleotide probe can alternatively comprise a second sequence specific to the polynucleotide of the particular organism, infectious agent, or biological component sought to be identified in the sample. This second sequence is complementary to a different specific sequence of the RNA and/or DNA of the particular organism, infectious agent, or biological component than the sequence to which the first polynucleotide probe is complementary.

XI. Label

The second polynucleotide probe is preferably labeled in order to easily detect its presence and facilitate the detection of the RNA and/or DNA hybridized to the first probe. A variety of chemical substances are available which can label a polynucleotide probe when attached to that probe. For example, a variety of radionuclides can be used, such as the radioisotopes $^{32}P$, $^{35}S$, $^{3}H$, and $^{125}I$. Enzymes or enzyme substrates can also be attached to the second polynucleotide probe in order to label it. Suitable enzymes include alkaline phosphatase, luciferase, and peroxidase.

Labels which provide a colorimetric indication or a radionuclide are preferred. Other labels which can be used include chemical compounds such as biotin, avidin, streptavidin, and digoxigenin. Colorimetric labels, such as fluorescein, are especially preferred because they avoid the health hazards and disposal problems associated with the use of radioactive materials. In a preferred embodiment, biotin is attached to the nucleotide probe, followed by an avidin, such as streptavidin, which is itself conjugated to an enzyme such as alkaline phosphatase. The presence of the enzyme can be detected by various substrates, such as ATTOPHOS, which provide a fluorescent marker that can be detected through fluorimetry.

Nucleic acids can also be "labeled" by staining them with a nucleic acid stain. Thus, where a relatively large amount of nucleic acids are present, ethidium bromide (EtBr) can be used to identify the presence of such nucleic acids. However, more sensitive stains are more preferable. Sensitive stains include various cyanine nucleic acid stains, such as POPO, BOBO, YOYO and TOTO, available from Molecular Probes (California). These stains are described, e.g., in Science, 257:885 (1992). Particularly preferred stains for use in the context of the present invention include the shorter wavelength forms, TOTO-1 and YOYO-1, still more preferably YOYO-1. As little as four picograms of stained DNA can be detected by visible fluorescence upon stimulation with a transilluminator or hand-held UV lamp. Thus, these stains provide a particularly easy and sensitive method of identifying the presence of nucleic acids.

Figure 1B:
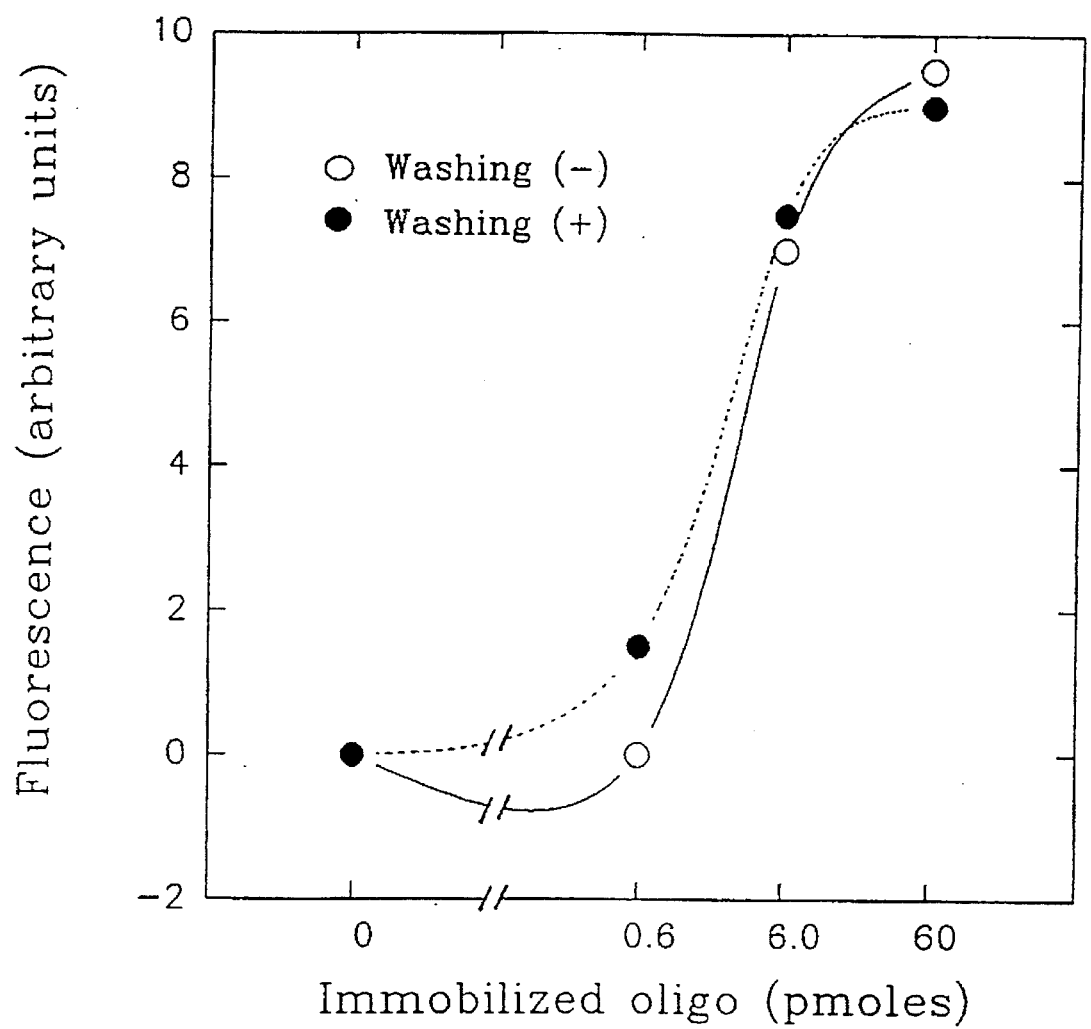
FIG. 1B is a graph showing the relationship between YOYO-1 fluorescence and amount of immobilized oligonucleotide.

We tested the ability of YOYO-1 to stain oligonucleotides immobilized to wells as discussed herein. We first immobilized various known amounts of oligonucleotides to wells and washed to remove non-immobilized oligonucleotides. We then added 1:1000 dilution of YOYO-1 in water. We then used a fluorimeter directly without washing. The relation between pmoles of oligonucleotide is shown in FIG. 1b with circles. We also incubated the TOTO-1 stained immobilized oligonucleotides for ten minutes, washed and added water, followed by use of the fluorimeter. The washed results are shown in dark circles in FIG. 1b, while results without washing are shown in open circles. It can be seen that washing does not significantly effect the amount of staining and that the amount of staining is related to the amount of oligonucleotide.

Figure 1C:
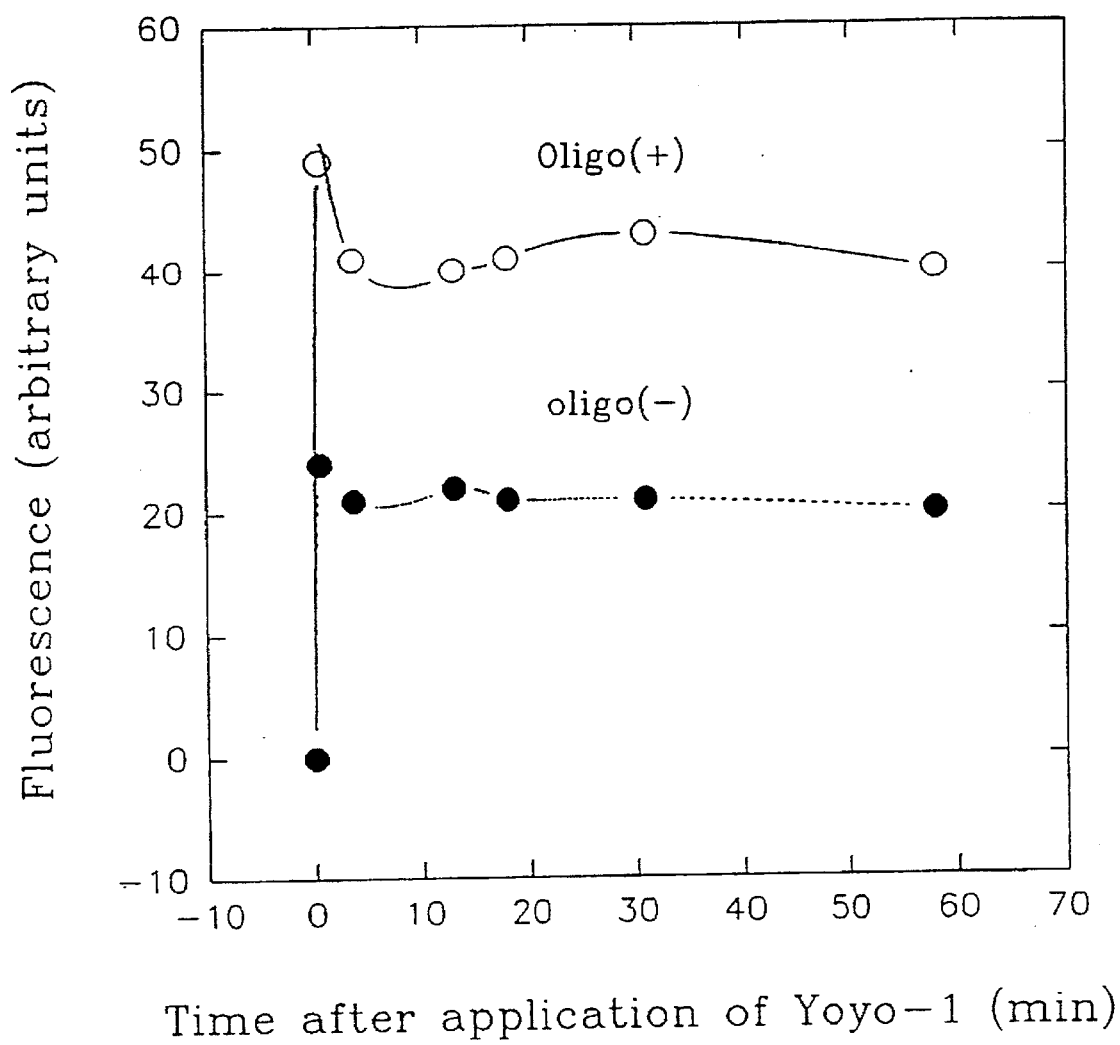
FIG. 1C is a graph showing the time course of YOYO-1 analysis.

We also tested the time course of YOYO-1 staining over the course of one hour. We included a control in which no oligonucleotide was immobilized to the plate. The oligonucleotide-immobilized plate is shown in open circles in FIG. 1c and the control in dark circles in that figure. It can be seen from FIG. 1c that after an initial spike, relatively constant staining is found.

Figure 1D:
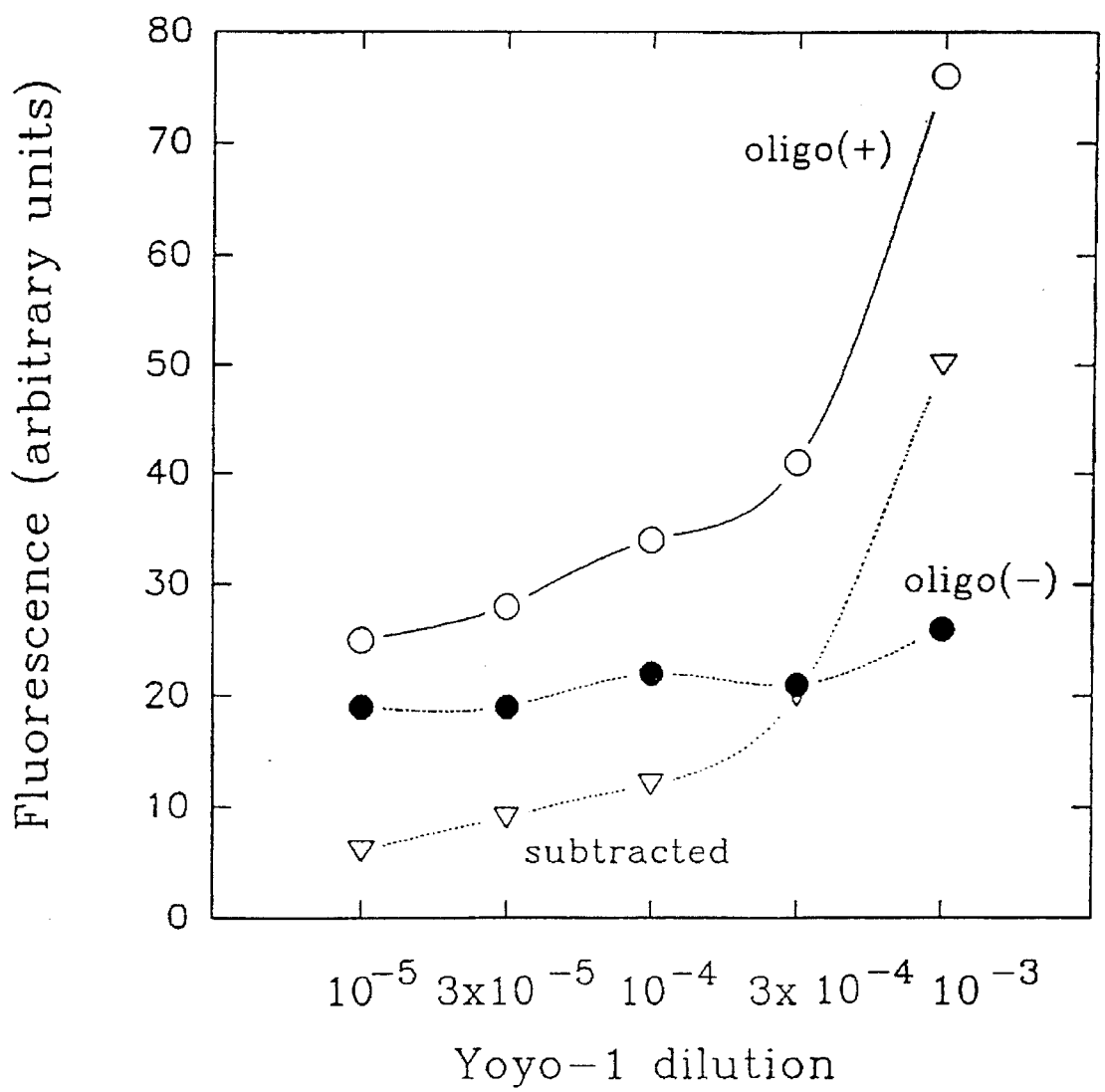
FIG. 1D is a graph showing the dose response of YOYO-1 concentration.

We further tested the dose response of constant amounts of oligonucleotides with oligonucleotides immobilized in wells (open circles in FIG. 1d) and control wells with no oligonucleotide (closed circles in FIG. 1d). The difference between the immobilized and non-immobilized is shown in FIG. 1d as triangles. It can be seen that a sharp increase in fluorescence occurs between $10^{-4}$ and $10^{-3}$ dilution.

Figure 1E:
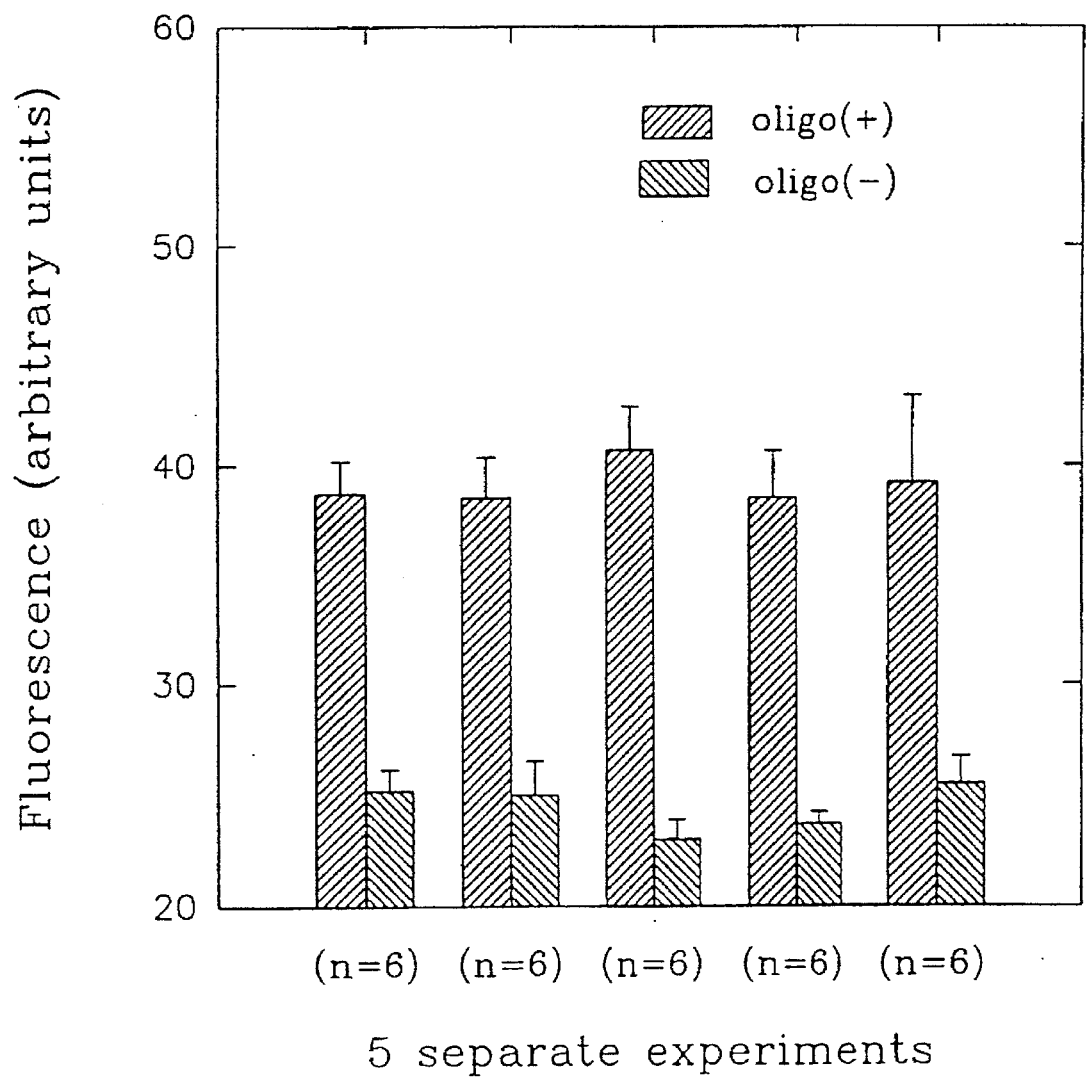
FIG. 1E is a bar graph showing the reproducibility of YOYO-1 staining based on quantitation of immobilized oligonucleotides.

We also tested the reproducibility of staining of both oligonucleotide-immobilized wells and non-immobilized wells. We repeated the experiment five times and graphically depicted the data for both oligonucleotide immobilized (+) and non-immobilized (−) wells in FIG. 1e. It can be seen that the data was substantially similar for each experiment.

Thus, the data depicted in FIGS. 1b–1e shows that use of YOYO-1 as a staining agent provides a reliable indication of the amount of oligonucleotide present.

Other labels known to the art can also be used. For example, a specific binding moiety which binds to a binding partner for that moiety can be used. For example, a binding moiety such as an antibody can be labeled with a marker and then bound to a binding partner, such as an antigen, on the second polynucleotide probe. An agonist and its receptor can also be used, as is known to the art. A receptor such as the norepinephrine receptor attached to the second polynucleotide probe can be detected by the addition of a labeled agonist for that receptor, in this case norepinephrine.

Example 5 shows one method of using a labeled common polynucleotide probe to identify the presence of rRNA.

EXAMPLE 5

Preparing, Labeling, and Hybridizing the Second Nucleotide Probe

The second nucleotide probe is an oligodeoxynucleotide prepared as in Example 1 comprising a sequence complementary to the following sequence: 5'-GAGGGAGCCTGAGAAACG-3' (SEQ ID NO:1). This sequence is complementary to the ribosomal RNA of a number of fungal species, including the ribosomal RNA to which the specific polynucleotide probe of Example 1 is complementary. This second nucleotide probe is labeled with fluorescein at either the 3' or 5' end of the probe. The 3' end is labeled using terminal transferase and FITC-dUTP. alternatively, the 5' end is labeled by chemical reaction with FITC. Fifty μl of Lysis Buffer including 0.5M NaCl and 1 μl of a solution containing the second polynucleotide probe to which fluorescein has been attached is added into each well and incubated at 39° for one hour, after which it is allowed to slowly cool (over 20–30 minutes).

XII. Determining the Presence of Organisms, Infectious Agents, or Biological Components in the Sample After the second polynucleotide probe has been hybridized to any RNA and/or DNA of the organism, infectious agent, or biological component present in the biological sample, substantially all of the solution containing the second probe is removed from the solid support by aspiration or in any other appropriate way, and the solid support is again washed to remove any unhybridized second polynucleotide. The presence of the particular organism, infectious agent, or biological component sought to be detected is then finally determined by detecting the presence of the second polynucleotide probe immobilized to the solid support via the RNA and/or DNA strand of the organism, infectious agent, or biological component being probed for, which is itself hybridized to the first polynucleotide probe. If the second polynucleotide probe is detected, this indicates that the biological sample contained RNA and/or DNA being tested for, and hence that the biological sample harbors the organism, infectious agent, or biological component sought to be identified in the sample.

In one embodiment of the present invention, a negative control experiment is performed when the biological sample is tested. The control experiment is run by performing the present method with the same steps and the same materials as when the biological sample is tested, except that no first polynucleotide is attached to the solid support on which the control experiment is performed.

A positive control experiment is also preferably run when performing the methods of the present invention. A positive control is run by performing the present method with the same materials and using the same steps, with the exception that the first polynucleotide probe immobilized to the solid support contains a sequence common to the RNA and/or DNA of a group of organisms, infectious agents, or biological components of which the organism, infectious agent, or biological component being probed for is a member. For example, if a species of fungus is being probed for, the first polynucleotide probe immobilized to the solid support of the positive control can contain a sequence common to the genus of fungi of which the species being probed for is a member. Thus, if any of the species of this genus of fungus are present in the biological sample, the solid support comprising the positive control will indicate the presence of a fungus in the sample.

EXAMPLE 5a

Identification of Subtypes of Jun Oncogenes in a Sample

In order to identify subtypes of jun oncogenes using subtype specific probes, approximately 10 picomoles (2 μl) of oligonucleotides specific to one of jun-B, c-jun, and jun-D jun oncogene subtypes (B-1258 (SEQ ID NO:730), C2147 (SEQ ID NO:470), and HUMD965 (SEQ ID NO:488)) were added into each of 3 wells of a plastic microtiter plate (No. 3490, made by Coster, Cambridge, Mass.) and mixed with 25 mM EDC (Pierce, Rockford, Ill.) overnight at 37° C. After the oligonucleotide-EDC solution was removed from the wells, 10 mM glycine was added into each well and incubated at 37° C. for 2 hours. Each of the wells was washed with 200 μl of water six times and then stored at 4° C. until use.

Approximately 50 μl of a solution containing approximately 1 mg/ml of each of jun-B, c-jun, and jun-D mouse jun oncogene cDNA (biotinylated) in reaction buffer (10 mM Tris, pH 8.0, 1 mM EDTA, and 0.5M NaCl) was placed in each of three wells in a microtiter plate. After incubating the wells at 37° C. for 2 hours, the wells were washed with the reaction buffer 3 times. Alkaline phosphatase-conjugated streptavidin (Clontech, Palo Alto, Calif.) was diluted 1:1000 with the reaction buffer, and 50 μl of the diluted solution was added into each well and incubated at room temperature for an additional 30 minutes. After the wells were washed w3ith the reaction buffer 3 more times, 50 μl of ATTOPHOS (JBL, San Luis Obispo, Calif.) was added into each well and incubated at room temperature for 10 minutes. The fluorescence of the individual wells was measured by CytoFluor 2300 (Millipore, Bedford, Mass.) at a filter setting of 485 nm for excitation and 590 nm for emission. As shown in FIG. 5a, each subtype-specific oligonucleotide hybridized only to the corresponding mouse jun oncogene subtype. Also, no appreciable cross-hybridization between subtypes occurred. Therefore, each of these probes is specific to only one subtype of jun oncogene.

XIII. Quantifying the Amount of an Organism, Infectious Agent, or Biological Component Contained in the Sample The amount of RNA and/or DNA in the biological sample from a particular organism or agent, or the amount of such RNA and/or DNA indicative of the presence of a particular biological component can be quantitated by measuring the amount of second polynucleotide probe bound to the solid support after being applied thereto in accordance with the method of the present invention. When testing for an organism or infectious agent, the amount of RNA and/or DNA in the sample can give a rough measurement of the number of organisms or infectious agents contained in the sample, and thus a rough estimate of the extent of an infection if the sample is from a diseased organism.

To quantify the amount of second polynucleotide probe attached to the solid support, a physical or chemical quantity or activity of the label on the second polynucleotide is measured. A number of techniques for measuring the label on a polynucleotide probe known to the art can be used, the technique used depending on the kind of label. Such techniques include measuring the optical density of the buffer solution, the emitted-light intensity of the buffer solution, or the amount of radiation given off by the immobilized second polynucleotide probe. The label itself can provide this indication or can require other compounds which bind thereto or which catalyze the label. Other mechanisms for detecting label include the use of compounds that can chemically react with the label, the detection of a colored label, the detection of light emission, the detection of radiation, or the catalytic ability of the label.

In one measurement technique, the label on the second polynucleotide is biotin. The presence of this label can be detected by reacting it with the enzymes peroxidase or alkaline phosphatase. These enzymes can be specifically directed to biotin by conjugation with avidin or streptavidin. The presence of the enzymes is then detected by the addition of an appropriate substrate to provide a detectable color-developing or light-emitting reaction. Alkaline phosphatase-labeled streptavidin can be readily obtained from the commercial market. One substrate for alkaline phosphatase is adamantyl-1,2-dioxetane phosphate (AMPPD). Upon reaction with the alkaline phosphatase, AMPPD will emit light at a wavelength of 447 nm. This light can be detected in accordance with techniques known in the art. A more preferred light emitting substrate for alkaline phosphatase is ATTOPHOS.

In the reaction between alkaline phosphatase and AMPPD, an enhancer such as 5-N-tetradecanoyl-aminofluorescein can be added. 5-N-tetradecanoyl-aminofluorescein has the ability to convert light of 477 nm wavelength to light of 530 nm wavelength, which is more readily detectable.

Other labels include an antigen, such as digoxigenin or an antibody. An antigen can be detected by its ability to bind to an antibody directed thereto. Such antibodies, or an antibody directly used to label the second polynucleotide probe, can be detected by their ability to bind a protein. The antibody itself can be labeled directly with a radionuclide, such as $^{125}I$, or can be labeled by binding thereto a protein labeled with the radionuclide. The radionuclide can then be detected in accordance with techniques well known in the art, such as using X-ray film or a radiation counter.

Well-known techniques for the detection of a label include detecting a label in a color-developing reaction with a spectrophotometer or fluorimeter. For example, fluorescein, which gives off a fluorescent pigment, can be used as a label, and the intensity of the pigment can be used to gauge the amount of label hybridized to target polynucleotides. The use of such color-developing reactions are preferred to using radioactive labels in the present methods because the problems associated with using radioactive nuclides are thereby avoided.

Other such techniques include the detection of a light emitting reaction using X-ray film or an instant camera. The emission reactions are recorded by X-ray film or instant camera film in the dark room. The X-ray film which is exposed by emission reactions is recorded as a blot, so that the shading of the blot can be measured by a densitometer. If one uses an instant camera such as a Polaroid, the picture is read by a scanner to decide the location of the blot on the computer, and the shading of the blot is determined using graphic analysis software.

An example of one embodiment of the present invention is illustrated in FIG. 2. As shown in that Figure, following the collection and lysis of a sample of biological materials from a human patient, the ribosomal RNA of a species of fungus sought to be detected is hybridized. Following hybridization, a specific sequence 24 of the strand of ribosomal RNA 22 to be detected is annealed to a complementary sequence 28 on a first polynucleotide probe 26. The first probe 26 is immobilized on a solid support 20.

After removing substantially all of the unhybridized portions of the sample, a second polynucleotide probe 34 is hybridized to the strand of ribosomal RNA 22 at a different sequence 30, which is preferably one that is common to a plurality of fungal species. The second probe 34 contains a sequence 32 that is complementary to the sequence 30. The second probe, in this diagram, also comprises a label 36 attached to the probe which facilitates the detection of the complex formed by the first probe 26, the second probe 34, the strand of ribosomal RNA 22, and the solid support 20.

Example 6 shows one method of measuring the amount of rRNA of a particular fungal species using a labeled common polynucleotide probe.

EXAMPLE 6

Measurement of Chemical Activities of the Labeled Second Nucleotide Probe

Following the hybridization described in Example 5, the hybridization solution (Lysis Buffer containing the labeled second polynucleotide probe) is removed by aspiration and the microtiter plate is washed once with 250 µl of fresh Lysis Buffer. A blocking buffer consisting of 0.05% (w/v) Tween 20, 500 mM NaCl, and 100 mM Tris-HCl, pH 7.5 is added into each well and incubated at room temperature for five minutes to reduced nonspecific binding. These solutions are then removed by aspiration.

The fluorescein on the second polynucleotide probe which is bound to the ribosomal RNA of the species of fungus being tested for, if present, is then visually detected to determine whether a fungus of that species was present in the biological sample. The approximate quantity of fungus present in the sample is then measured by determining the amount of fluorescein bound to the microtiter plate with a spectrophotometer or in a fluorimeter.

XIV. Using PCR to Detect Small Quantities of DNA or RNA in a Sample

We have also discovered an alternative procedure which is especially useful in the detection of minute quantities of an organism, infectious agent, or biological component in a sample. This alternative procedure makes use of the polymerase chain reaction (PCR) procedure to create multiple copies of a polynucleotide strand which is complementary and/or homologous to a biological component or a strand of RNA and/or DNA which belongs to an organism or infectious agent in the sample.

Figure 3:
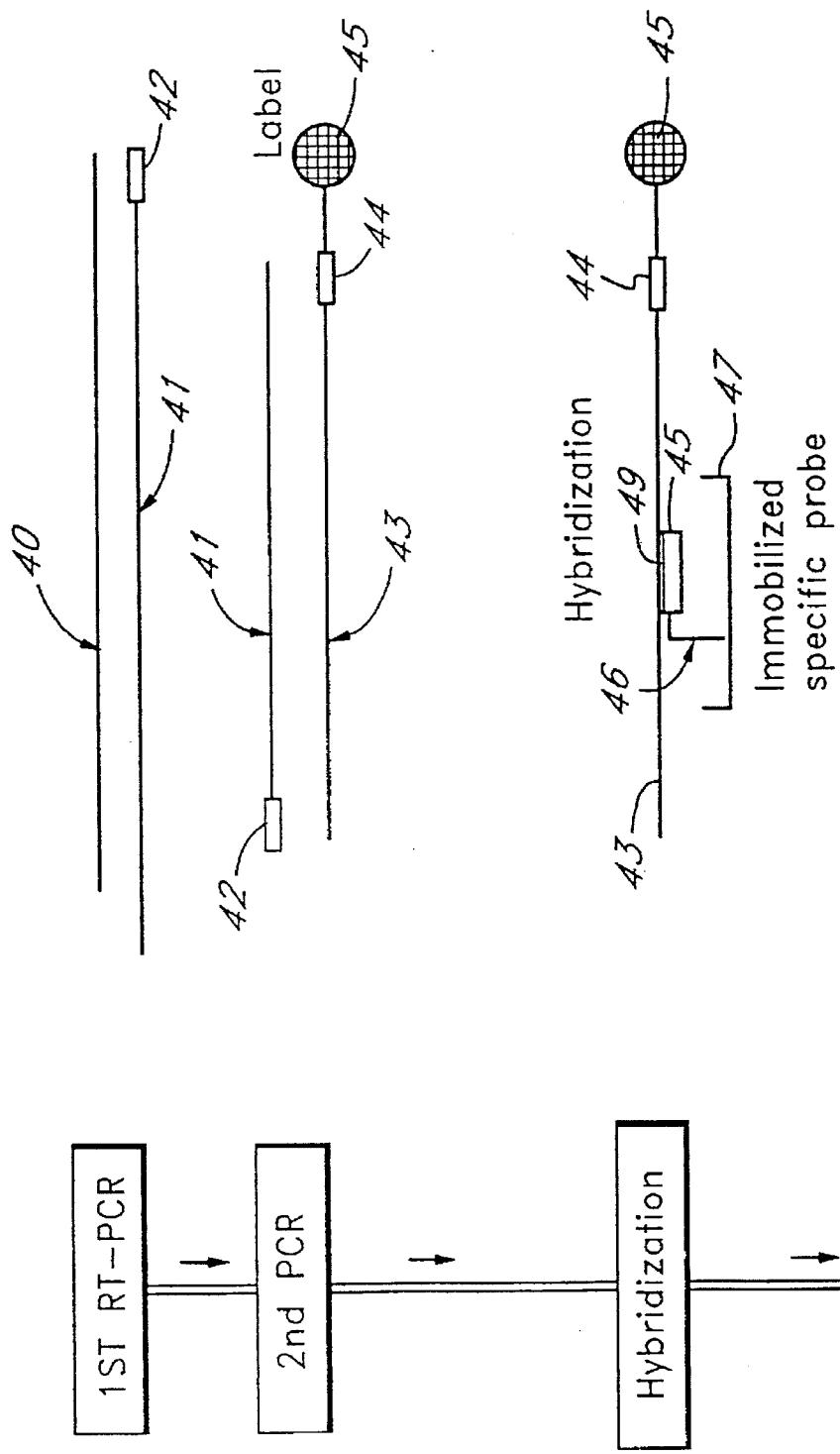
FIG. 3 is schematic representation of an embodiment of the method of the present invention in which PCR is used.

In an example of this embodiment of the present invention, shown in FIG. 3, a biological sample is first obtained as described previously. The sample is lysed so that the RNA and/or DNA of any organisms, infectious agents, or cells carrying biological components which are present in the sample can be probed. The lysed sample is then contacted with a first polynucleotide primer 42. This primer 42 is complementary to a sequence contained in the RNA or DNA of an organism, infectious agent, or biological component to be detected in the sample. The primer 42 is then contacted with an RNA or DNA strand 40 with which it is complementary and hybridized to that strand. The hybridizing of the primer 42 can be accomplished in the same manner as was previously described in relation to the hybridizing or annealing of polynucleotide probes.

The sequence complementary to the primer 42 can comprise, for example, a sequence specific to the DNA or RNA of an organism, such as the ribosomal RNA of a species of fungus. Such a sequence can also comprise a sequence specific to another infectious agent or to a biological component, such as an oncogene sequence. However, in another embodiment the primer 42 is complementary to a sequence located 3' of such a specific sequence, so that the primer 42 is positioned 5' of the specific sequence when it is annealed to a strand containing the specific sequence. In this way the sequence complementary to the specific sequence is incorporated when the primer 42 is extended.

In yet another embodiment, the primer 42 is complementary to a sequence common to a group of organisms, infectious agents, or biological components, such as a sequence common to a plurality of fungal species. In another example, the primer 42 is common to a number of related biological components, such as a plurality of subtypes of jun oncogenes. Thus, in this embodiment, the first polynucleotide primer 42 can be referred to as a common PCR primer.

After the common PCR primer 42 has been annealed to the RNA and/or DNA present in the sample, this primer is extended using the four nucleotide triphosphates and a polymerase enzyme, thereby producing a double-stranded polynucleotide including a complementary nucleotide strand 41 comprising cDNA and having a sequence complementary to the RNA and/or DNA in the sample from the organism, infectious agent, or biological component of interest. If the nucleotide sequence being probed for is contained in RNA, the polymerase is preferably a reverse transcriptase and the nucleotide triphosphates are deoxynucleotide triphosphates (dNTP's) so that cDNA complementary to the rRNA is produced. Further rounds of amplification can be accomplished by reannealing additional primer 42 to the strand of RNA or DNA 40 and then extending that primer. As will be clear to those of skill in the art, the first polynucleotide primer can also have a sequence specific to a particular organism, infectious agent, or biological component.

The first primer 42 is preferably extended using deoxynucleotides to form a strand of cDNA 41 that is complementary to the strand of RNA or DNA 40 in the sample. Using cDNA 41, amplification can also be accomplished by hybridizing to the strand of cDNA 41 a second polynucleotide primer 44 that is complementary to the newly synthesized complementary nucleotide strand 41. Thus, this second primer 44 is homologous to a portion of the RNA or DNA strand 40. This second primer 44 can preferably be common to the RNA or DNA of a plurality of organisms, infectious agents, or biological components and comprise a sequence different from that to which the first polynucleotide primer is complementary. Thus, in a preferred embodiment, the second primer 44 is a second common PCR primer, and the RNA and/or DNA of a plurality of organisms, infectious agents, or biological components can be amplified with it. Amplification is completed by extending the second primer 44 to produce a strand of cDNA 43 that is homologous to at least a portion of the strand of RNA or DNA 40 in a sample. This amplification step is also preferably repeated a plurality of times with further second primers 44.

These later rounds of amplification preferably use the four dNTP's in combination with a DNA polymerase so that during amplification, double-stranded DNA is produced which contains one strand of cDNA 43 homologous to the RNA or DNA of an organism, infectious agent, or biological component 40 present in the biological sample and one strand of cDNA 41 complementary to such homologous cDNA 43. Preferably, approximately 20 to 40 cycles of DNA synthesis are performed in order to produce an adequate amount of cDNA homologous to the RNA and/or DNA present in the sample for later detection. A DNA polymerase is used in the synthesis of such cDNA. This polymerase preferably has significant polymerase activity at temperatures above 50° C., such as Taq DNA polymerase.

Following these rounds of amplification, another round of amplification is preferably performed. In this second round of PCR, a third and fourth polynucleotide primer are used. One or both of these primers preferably contain a sequence that is homologous or complementary to a sequence specific to a particular organism, infectious agent, or biological component, in which case such primers can be called specific primers. However, when it is desired to identify or quantitate the presence of a group of organisms, infectious agents, or biological components, one or both of the third and fourth primers can contain a sequence complementary or homologous to a sequence common to a plurality of organisms, infectious agents, or biological components. When PCR is performed using third and fourth primers containing sequences specific to an organism, infectious agent, or biological component, amplification will occur in significant amounts only if RNA and/or DNA of the particular organism, infectious agent, or biological component being tested for is present in the biological sample and the initial amplification has produced cDNA corresponding to such RNA and/or DNA.

The amplification of sequences contained in the RNA and/or DNA of an organism, infectious agent, or biological component can be detected in several ways, as will be appreciated by those having ordinary skill in the art. For example, a common or specific primer can be labeled and the presence of the label in an extended polynucleotide can be detected. As shown in FIG. 3, for example, a label 45 can be attached to the primer 44, which is then extended to produce the homologous polynucleotide 43.

When it is desired to detect a specific organism, infectious agent, or biological component, the homologous polynucleotide strand 43 can then be contacted with and hybridized to a sequence 48 on a specific polynucleotide probe 46 which is complementary to a sequence 49 that is specific to a particular organism, infectious agent, or biological component and which is immobilized on a solid support 47, as in other embodiments of the present invention. Following this, the unhybridized portions of the sample are preferably washed from the solid support 47, and the labeled homologous polynucleotide 43 immobilized on the solid support 47 is detected. Alternatively, if the homologous polynucleotide 43 is not labeled, following the washing of the solid support 47 a second polynucleotide probe (not shown in FIG. 3) carrying a label can be hybridized to the homologous polynucleotide 43. This can also be followed by washing. After washing unhybridized second probe from the solid support, the labeled second probe can be detected using any of a variety of techniques. The homologous polynucleotide 43 will only be detected, of course, if it is hybridized to the immobilized polynucleotide probe 46.

As will be appreciated by those of skill in the art, the complementary cDNA strand 41 rather than the homologous polynucleotide 43 can also be annealed to a polynucleotide probe 46 immobilized on the solid support. In this method, the primer 42 is labeled rather than the primer 44. The strand 41 can then be detected directly, as described above, or can be detected by hybridizing a labeled polynucleotide to the strand 41.

Example 7 illustrates one method of identifying small quantities of the fungus Pneumocystis carinii in a sample.

EXAMPLE 7

Amplifying Ribosomal RNA Present in Minute Quantities with PCR

A sputum sample from a patient suspected of having pneumonia caused by the fungus Pneumocystis carinii is first lysed with Lysis Buffer and brought to a total volume of sample and lysis buffer of 50 82 1. This mixture is then added to a well of a microtiter plate to which a common probe (SEQ ID NO:1) has been immobilized, thereby contacting the probe with the mixture. The common probe is a polydeoxynucleotide complementary to a sequence common to the ribosomal RNA of a number of fungal species, including P. carinii. The sequence on the ribosomal RNA of Pneumocystis carinii to which this probe is complementary is located 3' of a specific sequence (SEQ ID NO:81) of such ribosomal RNA.

The common probe can then be hybridized to the fungal ribosomal RNA in the sample by incubating the mixture in the well at 39° C. for one hour and then cooling the mixture over 20–30 minutes. Following the annealing of the common probe to the ribosomal RNA, the probe is extended with a reverse transcriptase to produce a cDNA strand having a sequence complementary to the ribosomal RNA. The complementary strand is then melted off of the ribosomal RNA by heating the mixture to 94° C. for 1 to 2 minutes. This process is repeated several times in order to amplify the number of complementary strands.

Following the denaturation of the complementary strand from the ribosomal RNA, a second primer homologous to a sequence of the ribosomal RNA that is specific to Pneumocystis carinii is added to the mixture. The four dNTP's and a DNA polymerase capable of polymerase activity above 50° C. is added to the mixture. The mixture is then heated to a temperature below the $T_m$ of the second primer but high enough to assure specific binding of the primer, in this case approximately 50° C. After allowing enough time for the second primer to be extended, about 1–2 minutes, the mixture is heated to 94° C. for 1 to 2 minutes to melt the newly synthesized strand homologous to the ribosomal RNA of the sample from the complementary strand. This process is repeated from between 20–40 times, with the addition of primer as necessary.

Following this round of amplification, two labeled, specific primers are added to the mixture. One is complementary to a specific sequence on complementary strand, while the other is complementary to a sequence on the homologous strand. After annealing such primers to the complementary and homologous strands, these primers are extended with a polymerase in the same fashion as the second primer, after which such strands are melted off by raising the temperature of the mixture to 94° C. for 1 to 2 minutes. This process is also repeated between 20–40 times.

After the final round of amplification, the mixture is heated to melt off any newly synthesized strands from the templates from which they were produced, and the mixture is cooled to 37° C. and incubated at that temperature for an hour in order to allow the strands present in the mixture to anneal to a specific probe immobilized on the microtiter well. This probe is complementary to a specific sequence in the ribosomal RNA of Pneumocystis carinii and anneals to the ribosomal RNA of that fungus in addition to the synthesized sequences homologous to such ribosomal RNA.

Once the polynucleotide strands in the mixture have been allowed to hybridize to the specific probe, the non-hybridized portions of the mixture are removed by aspiration. The walls of the microtiter plate are then washed with Lysis Buffer to remove any non-specifically bound nucleotide strands from the well. The label attached to the specific primer is next detected in order to detect the presence of Pneumocystis carinii in the biological sample. If the label is detected, this indicates that the biological sample contained this fungus.

XV. Primers for Use in PCR

We have identified several probes and PCR primers for use in the present invention. In particular, sequences have been identified for detecting jun oncogenes and G protein sequences in humans and other animal species, as well as sequences for detecting substance P and Beta-receptor sequences. The design and use of such primers is described below.

A. Primers for Detecting Jun Oncogenes

It is well known that certain oncogenes, such as the jun oncogenes, are most rapidly expressed when cells are stimulated to proliferate. Therefore, the detection or quantification of the expression of jun oncogenes is a good marker for cellular mitogenic activity. Jun oncogenes were first reported by Maki, et al. (Proc. Natl. Acad. Sci. USA, 84:2848–2852 (1987)), and are currently known to exist in at least three different forms or subtypes, jun-B, c-jun, and jun-D. It is still unclear how these three jun subtypes are involved in cell growth, however, so that one has to analyze all three genes during cell growth in order to detect mitogenic activity. In addition, although it has been discovered that mice also carry three different jun oncogene subtypes, the nucleotide sequences of these three subtypes differ from the subtypes present in human cells (Ryder K., Nathans D., Proc. Natl. Acad. Sci. USA 85:8464–8467, 1988; Ryder K. et al., Proc. Natl. Acad. Sci., USA 85:1487–1491, 1988; Hattori K. et al., Proc. Natl. Acad. Sci. USA 85:9148–9152, 1988; Schuette J. et al., Cell, 59:987–997, 1989).

In order to design sense and anti-sense PCR primers for detecting jun oncogenes in both humans and mice, sequences were designed with the following considerations in mind:

(a) The nucleotide sequences should be common to the three subtypes of jun oncogenes (jun-B, c-jun and jun-D), with a maximum of 4 base mismatches.

(b) The nucleotide sequences should be common to both humans and mice, with a maximum of 4 base mismatches.

(c) At least 5 bases at the 3' end of the primers should be 100% identical to sequences in all three jun subtypes in both humans and mice.

(d) The length of the nucleotide sequences of both the sense primers and the anti-sense primers should be between about 17 and 50 bases.

(e) The difference in $T_m$ between the sense primers and anti-sense primers and their corresponding sequences should be within 2° C.

(f) There is no complementary structure more than 4 bases long in either the sense or the anti-sense primer.

(g) There should be no complementary structure more than 4 bases long between the sense and the anti-sense primer.

(h) Both the sense and the anti-sense primers should span part of the coding sequence of their complementary polynucleotides.

(i) The length of polynucleotide to be amplified should be greater than 200 bases.

(j) The nucleotide sequence homology of amplified genes among the three subtypes of jun oncogenes should not be greater than 80%.

DNA fragments (both sense and anti-sense primers) which satisfied the above conditions were investigated and several candidate oligonucleotides were synthesized. One set of primers which fit these parameters particularly well is the sense primer 5'-CCCTGAAGGAGGAGCCGCAGAC-3' (SEQ ID NO:733) and the anti-sense primer 5'-CGTGGGTCAAGACTCTGCTTGAGCTG-3' (SEQ ID NO:734). The homology between the sense primer SEQ ID NO:733 and several jun gene subtypes is shown in Table 2 below.

TABLE 2

| | | Sense primer<br>5'-CCCTGAAGGAGGAGCCGCAGAC-3' |
|---|---|---|
| Mouse | jun-B | --T-T--A---------------<br>(SEQ ID NO:735) |
| | c-jun | ----------A------------<br>(SEQ ID NO:736) |
| Human | jun-B | --T-C---------A--------<br>(SEQ ID NO:737) |
| | c-jun | ------------------T----<br>(SEQ ID NO:738) |

—: indicates identical base to the sense primer.

As an alternative to the sense primer SEQ ID No:733 shown in Table 2, 5'-XCCCTGAAGGAGGAGCCGCAGAC-3' (SEQ ID No.739) can also be used as a primer for detecting jun oncogenes. In this sequence, X represents a primary amine residue, a nucleotide sequence recognized by a restriction endonuclease, or an RNA promoter sequence. The attachment of a restriction site to the 5' end of the PCR primers is useful for the cloning of amplified genes, while the attachment of RNA promoter sequences at such 5' ends is useful in RNA transcription and RNA transcription-based amplification, as is known to those of skill in the art. Preferably, the RNA promoter is either a T7, SP6, or T3 RNA promoter sequence. The attachment of a primary amine at 5' end can also be useful for coupling reactions, whereby the primer can be attached to labeling compounds or to solid supports via the primary amine group. Such primary amine residues can be added onto the 5' end of a nucleotide during oligonucleotide synthesis. The antisense analog 5'-XCGTGGGTCAAGACTTCTGCTTGAGCTG-3' (SEQ ID No:740) can also be used to probe for the different jun gene subtypes, where X represents a primary amine residue, nucleotide sequence recognized by a restriction enzyme, or RNA promoter sequence.

The DNA fragments for the sense primer and anti-sense primer in this invention can be easily synthesized using a DNA synthesizer. These synthesized oligonucleotides can be purified by high pressure liquid chromatography or gel electrophoresis.

The test material to be analyzed is usually total RNA or purified mRNA from cells or tissues. If desired, cells or tissues can be tested in their natural state without any pretreatment. In the case of drug testing, a drug can first be administered to cells or to tissues in a test tube. A drug can alternatively be administered (through intravenous injection, subcutaneous injection, intramuscular injection, oral administration, or intra-abdominal injection) to a laboratory animal, after which cells or tissues are removed from the animal.

Total RNA or mRNA can be purified through standard protocols, such as those described in Molecular Cloning, or by using a commercially available kit such as FastTrack from Invitrogen (San Diego). In either case, in order to avoid introducing any RNase into a solution containing RNA, a researcher's hands should be protected with vinyl gloves, and the instruments used for experiments should not be touched with bare hands. Also, any glass containers to be used in the experiments should be heated prior to use at approximately 250° C. for at least 4 hours. Furthermore, any water to be used in the procedures should be treated with 0.1% diethyl pyrocarbonate (DEPC) incubated overnight at 37° C. and autoclaved.

The cDNA to be synthesized from mRNA is made using reverse transcriptase, as described in Molecular Cloning. Once such cDNA has been generated, it is mixed with sense primer, antisense primer, 4 types of deoxynucleotides (dATP, dCTP, dGTP and dTTP), Taq polymerase, inorganic salts, and other necessary materials, and a PCR reaction is undertaken in a thermal cycler (Perkin-Elmer Cetus).

In order to analyze the genes amplified in this way, it is appropriate to use electrophoresis. After the amplified gene undergoes electrophoresis in an agarose gel, the DNA is stained with ethidium bromide. The amplified DNA band will be then visible under fluorescent light. After taking photographs of the DNA band, it is also possible to quantify the intensity of each DNA band by scanning such photographs and analyzing the scanned picture with a commercially available system such as Stratascan (Stratagene, La Jolla). Furthermore, after agarose gel electrophoresis, amplified genes can be transblotted onto membranes, and subtypes of specific jun genes can be detected by hybridizing the blotted membranes with labeled probes followed by exposing labeled signals, such as $^{32}P$ or chemiluminescence, to either Polaroid films or X-ray films (i.e., doing a Southern blot).

As with the other polynucleotides that can be detected in accordance with the methods of the present invention, a variety of jun sequences can serve as sense or antisense primers for PCR methods or as probes for the detection of DNA or RNA as described herein. A method for the identification of such sequences that are either common to a variety of jun oncogenes or specific to a particular species is provided hereinbelow. In the preferred embodiment of this method of identification, a computer program is used to identify the sequences. Through use of such a program, we have identified a large number of both common and specific primers and probes. Provided as Tables XVII through XXII and XXX through XXXII are various sense sequences, i.e., sequences homologous or approximately homologous to sequences found in an organism, infectious agent, or biological component, which have been identified through the use of such a computer program as being useful as jun gene probes and primers.

All of the sequences listed in these tables are useful within the context of the PCR methods of the present invention. The complementary antisense sequences are also useful as both probes and/or PCR primers in certain aspects of the invention. As will be known by those having ordinary skill in the art, for common probes that are similar but not identical to target sequences, stringency conditions can be varied (e.g. by changes in temperature and salinity) so that such probes will hybridize or fail to hybridize with a particular target sequence. Thus, also included within the present invention are sequences that are capable of hybridizing with the same sequences as either the sense sequences listed or their anti-sense counterparts. Additional probes for jun genes include the following:

| Common jun gene probes | |
|---|---|
| 5'-CCATGTCGATGGGGGACAGCGG-3' | SEQ ID NO:741 |
| 5'-CTGTTTAAGCTGCGCCACCTG-3' | SEQ ID NO:742 |
| 5'-GTCTGCGGCTCCTCCTTCAGGG-3' | SEQ ID NO:743 |
| 5'-CGTGGGTCAAGACTTTCTGCTTGAGCTG-3' | SEQ ID NO:744 |
| Specific probes | |
| B type: 5'-CACTTGGTGGCCGCCAG-3' | SEQ ID NO:745 |
| C type: 5'-GAGCATGTTGGCCGTGG-3' | SEQ ID NO:746 |
| Human D type: 5'-GATGCGCTCCTGCGTGT-3' | SEQ ID NO:747 |
| Mouse D type: 5'-GCCTGTTCTGGCTTTTGAGGG-3' | SEQ ID NO:748 |

EXAMPLE 8

Synthesis of DNA fragments (sense and anti-sense primer) and amplification of mouse clones of jun oncogenes SEQ ID No:728 (S943-2) and SEQ ID No:729 (AS1132-2) were synthesized with a 380 B type DNA synthesizer (Applied Biosystems Co.). After treatment with ammonium hydroxide at 55° C. overnight, the synthesized oligonucleotides were dried in a Speed-Vac (Savant Co.), and the concentration of each oligonucleotide was adjusted to 1 microgram/ml with water. These oligonucleotides were then at −20° C. until use.

One microliter (containing approximately 10 ng) of one of the three types of mouse jun clones (jun-B, c-jun, or jun-D, obtained from ATCC), was placed in each of three reaction tubes. To each of these reaction tubes was then added 1 microliter of sense primer SEQ ID No:728, 1 microliter of anti-sense primer SEQ ID No:729, 5 microliters of 10× buffer for PCR (Promega), 1 microliter of 25 mM magnesium chloride, 4 microliters of 10 mM dNTP mix, and 0.5 microliters of Taq polymerase (Promega) were mixed, and water was added up to a total volume of 50 microliters. After adding two drops of mineral oil to each tube, PCR was undertaken using the thermal cycler, model 480 (Perkin-Elmer Cetus). After the reaction mixture was heated at 95° C. for 10 minutes, PCR was carried out with the following cycles 30 times: annealing at 55° C. for 1.5 minutes, extension at 72° C. for 4 minutes, and denaturing at 95° C. for 1.5 minutes.

After PCR, 10 microliters of the sample was mixed with 1 microliter of 10× loading buffer (0.25% bromophenol blue, 0.25% xylenecyanol FF, and 15% Ficoll, Type 400), and electrophoresis was carried out on a 1.5% agarose gel containing 5 microgram/ml ethidium bromide. After electrophoresis, the amplified DNA bands were visualized by an ultraviolet light.

As shown in FIG. 3a, the clones jun-B, c-jun, and jun-D were amplified using SEQ ID NO:728 and SEQ ID NO:729, and a single band for the amplified DNA was observed at the position of approximately 270 bp in each case. This indicates that the above-mentioned set of primers can recognize and amplify all three types of mouse jun oncogenes, jun-B, c-jun and jun-D.

EXAMPLE 9

The effect of pretreatment with EGF on expression of jun oncogenes in human mononuclear leukocytes The following protocol describes the effect of using EGF to stimulate the production of jun oncogene mRNA:

(1) Pretreatment of human leukocytes with EGF. 40 ml of phosphate buffered saline (PBS) is added to 20 ml of heparinized human blood and mixed. 10 ml each of this sample is overlayered onto 3 ml of IsoLymph, then centrifuged for 30 minutes at 400×g. After washing the pellet three times with PBS, the pellet is resuspended in 3 ml of PBS. 1 ml each of this sample is then placed into three tubes (No. 1 to No. 3). 1 ml of PBS is placed in a fourth tube as control. The four tubes are incubated for 10 minutes at 37° C., and EGF (Epidermal Growth Factor) is then placed in tube No. 1 at a final concentration of 30 ng/ml. After 15 minutes, EGF is placed in the same manner in tube No. 2, and incubated for another 5 minutes. After 5 min, RNA is extracted from all 4 tubes simultaneously. Thus, the time period of the pretreatment of human leukocytes by EGF is 20 minutes for tube No. 1, 5 minutes for tube No. 2, and 0 minutes for tube No. 3.

(2) Extraction of RNA from cells. The above four tubes are taken out and subjected to centrifugation by a microfuge for 10 seconds. Then, the supernatant is discarded and the below described lysis buffer is added to the pellet. The lysis buffer and pellet are thoroughly mixed, after which the mixture is incubated for 30 minutes at 45° C.

Contents of lysis buffer:

10 mM EDTA pH 8.0

0.5% SDS (with bacteria removed by non-bacterial filter)

0.2M NaCl

DEPC treated water

RNA inhibitor 500 unit s/ml

Vanadyl Complex 10 mM

Proteinase K 200 microgram/ml (3) Purification of mRNA. After 5M NaCl is added to the above cell lysates to obtain a final concentration of 0.5M, oligo (dT) cellulose (Stratagene Co.) is added, and is reacted for 30 minutes at room temperature. Then, after washing the cellulose in 10 ml binding buffer (20 mM Tris-HCl, pH 7.6, 1 mM EDTA, 0.5M NaCl) 5 times, 0.35 ml of DEPC treated water is added, and mRNA is eluted from the solid phase. Then, 53 microliters of 2M sodium acetate and 2.5 times the volume of ethanol are added, and after cooling in dry ice for 20 minutes, this mixture is centrifuged at 15,000 rpm for 20 minutes. After washing the pellet in 75% ethanol one time, the pellet is dried and then dissolved in 10 microliters of DEPC treated water. The resulting mixture contains mRNA from the cells being tested.

(4) Synthesis of cDNA. 50 mM Tris-HCl (pH 8.3), 75 mM KCl, 3 mM magnesium chloride, 10 mM DTT, 0.5 mM dNTP (dATP, dCTP, dGTP, dTTP), 50 micrograms/ml oligo (dT) primer, and 10,000 units/ml reverse transcriptase are added to 10 microliters of the mRNA obtained above to a total volume of 20 microliters, and this undergoes a reaction for one hour at 37° C. After the reaction, 20 microliters of a phenol:chloroform:isoamyl alcohol mixture is added, and the mixture is cooled for 20 minutes in dry ice to precipitate the cDNA. After centrifugation for 20 minutes at 10,000 rpm, the pellet is washed one time in 75% ethanol. Then, after drying, the pellet is dissolved in 20 microliters of autoclaved water to form a cDNA solution, and stored at −20 degrees C.

(5) PCR. One microliter each of sense primer SEQ ID NO:733 and anti-sense primer SEQ ID NO:740 (1 mg/ml) for jun gene amplification are added with 2 microliters of the cDNA solution above. After mixing this with 50 mM KCl, 10 mM Tris-HCl (pH 8.4), 2.0 mM magnesium chloride, 100 micrograms/ml gelatin, and 0.2 mM dNTP, 2.5 units of Taq polymerase are added (final volume is 50 ml). After the reaction mixture is heated at 95° C. for 10 minutes, PCR is carried out with the following cycles 30 times: annealing at 55° C. for 1.5 minutes, extension at 72° C. for 4 minutes, and denaturing at 95 degrees C for 1.5 minutes.

(6) Agarose gel electrophoresis. After completing PCR, 10 microliters of the reacted solution is taken and electrophoresed in the same method as described in example 1. The results showed that in the leukocytes which did not undergo treatment with EGF (i.e., the sample which underwent 0 treatment time in tube No. 3) is found to have a minimal band for the amplified DNA at the position of about 270 bp size. However, it has been found that the band of amplified DNA was increased after 5 min, then returns to basal levels within 20 min.

EXAMPLE 10

Effect of pretreatment with PHA on jun gene expression in human leukocytes

In the place of EGF, PHA (at a final concentration of 10 micrograms/ml) is utilized and the pretreatment times are set at 0 minutes, 5 minutes, 15 minutes, and 30 minutes. The procedures followed in Example 2 are then followed. As a result, with the pretreatment with PHA done at 15 minutes, it was found that the band for the amplified DNA at the position of approximately 270 bp was maximized, but for the time periods afterwards, this band decreased in intensity and therefore in the quantity of DNA it contained.

B. Primers for Detecting G Protein Sequencer

Cell surface receptors for hormones and neurotransmitters are known to be coupled to intracellular heterotrimeric GTP-binding proteins (G proteins) composed of $\alpha, \beta$ and $\tau$ subunits. Once receptors are activated by specific ligands, receptor-coupled G proteins transduce signals to intracellular secondary effector systems, such as adenylyl cyclase, phospholipase C, and ion channels.

G proteins are believed to be involved in causing various disease states. For example, a genetic deficiency of $G_s$ proteins is the molecular basis of hereditary osteodystrophy. Pituitary tumors in acromegalic patients have been shown to contain mutant Gs proteins. G proteins are also involved in invasive and metastatic melanoma cells. Rat models of streptozotocin-induced experimental diabetes suggest that the levels of mRNA for various subclasses of $G\alpha$ proteins are significantly altered from normal control rats. Furthermore, cellular functions of pertussis toxin-sensitive G proteins were shown to be significantly impaired in atherosclerotic porcine coronary arteries, while G protein function in leukocytes of patients with mania was hyperfunctional. However, currently available immunological detection methods (Western blots) and mRNA detection methods (Northern blots) are not sensitive and require a lot of cellular material, making it difficult to study the role of G proteins in such diseases.

Although G proteins have been analyzed extensively from a biochemical and immunological point of view using various antibodies, antibody production without any cross-reactivity among various subclasses or with high species specificity has been quite difficult to obtain. Therefore, recent experiments have focused on Northern blot analyses to identify G protein-specific mRNA from various tissues or cells in different species. However, Northern blots require experienced handling and protection from RNase contamination, in addition to a large amount of starting cellular materials.

In contrast to these conventional methods, PCR technology is more convenient and practically useful, because it requires less material than a Northern blot analysis and has great sensitivity. However, it is difficult for PCR to quantify the amount of DNA or mRNA in starting materials.

Figure 6:
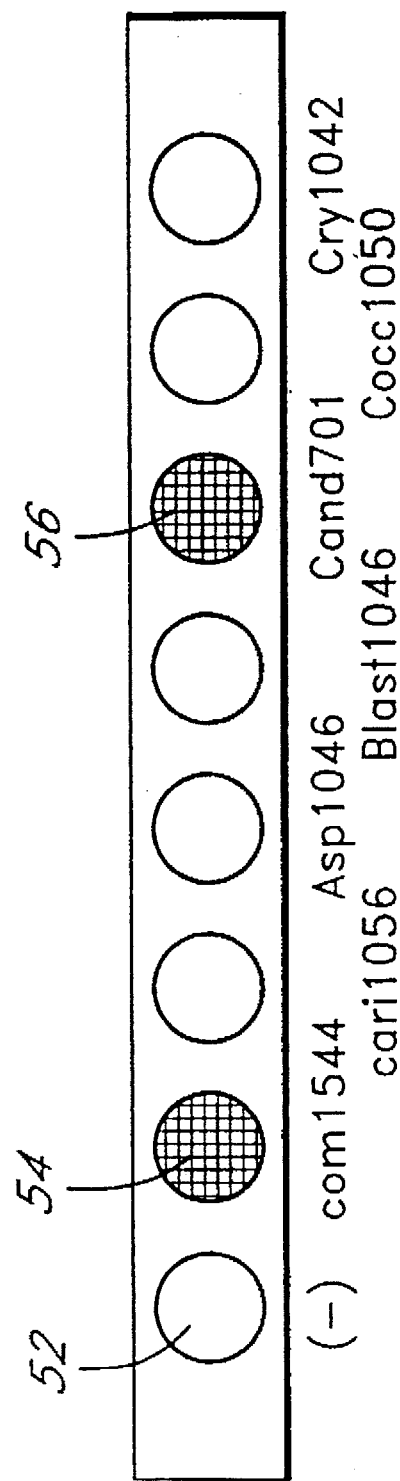
FIG. 6 is a schematic representation of an example of a microtiter plate used in the methods of the present invention.

We have identified two highly conserved oligonucleotide sequences among five different $\alpha$ subunits of G proteins, SEQ ID NO:528 and SEQ ID NO:731, which can be used as PCR primers. These sequences are able to amplify the sequences of all the subclasses of G proteins under the same PCR conditions, including G protein sequences obtained from a mixture of rat $G\alpha$ protein clones and cDNAs derived from various human tissues. Interestingly, the final PCR products obtained using the novel G-protein PCR primers of the present invention reflect the relative composition of each of the subclasses of $G\alpha$ proteins present in the starting materials. This is probably because the five different $G\alpha$ proteins cDNAs are amplified at a similar rate with a single set of PCR primers under the same PCR conditions. If known mixtures of each of the subclasses of $G\alpha$ protein clones are assayed together with unknown test samples, as shown in FIG. 6, the relative composition of $G\alpha$ proteins can be determined fairly precisely. Therefore, the present method is ideal for the characterization of $G\alpha$ proteins in various tissues and cells.

Performing PCR with the primers of the present invention is also useful in clinical and diagnostic assays in the detection of disease. Since G protein abnormalities have been associated with hereditary diseases, cancer, forms of diabetes, and other diseases, the present PCR primers for detecting and quantifying G proteins can be used to detect these diseases and assess their severity.

We have identified $G_{i-1}$, $G_{i-2}$, $G_{i-3}$, $G_s$ and $G_0$ using the PCR primers of the present invention (SEQ ID NO:528 and SEQ ID NO:731). Although recent cloning has identified more subclasses of G proteins, all of these newly identified G protein cDNAs showed a high degree of homology to other known G proteins. Therefore, it is expected that the primers of the present invention will amplify these subclasses as well, and that the present PCR the present PCR technique can also be applied to these new G proteins. Moreover, this PCR method can be utilized to clone unique G protein genes as well.

We designed two 22-mer oligonucleotides, $G_2$ (SEQ ID NO:528) and $G_4$ (SEQ ID NO:731), as PCR primers for the detection of G protein sequences. As shown in Table 3, these oligonucleotides contain sequences which are highly conserved among five different $G\alpha$ protein cDNAs, having only 0–4 base mismatches per sequence. No mismatch was found in the 4 bases at the 3' end of the $G_2$-sense and $G_4$-antisense sequences. Furthermore, $G_2$ and $G_4$ have no self-complementary sequences more than 3 base pairs in a row (data not shown). In order to analyze whether $G_2$ and $G_4$ are common to all the $G\alpha$ proteins, but not to other unrelated sequences, a homology search (DNASIS) of $G_2$ and $G_4$ sequences was carried out against all mammalian sequences in GenBank. As a result, $G_2$ and $G_4$ were found to be common to all the types of Gα proteins and rhodopsins of various species, but less homologous to other unrelated sequences (data not shown).

PCR was first carried out at different annealing temperatures ranging from 37° C. to 65° C. using the λgt10 library of human HL-60 cells. As a result, PCR products were seen only at 45° C. and 55° C. with a size of approximately 500 bp (data not shown), which was similar to theoretical values (576 to 524 bp) (see Table 3 above). Therefore, all the PCR was then carried out at an annealing temperature of 45° C.

Figure 5:
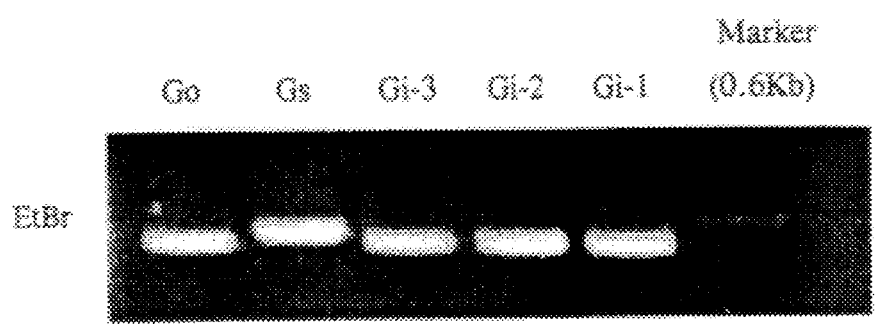
FIG. 5 is a picture of a gel showing the outcome of an experiment in which cloned rat $G_{i-1}$, $G_{1-2}$, $G_{i-3}$, $G_s$, and $G_o$ G protein subtypes were amplified using SEQ ID NO:528 and SEQ ID NO:731.

As shown in FIG. 5, cloned rat Gα protein cDNAs ($G_{i-1}$, $G_{i-2}$, $G_{i-3}$, $G_s$, $G_0$) were successfully amplified using the same set of PCR primers ($G_2$ and $G_4$) with a size of approximately 500 bp in 1.2% agarose gels stained with ethidium bromide. According to the computer analysis (DNASIS), the nucleotide sequences of the amplified PCR products were less homologous among five Gα proteins with the percentage of similarity ranging from 76.8% to 47.6%. This indicates that after PCR amplification, each of the components of Gα proteins can be identified by Southern blot analysis, even though the sizes of the PCR products generated are very similar among the five Gα proteins. Therefore, another PCR was carried out in which 35% of the dTTP was replaced with biotin-conjugated dUTP in order to prepare subclass-specific, biotin-labeled probes. Southern membranes were then probed with these biotin-PCR products. As shown in FIG. 5, these biotin-PCR probes were highly specific to each Gα protein subclass with washing temperature at 65° C. At low stringent washing, these probes cross-hybridized with other subclasses of Gα proteins (data not shown).

By using the $G_2$ and $G_4$ sequences, all the subclasses of Gα protein cDNA were amplified with PCR when an equal amount of $G_{i-1}$, $G_{i-2}$, $G_{i-3}$ and $G_0$ were present in test samples (FIG. 6, lane 4, 5, 10). However, if all the concentrations of Gα protein cDNA are abundant, $G_0$ is less amplified (FIG. 6, lane 10), probably because the number of mismatches between $G_0$ and $G_4$ is higher than others between $G_4$ and the $G_2$ sequences. If 1 or 2 of the 5 Gα protein cDNAs were present in smaller quantities than the others, the amounts of amplified cDNA were relatively correlated with the starting concentrations of cDNAs (FIG. 6, lane 1, 2, 3, 8, 9). Furthermore, if 1 of 5 of the Gα proteins' cDNA is more abundant than that of the others, this G protein gene was amplified more than others (FIG. 6, lane 6, 7).

Figure 7:
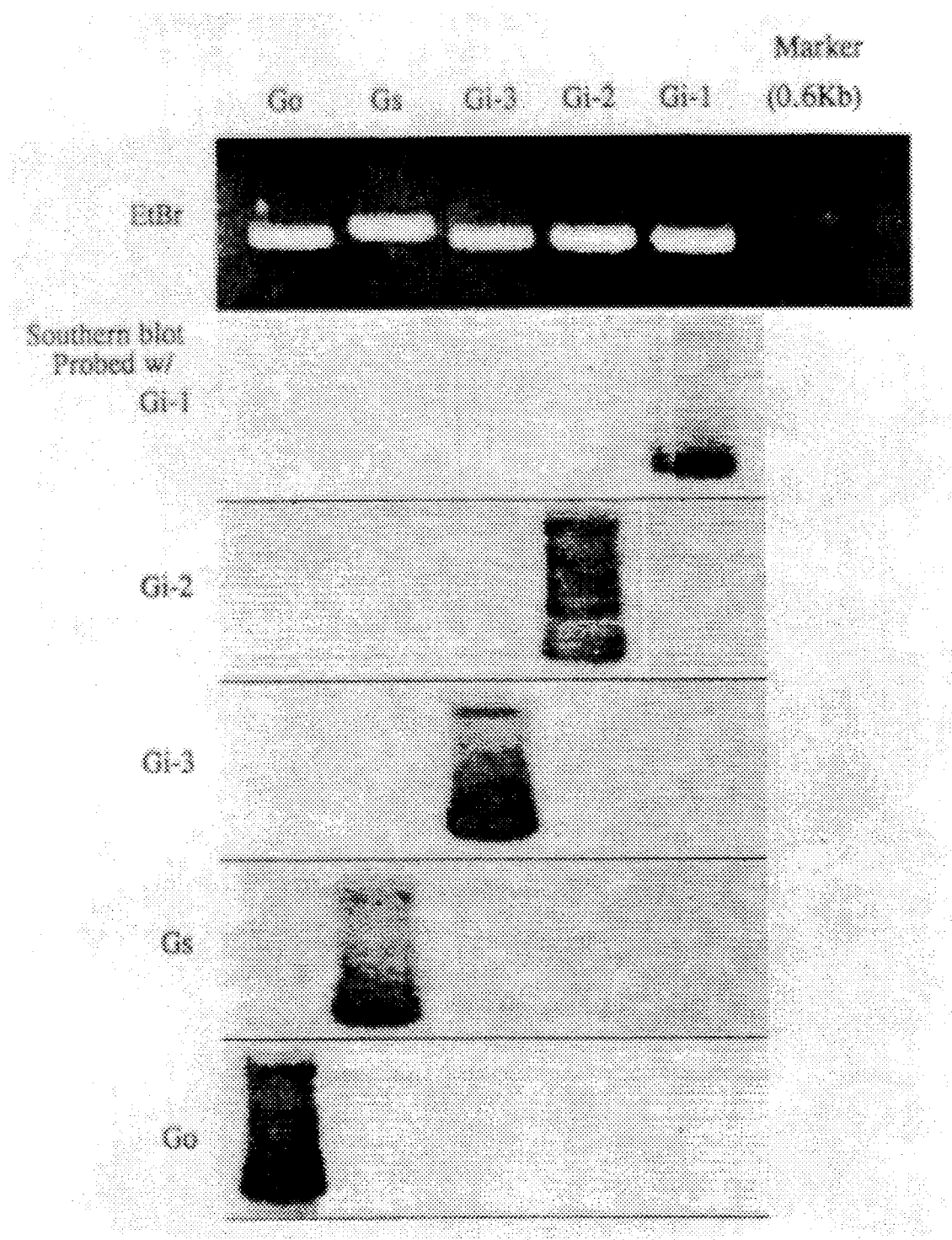
FIG. 7 is a picture of the gel referred to in FIG. 5 which also provides Southern blots using each of the five G protein sequences as a probe.
Figure 7A:
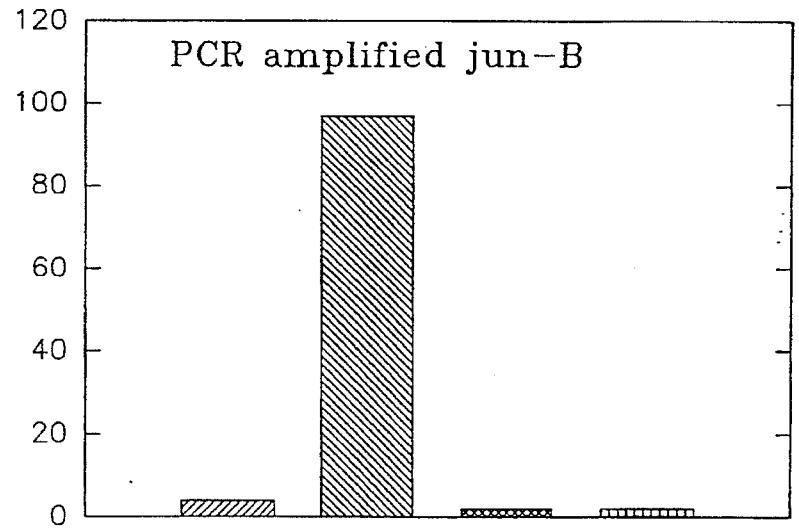
FIGS. 7A–7C are graphic representations of the results of an experiment which shows that SEQ ID NO:470, SEQ ID NO:488, and SEQ ID NO:730 can be used to detect specific subtypes of jun oncogenes.
Figure 7B:
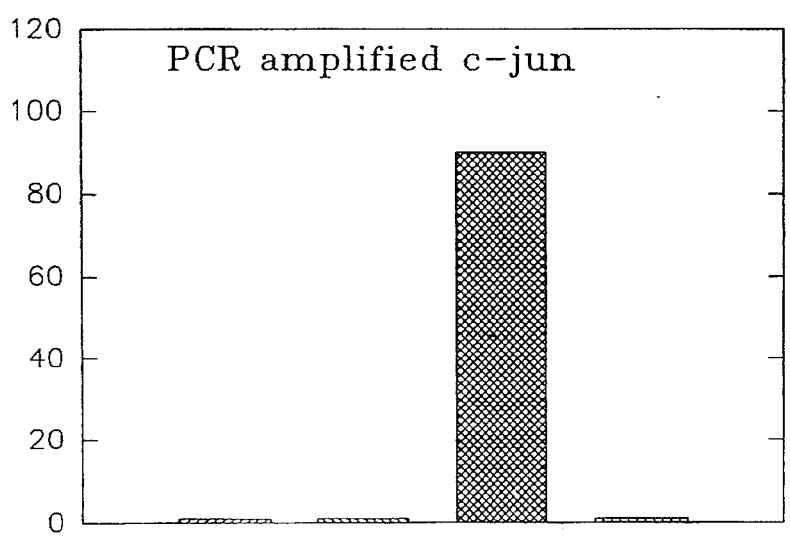
Figure 7C:
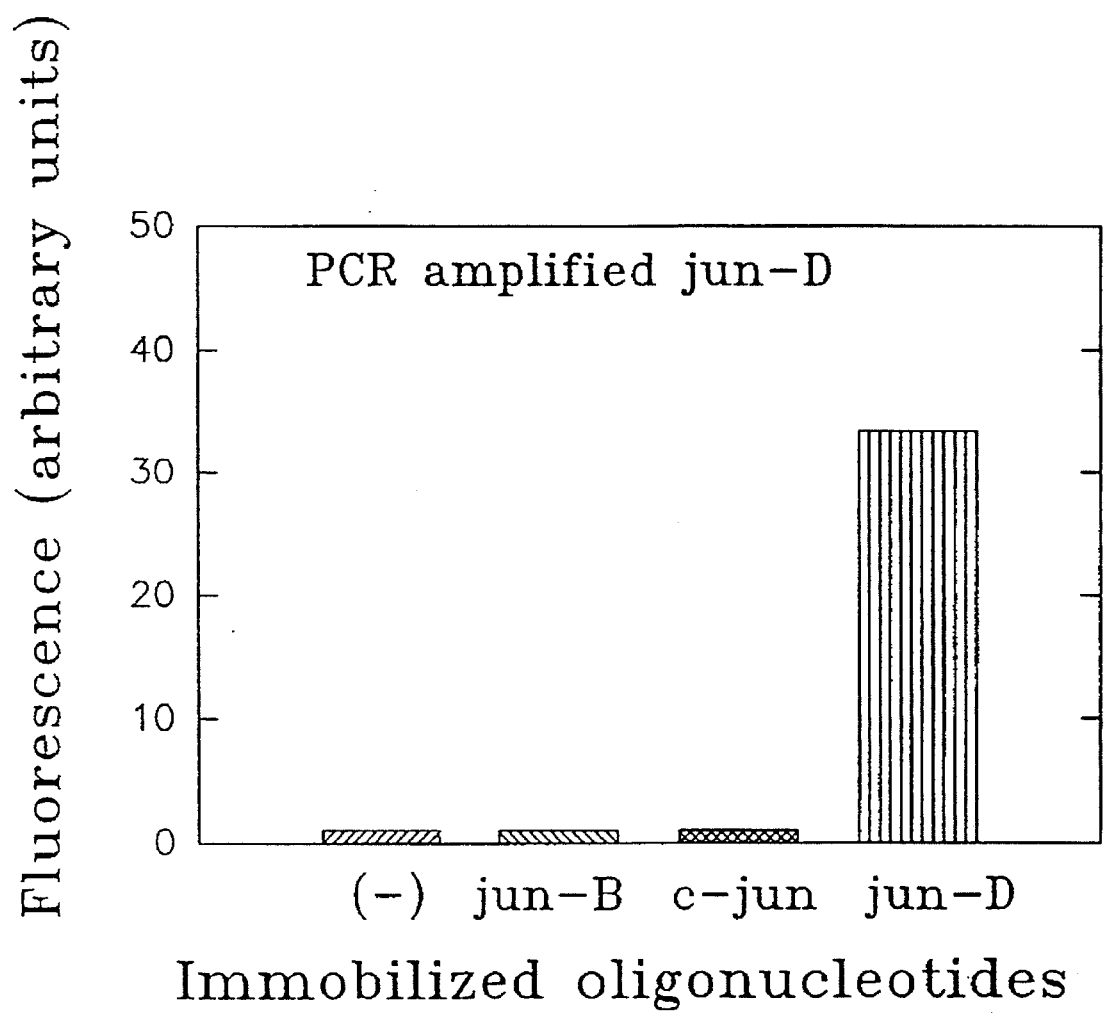
Figure 9:
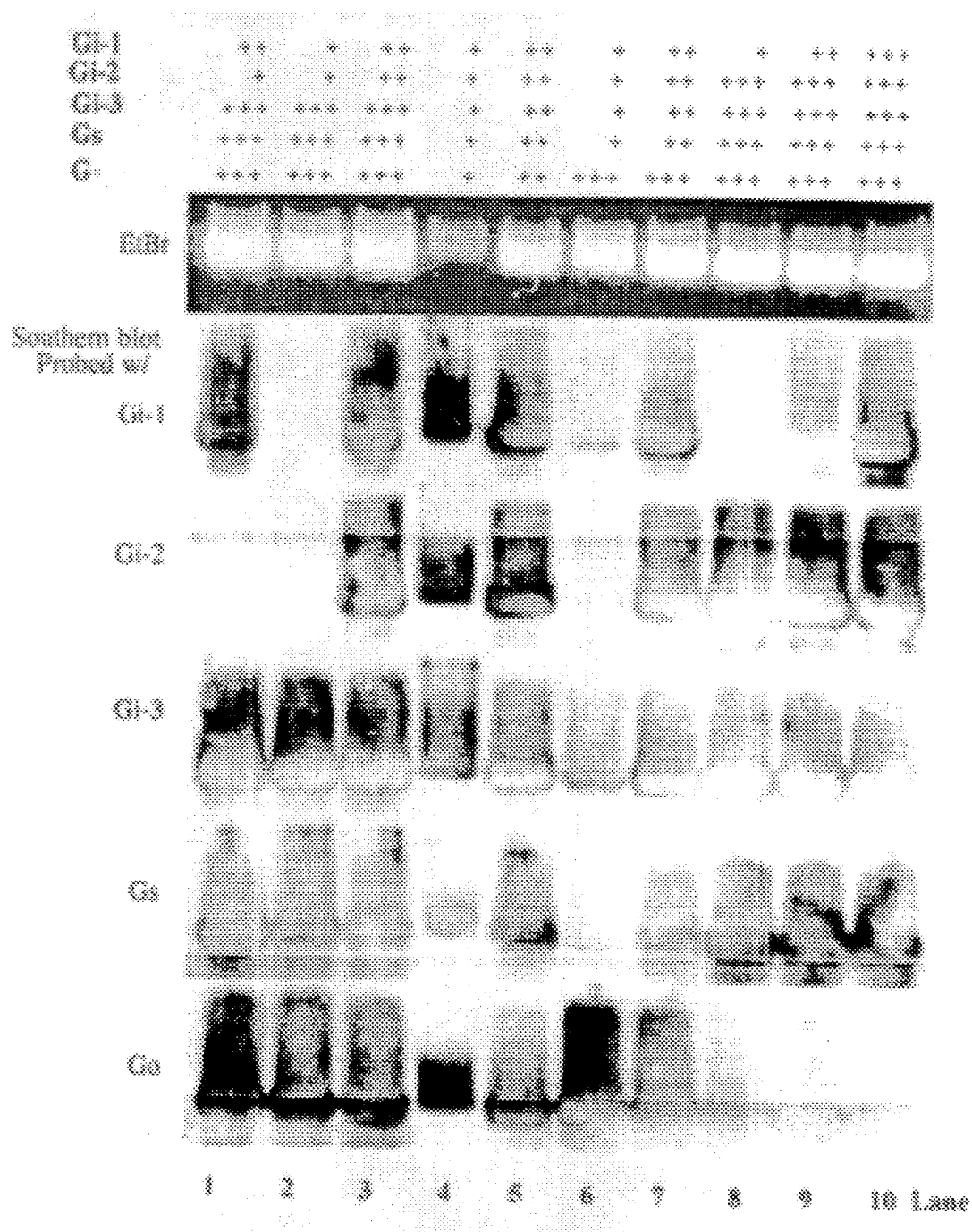
FIG. 9 shows a gel of AZAP cDNA libraries from rate pituitary (P), kidney (K) and intestinal (I) amplified with each of five different G protein primers, as indicated.
Figure 9:
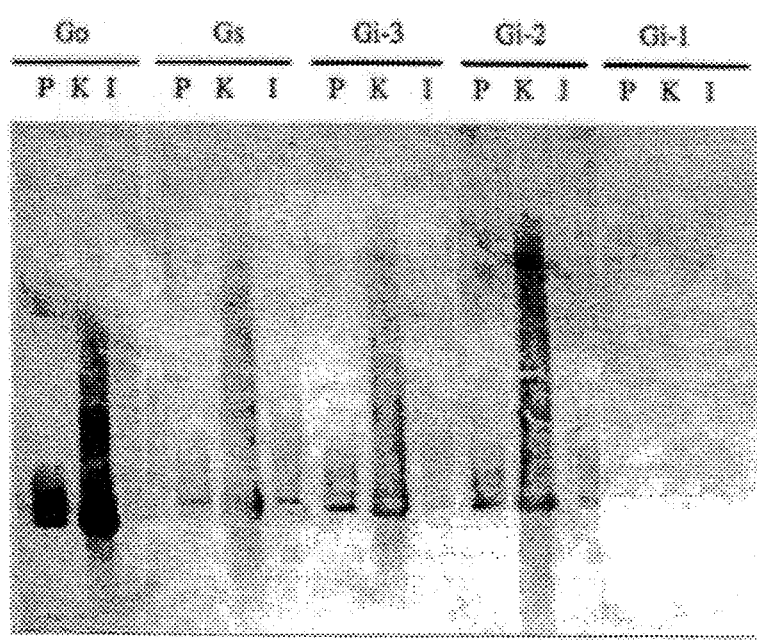
Figure 10:
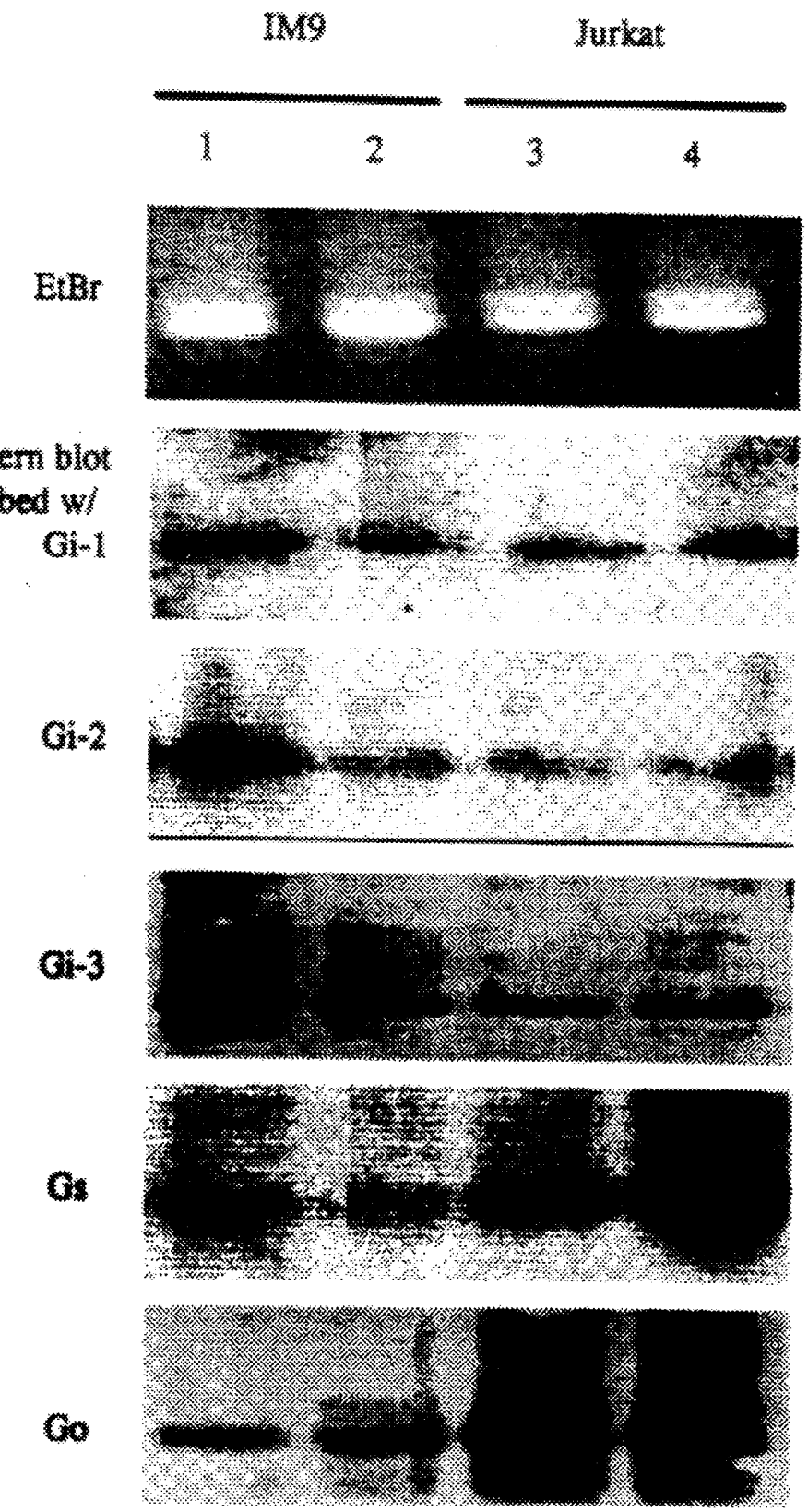
FIG. 10 shows a gel of 500 bp DNA from cDNAs of human IM9 and Jurkat cells amplified with $G_2$ and $G_4$ PCR primers.

Using this PCR method, Gα protein genes were amplified not only from cloned cDNAs, but also from various rat cDNAs (FIG. 7). In λZAP cDNA libraries from rat pituitary glands and cDNA from rat kidney KNRK cells, $G_0$ was more abundant than $G_s$, $G_{i-2}$ and $G_{i-3}$, and $G_{i-1}$ was undetectable (FIG. 7, lane 1, 2). λZAP cDNA library of rat intestine contained more $G_{i-2}$, $G_{i-3}$, and $G_s$ and $G_0$ (FIG. 7, lane 3).

TABLE 3

Two consensus oligonucleotides (G2 and G4) among five different cDNAs of G protein α subunits.

Consensus sequence (# of mismatch)

| | G2<br>AGCACCATTGTGAAGCAGATGA | | Length (bp) | G4<br>TGTTTGATGTGGGAGGCCAGAG | |
|---|---|---|---|---|---|
| Gi-1 | AGCACaATTGTGAAGCAGATGA | (1) | 476 | TGTTTGACGTGGGAGGCCAGAG | (1) |
| Gi-2 | AGCACCATcGTcAAGCAGATGA | (2) | 479 | TGTTTGATGTGGGtGGtCAGcG | (3) |
| Gi-3 | AGtACtATTGTGAAaCAGATGA | (3) | 476 | TGTTTGATGTaGGtGGCCAaAG | (3) |
| Gs | AGCACCATTGTGAAGCAGATGA | (0) | 524 | TGTTcGATGTGGGcGGCCAGcG | (3) |
| Go | AGCACCATTGTGAAGCAGATGA | (0) | 479 | TGTTTGAcGTtGGgGGCCAGcG | (4) |

According to the sequence analyses, the PCR products of rat $G_{i-1}$, $G_s$ and $G_0$ sequence amplification exhibited a high degree of homology to human G protein cDNAs, see Table 4 below). Furthermore, as shown in FIG. 8, PCR with a pair of $G_2$ and $G_4$ primers could amplify 500 bp DNA from cDNAs of human IM9 and Jurkat cells. Unlike rat cDNAs (FIG. 7), both IM9 and Jurkat cells contained all the subclasses of Gα proteins (FIG. 8). However, $G_{i-3}$ is relatively more abundant in IM9 cells, while $G_s$ and $G_0$ were more in Jurkat cells than IM9 cells (FIG. 8).

TABLE 4

Nucleotide sequence similarity of PCR products between rat and human G proteins.

| | Length (bp) | | No. of | |
|---|---|---|---|---|
| | Rat | Human | mismatch | % Similarity |
| Gi-1 | 476 | 476 | 62 | 87.0% |
| Gi-2 | 479 | 479 | 44 | 90.8% |
| Gi-3 | 476 | 476 | 40 | 91.6% |
| Gs | 524 | 482 | 52 | 89.2% |
| Go | 479 | 479 | 39 | 91.9% |

Example 10 describes a method of amplifying and detecting G proteins with another set of PCR primers of the present invention, G2-S and G4-AS.

EXAMPLE 10

Amplifying G Proteins With PCR Primers
Materials

The cDNAs of rat G protein α subunits ($G_{i-1}$, $G_{i-2}$, $G_{i-3}$, $G_s$ and $G_0$) were provided by Dr. R. R. Reed (Johns Hopkins Univ., Md.). λZAP libraries of rat pituitary and intestine were provided by Dr. D. G. Payan (Univ. Calif. San Francisco). Kirsten murine sarcoma virus transformed rat kidney cells (KNRK), human IM9 B-lymphocytes and human Jurkat T-lymphocytes were obtained from American Type Tissue Culture Collection, Rockville, Md.). Cell culture media, Superscript (Gibco/BRL, Gaithersburg, Md.), reagents for PCR (Promega, Madison, Wis.), ECL (Amersham, Arlington Height, Ill.), Genius, Lumi-Phos 530 (Boehringer-Mannheim, Indianapolis, Ind.), FastTrack (Invitrogen San Diego, Calif.), λgt10 library of human HL-60 cells, biotin-dUTP, alkaline phosphatase-conjugated streptavidine (Clontech, Palo Alto, Calif.), dNTP (Pharmacia, Piscataway, N.J.) were obtained from the designated suppliers. Other chemicals were purchased from Sigma (St. Louis, Mo.).

Cell culture. KRNK cells were grown in Dulbecco's modified Eagles medium containing 10% fetal calf serum, 100 U/ml penicillin and 100 μg/ml streptomycin at 37° C. in 5% $CO_2$/95% air. Cells were fed every other day and passaged at 70–90% confluency with 0.1% trypsin in $CA^{2+}$—$Mg^{2+}$-free saline containing 0.02% EDTA. IM9 and Jurkat cells was grown in RPMI 1640 containing 10% fetal calf serum, 100 U/ml penicillin and 100 μg/ml streptomycin at 37° C. in 5% $CO_2$/95%. Cell viability was more than 90% as assessed by the exclusion of trypan blue.

Primer design. Rat clones of Gα proteins ($G_{i-1}$ (RATBPGTPB), $G_{i-2}$ (RATBPGTPA), $G_{i-3}$ (RATBPGTP), $G_s$ (RATBPGTPD), and $G_O$ (RATBPGTPC) were retrieved from GenBank release 65.0 (HIBIIO, Hitachi America, Brisbane, Calif.). The nucleotide sequence similarity among these clones were then analyzed by the multiple alignment program (DNASIS, Hitachi). We have initially identified 7 highly conserved areas among them. These conserved nucleotide sequences were then analyzed against all mammalian sequences in GenBank in order to identify other similar sequences. The designed oligonucleotides G2-S (SEQ ID NO:528) and G4-AS (SEQ ID NO:731) were synthesized by Genosys Biotechnologies (Woodlands, Tex.), and suspended in water at 100 pg/ml.

PCR. One μl of the template DNA was mixed with 1 mM each of dATP, dGTP, dCTP and dTTP, 1 μl of each PCR primers, 1 μl of 25 mM $MgCl_2$, 5 μl PCR buffer, and 0.5 μl of Taq polymerase (18). PCR was then carried out in a DNA thermal cycler (model 480, Perkin-Elmer Cetus, Norwalk, Conn.) with 30 cycles of annealing temperature at ranging from 37° C. to 65° C. for 1.5 min, 72° C. extension for 4 min followed by 95° C. denaturization for 1.5 min. In separate experiments, 35% of dTTP was replaced with biotin-dUTP in order to prepare biotin-labeled probes.

Southern blot. PCR products were separated by electrophoresis in 1.2% agarose, and stained with ethidium bromide (19). Gels were then depurinated in 0.25N HCl for 30 minutes and denatured in 0.5N NaOH containing 1.5M NaCl for 30 minutes. The gels were then neutralized with 1.0M Tris, pH 7.6 containing 1.5M NaCl for 30 minutes. Gels were then placed onto nylon membranes (MagnaGraph, MSI, Westboro, Mass.) prewetted in 10× SSPE for 10 min, and DNA was transferred onto membranes by positive pressure at 75 mmHg for 60 minutes (Posiblot, Stratagene, La Jolla, Calif.). The DNA from the gel was then cross-linked to the membranes with ultraviolet light at 120 mjoules (Stratalinker, Stratagene), and the membranes were incubated with hybridization buffer (ECL) containing 5% blocking reagent (ECL) and 0.5M NaCl at 40° C. for more than 1 hour. Heat denatured biotin-labeled PCR probes were then added, and hybridization was continued overnight. The membranes were washed four times for 15 minutes each time with primary wash buffer (0.5×SSPE, 36 w/v% urea, 0.4 w/v% SDS) at 45°–65° C., then washed twice for 5 minutes with secondary wash buffer (2× SSPE) at room temperature, and were incubated with the blocking buffer (Genius) for at least 3 hours at room temperature. Alkaline phosphatase-conjugated streptavidine (1:5,000 dilution) was then added, and incubation was continued for an additional 30–60 minutes at room temperature. The membranes were washed four times for 15 minutes with buffer A (100 mM Tris, pH 7.5, 150 mM NaCl) at room temperature, were washed for 2 minutes once with buffer C (100 mM Tris, pH 9.5, 100 mM NaCl, 50 mM $MgCl_2$), and soaked in Lumi-Phos 530 for approximately 1–2 minutes. The membranes were then wrapped with transparency films, and chemiluminescent signals were allowed to expose X-ray films (XAR-5, Kodak, Rochester, N.Y.) for between 10 minutes and 1 hour.

mRNA preparation and cDNA synthesis. The cells were washed with phosphate buffered saline three times, homogenized in lysis buffer (FastTrack), and then incubated at 45° C. for 1 hour to eliminate any RNase activity. NaCl concentrations were adjusted at 0.5M, and an oligo (dT) cellulose tablet was added to lysis buffer. Incubation was then continued at room temperature for an additional 40 minutes. After oligo (dT) cellulose was washed with binding buffer (FastTrack) four times, bound mRNA was eluted with DEPC-treated water. Concentrations of mRNA were determined in a spectrophotometer (Hitachi, U-2000, Irvine, Calif.) at $OD_{260}$. The first strand cDNA was synthesized from a template mRNA in the presence of 50 mM Tris, pH 8.3, 75 mM KCl, 3 mM $MgCl_2$, 10 mM DTT, 0.5 mM each of dATP, dCTP, dGTP, and dTTP, poly (dT) as a primer, and reverse transcriptase (Superscript) at 37° C. for 1 hour. Second strand cDNA was then synthesized in the same tube, containing 25 mM Tris, pH 7.5, 100 mM KCl, 5 mM $MgCl_2$, 10 mM $(NH_4)_2SO_4$, 0.15 mM β-$NAD^+$, 250 μM each of dATP, dGTP, dCTP and dTTP, 1.2 mM DTT, 65 U/ml DNA ligase, 250 U/ml DNA polymerase, and 13 U/ml RNase H (Superscript) for 2 hours at 16° C. Synthesized cDNAs were then extracted once with an equal volume of phenol:chloroform:isoamyl alcohol (25:24:1), precipitated with ethanol, and resuspended in $H_2O$.

Graphic presentation. Data on Polaroid films and X-ray films was scanned by Stratascan (Stratagene) with optimization of signal-to-noise ratio, then edited with desk top publishing software (PageMaker, Aldus, Seattle, Wash.). As shown in FIG. 3b, the combination of SEQ ID NO:528 and SEQ ID NO:731 can amplify all of the subtypes of G protein α subunits.

It will be evident to one having ordinary skill in the art that a variety of sequences could serve as sense or antisense primers for PCR methods or as probes for the detection of DNA or RNA as described herein. A method for identification of such sequences that are either common to a variety of G proteins or specific to a particular species is provided hereinbelow. In the preferred embodiment of this method of identification, a computer program is used to identify the sequences. Through use of such a program, we have identified a large number of both common and specific primers and probes. Provided as Tables XXIII through XXIX and XXXIII through XXXVII are various sense sequences identified through the use of such a program that are useful as G protein probes and primers.

All of the sequences listed in these tables are useful within the context of the PCR methods of the present invention. The complementary antisense sequences are also useful in certain aspects of the invention. As will be known having ordinary skill in the art, for common probes that are similar, but not identical to target sequences, stringency conditions can be varied (e.g. by changes in temperature and salinity) so that such probes will hybridize or fail to hybridize with a particular target sequence. Thus, also included within the present invention are sequences that are capable of hybridizing with the same sequences as either the sense sequences listed or their anti-sense counterparts. Additional probes for G protein also include the following:

| Common G protein probes | |
| --- | --- |
| 5'-CTCTGGCCTCCCACATCAAACA-3' | SEQ ID NO:749 |
| 5'-TCATCTGCTTCACAATGGTGCT-3' | SEQ ID NO:750 |
| Specific probes (Human & Rat common) | |
| Gi-1   5'-GTTTTCACTCTAGTTCTGAGAACATC-3' | SEQ ID NO:751 |
| Gi-2   5'-CAAAGTCGATCTGCAGGTTGC-3' | SEQ ID NO:752 |
|        5'-ATGGTCAGCCCAGAGCCTCCGG-3' | SEQ ID NO:753 |
| Gi-3   5'-GTCTTCACTCTCGTCCGAAGA-3' | SEQ ID NO:754 |
| Gs     5'-GCCTTGGCATGCTCATAGAATT-3' | SEQ ID NO:755 |
|        5'-TTCATCCTCCCACAGAGCCTTG-3' | SEQ ID NO:756 |
| Go     5'-CGCATCATGGCAGAAAGCAG-3' | SEQ ID NO:757 |

C. Primers for Detecting Other Biological Components

Another example of a primer or probe for detecting a biological component is a sequence specific for the mRNA of substance P. Substance P is a neurotransmitter expressed by nerves that are involved in pain receptor pathways. We have discovered that the sequence 5'-TGGTACGCTTTCTCATAAGTCC-3' (SEQ ID NO:758) is very specific for Substance P.

Another biological component which can be probed for is the mRNA for the β receptor. The β receptor is a protein located in human nerve tissue. In particular, abnormalities in the $\beta_2$ receptor has been found to be closely correlated with asthma. Thus, measuring the mRNA for $\beta_2$ receptor can be used to determine the pathophysiology of asthma patients, and could also be used to assess the effectiveness of anti-asthma agents. We have found that the sequence 5'-ATGCTGGCCGTGACGCACAGCA-3' (SEQ ID NO:759) is common to a number of human subtypes of β receptor, including β1 (only one mismatch), β2 (no mismatches), and β3 (2 mismatches). Thus, SEQ ID NO:759 can be used to probe for all three of these subtypes of β receptor.

XVI. Identifying PCR Primers and Probes

PCR primers and probes for use in the methods of the present invention can be identified in any way known to the art. Preferably, however, such probes and primers are identified by a computer. We have developed a novel computer system for identifying the sequences to be used in such probes and primers. This system is an automated system which allows the user to calculate and design extremely accurate oligonucleotide probes and PCR primers.

The software of the present invention runs under Microsoft Windows® on IBM® compatible personal computers (PC's). This invention allows a researcher to design oligonucleotide probes based on the GenBank database of DNA and mRNA sequences. The present invention further allows examination of probes for specificity or commonality with respect to a user-selected target gene sequences. Hybridization strength between a probe and a target subsequence of DNA or mRNA can be estimated through a hybridization strength model. Quantitatively, hybridization strength is given as the melting temperature (Tm).

Two models for estimating hybridization strength models are supported by this invention: 1) the Mismatch Model and 2) the H-Site Model. In either case, the user can select the following calculations for each probe, results of which are then made available for display and analysis: 1) Sequence, Melting Temperature (Tm) and Hairpin characteristics (a hairpin is a nucleotide sequence that is homologous to itself and can "fold back" with one portion of the probe hybridizing to another portion of the same probe); 2) Hybridization to other species within the preparation mixture; and (3) Location and Tm for the strongest hybridizations. The results of the invention's calculations are then displayed on a Mitsuhashi Probe Selection Diagram (MPSD) which is a graphic display of all potential hybridizations between the target mRNA and the probe sequences in the preparation.

The Main OligoProbe Design Station dialog window controls all user-definable settings in the program. The user is offered a number of options at this window. The File option allows the user to print, print in color, save selected probes, and exit the program. The Preparation option allows the user to open and create preparation (PRP) files. The Models option allows the user to chose between the two hybridization models currently supported by the OligoProbe DesignStation: 1) the H-Site Model and 2) the Mismatch Model.

If the user selects the H-Site Model option, the melting temperature for each probe and the nucleation threshold parameters can be set. The nucleation threshold is the number of base pairs constituting a nucleation site (a subsequence with an exact match). If the user selects the Mismatch Model option, the probe length and mismatches (N) can be set.

Mismatch Model

The Mismatch Model is used for designing DNA and mRNA probes utilizing sequence database information from sources such as GenBank. In this Model, hybridization strength is related only to the number of base pair mismatches between a probe and its target. Generally, the more mismatches a user allows when setting parameters, the more probes will be identified. The Mismatch Model does not take into account the GC content of candidate probes so there is no calculation of the probe's binding strength.

The basic technologies employed by the Mismatch model are hashing and continuous seed filtration. Hashing involves the application of an algorithm to the records in a set of data to obtain a symmetric grouping of the records. When using an indexed set of data such as a database, hashing is the process of transforming a record key to an index value for storing and retrieving a record. The Mismatch Model is essentially a quick process for determining exact and inexact matching between DNA and mRNA sequences to support the Mitsuhashi Probe Selection Diagram (MPSD).

The algorithm used by the Mismatch Model is based on the Waterman-Pevzner Algorithm (WPALG), which is a computer-based probe selection process. Essentially, this is a combination of new and improved pattern matching processes. See Hume and Sunday (1991, Ref. 4), Landau et al (1986–1990, Refs. 6, 7, 8), Grossi and Luccio (1989, Ref. 3), and Ukkonen (1982, Ref. 14).

There are three principal programs that make up the Mismatch Model in this implementation of the invention. The first is designated by the inventors as "k_diff." WPALG uses k_diff to find all locations of matches of length greater than or equal to one (1) (length is user-specified) with less than or equal to k number of mismatches (k is also user-specified) between the two sequences. If a candidate oligonucleotide probe fails to match that well, it is considered unique. k_diff uses hashing and continuous seed filtration, and looks for homologs by searching GenBank and other databases with similar file formats. The technique of continuous seed filtration allows for much more efficient searching than previously implemented techniques.

A seed is defined in this invention to be a subsequence having a length equal to the longest exact match in the worst case scenario. For example, suppose the user selects a probe length (1) of 18, with 2 or fewer mismatches (k). If a match exists with 2 mismatches, then there must be a perfectly matching subsequence of length equal to 6. Once the seed length has been determined, the Mismatch Model looks at all substrings of that seed length (in this example, the seed length would be 6), finds the perfectly matched base pair subsequence of length equals 6, and then looks to see if this subsequence extends to a sequence of length equal to the user selected probe length (i.e., 18 in this example). If so, a candidate probe has been found that meets the user's criteria.

Where the seed size is large (i.e., a long string of unique nucleotides), the program allocates a relatively large amount of memory for the hash table. This invention has an option that allows memory allocation for GenBank entries just once at the beginning of the program, instead of reallocating memory for each GenBank entry. This reduces input time for GenBank entries by as much as a factor of two (2), but this method requires the user to know the maximum GenBank entry size in advance.

A probe is found to hybridize if it has k or fewer mismatches with a target sequence from the database or file searched. The hit extension time for all appropriate parameters of the Mismatch Model has been found by experimentation to be less than thirty-five (35) seconds, except in one case where the minimum probe length (1) was set to 24 and the maximum number of mismatches (k) was set to four (4). This situation would rarely be used in real gene localization experiments because the hybridization conditions are too weak.

H-Site Model

In this embodiment of the invention, the second hybridization strength model is termed the H-Site Model. One aspect of the H-Site Model uses a generalization of an experimental formula to analize nucleotide binding strength. The basic formula on which this aspect of the model is built is as follows:

$$Tm = 81.5 - 16.6(\log[Na]) - 0.63\%(\text{formamide}) + 0.41\ (\%(G+C)) - 600/N$$

In this formula, log[Na] is the log of the sodium concentration, %(G+C) is the fraction of matched base pairs which are G–C complementary, and N is the probe length. This formula relates the fact that melting temperature is a function of both probe length and percent GC content. This basic formula has been modified in this invention to account for the presence of mismatches. Each percent of mismatch reduces the melting temperature by an average of 1.25° (2° C. for an AT mismatch, and 4° C. for a GC mismatch). This formula is, however, an approximation. The actual melting temperature might potentially differ from this approximation, especially for short probes or probes with a relatively large number of mismatches.

Hybridization strength in the H-Site Model is related to each of the following factors: 1) "binding region"; 2) type of mismatch (GC or AT substitution); 3) length of the probe; 4) GC content of the binding region; and 5) existence of a "nucleation site" (a subsequence with an exact match). The type of mismatch and GC content of the binding region from each sequence contributes to a candidate probe's binding strength. The binding strength from each probe is thereby determined enabling the user to select an optimal probe.

The fundamental assumption of the H-Site Model is that binding strength is mostly determined by a paired subsequence of the probe and target, called the binding region. If the subsequence binding region contains more GC pairs than AT pairs, the binding strength will be higher due to the greater number of hydrogen bonds between G and C bases (three bonds) in comparison to A and T bases (two bonds). Thus, GC rich probes have a higher melting temperature and subsequently form stronger hybridizations.

In the H-Site Model the program determines optimal probes, ideally without any mismatches to the target gene. With this model, however, a candidate probe can have more AT mismatches if the sequence is GC rich. The amount of allowable AT mismatches in a specific sequence is determined in the present invention program by looking primarily at subsequence regions of the probe and target that match without penalizing the probe for areas that mismatch. If the mismatches are located at either or both of the ends of the binding region, there is little effect on the overall stability of the base-pairing. Centrally located mismatches in the binding region are much more deleterious, as this will significantly lower the binding strength of the probe.

The formula cited above for the melting temperature applies within the binding region. The length of the probe is used to calculate percentages, but all other parameters of the formula are applied to the binding region only. The H-Site Model further assumes the existence of a nucleation site. The length of this nucleation site may be set by the user. Typically, a value of 8 to 10 base pairs is used. To complete the H-Site Model, the binding region is chosen so as to maximize the melting temperature Tm among all regions containing a nucleation site, assuming one exists (otherwise, Tm=0).

The H-Site Model is more complex than the Mismatch Model discussed above in that hybridization strength is modeled as a sum of multiple subsequence contributions, with matches generally providing positive binding energy and mismatches generally providing negative binding energy. The exact binding energies to be used depend only on the matched or mismatched pair. These coefficients may be specified by the user, although in the current version of this invention these coefficients are not explicitly user-selectable, but rather are selected to best fit the hybridization strength formulas developed by Itakura et al (1984, Ref. 5), Bolton and McCarthy (1962, Ref. 2), Benner et al (1973, Ref. 1), and Southern (1975, Ref. 13).

A unique aspect of the H-Site Model is that hybridization strength is determined by the optimal binding region between the candidate probe and binding locus. This binding region is called the hybridization site, or h-site, and is selected so as to maximize overall hybridization strength, so that mismatches outside the binding region do not detract from the estimated hybridization strength. Several other unique features of the H-Site Model include the fact that it is more oriented toward RNA and especially cDNA sequences than DNA sequences, and the fact that the user has control over preparation and environmental variables.

The emphasis on RNA and cDNA sequences allows the user to concentrate on coding regions of genes, rather than necessitating sorting through all of a genomic sequence for the desired probe. The enhanced user control over environmental and preparation variables allows the user to more accurately simulate laboratory conditions that closely correspond with any experiments he or she is conducting. Further, this implementation of the invention does some preliminary preprocessing of the GenBank database to sort out and select the cDNA sequences. This is done by locating a keyword (in this case CDS) in each GenBank record, thereby eliminating any sequences containing introns.

Figure 14:
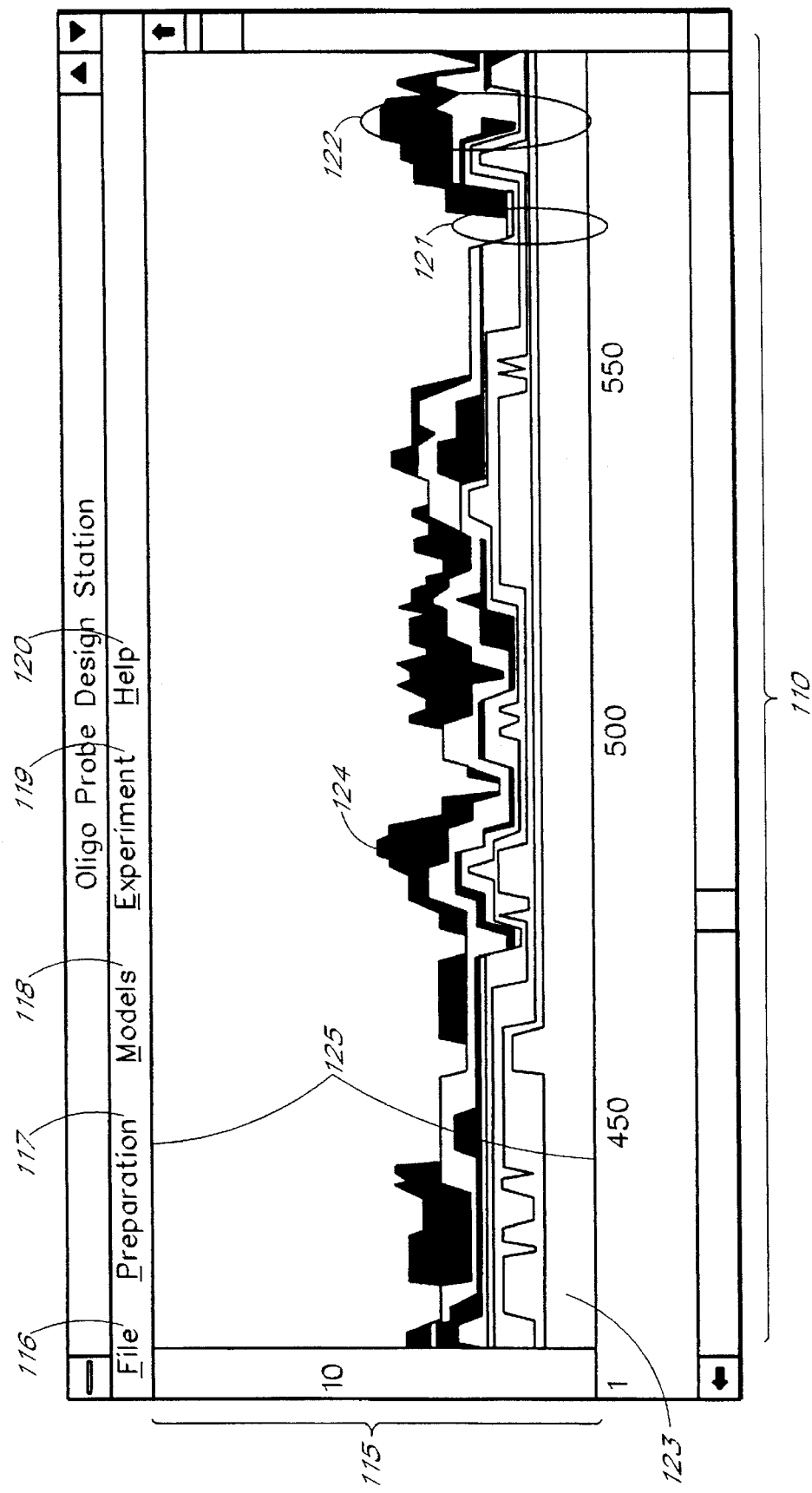
FIG. 14 is a display screen representation of the Mitsuhashi probe selection diagram.

The Mitsuhashi Probe Selection Diagram (MPSD), FIG. 14, is a key feature of this invention, as it is a unique way of visualizing the results of the probe designed by the Mismatch and H-Site Models. It is a graphic display of all of the hybridizations of candidate oligonucleotide probes and the target with all sequences in the preparation. Given a gene sequence database and a target mRNA sequence, the MPSD graphically displays all of the candidate probes and their hybridization strengths with all sequences from the database. In the present implementation, each melting temperature is displayed as a different color, from red (highest Tm) to blue (lowest Tm). The MPSD allows the user to see visually the number of false hybridizations at various temperatures for all candidate probes, and the sources of these false hybridizations (with a loci and sequence comparison). A locus may be a specific site or place, or, in the genetic sense, a locus is any of the homologous parts of a pair of chromosomes that may be occupied by allelic genes.

These probes may then be used to test for the presence of precursors of specific proteins in living tissues. The oligonucleotide probes designed with this invention may be used for medical diagnostic kits, DNA identification, and potentially continuous monitoring of metabolic processes in human beings. The present implementation of this computerized design tool runs under Microsoft® Windows™ v. 3.1 (made by Microsoft Corporation; Redmond, Wash.) on IBM® compatible personal computers (PC's).

The H-Site Model of this invention is unique in that it offers a multitude of information on selected probes and original and distinctive means of visualizing, analyzing and selecting among candidate probes designed with the invention. Candidate probes are analyzed using the H-Site Model for their binding specificity relative to some known set of mRNA or DNA sequences, collected in a database such as the GenBank database. The first step involves selection of candidate probes at some or all the positions along a given target. Next, a melting temperature model is selected, and an accounting is made of how many false hybridizations each candidate probe will produce and what the melting temperature of each will be. Lastly, the results are presented to the researcher along with a unique set of tools for visualizing, analyzing and selecting among the candidate probes.

This invention is both much faster and much more accurate than the methods that are currently in use. It is unique because it is the only method that can find not only the most specific and unique sequence, but also the common sequences. Further, it allows the user to perform many types of analysis on the candidate probes, in addition to comparing those probes in various ways to the target sequences and to each other.

Therefore, it is the object of this invention to provide a practical and user-friendly system that allows a researcher to design both specific and common oligonucleotide probes, and to do this in less time and with much more accuracy than currently done.

Figure 11:
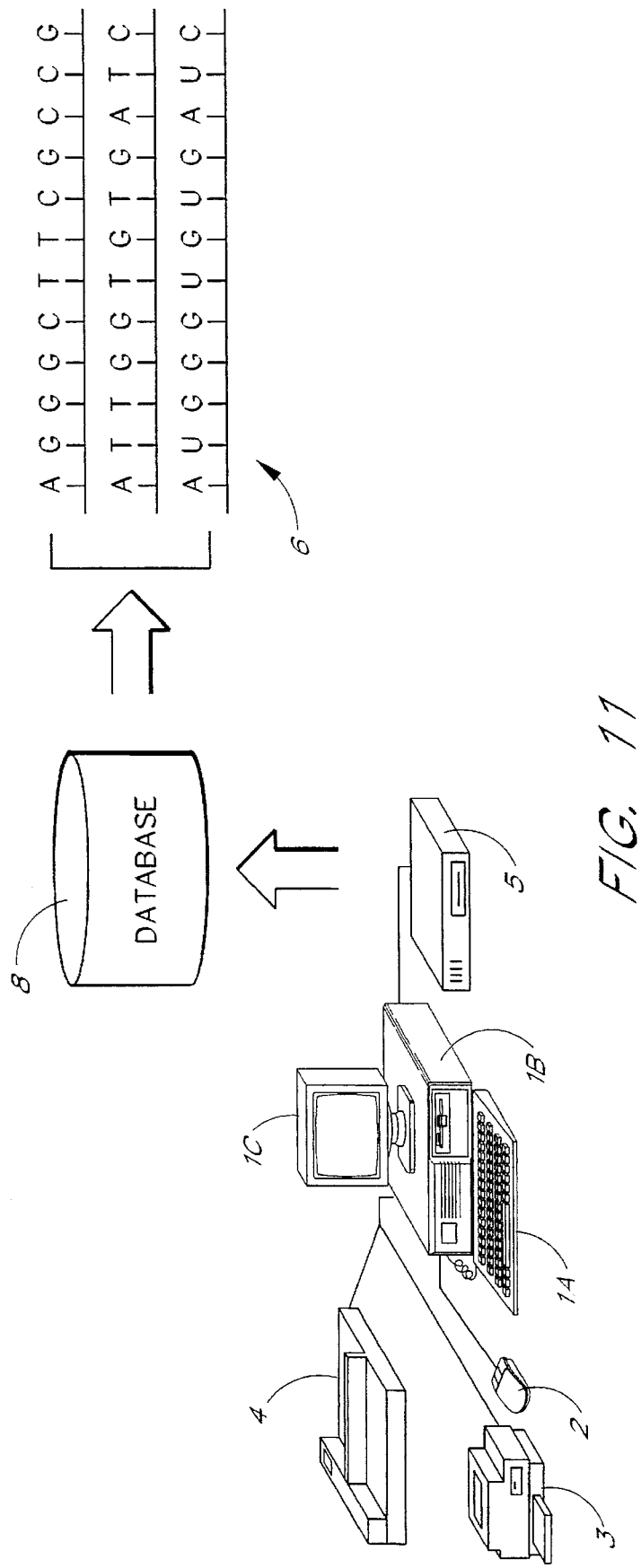
FIG. 11 is a simplified block diagram of a computer system illustrating the overall design of this invention.

This invention is employed in the form best seen in FIG. 11. There, the combination of this invention consists of an IBM® compatible personal computer (PC), running software specific to this invention, and having access to a distributed database with the file formats found in the GenBank database and other related databases.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

The preferred computer hardware capable of operating this invention involves of a system with at least the following specifications (FIG. 11): 1) an IBM® compatible PC, generally designated 1A, 1B, and 1C, with an 80486 coprocessor, running at 33 Mhz or faster; 2) 8 or more MB of RAM, 1A; 3) a hard disk 1B with at least 200 MB of storage space, but preferably 1 GB; 4) a VGA color monitor (1C) with graphics capabilities of a size sufficient to display the invention's output in readable format, preferably with a resolution of 1024×768; and 5) a 580 MB CD ROM drive 5 (1B of FIG. 11 generally refers to the internal storage systems included in this PC, clockwise from upper right, two floppy drives, and a hard disk). Because the software of this invention preferably has a Microsoft® Windows™ interface, the user will also need a mouse 2, or some other type of pointing device.

The preferred embodiment of this invention would also include a laser printer 3 and/or a color plotter 4. The invention may also require a modem (which can be internal or external) if the user does not have access to the CD ROM versions of the GenBank database 8 (containing a variable number of gene sequences 6). If a modem is used, information and instructions are transmitted via telephone lines to and from the GenBank database 8. If a CD ROM drive 5 is used, the GenBank database (or specific portions of it) is stored on a number of CDs.

The computer system should preferably have at least the Microsoft® DOS version 5.0 operating system running Microsoft® Windows™ version 3.1. All of the programs in the preferred embodiment of the invention were written in the Borland® C++ (Borland International, Inc.; Scotts Valley, Calif.) computer language. It should be noted that subsequently developed computers, storage systems, and languages may be adapted to utilize this invention and vice versa.

This inventive computer program is designed to enable the user to access DNA, mRNA and cDNA sequences stored either in the GenBank or in databases with similar file formats. GenBank is a distributed flat file database made up of records, each record containing a variable number of fields in ASCII file format. The stored database itself is distributed, and there is no one database management system (DBMS) common to even a majority of its users. One general format, called the line type format, is used both for the distributed database and for all of GenBank's internal record keeping. All data and system files and indexes for GenBank are kept in text files in this line type format.

The primary GenBank database is currently distributed in a multitude of files or divisions, each of which represents the genome of a particular species (or at least as much of it as is currently known and sequenced and publicly available). The GenBank provides a collection of nucleotide sequences as well as relevant bibliographic and biological annotation. Release 72.0 (6/92) of the GenBank CD distribution contains over 71,000 loci with a total of over ninety-two (92) million nucleotides. GenBank is distributed by IntelliGenetics, of Mountain View, Calif., in cooperation with the National Center for Biotechnology Information, National Library of Medecinge, in Bethesda, Md.

1. Overall Description of the OligoProbe DesignStation a. General Theory

The intent of this invention is to provide one or more fast processes for performing exact and inexact matching between DNA sequences to support the Mitsuhashi Probe Selection Diagram (MPSD) discussed below, and other analysis with interactive graphical analysis tools. Hybridization strength between a candidate oligonucleotide probe and a target subsequence of DNA, mRNA or cDNA can be estimated through a hybridization strength model. Quantitatively, hybridization strength is given as the melting temperature (Tm). Currently, two hybridization strength models are supported by the invention: 1) the Mismatch Model and 2) the H-Site Model.

b. Inputs i. Main OligoProbe DesignStation Dialog Window

Figure 12A:
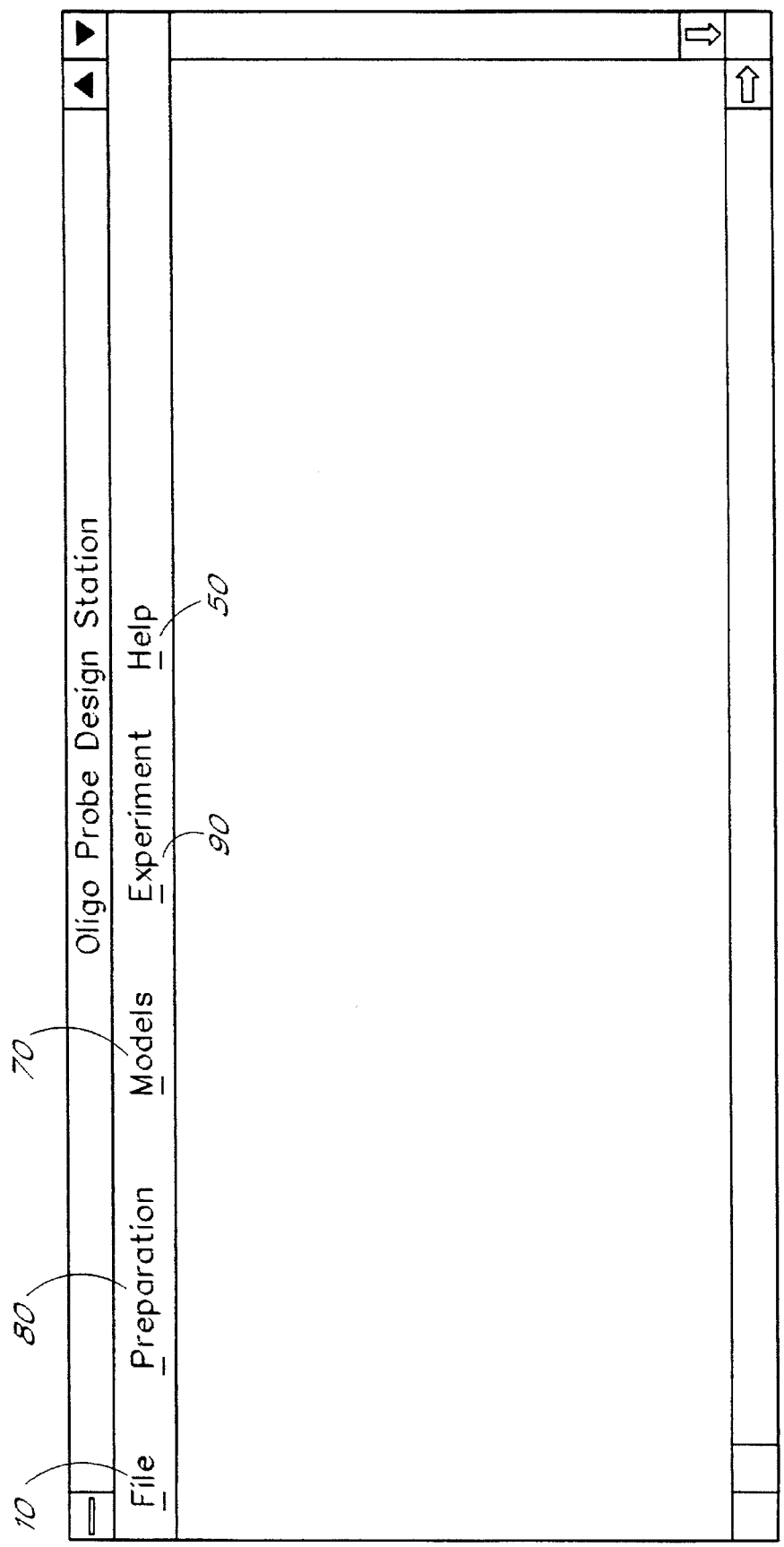
Figure 12B:
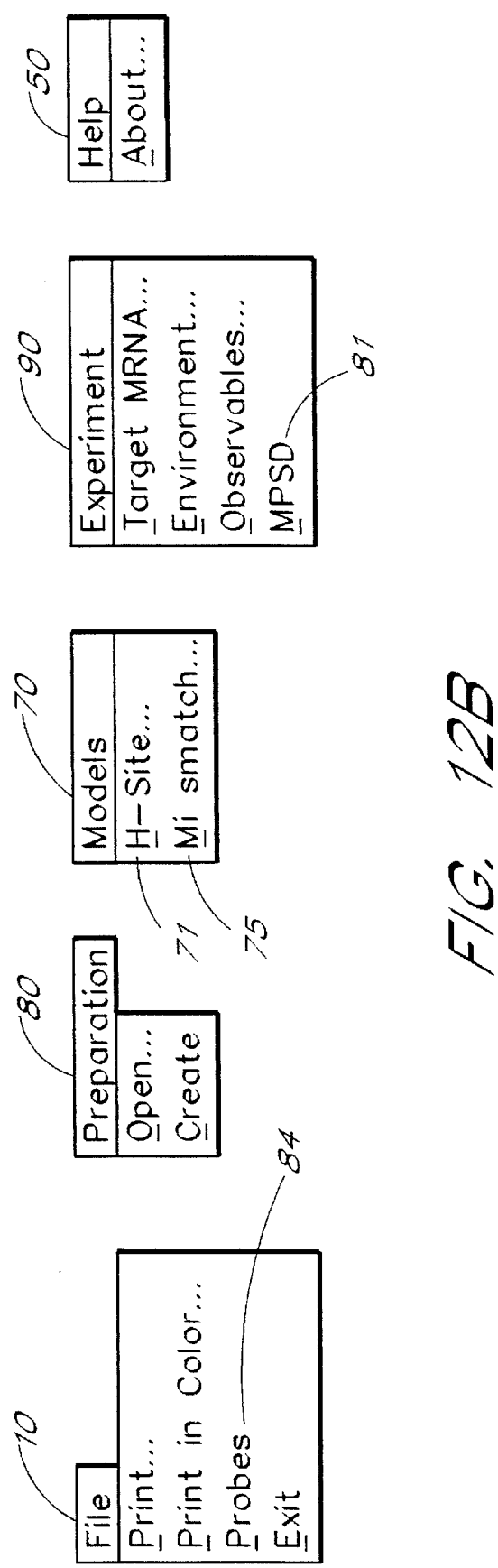

The Main OligoProbe DesignStation dialog window, FIG. 12, controls all user-definable settings. This window has a menu bar offering five options: 1) File 10; 2) Preparation 80; 3) Models 70; 4) Experiment 90; and 5) Help 50. The File 10 option allows the user to print, print in color, save selected probes, and exit the program. The Preparation 80 option allows the user to open and create preparation (PRP) files.

The Models 70 option allows the user to chose between the two hybridization models currently supported by the OligoProbe DesignStation: 1) the H-Site Model 71 and 2) the Mismatch Model 75. If the user selects the H-Site Model 71 option, the left hand menu of FIG. 12C is displayed and the user sets the following model parameters: 1) the melting temperature Tm 72 for which probes are being designed (i.e., the melting temperature that corresponds to a particular experiment or condition the user desires to simulate); and 2) the nucleation threshold 73, which is the number of base pairs constituting a nucleation site. If the user selects the Mismatch Model 75 option, the right hand menu of FIG. 12C is displayed and the user sets the following model parameters: 1) probe length 76, which is the number of base pairs in probes to be considered; and 2) mismatch N 77, which is the maximum number of mismatches constituting a hybridization. Computation of the user's request takes longer with the H-Site Model if the threshold 73 setting is decreased, but longer with the Mismatch Model if the number of mismatches K 77 is increased.

In addition, for both Model options the user chooses the target species 11 DNA or mRNA for which probes are being designed and the preparation 12, a file of all sequences with which hybridizations are to be calculated. A sample of a target species file is shown in FIG. 37 (humbjunx.cds), while a sample of a preparation file is shown in FIG. 38 (junmix.seq). Each of these inputs is represented by a file name and extension in standard DOS format. In the target species and preparation fields, the file format follows the GenBank format with each of the fields having a default file extension. Pressing the "OK" button 91 (FIG. 12C) will initiate processing, while pressing the "Cancel" button 93 will stop the processing.

The Experiment 90 option and the Help 50 option are expansion options not yet available in the current implementation of the invention.

c. Processing

Figure 13A:
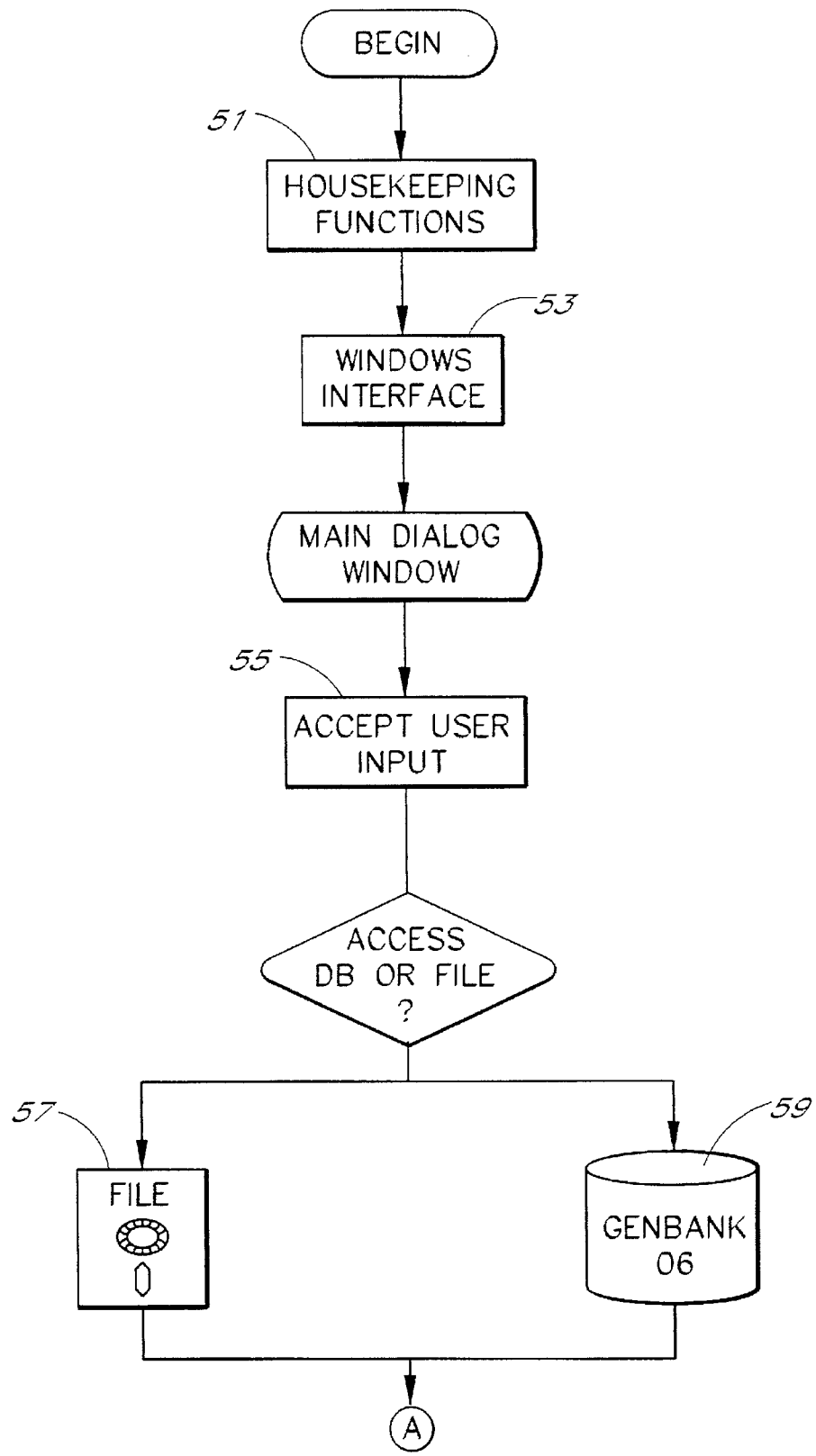
FIGS. 13A and 13B are flow charts of the overall invention illustrating the program and the invention's sequence and structure.
Figure 13B:
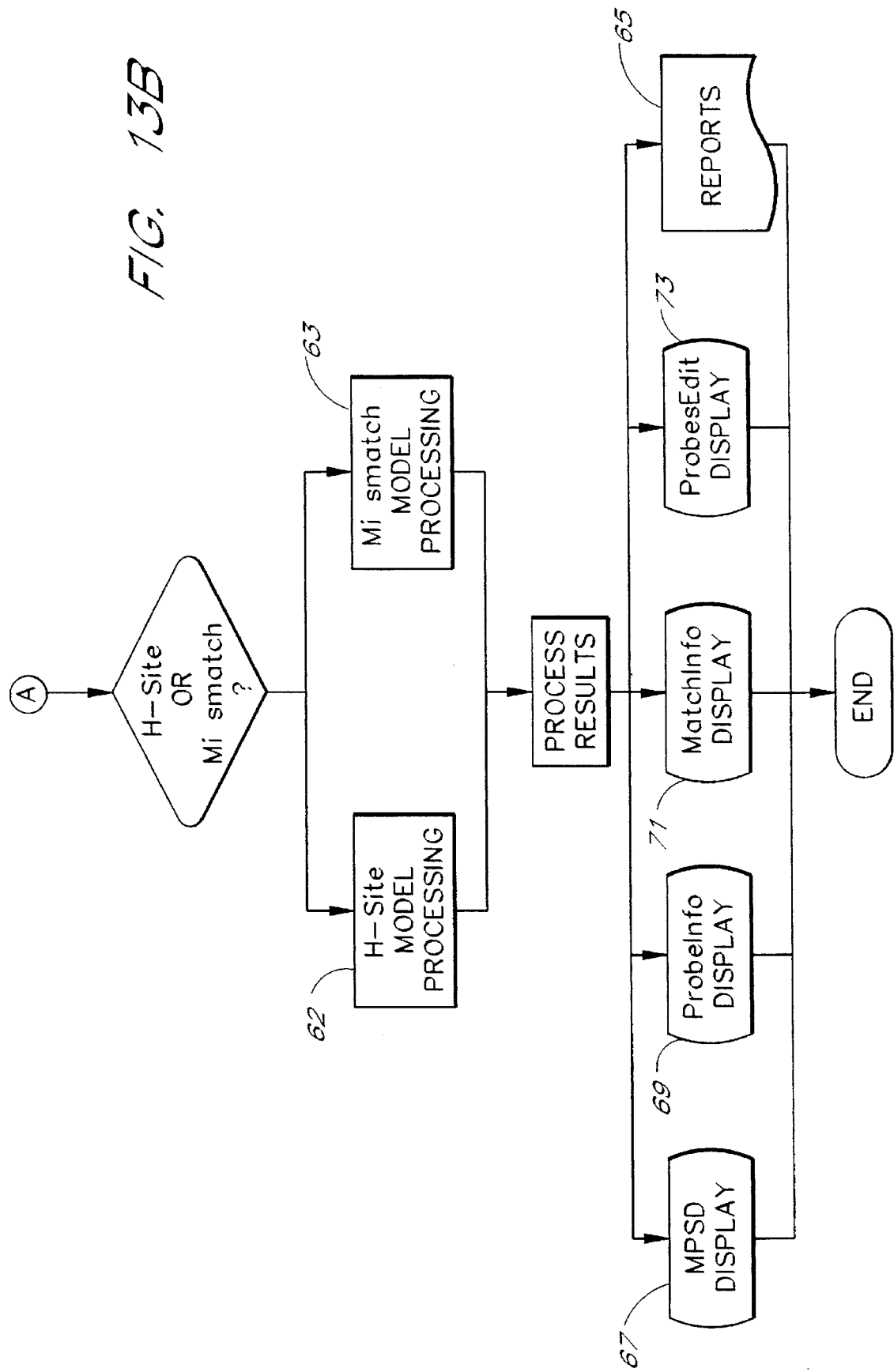

FIG. 13 is a flow chart of the overall OligoProbe DesignStation Program, illustrating its sequence and structure. Generally, the main or "control" program of the OligoProbe DesignStation performs overall maintenance and control functions. This program, as illustrated in FIG. 13, accomplishes the general housekeeping functions 51, such as defining global variables. The user-friendly interface 53, carries out the user-input procedures 55, the file 57 or database 59 access procedures, calling of the model program 62 or 63 selected by the user, and the user-selected report 65 or display 67, 69, 71 and 73 features. Each of these features is discussed in more detail in later sections, with the exception of the input procedures, which involves capturing the user's set-up and control inputs.

d. Outputs i. The Mitsuhashi Probe Selection Diagram Window

The Mitsuhashi Probe Selection Diagram (MPSD), FIG. 14, is a key feature of the invention as it is a unique way of visualizing the results of the program's calculations. It is a graphic display of all of the hybridizations of probes with the target oligonucleotides in the preparation. Specifically, given a nucleotide sequence database and a target mRNA, the MPSD graphically displays all of the candidate probes and their hybridization strengths with all sequences from the nucleotide database. The MPSD allows the user to visualize the number of false hybridizations at various temperatures for all candidate probes, and the sources of these false hybridizations (with a loci and sequence comparison).

For each melting temperature selected, a graph showing the number of hybridizations for each probe is displayed. In the preferred embodiment, the graphs are color coded. In this implementation of the invention, the color red 123 identifies the highest melting temperature and the color blue 124 identifies the lowest melting temperature. Each mismatch results in a reduction in the Tm value. The melting temperature is also a function of probe length and percent GC content. Within the window, the cursor 125 shape is changed from a vertical line bisecting the screen to a small rectangle when the user selects a particular probe. The current probe is defined to be that probe under the cursor position (whether it be a line or a rectangle) in the MPSD window. More detailed information about the current probe is given in the ProbeInfo and MatchInfo windows, discussed below. Clicking the mouse button 2 once at the cursor 125 selects the current probe. Clicking the mouse button 2 a second time deselects the current probe. Moving the cursor across the screen causes the display to change and reflect the candidate probe under the current cursor position.

The x-axis 110 of the MPSD, FIG. 14, shows the candidate probes' starting positions along the given mRNA sequence. The user may "slide" the display to the left or right in order to display other probe starting positions. The y-axis 115 of the MPSD displays the probe specificity, which is calculated by the program.

The menu options 116, 117, 118, 119, and 120 available to the user while in the MPSD, FIG. 14, and are displayed along a menu bar at the top of the screen. The user can click the mouse 2 on the preferred option to briefly display the option choices, or can click and hold the mouse button on the option to allow an option to be selected. The user may also type a combination of keystrokes in order to display an option in accordance with well-known computer desk top interface operations. This combination usually involves holding down the ALT key while pressing the key representing the first letter of the desired option (i.e, F, P, M, E or H).

The File option 116 allows the user to specify input files and databases. The Preparation option 117 allows the user to create a preparation file summarizing the sequence database. The Models option 118 allows the user to specify the hybridization model (i.e., H-Site or Mismatch) and its parameters. The Experiment option 119 and the Help option 120 are not available in the current implementation of this invention. These options are part of the original Main OligoProbe DesignStation dialog window, FIG. 12.

Areas on the graphical display of the MPSD, FIG. 14, where the hybridizations for the optimal probes are displayed are lowest and most similar, such as shown at 121, indicate that the particular sequence displayed is common to all sequences. Areas on the graphical display of the MPSD where the hybridizations for the optimal probes are displayed are highest and most dissimilar, such as shown at 122, indicate that the particular sequence displayed is extremely specific to that particular gene fragment. The high points on the MPSD show many loci in the database, to which the candidate probe will hybridize (i.e., many false hybridizations). The low points show few hybridizations, at least relative to the given database. Specifically, the sequence shown at 121 would reflect a probe common to all of the gene fragments tested, such that this probe could be used to detect each of these genes. The sequence shown at 122 would reflect a probe specific to the particular gene fragment, such that this probe could be used to detect this particular gene and no others.

ii. The ProbeInfo and MatchInfo Window

Figure 15:
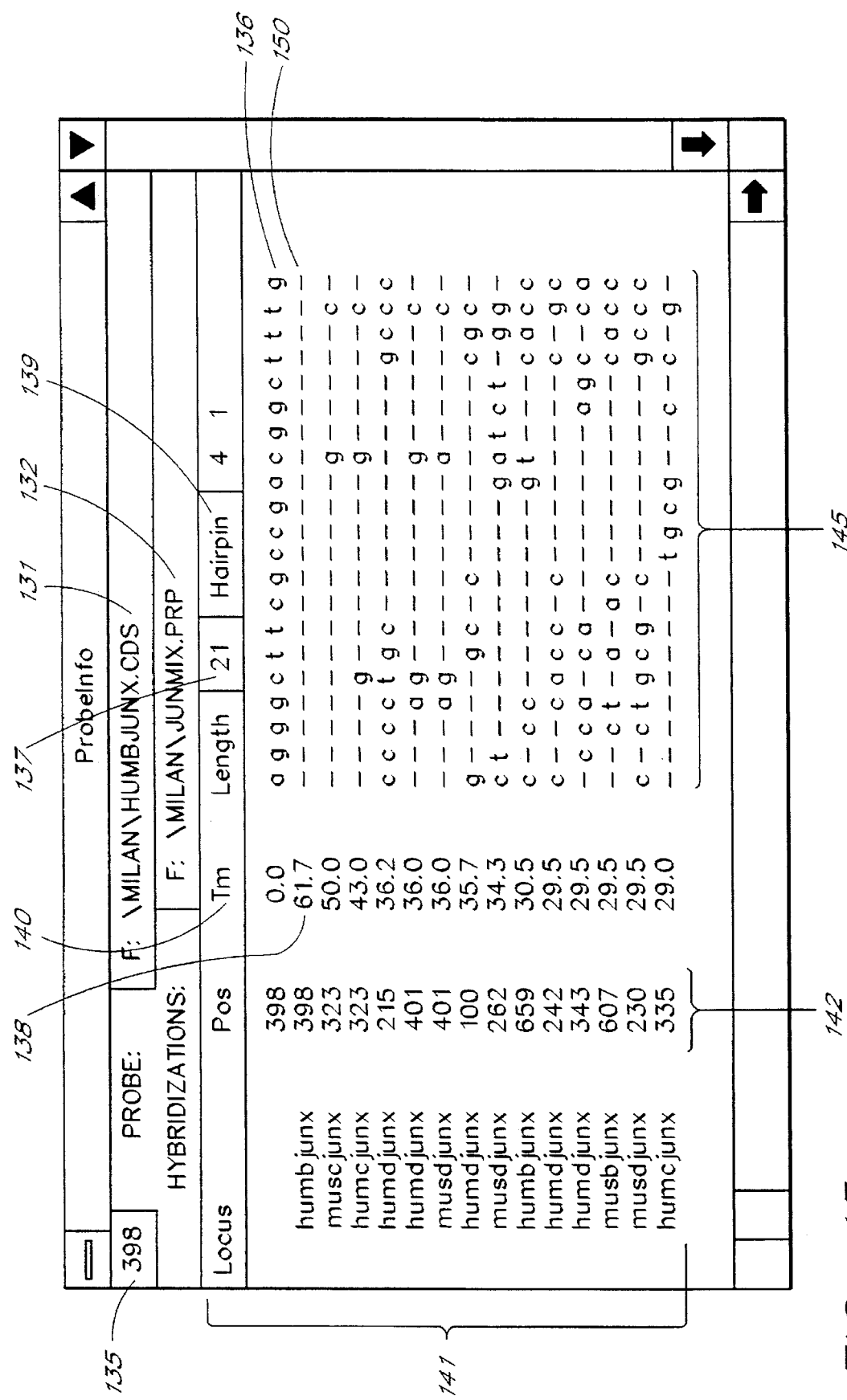
FIG. 15 is a display screen representation of the probeinfo and matchinfo window.

The combined ProbeInfo and MatchInfo Window, FIG. 15, displays detailed information about the current candidate probe. The upper portion of the window is the ProbeInfo window, and the lower portion is the MatchInfo window. The ProbeInfo window portion displays the following types of information: the target locus (i.e., the mRNA, cDNA, or DNA from which the user is looking for probes) is displayed at 131, while the preparation used for hybridizations is displayed at 132. In the example shown in FIG. 15, the target locus 131 is the file named HUMBJUNX.CDS, which is shown as being located on drive F in the subdirectory MILAN. The preparation 132 is shown as being the file designated JUNMIX.PRP, which is also shown as being located on drive F in the subdirectory MILAN. The JUN-MIX.PRP preparation in this example is a mixture of human and mouse jun loci.

The current and optimal probe's starting position is shown at 135. The current candidate oligonucleotide probe is defined at 136, and is listed at 137 as having a length of 21 bases. The melting temperature for the probe 136 as hybridized with the targets is shown in column 140. The melting temperature for the optimal probe is given as 61.7 degrees C at 138. The ProbeInfo Window FIG. 15 also displays hairpin characteristics of the probe at 139. In the example shown, the ProbeInfo Window shows that there are four (4) base pairs involved in the worst hairpin, and that the worst hairpin has a length of one (1) (see FIG. 15, at 139).

The MatchInfo Window portion displays a list of hybridizations between the current probe and species within the preparation file, including hybridization loci and hybridization temperatures. The hybridizations are listed in descending order by melting temperature. The display shows the locus with which the hybridization occurs, the position within the locus, and the hybridization sequence.

In the MatchInfo window portion, the candidate probe 136 is shown at 150 as hybridizing completely with a high binding strength. This is because the target DNA is itself represented in the database in this case, so the candidate probe is seen at 150 to hybridize with itself (a perfect hybridization). The locus of each hybridization from the preparation 132 are displayed in column 141, while the starting position of each hybridization is given in column 142. The calculated hybridizations are shown at 145.

iii. The ProbesEdit Window

The ProbesEdit Window, FIG. 16, is a text editing window provided for convenient editing and annotation of OligoProbe DesignStation text file output. It is also used to accumulate probes selected from the MPSD, FIG. 14, by mouse button 2 clicks. Standard text editing capabilities are available within the ProbesEdit Window. The user may accumulate selected probes in this window (see 155 for an example) and then save them to a file (which will bear the name of the preparation sequence with the file extension of "prb" 156, or may be another file name selected by the user). A sample of this file is shown in FIG. 16A.

iv. Miscellaneous Output

The present embodiment of this invention also creates two output files, currently named "test.out" and "test1.out", depending upon which model the user has selected. The first file, "test.out", is created with both the Mismatch Model and the H-Site Model. This file is a textual representation of the Mitsuhashi Probe Selection Diagram (MPSD). It breaks the probe sequence down by position, length, delta Tm, screensN, and the actual probe sequence (i.e., nucleotides). An example of this file created by the Mismatch Model is shown in FIG. 30, and example created by the H-Site Model is shown in FIG. 34a. The second file, "test1.out", is created only by the H-Site Model. This file is a textual representation of the ProbeInfo and MatchInfo window that captures all hybridizations, along with their locus, starting position, melting temperature, and possible other hybridizations. A partial example of this file is shown in FIG. 34b (10 pages out of a total of 190 pages created by the H-Site Model).

2. Description of the Mismatch Model Program a. Overview

In this invention, one of the hybridization strength models is termed the Mismatch Model (see FIG. 12 for selection of this model). The basic operation of this model involves the techniques of hashing and continuous seed filtration, as defined earlier but described in more detail below. The essence of the Mismatch Model is a fast process for doing exact and inexact matching between nucleotide sequences to support the Mitsuhashi Probe Selection Diagram (MPSD). There are a number of modules in the present implementation of the Mismatch Model contained in this invention, the most significant of which are shown in the flow chart in FIG. 17 and in more detail in FIGS. 18 through 28. The main k_diff module shown in the flow chart in FIG. 18 is a structured program that provides overall control of the Mismatch Model, calling various submodules that perform different functions.

b. Inputs

The user-selected input variables for this model are minimum probe length 76 (which is generally from 18 to 30) and maximum number of mismatches 77 (which generally is from 1 to 5). These inputs are entered by the user in the Main OligoProbe DesignStation Dialog Window, FIG. 12C.

c. Processing i. k_diff Program

Some terms of art need to be defined before the processing performed by this module can be explained. A hash table basically is an array or table of data. A linked list is a classical data structure which is a chain of linked entries and involves pointers to other entry structures. Entries in a linked list do not have to be stored sequentially in memory, as is the case with elements contained in an array. Usually there is a pointer to the list associated with the list, which is often initially set to point to the start of the list. A pointer to a list is useful for sequencing through the entries in the list. A null pointer (i.e., a pointer with a value of zero) is used to mark the end of the list.

Figure 17:
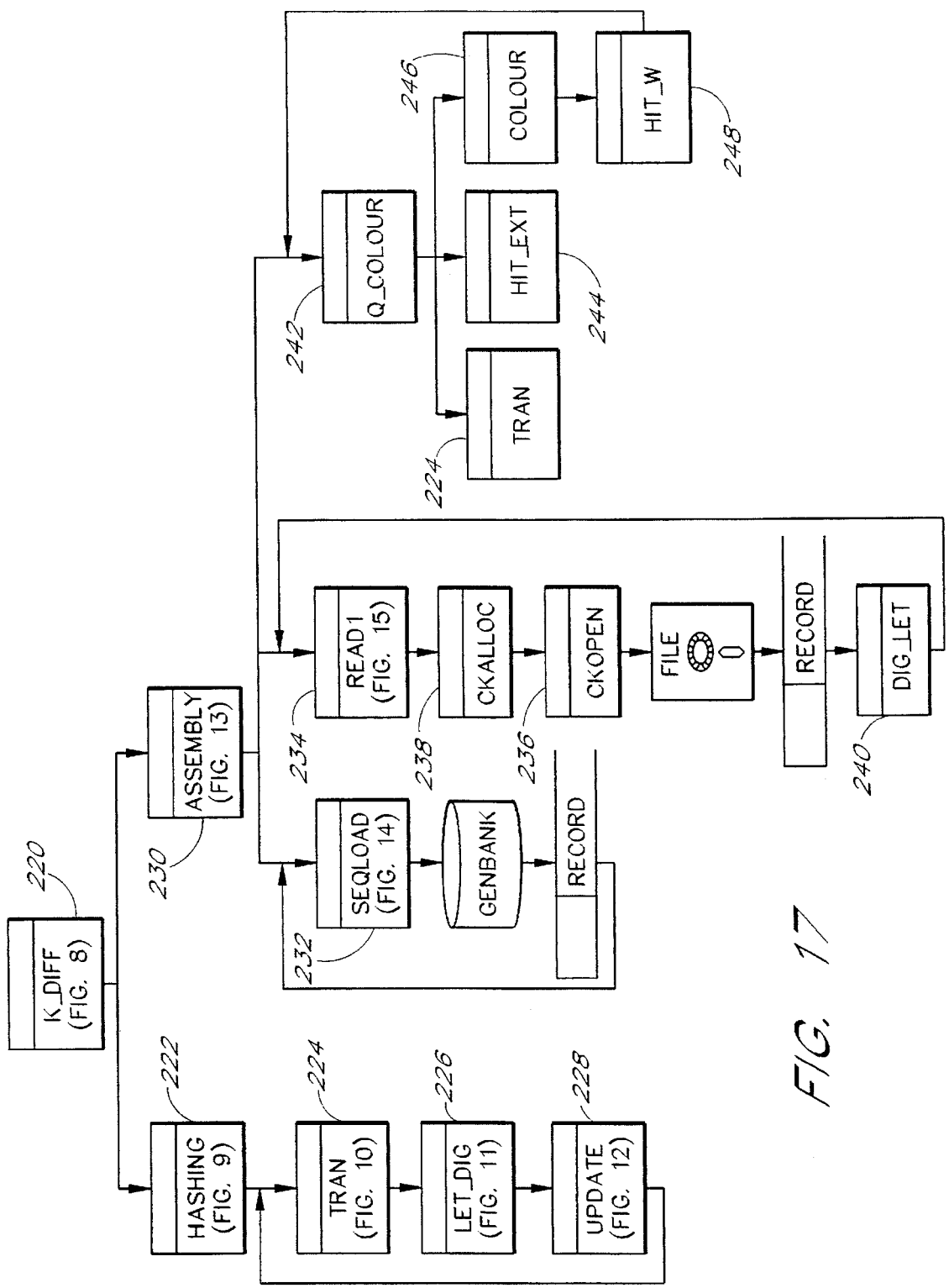
FIG. 17 is a flow chart of the overall k_diff program of the Mismatch Model of this invention, including its sequence and structure.
Figure 18A:
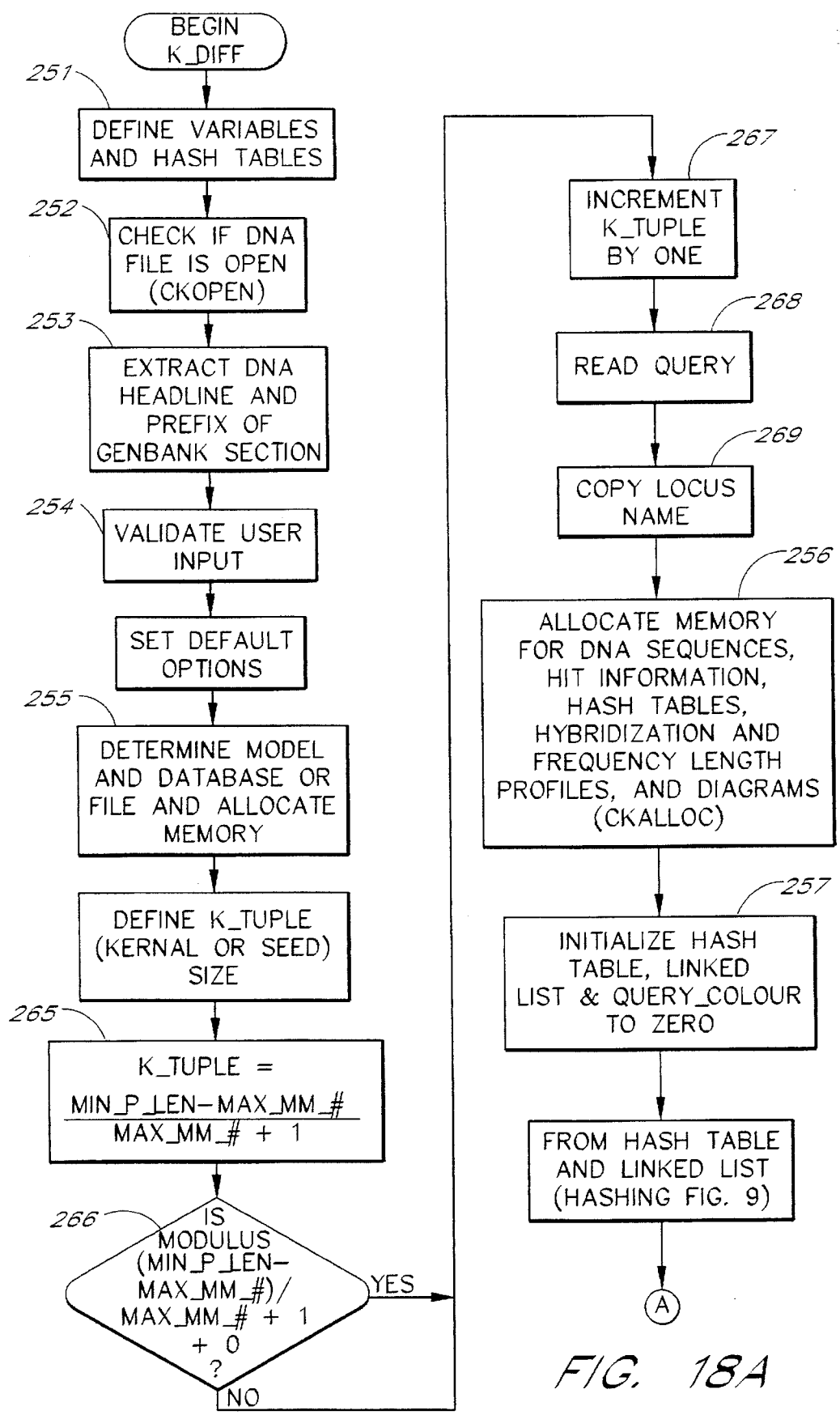
FIGS. 18A–18B are flow charts of the k_diff module of this invention.
Figure 18B:
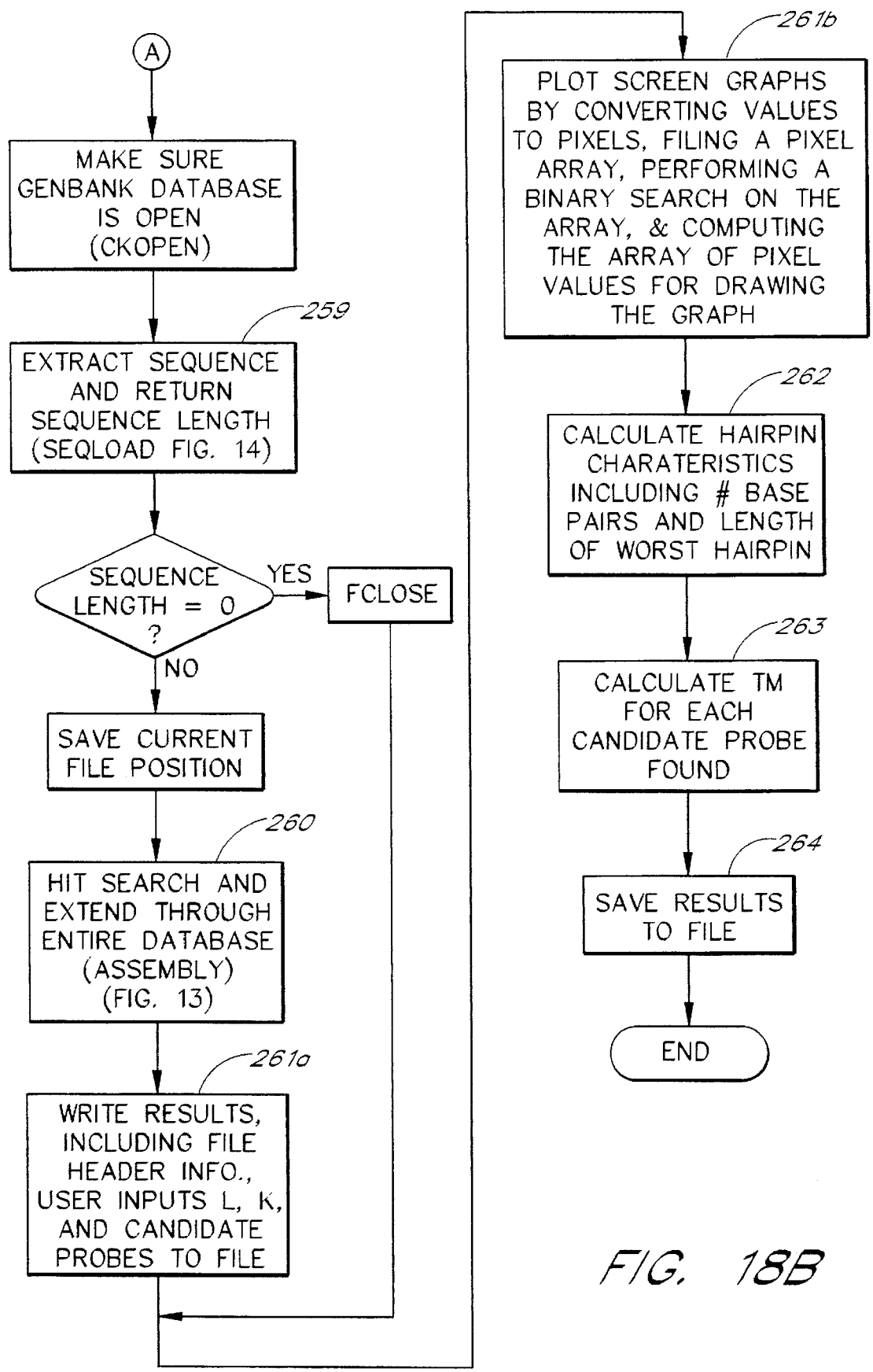

As the flow charts in FIGS. 17 and 18 illustrate, the general process steps and implemented functions of this model can be outlined as follows:

Step 1: First, create a hash table and linked list from the query (FIG. 17, hashing module 222).

Step 2: Next, while there are still GenBank entries available for searching (FIG. 17, assembly module 230):

Step 2a: Read the current GenBank entry (record) sequence of user-specified length (FIG. 17, seqload module 232), or read the current sequence (record) from the file selected by the user (FIG. 17, read1 module 234).

Step 2b: For the current sequence for each position of the sequence from the first position (or nucleotide) to the last position (or nucleotide) (incrementing the position number once each iteration of the loop) (FIG. 17, q_colour module 242), Step 2c: set the variable dna_hash equal to the hash of the current position of the current sequence (FIG. 17, q_colour module 242).

Step 2d: While not at the end of the linked list for dna_hash (FIG. 17, q_colour module 242), Step 2e: set the query_pos equal to the current position of dna_hash in the linked list (FIG. 17, q_colour module 242) and Step 2f: Extend the hit with the coordinates (query_pos, dna_pos) (FIG. 17, hit_ext module 244), Step 2g: If there exists a k_mismatch in the current extended hit (FIG. 17, colour module 246), then Step 2h: print the current hit (FIG. 17, q_colour module 242), and repeat from Step 2.

As this illustrates, there are three (3) basic looping or iteration processes with functions being performed based on variables such as whether the GenBank section end has been reached (the first "WHILE" loop, Step 2), whether the end of the current DNA entry has been reached (the "FOR" loop, Step 2b), and whether the end of the dna_hash linked list has been reached (the second "WHILE" loop, Step 2d). A "hit" will only be printed if there are k_mismatches in the current extended hit.

FIGS. 18 through 28 illustrate the functions of each of the modules of the present embodiment of this invention, all of which were generalized and summarized in the description above. FIG. 18, which outlines the main "k_diff" module, shows that this module is primarily a program organization and direction module, in addition to performing routine "housekeeping" functions, such as defining the variables and hash tables 251, checking if the user-selected gene sequence file is open 252, extracting needed identification information from the GenBank 253, and ensuring valid user input 254. This module also performs a one-time allocation of memory for the gene sequences, and allocates memory for hit information, hashing, hybridization and frequency length profiles and output displays, 255 & 256. The "k_diff" module also initializes or "zeros out" the hashing table, the linked hashing list and the various other variables 257 in preparation for the hashing function. In addition, this module forms the hash tables 258 and extracts a sequence and finds the sequence length 259.

One of the most important functions performed by the "k_diff" module is to define the seed (or kernel or k_tuple) size. This is done by setting the variable k_tuple equal to (min_probe_length−max_mismatch_#)/(max_mismatch+#+1) FIG. 18 at 265. Next, if the remainder of the aforementioned process is not equal to zero 266, then the value of the variable k_tuple is incremented by one 267. The resulting value is the size of the seed. The module then reads the query 268 and copies the LOCUS name 269 for identification purposes (a definition of the term locus is given earlier in the specification).

The "k_diff" module FIG. 18 also calls the "assembly" module 260, writes the results to a file 261a, plots the results 261b (discussed below), calculates the hairpin characteristics 262 (i.e., the number of base pairs and the length of the worst hairpin) and the melting temperature (Tm) for each candidate probe 263, and saves the results to a file 264.

The screen graphs are plotted 261b by converting the result values to pixels, filing a pixel array and performing a binary search into the pixel array. Next, given the number of pixels per probe position and which function is of interest to the user (i.e., the three mismatch match numbers), the program interpolates the values at the value of (pixelsPerPositionN-1) and computes the array of pixel values for drawing the graph. These values are then plotted on the MPSD.

Figure 19:
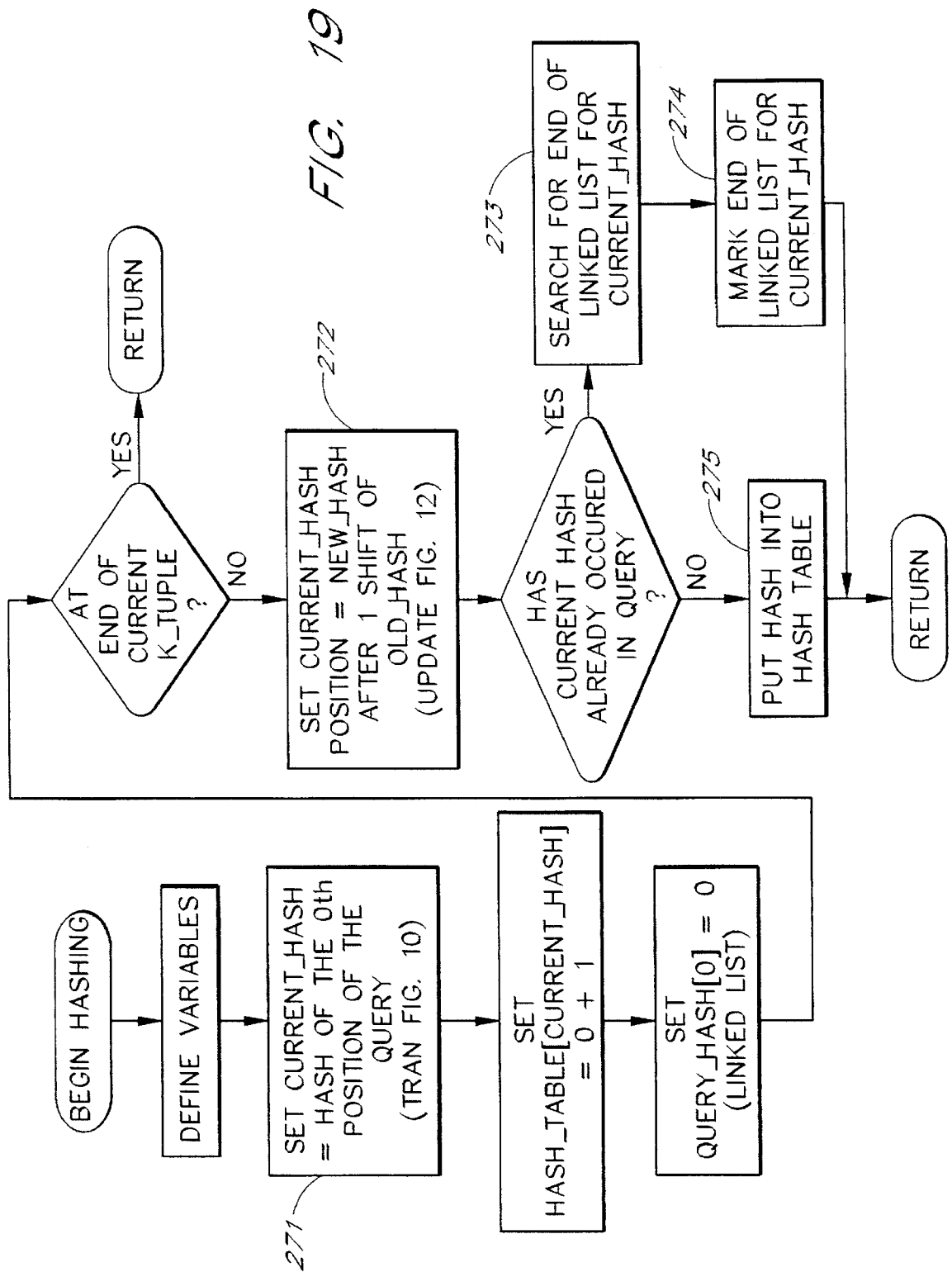
FIG. 19 is a flow chart of the hashing module of this invention.

The "hashing" module, FIG. 19, performs hashing of the query. In other words, it creates the hash table and linked list of query positions with the same hash. The variable has_table[i] equals the position of the first occurrence of hash i in the query. If i does not appear in the query, hash_table[i] is set to zero.

Figure 20:
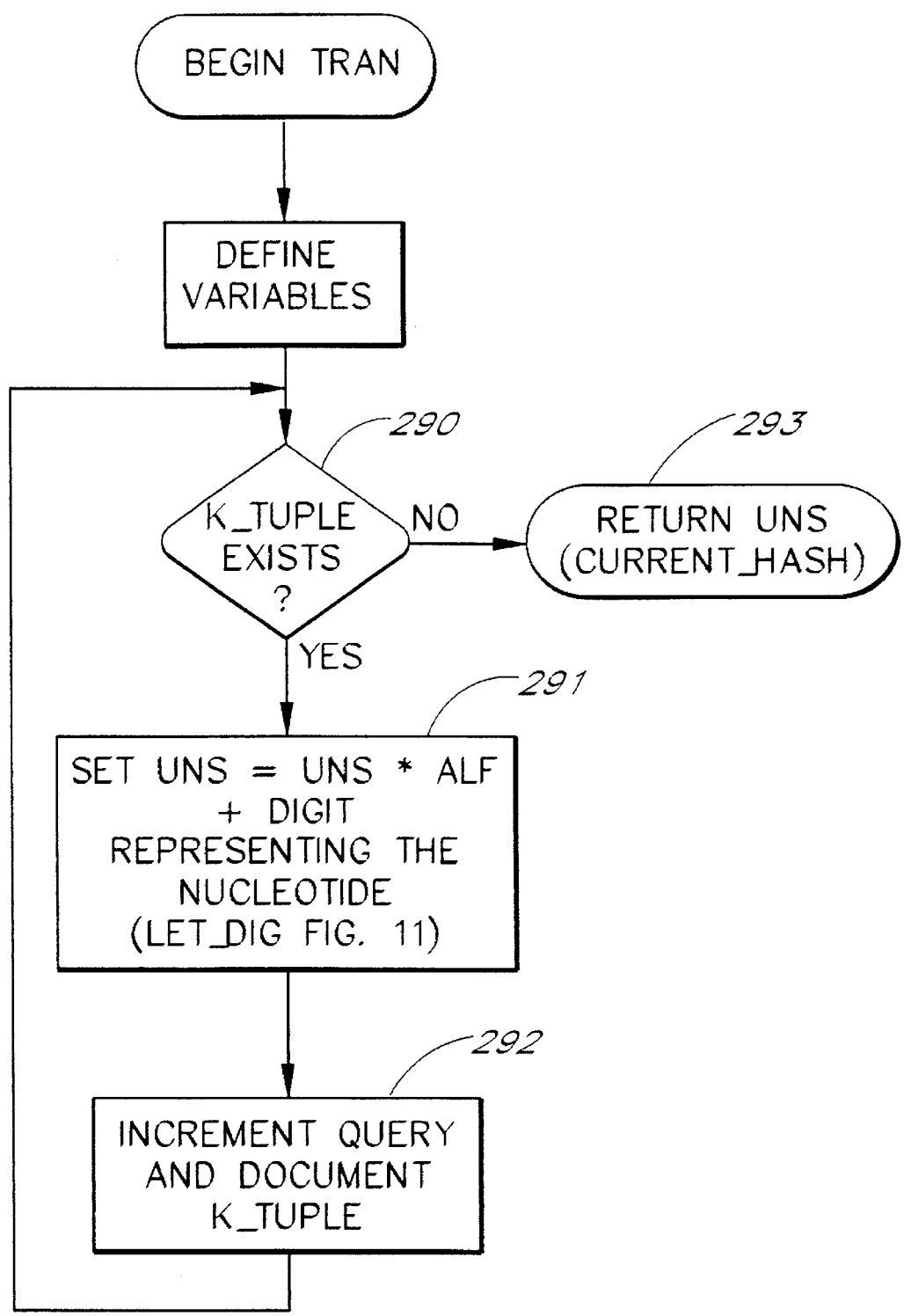
FIG. 20 is a flow chart of the tran module of this invention.

The "tran" module, FIG. 20, is called by the "hashing" module 271, and performs the hashing of the sequence of k_tuple (kernel or seed) size. If the k_tuple exists (i.e., its length is greater than zero), the variable uns is set equal to uns*ALF+p 291. The variable p represents the digit returned by the "let_dig" module FIG. 21 that represents the nucleotide being examined. ALF is a constant that is set by the program in this implementation to equal four. The query pointer is then incremented, while the size of k_tuple (the seed) is decremented 292. This process is repeated until the sequence of k_tuple has been entirely hashed. Then the "tran" module returns the variable current_hash 293 to the "hashing" module FIG. 19.

Figure 21:
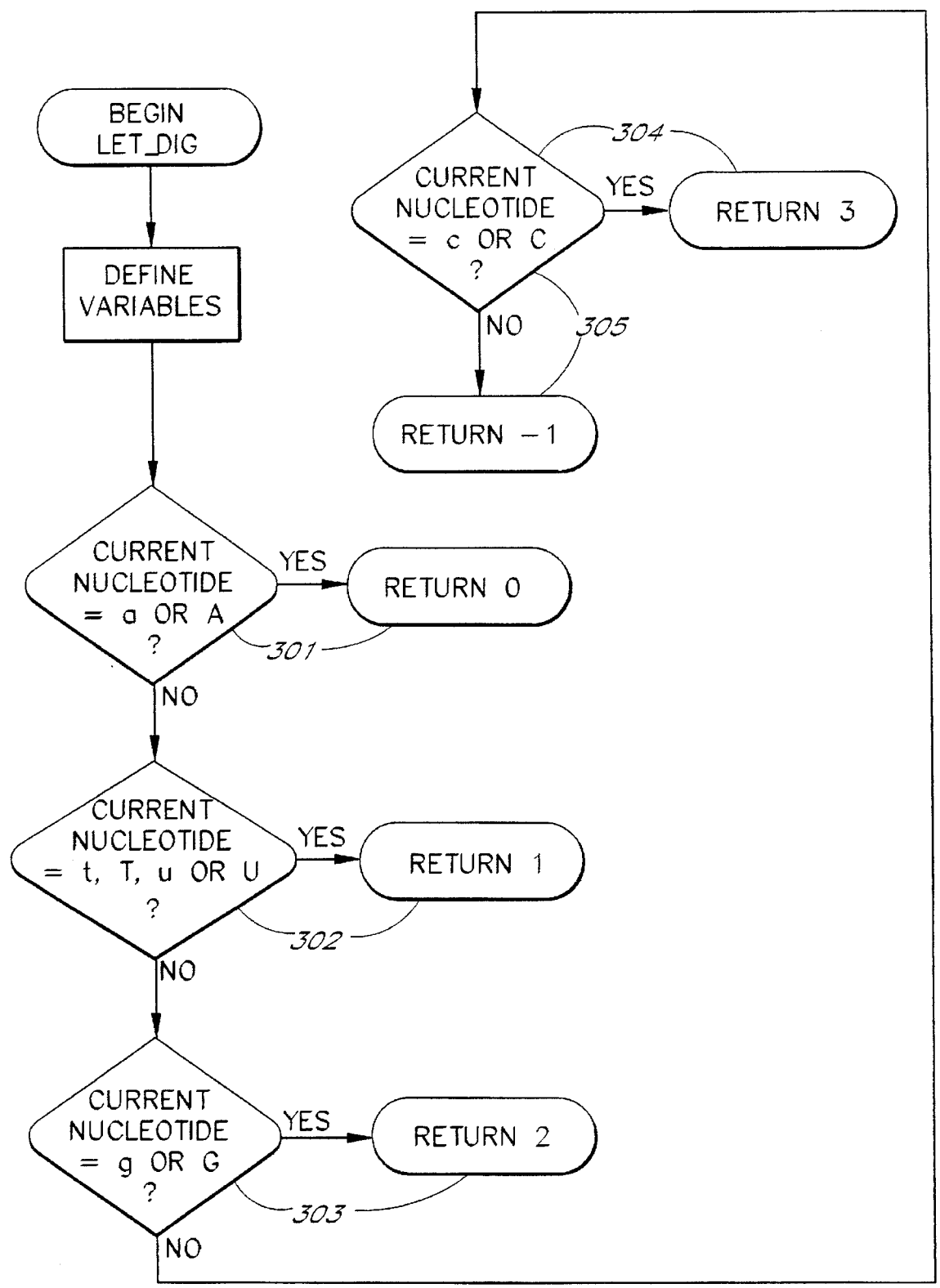
FIG. 21 is a flow chart of the let_dig module of this invention.
Figure 22:
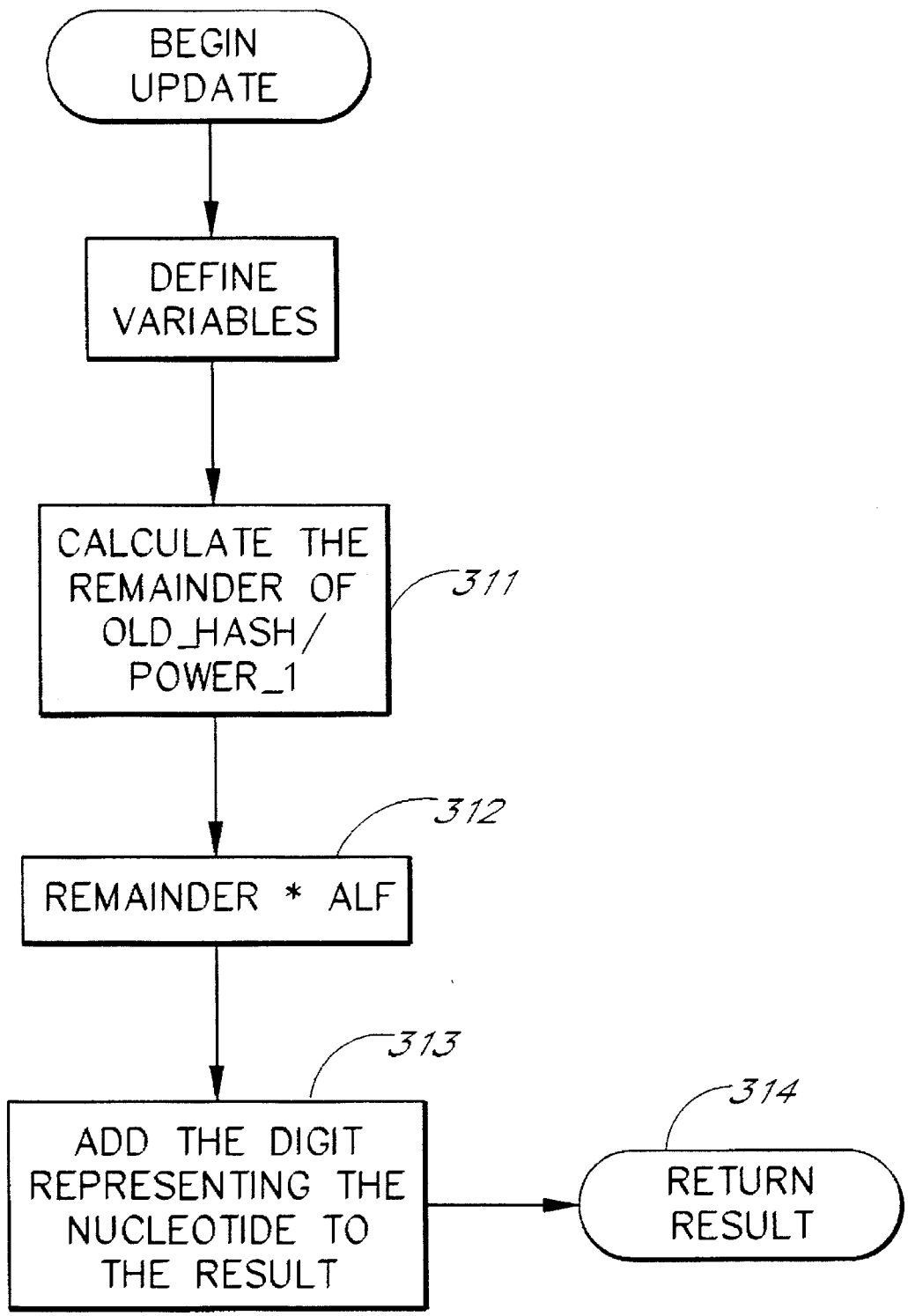
FIG. 22 is a flow chart of the update module of this invention.

The "let_dig" module, FIG. 21, is called by the "tran" module 291, and transforms the nucleotides represented as the characters "A", "T", "U", "G" and "C" in the GenBank and the user's query into numeric digits for easier processing by the program. This module transforms "a" and "A" into "0" 301, "t", "T", "u" and "U" into "1" 302, "g" and "G" into "2" 303, and "c" and "C" into "3" 305. If the character to be transformed does not match any one of those listed above, the module returns "−1" 305. The "hashing" module, FIG. 19, then calls the "update" module 272, FIG. 22, which updates the hash with a sliding window (i.e., it forms a new hash after shifting the old hash by "1"). The remainder of old_hash divided by power_1 is calculated 311 (a modulus operation), the remainder is multiplied by ALF 312 (i.e., four), and then the digit representing the nucleotide is added to the result 313. The "update" module then returns the result 314 to the "hashing" module FIG. 19.

If the current hash has already occurred in the query, the program searches for the end of the linked list for the current hash 273 and marks the end of the linked list for the current hash 274. If the current hash has not already occurred in the query, the program puts the hash into the hash table 275. The resulting hash table and linked list are then returned to the "k_diff" module, FIG. 18 at 258.

Figure 23A:
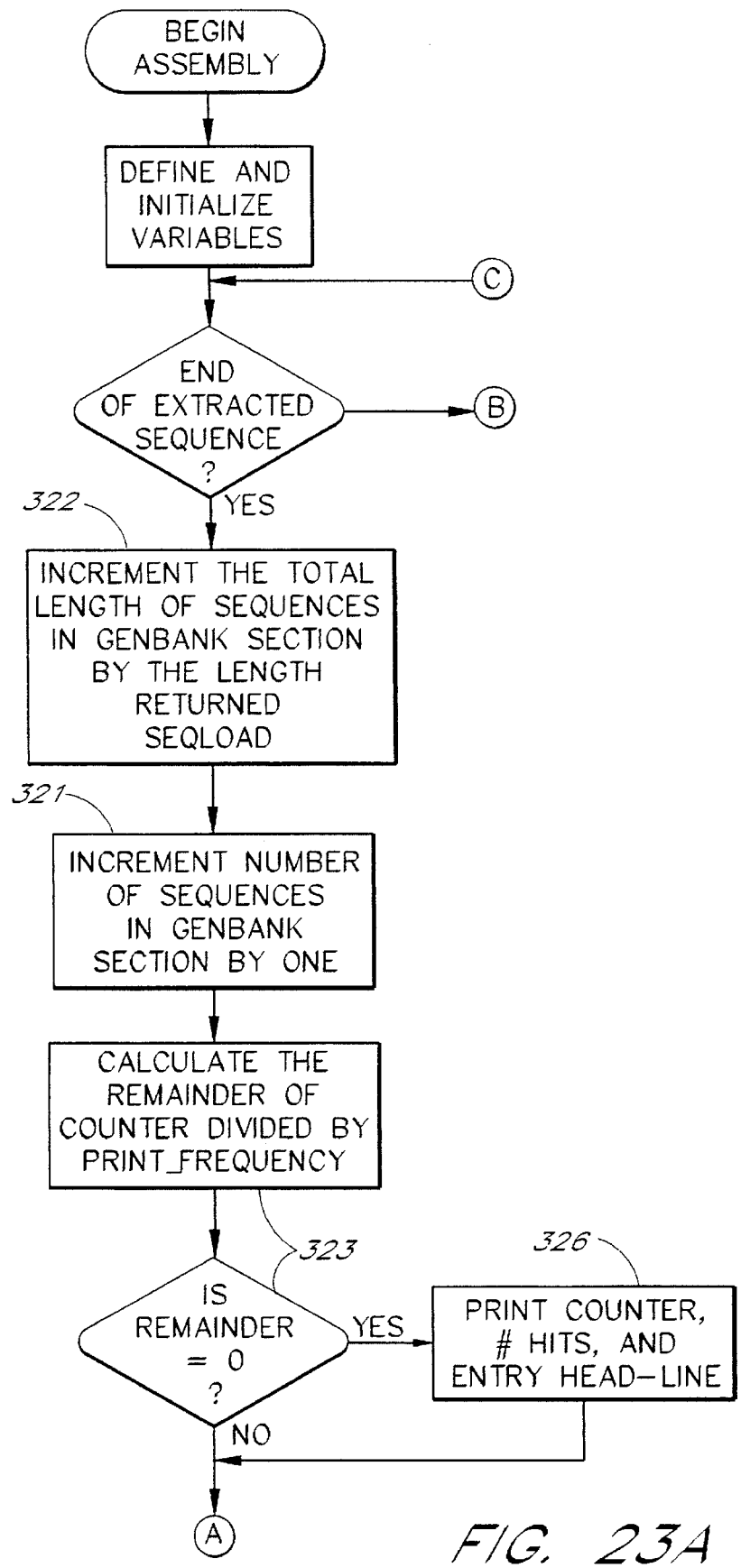
FIGS. 23A–23B are flow charts of the assembly module of this invention.
Figure 23B:
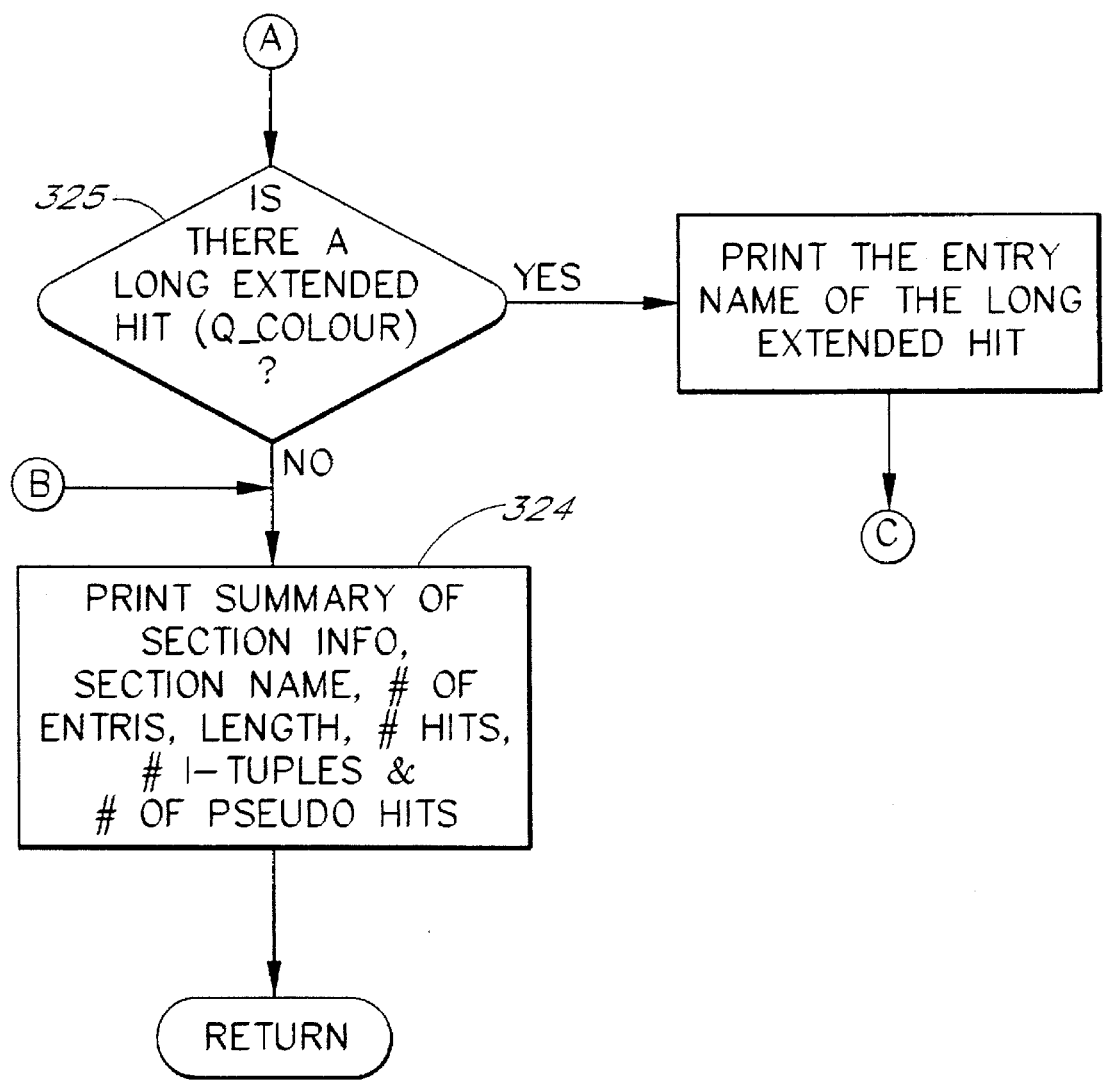

The "assembly" module, FIG. 23, extracts sequences from the GenBank and performs hit locating and extending functions. This module is called by the "k_diff" module FIG. 18 at 260 if the user has chosen to use the database to locate matches. The output from the "assembly" module (FIG. 23) tells the user that the section of the database searched contains E number of entries 321 of S summary length 322 with H number of hits 323. Further, the program tells the user that the number of considered 1-tuples equals T 324. The entry head line is also printed 326.

Figure 24A:
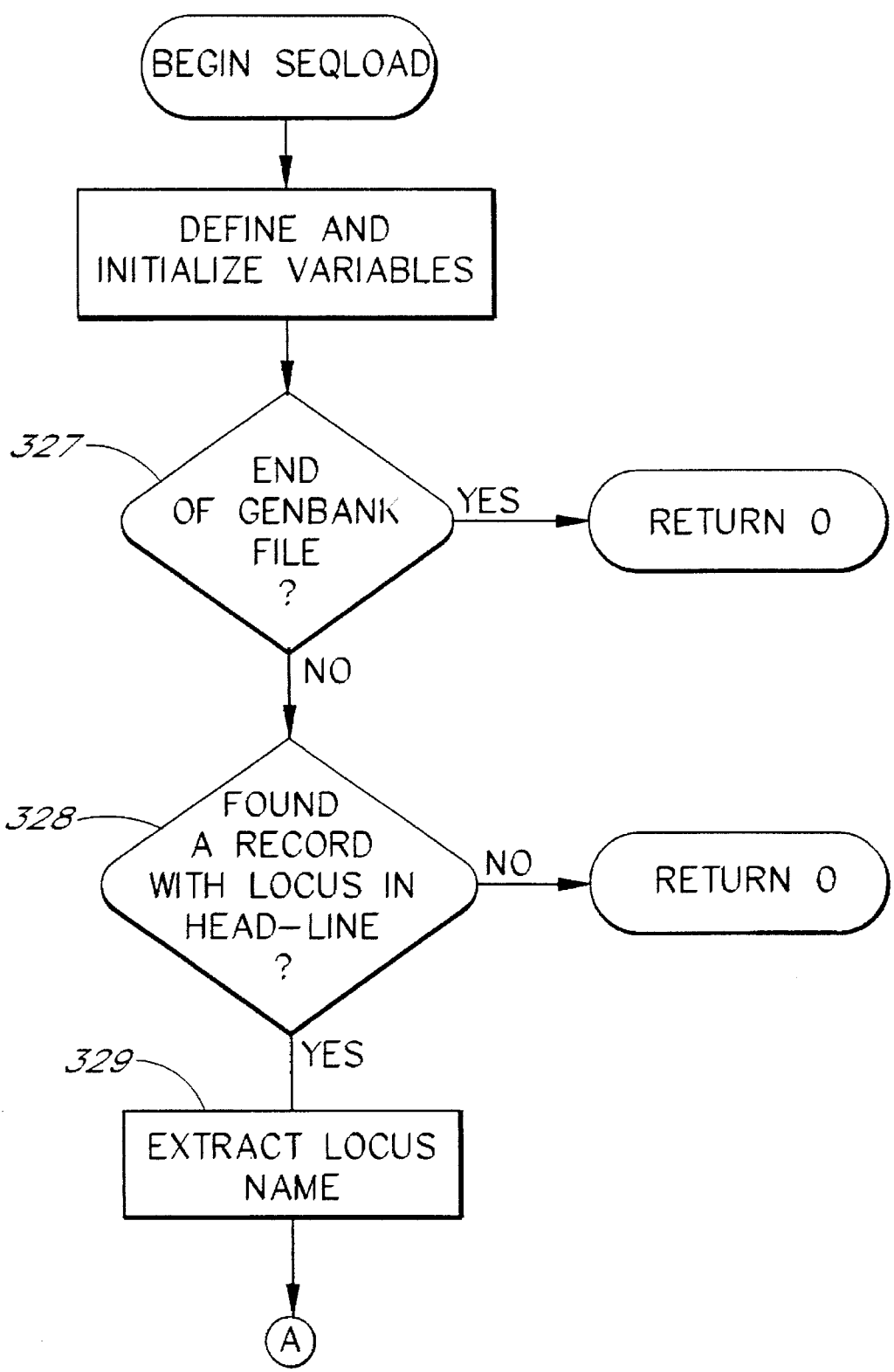
FIGS. 24A–24B are flow charts of the seqload module of this invention.
Figure 24B:
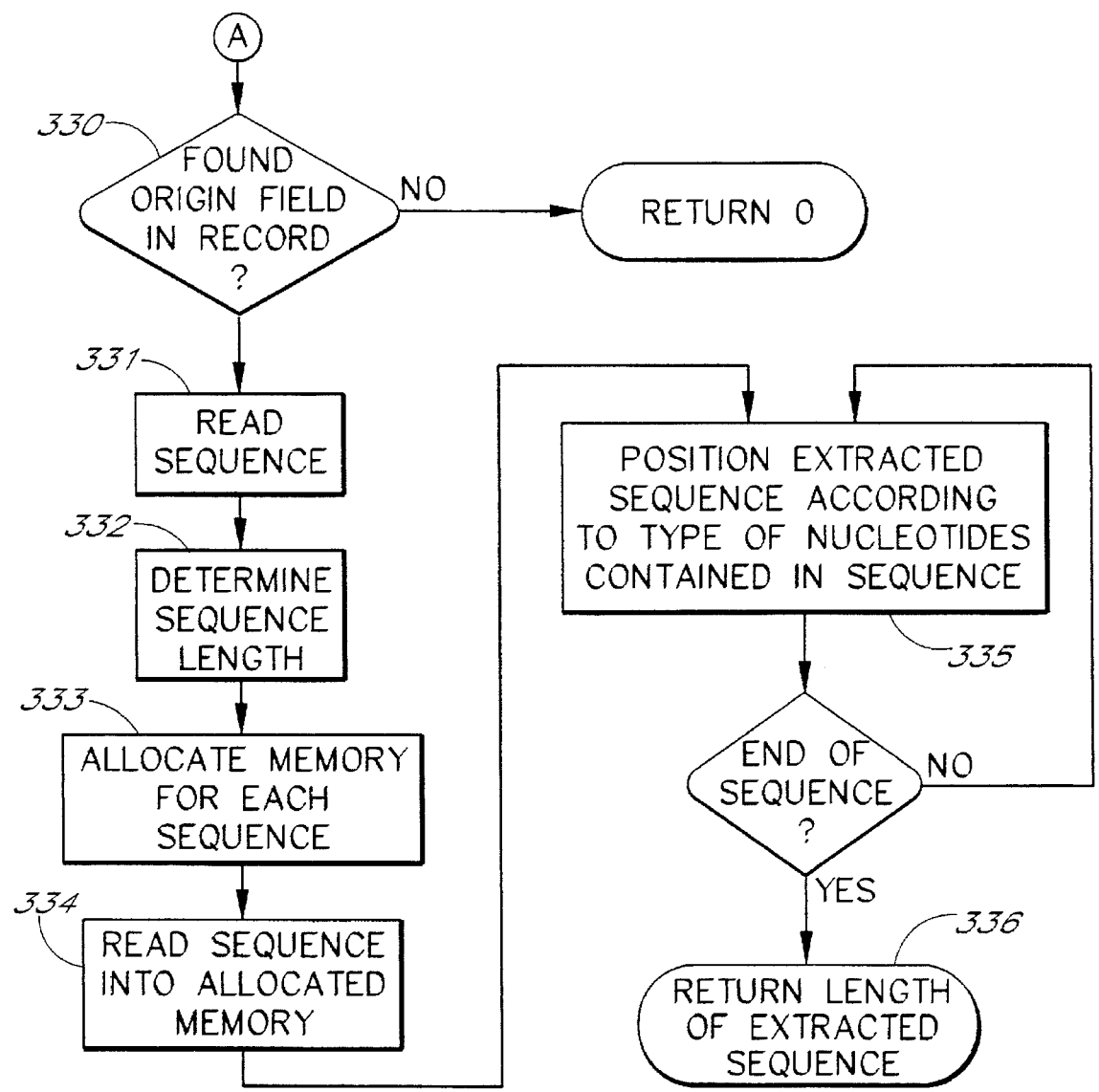

The "seqload" module, FIG. 24, is called by the "k_diff" module FIG. 18 at 259 once the query hash table and linked list have been formed by the "hashing" module FIG. 19. The "seqload" module FIG. 24 checks to see if the end of the GenBank file has been reached 327, and, if not, searches until a record is found with LOCUS in the headline 328. Next, the LOCUS name is extracted 329 for identification purposes, and the program searches for the ORIGIN field in the record 330.

The program then extracts the current sequence 331 from the GenBank and performs two passes on each sequence. The first is to determine the sequence length 232 and allocate memory for each sequence 333, and the second pass is to read the sequence into the allocated memory 334. Since the sequences being extracted can contain either DNA nucleotides or protein nucleotides, the "seqload" module can recognize the characters "A", "T", "U", "G", and "C". The bases "A", "T", "G" and "C" are used in DNA sequences, while the bases "A", "U", "G" and "C" are used in RNA and mRNA sequences. The extracted sequence is then positioned according to the type of nucleotides contained in the sequence 335, and the process is repeated. Once the end of the sequence has been reached, the "seqload" module returns the sequence length 336 to the "k_diff" module FIG. 18.

Figure 25A:
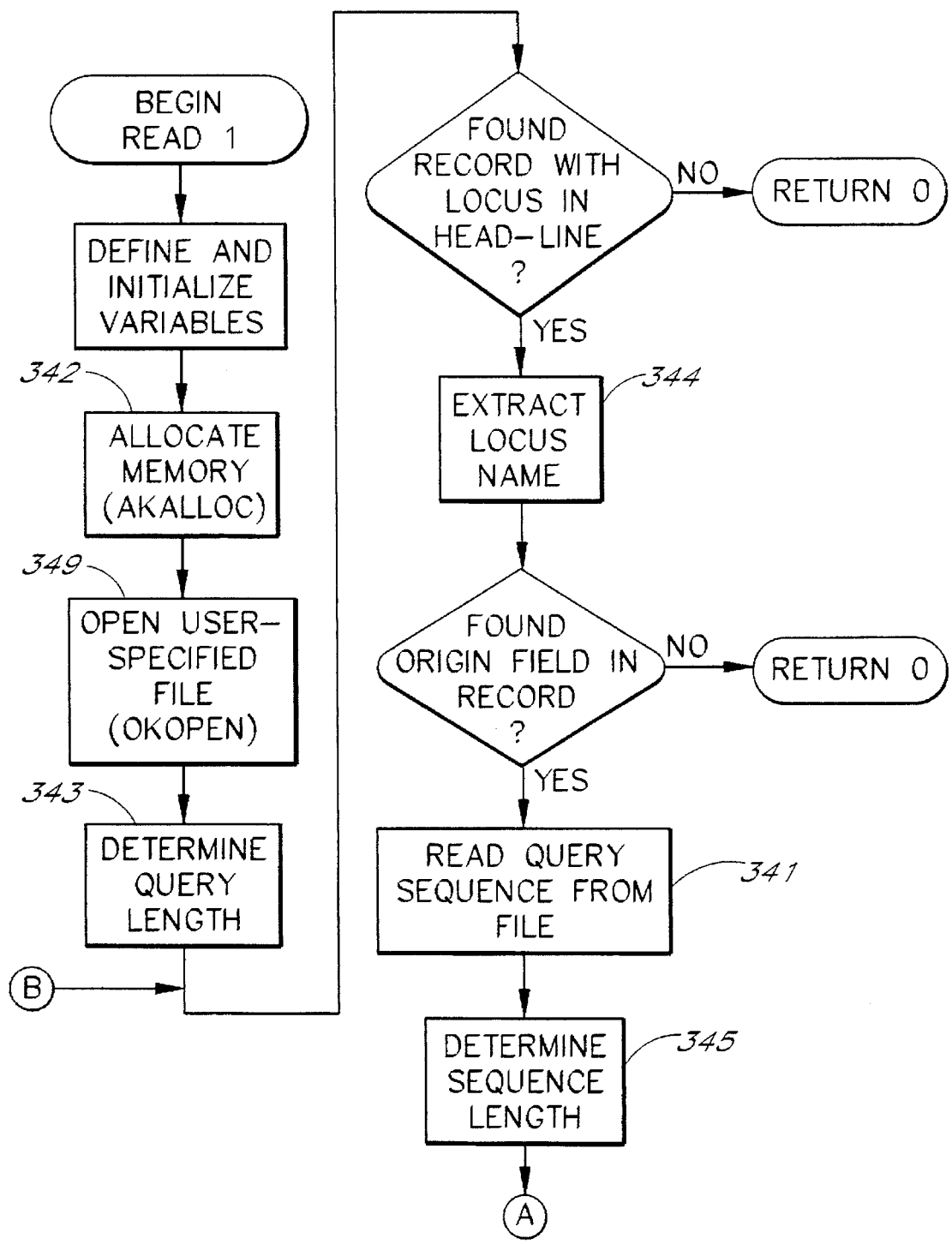
FIGS. 25A–25B are flow charts of the read1 module of this invention.
Figure 25B:
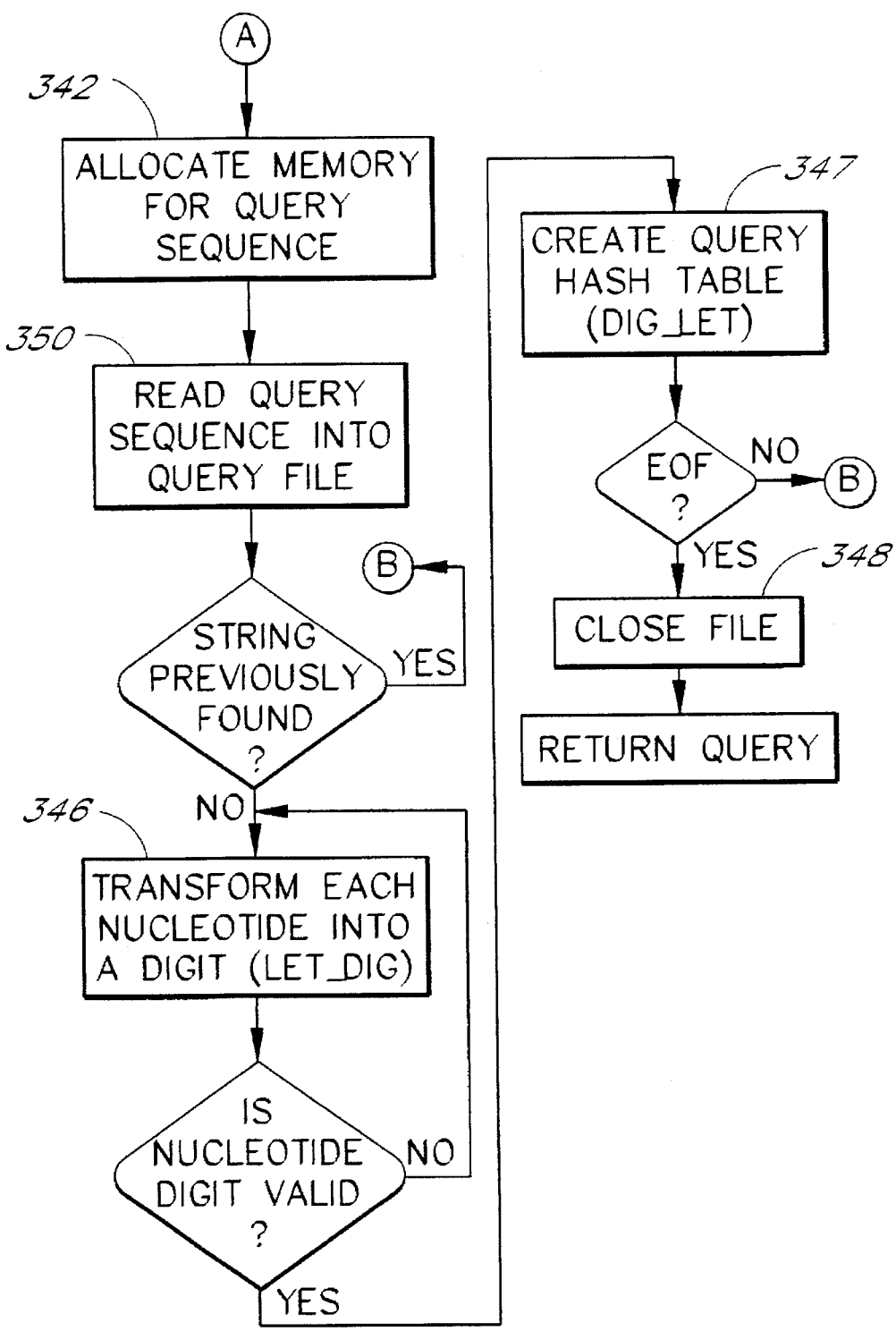

If the user has chosen to use one or more files to locate matches, rather than the database, the "read1" module, FIG. 25, rather than the "seqload" module FIG. 24, is called by the "k_diff" module FIG. 18. The "read1" module, FIG. 25, reads the sequence from the user specified query file 341 and allocates memory 342. This module also determines the query length 343, extracts sequence identification information 344, determines the sequence length 345, transforms each nucleotide into a digit 346 by calling the "let_dig" module FIG. 21, creates the query hash table 347 by calling the "dig_let: module FIG. 26, and closes the file 348 once everything has been read in.

First, the "read1" module FIG. 25 allocates space for the query 342. To do this, the "ckalloc" module, FIG. 25 at 342, is called. This module allocates space and checks whether this allocation is successful (i.e., is there enough memory or has the program run out of memory). After allocating space, the "read1" module FIG. 25 opens the user-specified file 349 (the "ckopen" module, FIG. 25 at 349, is called to ensure that the query file can be successfully opened 349), determines the query length 343, locates a record with LOCUS in the head-line and extracts the LOCUS name 344 for identification purposes, locates the ORIGIN field in the record and then reads the query sequence from the file 341. Next, the sequence length is determined 345, memory is allocated for the sequence 342, and the sequence is read into the query file 350. If the string has previously been found, processing is returned to 344. If not, then each character in the query file is read into memory 350.

Figure 26:
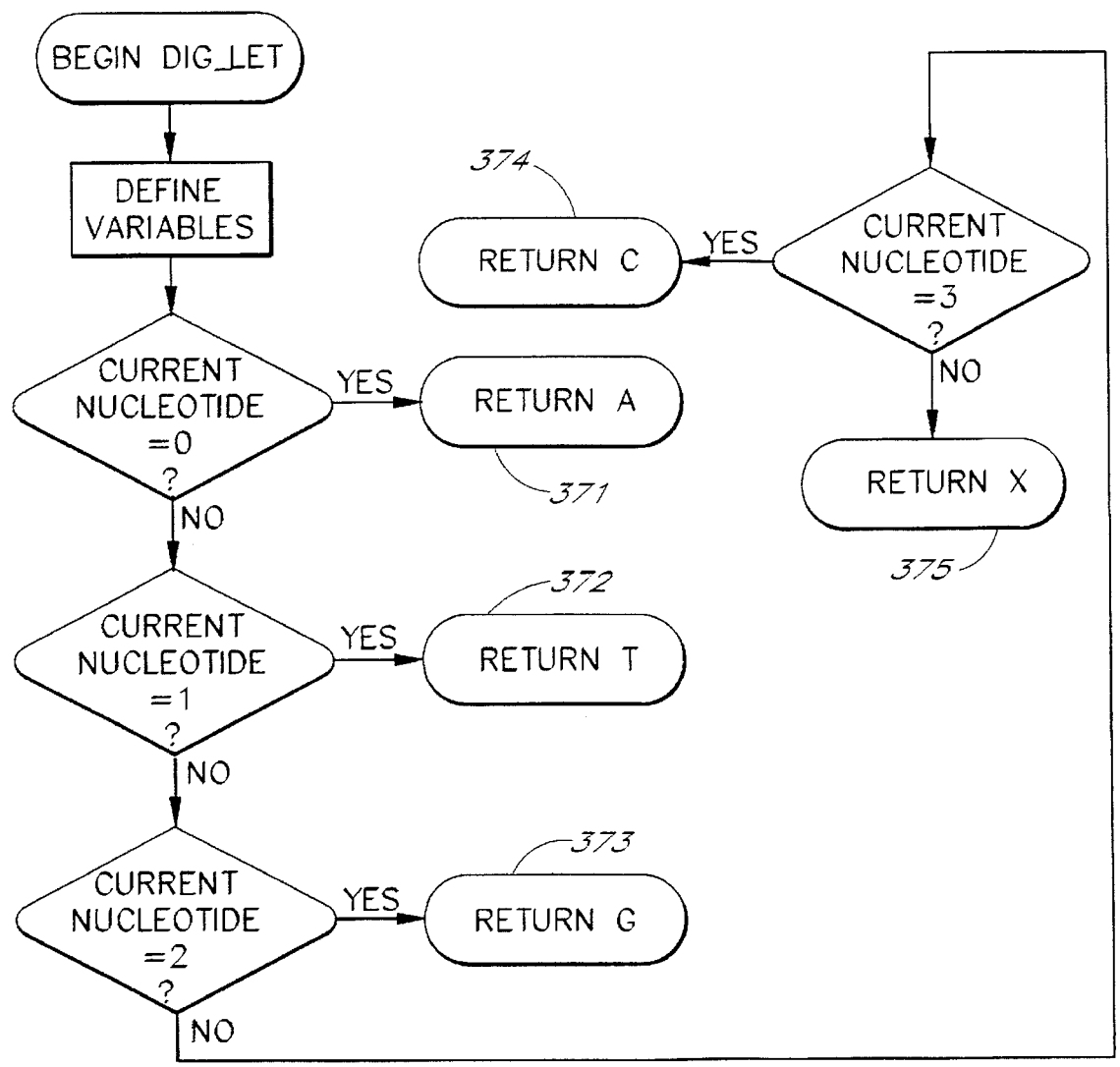
FIG. 26 is a flow chart of the dig_let module of this invention.

The characters are transformed into digits 346 using the "let_dig" module, FIG. 21, until a valid digit has been found, and then the hash table containing the query is set up 347 using the module "dig_let", FIG. 26 which transforms the digits into nucleotides represented by the characters "A" 371, "T" 371, "G" 373 "C" 374 and "X" 375 as a default. If the end of the file has not been reached, processing is returned to 344. If it has, the file is closed 348 and the query is then returned to the "read1" module FIG. 25 at 347.

The "q_colour" module, FIG. 17 (FIG. 23 at 325), is called by the "assembly" module FIG. 23 after the current sequence has been extracted from the GenBank. The "q_colour" module FIG. 27 performs the heart of the Mismatch Model process in that it performs the comparison between the query and the database or file sequences. If the module finds that there exists a long (i.e., greater than the min_hit_length) extended hit, it returns a "1" to the "assembly" module FIG. 24. Otherwise, the "q_colour" module, FIG. 27, returns a "0".

In the "q_colour" module, FIG. 27, all DNA positions are analyzed in the following manner. First, the entire DNA sequence is analyzed 391 to see whether each position is equal to zero 392 (i.e., whether it is empty or the sequence is finished). If it is not equal to zero 393, the "q_colour" module FIG. 30 calls the "tran" module, FIG. 20 described above, which performs the hashing of k_tuples. The "tran" module FIG. 20 calls other modules which transform the nucleotides represented by characters into digits for easier processing by the program and then updates the hash with a sliding window. If the position is equal to zero, the current_hash position is set to new_has after one shift of old_hash 390 by calling the "update" module FIG. 22.

If the nucleotide at the current hash position is equal to zero, processing is returned to 391. If not, the query position is set equal to (nucleotide at current hash position −1). Next, the "q_colour" module FIG. 27 looks for the current hash in the hash table 394. If the current k_tuple does not match the query 395, then the next k_tuple is considered 395, and processing is returned to 391. If the current k_tuple does match the query, then the program checks the hit's (i.e., the match's) vicinity 396 by calling the "hit_ext" module, FIG. 28 to determine if the hit is weak. The inventors have found that if the code for the module "hit_ext" is included within the module "q_colour", rather than being a separate module utilizing the parameter transfer machinery, 25% of CPU time can be saved.

Figure 27A:
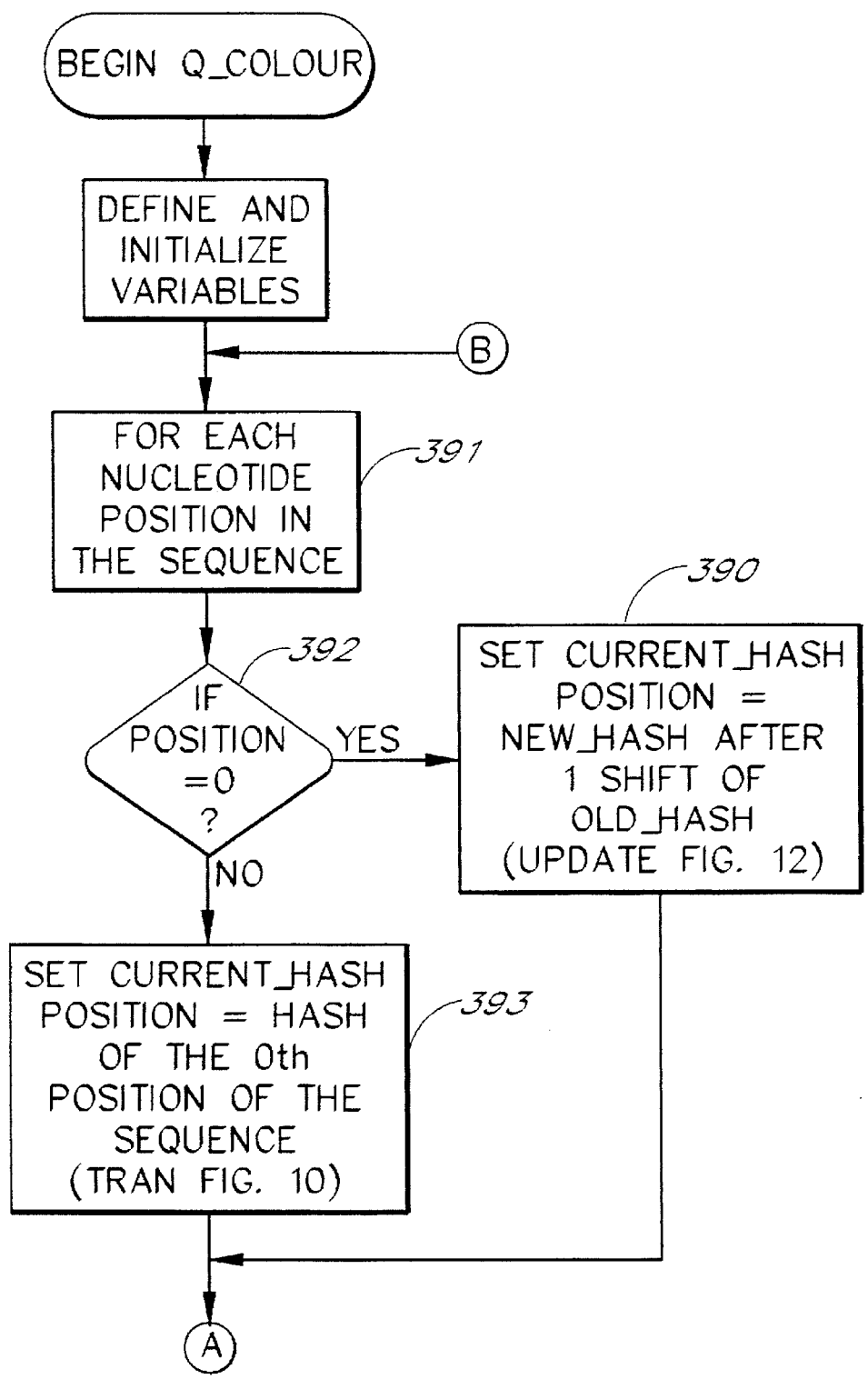
FIGS. 27A–27B are flow charts of the q_colour module of this invention.
Figure 27B:
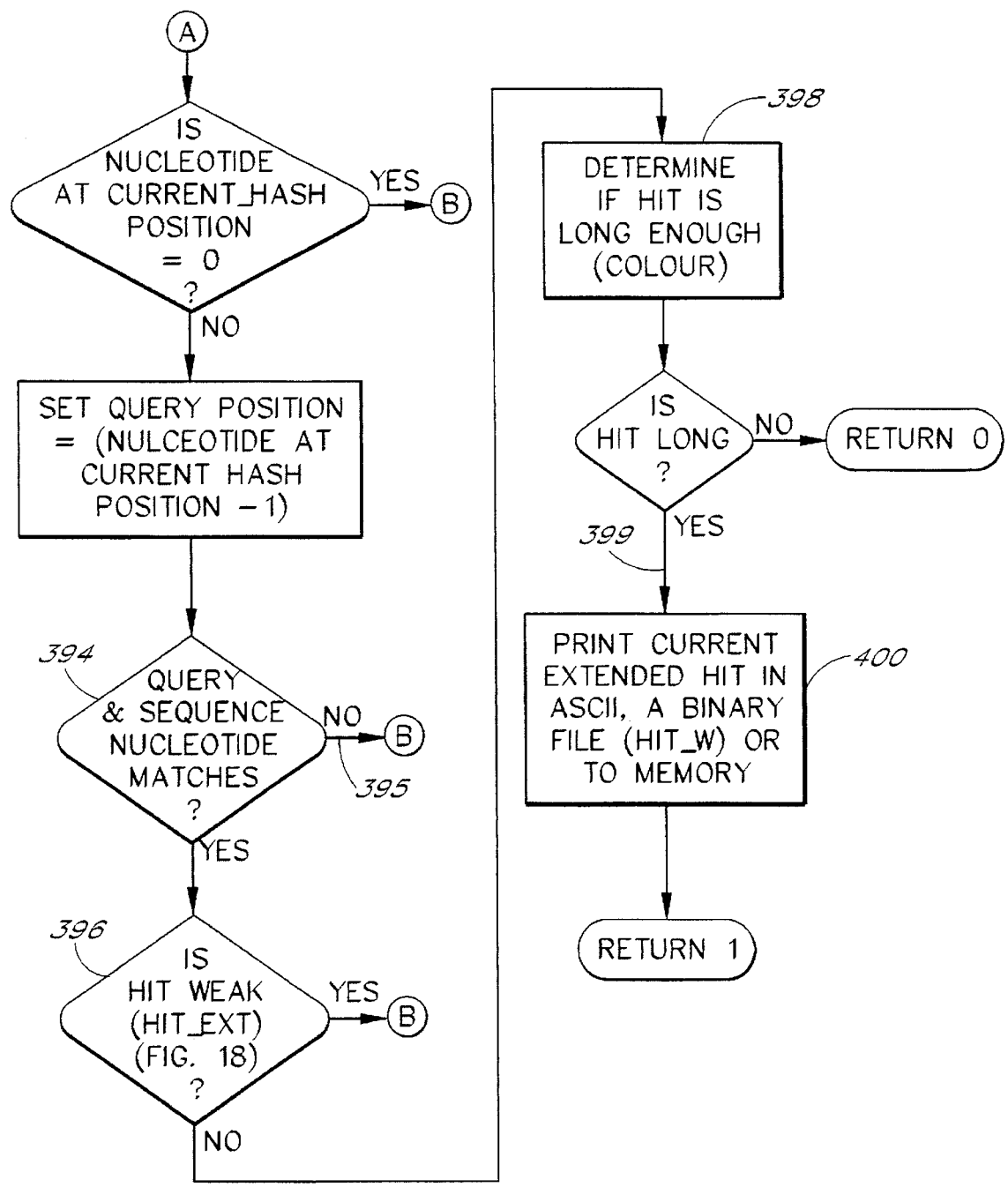
Figure 28:
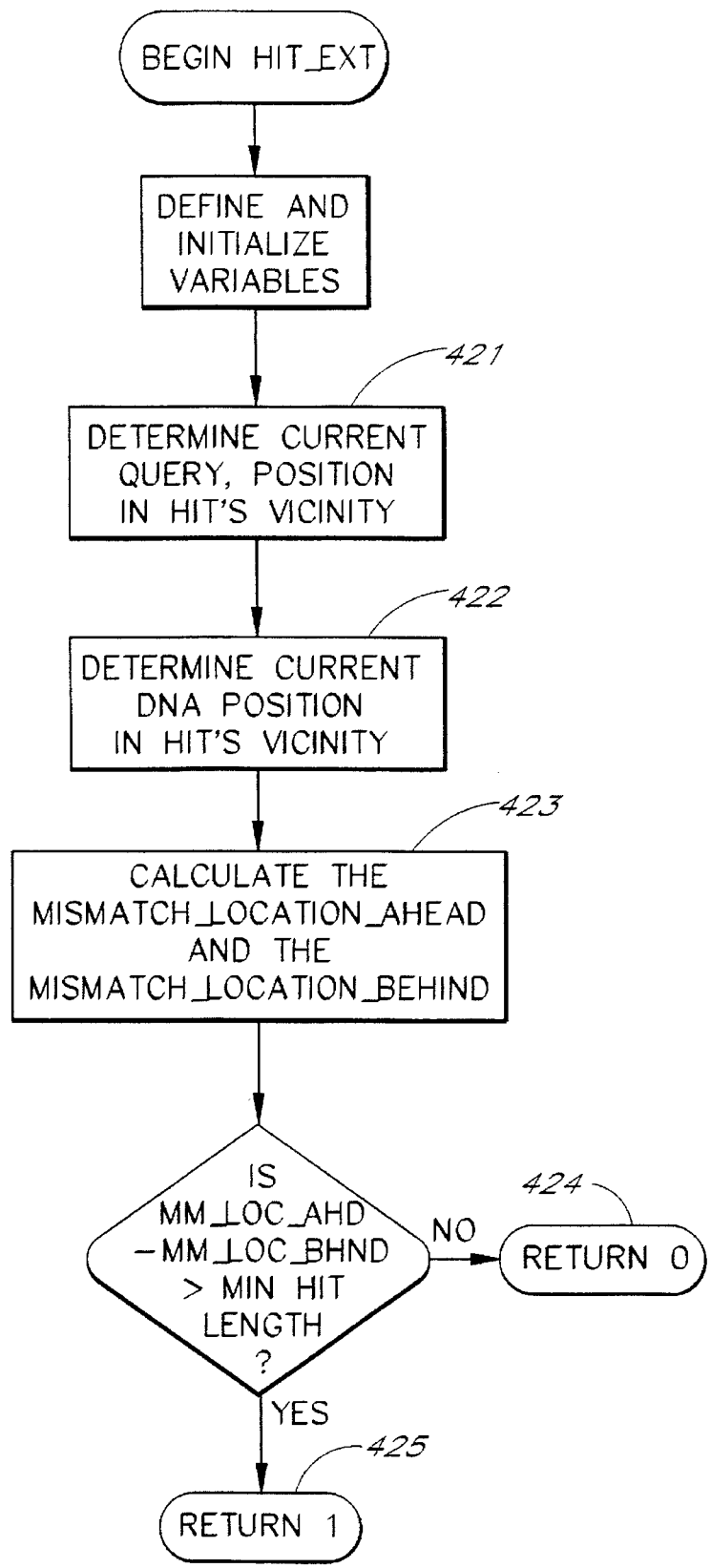
FIG. 28 is a flow chart of the hit_ext module of this invention.

The "hit_ext" module FIG. 28 determines the current query position in the hit's vicinity 421, determines the current DNA position in the hit's vicinity 422, and creates the list of mismatch positions (i.e., the mismatch_location_ahead 423, the mismatch_location_behind 423 and the kernel match location). If the hit is weak 424, the "hit_ext" module FIG. 28 returns "0" to the "q_colour" module FIG. 27. If the hit has a chance to contain 425, the module returns "1" to the "q_colour" module FIG. 27. A hit has a chance to contain, and is therefore not considered weak, if the mismatch_location_ahead—the mismatch_location_behind is greater than the min_hit_length. If not, it is a short hit and is too weak.

Figure 29:
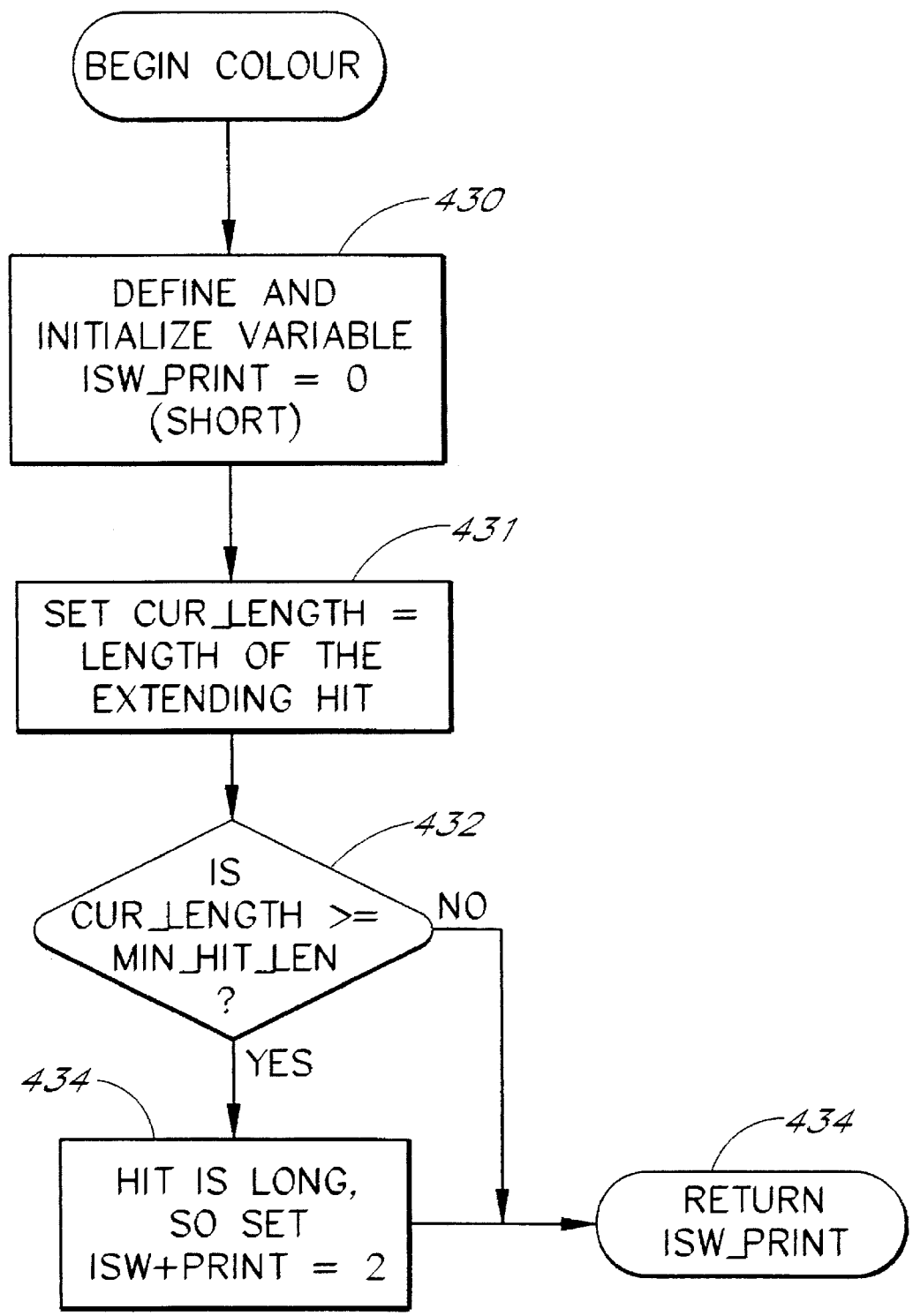
FIG. 29 is a flow chart of the colour module of this invention.

If the "hit_ext" module FIG. 28 tells the "q_colour" module FIG. 27 that the hit was not a weak one, then the "q_colour" module determines whether the current hit is long enough 398 by calling the "colour" module FIG. 29. The "colour" module FIG. 29 performs query_colour modification by the hit data, starting at pos_query and described by mismatch_location_ahead and mismatch_location_behind. After the variables to be used in this module are defined, variable isw_print (which is the switch indicating the hit length) is initialized to zero 430. The cur_length is then set equal to the length of the extending hit 431 (mismatch_location_behind[i] +mismatch_location_ahead[j]−1). Next, if cur_length is greater than or equal to the min_hit_length 432 (i.e., the minimum considered probe size), the hit is considered long and isw_print is set equal to two 433. The value of isw_print is then returned 434 to the "q_colour" module FIG. 27.

If the length of the extending hit is longer than the min_hit_length, the hit is considered long 399. Otherwise, the hit is considered short. If the hit is short, nothing more is done to the current hit and the module begins again. If, on the other hand, the hit is considered long 399, the "q_colour" module FIG. 27 prints the current extended hit 400. The current extended hit can be printed in ASCII, printed in a binary file, or printed to a memory file. The "q_colour" module FIG. 27 then repeats until the end of the linked list is reached.

d. Outputs

The output of the k_diff program may be either a binary file containing the number of extended hits and the k_mismatch hit locations (see FIG. 30), or the output may be kept in memory without writing it to a file. See Section 1(d)(iv) for more detail.

3. Description of the H-Site Model Program a. Overview

In this invention, the second hybridization strength model is termed the H-Site Model (see FIG. 12 for user selection of this model). The formula used in the H-Site Model is an expression of the fact that melting temperature Tm is a function of both probe length and percent of GC content. This basic formula has been modified in this invention to account for the presence of mismatches. Each percent of mismatch reduces the melting temperature Tm by an average of 1.25 degrees (2 degrees C for an AT mismatch, and 4 degrees C for a GC mismatch).

In addition, this implementation of the invention does some preliminary preprocessing of the GenBank database to sort out and select the cDNA sequences. This is done by locating a keyword (in this case CDS) in each GenBank record.

There are a number of modules in the present embodiment of the H-Site Model contained in this invention. Each step of the processing involved in the H-Site Model is more fully explained below, and is accompanied by detailed flow charts.

b. Inputs

There are two basic user-selected inputs for the H-Site Model (see FIG. 12C): 1) the melting temperature Tm 72 for which probes are being designed (i.e., the melting temperature that corresponds to a particular experiment or condition the user desires to simulate); and 2) the nucleation threshold 73, which is the number of base pairs constituting a nucleation site. The user is also required to select the 1) target species 11 gene sequence(s) (DNA, mRNA or cDNA) for which probes are being designed; 2) the preparation 12 of all sequences with which hybridizations are to be calculated; and 3) the probe output file 13. The preparation file is the most important, as discussed below.

c. Organization of the M-Site Model Program

The current implementation of the H-Site Model program of this invention is distributed between five files containing numerous modules. The main file is designated by the inventors as "ds.cpp" in its uncompiled version. This file provides overall control to the entire OligoProbe Design-Station invention. It is divided into six sections. Section 0 defines and manipulates global variables. Section 1 controls general variable definition and initialization (including the arrays and memory blocks). It also reads and writes buffers for user input selections, and constructs multi buffers.

Section 2 sets up and initializes various "snippet" variables (see section below for a complete definition of the term snippet), converts base pair characters to a representation that is 96 base pairs long and to ASCII base pair strings, and performs other sequence file manipulation such as comparing snippets. This section also reads the sequence format file, reads base pairs, checks for and extracts sequence identification information (such as ORIGIN and LOCUS) and filters out sequences beginning with numbers.

Section 3 involves preparation file manipulation. This section performs the preprocessing on the PRP file discussed above. It also merges and sorts the snippet files, creates a PRP file and sorts it, and outputs the sorted snippets. Next, this section streams through the PRP file.

Section 4 contains the essential code for H-Site Model processing (see FIGS. 31 through 33 for details, discussed below). Streams are set up, and then RIBI comparisons are performed for hybridizations (see file "ribi.cpp" for definitions of RIBI search techniques). Next, probes are generated, binding strength is converted to melting temperature, and hybridizations are calculated and stored (including hybridization strength). Lastly, other H-Site calculations are performed.

Section 5 is concerned with formatting and presenting diagnostic and user file (test.out, test1.out, and test2.out files) output. This section also handles the graphing functions (the MPSD diagram in particular). In addition, this section calculates the hairpin characteristics for the H-Site Model candidate probes.

The second H-Site Model file, designated as "ds.h" defines data variables and structures. Section 1 of this file concerns generic data structures (including memory blocks and arrays, and file inputs and outputs). Section 2 defines the variables and structures used with sequences, probes and hybridizations. Section 3 defines variables and structures concerned with protocols (i.e., function prototypes, graphing, etc.).

The third H-Site Model file, designated as "funcdoc.txt", contains very detailed documentation for this implementation of the H-Site Model program. Numerous variables and structures are also defined. The flow of the program is clearly shown in this file.

The fourth H-Site Model file, designated as "ribi.h" handles the sequence comparisons. The fifth and last H-Site Model file, designated as "ribi.cpp", performs internal B-Tree indexing. Definitions of Red-black Internal Binary Index (RIBI) searching are found in this file. Definitions are also included for the concepts keyed set, index, binary tree, internal binary index, paths, and red-black trees. Implementation notes are also included in this file.

d. Processing

Implementation of the H-Site Model in this invention is done in three stages. First, the invention creates the preparation (PRP) file, which contains all relevant information from the sequence database. This is the preprocessing stage discussed above. Next, the target is prepared by the program. Lastly, the invention calculates the MPSD data using the PRP file and target sequence to find probes.

i. Creation of the Preprocessed Preparation File

Figure 31:
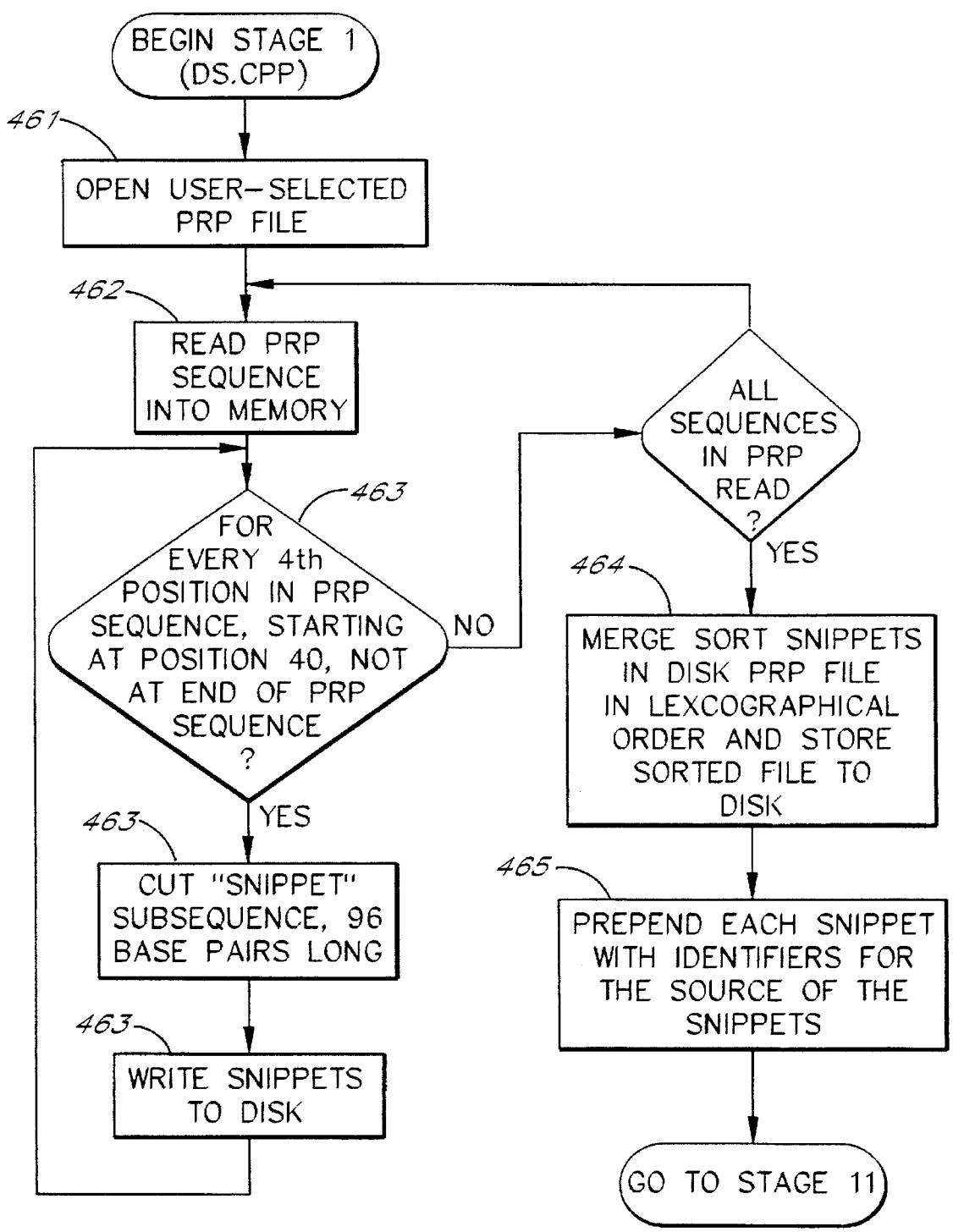
FIG. 31 is a flow chart of the H-Site Model, stage I, covering the creation of a preprocessed preparation file of this invention.

FIG. 31. Step 1: The program first opens the sequence database for reading into memory 461, 462. Step 2: Next, as sequence base pairs are read in 462, "snippets" are saved to disk 463, along with loci information. A snippet is a fixed-length subsequence of a preparation sequence. The purpose of snippets is to allow the user to examine a small portion of a preparation sequence together with its surrounding base pairs. Snippets in the implementation of this invention are 96 base pairs long (except for snippets near the end or beginning of a sequence, which may have fewer base pairs). The "origin" of the snippet is in position 40. For snippets taken near the beginning of a sequence, some of the initial 40 bases are undefined. For snippets near the end of a sequence, some of the final 55 bases are undefined. Snippets are arranged in the preparation file (PRP) in sorted order (lexicographical order beginning at position 40). In this invention, the term "lexicographical order" means a preselected order, such as alphabetical, numeric or alphanumeric. In order to conserve space, snippets are only taken at every 4th position of the preparation sequence.

Step 3: The snippets are merge sorted 464 to be able to search quickly for sequences which pass the "screen", discussed below. Step 4: The merged file is prepended with identifiers for the sources of the snippets 465. This is done to identify the loci from which hybridizations arise.

ii. Target Preparation

Figure 32:
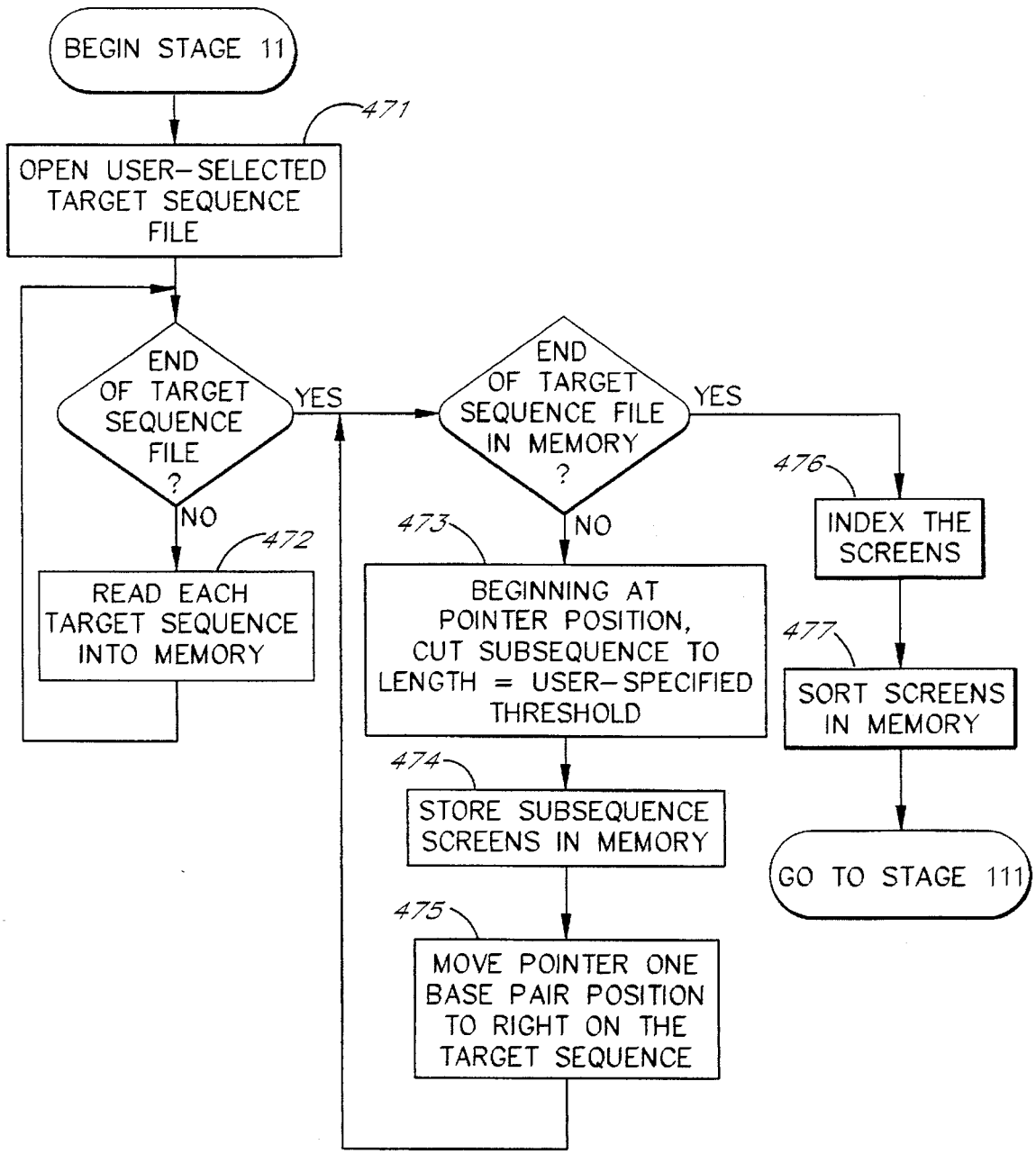
FIG. 32 is a flow chart of the H-Site Model, stage II, covering the preparation of the target sequence(s)
Figure 33A:
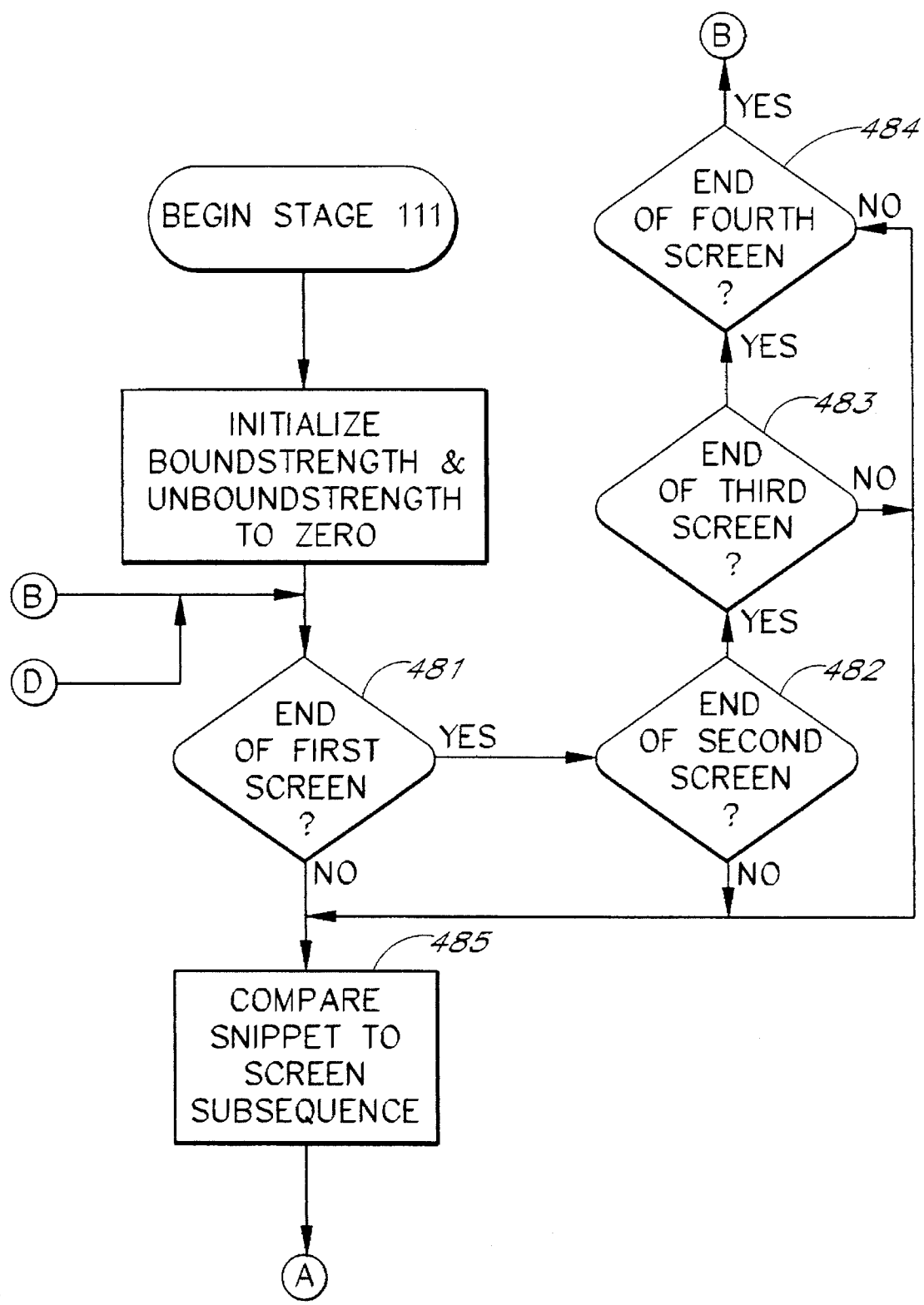
FIGS. 33A–33D are flow charts of the H-Site Model, stage III, covering the calculation of MPSD data.
Figure 33B:
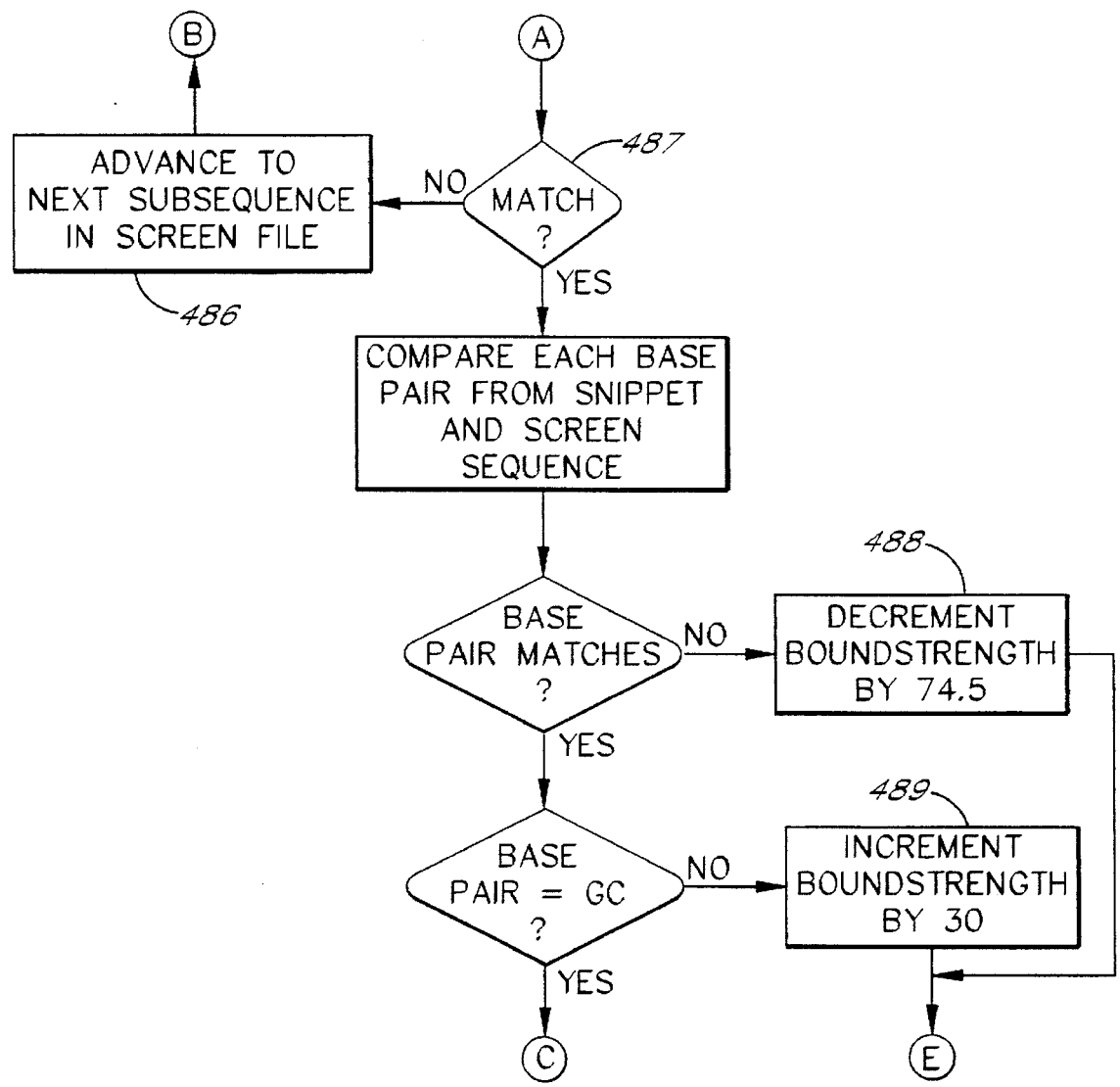
Figure 33C:
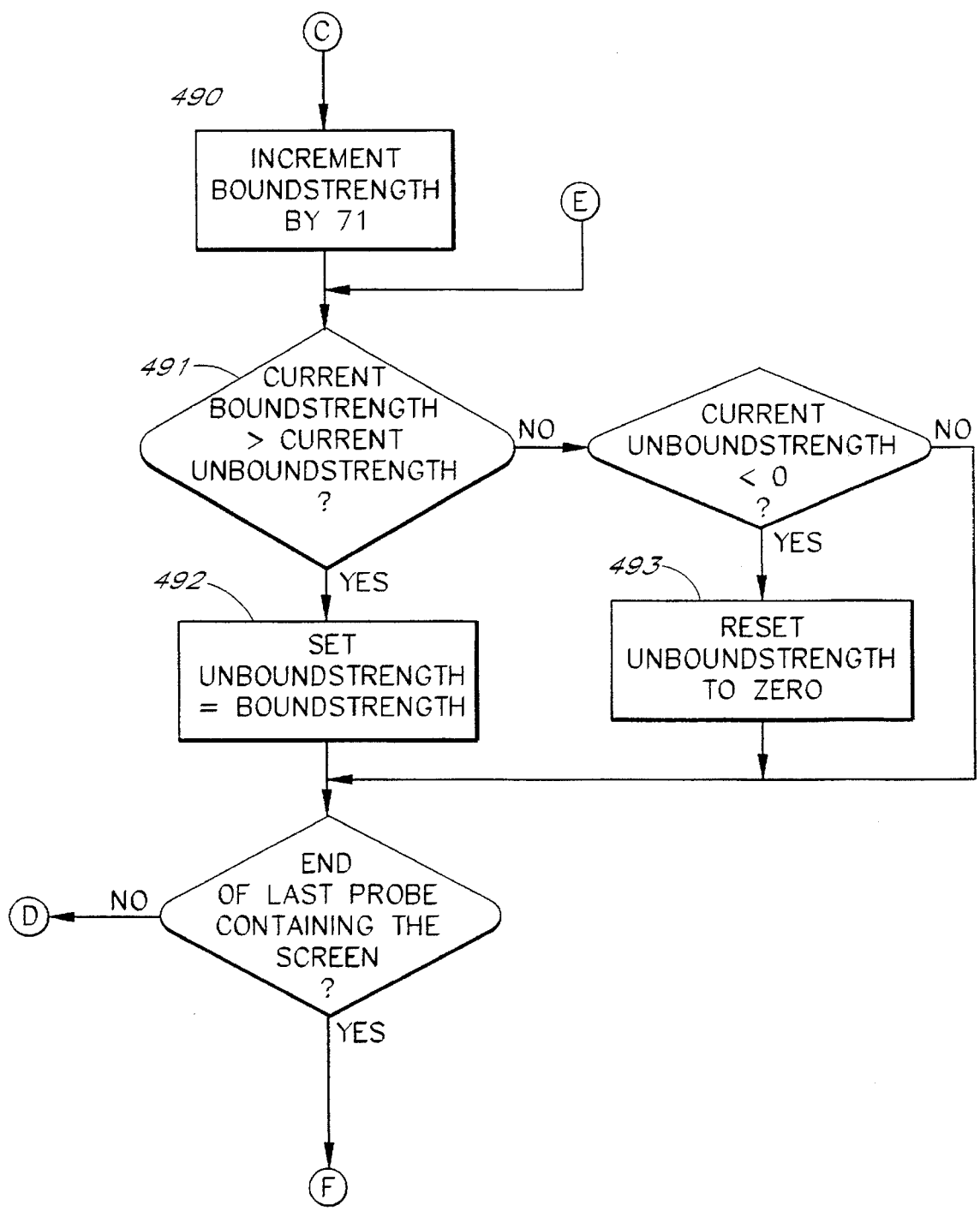
Figure 33D:
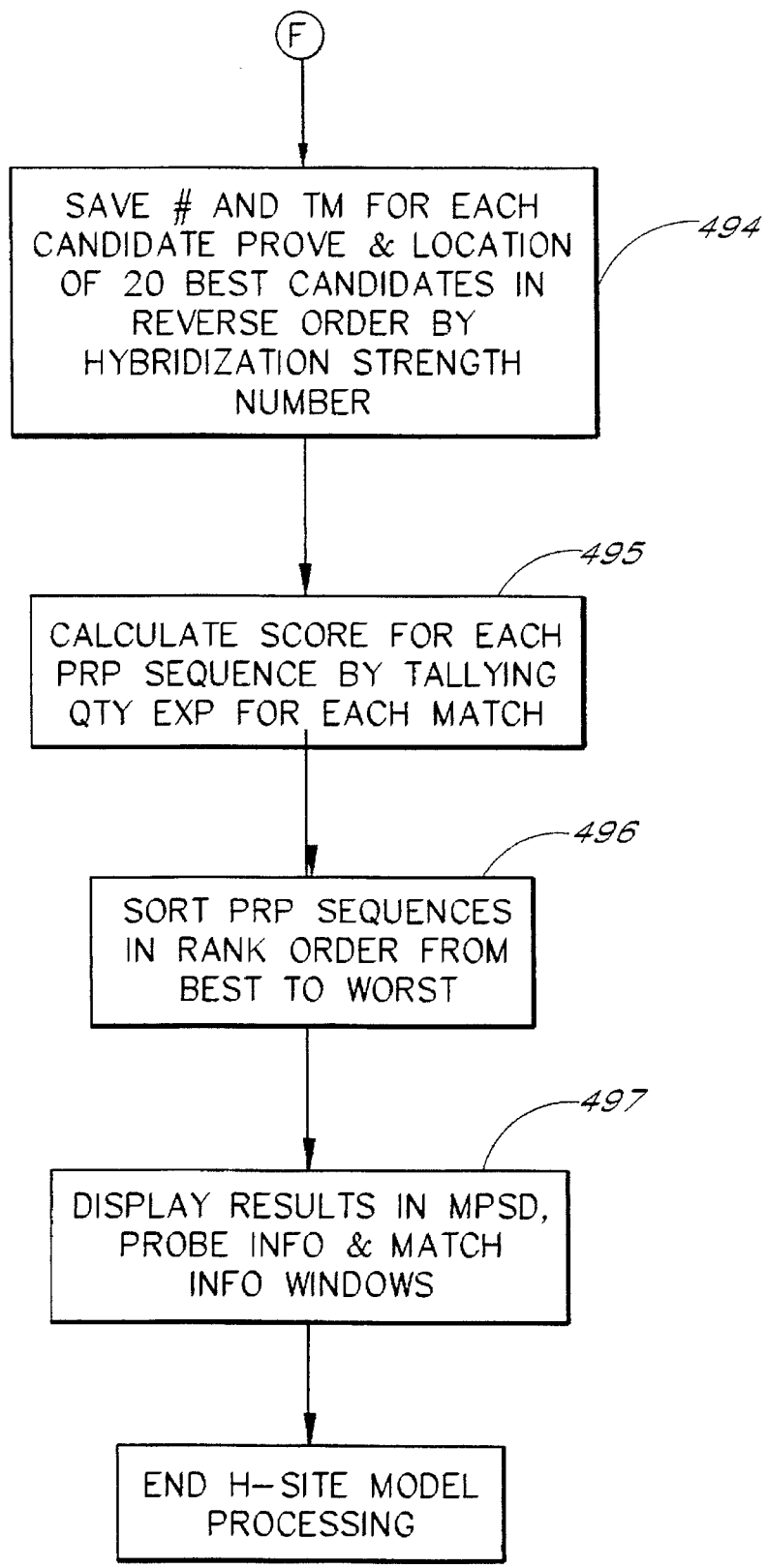

FIG. 32. Step 1: The target sequence file is opened 471 and read into memory 472. For each position in the target mRNA, the probe defined at that starting position is the shortest subsequence starting at that position whose hybridization strength is greater than the user specified melting temperature Tm. Typically, the probes are of length 18 to 50. Step 2: Four lists of "screens" are formed 473, 474, 475, each shifted by one base pair 475 to correspond to the fact that snippets are only taken at every four base pairs. A screen is a subsequence of the target mRNA of length equal to the screening threshold specified by the user. The screens are then indexed 476 and sorted in memory 477.

iii. Calculation of the MPSD Data

FIG. 33. Step 3: This step is the heart of the process. Step 3a: The program streams through the following five items in sync, examining them in sequential order: the snippet file and the four lists of screens 481–484. Step 3b: Each snippet is compared to a screen 485. Step 3c: If the snippet does not match, whichever stream is behind is advanced 486 and Step 3b is repeated. If the snippet does match, Step 4 is performed.

Step 4: If a snippet and a matching screen were found in Step 3b 487, the hybridization strength of the binding between the sequence containing the snippet and all of the probes containing the screen is calculated (see Step 5). Double counting is avoided by doing this only for the first matched screen containing the probe. Each pair of bases is examined and assigned a numerical binding strength. An AT pair would be assigned a lower binding strength than a GC pair because AT pairs have a lower melting temperature Tm. The process is explained more fully below at Step 5b.

Step 5: The hybridization strengths between sequence and all the probes containing it are calculated using a dynamic programming process. The process is as follows: Step 5a: Begin at the position of the first probe containing the given screen but not containing any other screens which start at an earlier position and also match the sequence. This is done to avoid double counting. Two running totals are maintained: a) boundStrength, which represents the hybridization strength contribution which would result if the sequence and probe were to match exactly for all base pairs to the right of the current position, and b) unboundStrength, which represents the strength of the maximally binding region. Step 5b: At each new base pair, the variable boundStrength is incremented by 71 if the sequence and probe match and the matched base pair is GC 489, incremented by 30 if the matched base pair is AT 490 (i.e., this number is about 42.25% of the first number 71), and decremented by 74.5 if there is not a match 488 (i.e., this number is about 5% larger than the first number 71). Step 5c: If the current boundStrength exceeds the current unboundStrength 491 (which was originally initialized to zero), a new binding region has been found, and unboundStrength is set equal to boundStrength 492. Step 5d: If the current boundStrength is negative, boundStrength is reset to zero 493. Step 5e: If the current position is at the end of a probe, the results (the hybridization strengths) are tallied for that probe. Step 5f: If the current position is at the end of the last probe containing the screen, the process stops.

Step 6: A tally is kept of the number and melting temperature of the matches for each candidate probe, and the location of the best 20 candidates, using a priority queue (reverse order by hybridization strength number) 494. Step 7: A numerical "score" is kept for each preparation sequence by tallying the quantity exp (which can be expressed as $\Sigma e^{-Tm}$) for each match 495, where Tm is the melting temperature for the "perfect" match, the probe itself. In other words, the probe hybridizes "perfectly" to its target.

Step 8: Hairpins are calculated by first calculating the complementary probe. In other words, the order of the bases in the candidate probe are reversed (CTATAG to GATATC), and complementary base pairs are substituted (A for T, T for A, G for C, and C for G, changing GATATC to CTATAG in the above example). Next, the variable representing the maximum hairpin length for a candidate probe is initialized to zero, as is the variable representing a hairpin's distance. For each offset, the original candidate probe and the complementary probe just created are then aligned with each other and compared. The longest match is then found. If any two matches have the same length, the one with the longest hairpin distance (i.e., the number of base pairs separating the match) is then saved.

Step 9: The preparation sequences are then sorted 496 and displayed in rank order, from best to worst 497. Step 10: The resulting MPSD, which includes all candidate probes, is then displayed on the screen. Step 11: The best 20 matches are also printed or displayed in rank order, as the user requests 497.

e. Outputs

The outputs of the H-Site Model are fully described in Section 1(d)(iv), above, and illustrated in FIGS. 14 through 16. Samples of the two output files created by the H-Site Model are shown in FIGS. 34A and 34B.

4. Description of the Mitsuhashi Probe Selection Diagram Processing

Figure 35:
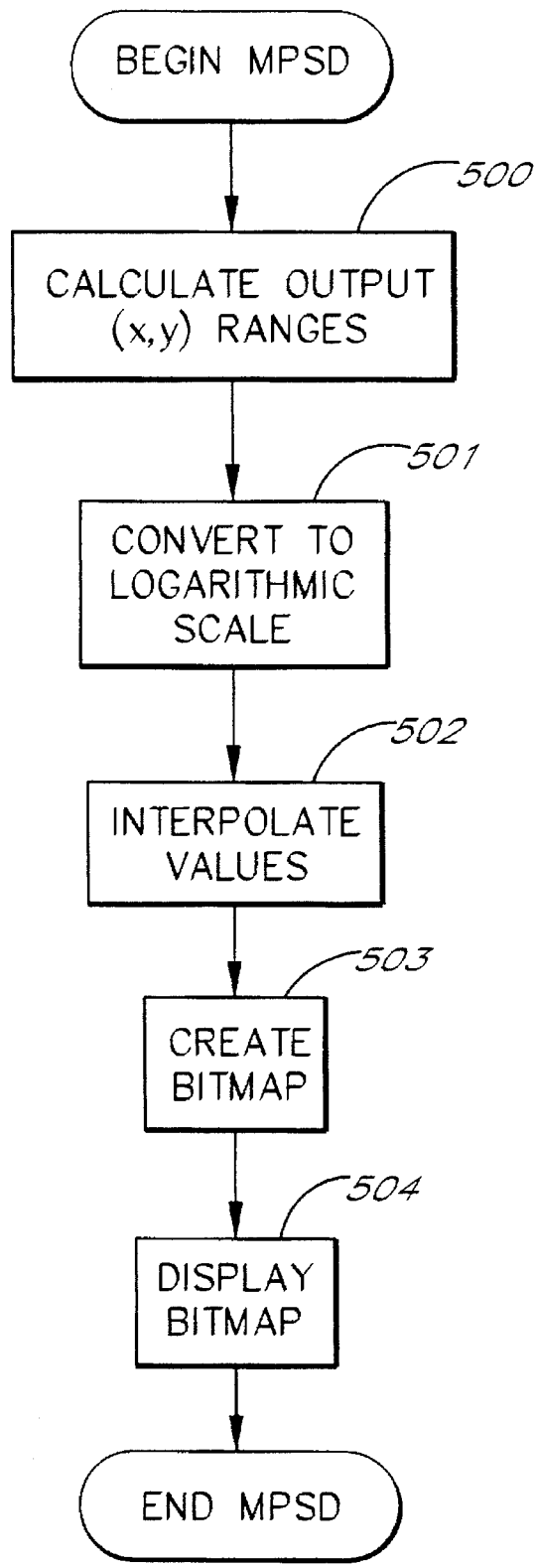
FIG. 35 is a flow chart of the processing used to create the Mitsuhashi probe selection diagram (MPSD)

Once the Mitsuhashi Probe Selection Diagram (MPSD) data has been calculated by the H-Site Model program (see stage three and FIG. 33, discussed above), it is necessary to convert this data to pixel format and plot a graph. An overview of this process is shown in FIG. 35. First, the program calculates the output (x,y) ranges 500. Next, these are converted to a logarithmic scale 501. The values are then interpolated 502, and a bitmap is created 503. Lastly, the bitmap is displayed on the screen 504 in MPSD format (discussed above in section 1(e)(i)). A sample MPSD is shown in FIG. 14.

5. Description of the MatchInfo Window Processing

Figure 36:
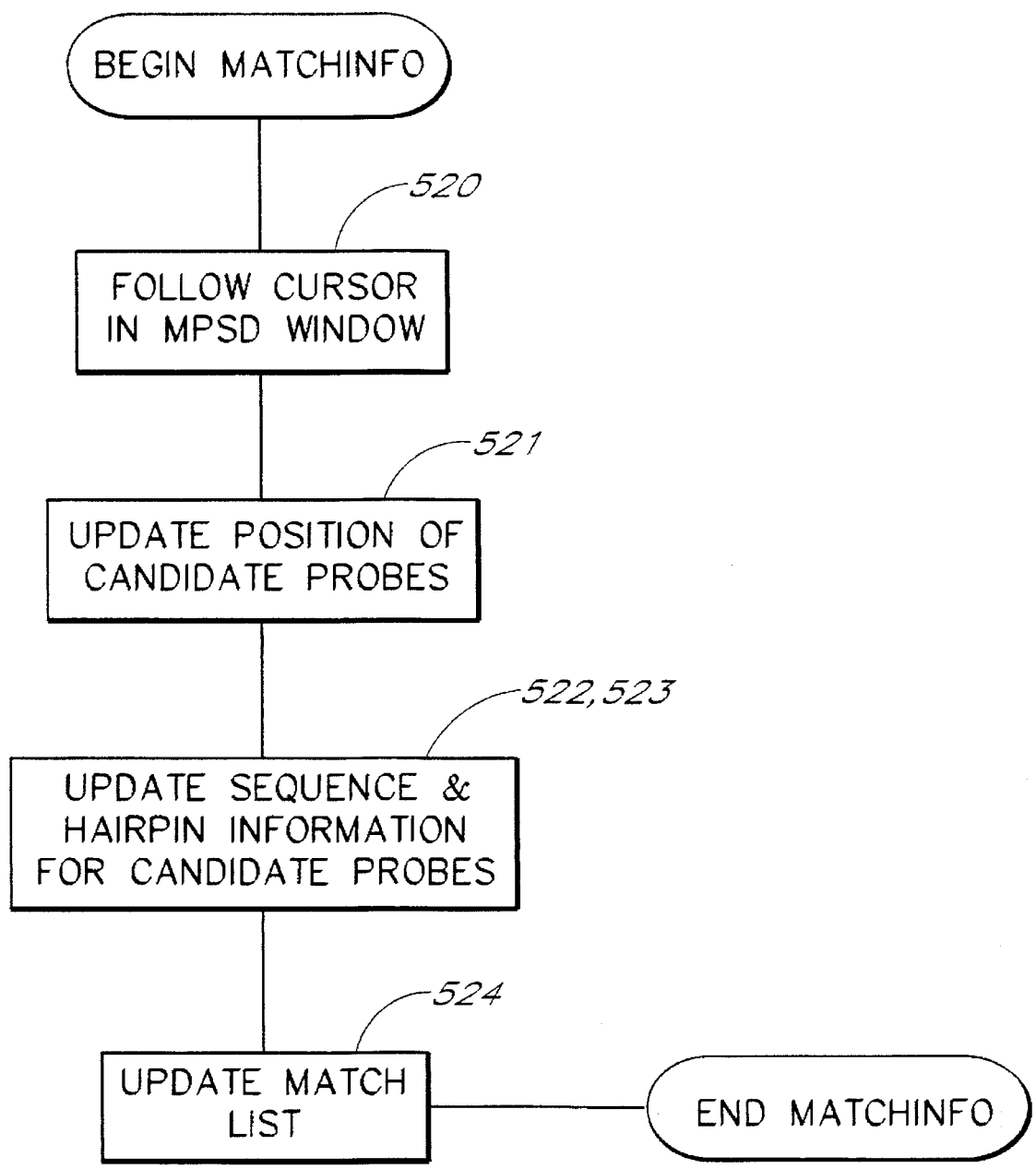
FIG. 36 is a flow chart of processing used to create the matchinfo window.

The ProbeInfo and MatchInfo windows are discussed in great detail in Section 1(e)(ii), and a sample of these windows is shown in FIG. 15. An overview of the processing involved in creating the MatchInfo portion of the window is given in the flow chart in FIG. 36. First, as the user moves the MPSD cursor 570 (seen as a vertical line bisecting the MPSD window), the program updates the position of the candidate probe shown under that cursor position 521. Next, based upon the candidate probe's position, the program updates the sequence 522 and hairpin information 523 for that probe. This updated information is then displayed in an updated match list 524, shown in the MatchInfo window.

XVII. Detection Kits

The present invention can preferably be embodied in a kit for the detection of an organism, infectious agent, or biological component contained in a biological sample. Such a kit can take a variety of forms, as will be apparent to those of skill in the art.

In one embodiment, the present invention comprises a kit for identifying the presence of a particular species of fungus in a biological sample. Such a kit includes at least one specific polynucleotide probe and a common probe, as described above. In a preferred embodiment, a plurality of specific probes are included, and such probes are preferably immobilized on one or more solid supports. In a more preferred embodiment, each of the plurality of specific probes is immobilized on a different solid support. For example, a microtiter plate having a plurality of wells can have a different polynucleotide probe immobilized to each well. If such probes contain sequences specific to the ribosomal RNA of different species of fungi, the kit can be used to test a single biological sample for the presence of a plurality of fungi.

Figure 4:
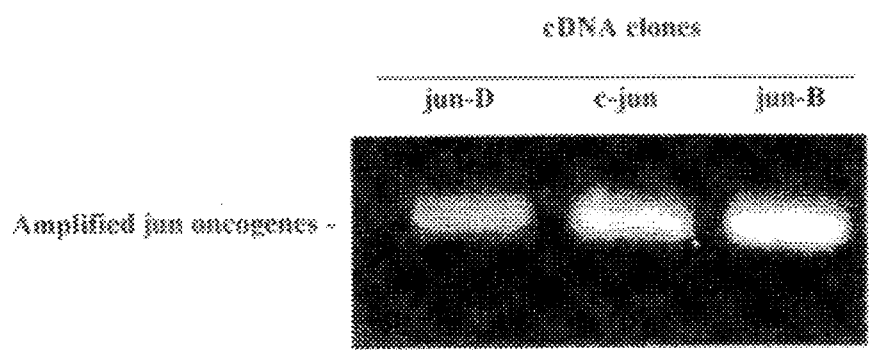
FIG. 4 is a picture of a gel showing the outcome of an experiment in which jun-D, c-jun, and jun-D jun oncogene subtypes were amplified using SEQ ID NO:728 and SEQ ID NO:729.

An example of such a kit using microtiter wells as the solid supports is shown schematically in FIG. 4. In this figure, the presence of the ribosomal RNA of a particular species of fungus, in this case *Candida albicans*, is detected in a well 56, which is darkened to show a positive result. No probe has been immobilized to well 52 in order to provide a negative control. Well 54, on the other hand, has immobilized to its walls a common probe, such as SEQ ID NO:1, which is complementary to a sequence present in the ribosomal RNA of the fungi being tested for. This provides a positive control, since well 54 should show a positive result whenever a positive result is detected in well 56 or any of the other wells in this embodiment of the kit.

Well 54 also provides a means of detecting the presence of fungi which do not contain the specific ribosomal RNA sequences being probed by the specific polynucleotide probes. For example, if a mutant strain of *Candida albicans* which does not contain the specific sequence complementary to the probe used in well 56 is present in a sample tested with the kit illustrated in FIG. 4, well 56 would not show a positive result. Well 54 would, however, indicate the presence of a fungal pathogen, as long as the mutant strain did not contain a mutation in the common sequence detected in well 54 which interfered with the hybridization of that sequence to the common probe immobilized to the walls of well 54.

In addition to specific probes, common probes, and solid supports, other elements can also be included in the present kit. For example, appropriate buffers for hybridizing DNA or RNA to the probes in the kit can be included. Labels, as described above, can also be incorporated which are attached to a common probe.

In an alternative embodiment, the kit can include PCR primers such as those previously described. Such a kit could comprise a common primer and a specific primer, 2 common primers, or 2 specific primers identified through the method of the present invention. Other components, such as a reverse transcriptase, a DNA polymerase like Taq polymerase and dNTP's can also be included in this embodiment of the present kit.

The forgoing embodiments of the kit of the present invention can be adapted to perform the methods of the present invention that involve PCR as well. In this embodiment, the kit additionally includes a reverse transcriptase and a polymerase, preferably a DNA polymerase that has significant polymerase activity at temperatures above 50° C., such as Taq DNA polymerase.

XVIII. Conclusion

All references cited herein are hereby explicitly incorporated by this reference thereto. Although the invention has been described with reference to certain particular exemplary embodiments of various aspects, these embodiments are intended only to illustrate and not to limit the present invention. Accordingly, the scope of the present invention is to be determined upon reference to the appended claims.
GTCCACCGCGTCGAATTTGTC

TABLE I

Common probe (Com-392)* for Fungi

| Species | | GenBank name | Com-392 GAGGGAGCCTGAGAAACG |
|---|---|---|---|
| I. Fungi | | | |
| *Pneumocystis carinii* | | PMC16SRR1 | -------------------- |
| *Cryptococcus neoformans* | | CPCDA | -------------------- |
| *Coccidiodes immitis* | | COIDA | -------------------- |
| *Blastomyces dermatitidis* | | BLODA | -------------------- |
| *Aspergillus* | *fumagatus* | ASNDA | -------------------- |
| | *fumigatus* | ASNRR5SS | -------------------- |
| | *fumigatus* | ASNRRSSB | -------------------- |
| *Candida* | *albicans* | YSASRSUA | -------------------- |
| | *albicans* | YSAL16S | -------------------- |
| | *lusitaniae* | YSASRRNAA | -------------------- |
| | *lusitaniae* | YSASRSUE | -------------------- |
| | *kefyr* | YSASRSUB | -------------------- |
| | *krusei* | YSASRRNAC | -------------------- |
| | *krusei* | YSASRSUD | |
| | *tropicalis* | YSASRRNAB | -------------------- |
| | *tropicalis* | YSASRSUG | -------------------- |
| | *viswanathii* | YSASRSUH | -------------------- |
| | *parapsilosis* | YSASRSUF | -------------------- |
| | *guilliermondii* | YSASRSUC | -------------------- |
| | *glabrata* | YS5CRRNAS | -------------------- |

*Com-392 is identical among 107 different rRNAs registered in GenBank

TABLE II

Common probe (Com-419)* for Fungi

| Species | | GenBank name | Com-419<br>TCCAAGGAAGGCAGCAGG |
|---|---|---|---|
| I. Fungi | | | |
| *Pneumocystis carinii* | | PMC16SRR1 | ──────────────── |
| *Cryptococcus neoformans* | | CPCDA | ──────────────── |
| *Coccidiodes immitis* | | COIDA | ──────────────── |
| *Blastomyces dermatitidis* | | BLODA | ──────────────── |
| *Aspergillus* | *fumagatus* | ASNDA | ──────────────── |
| | *fumigatus* | ASNRR5SS | ──────────────── |
| | *fumigatus* | ASNRRSSB | ──────────────── |
| *Candida* | *albicans* | YSASRSUA | ──────────────── |
| | *albicans* | YSAL16S | ──────────────── |
| | *lusitaniae* | YSASRRNAA | ──────────────── |
| | *lusitaniae* | YSASRSUE | ──────────────── |
| | *kefyr* | YSASRSUB | ──────────────── |
| | *krusei* | YSASRRNAC | ──────────────── |
| | *krusei* | YSASRSUD | ──────────────── |
| | *tropicalis* | YSASRRNAB | ──────────────── |
| | *tropicalis* | YSASRSUG | ──────────────── |
| | *viswanathii* | YSASRSUH | ──────────────── |
| | *parapsilosis* | YSASRSUF | ──────────────── |
| | *guilliermondii* | YSASRSUC | ──────────────── |
| | *glabrata* | YS5CRRNAS | ──────────────── |

*Com-419 is identical among 123 different rRNAs registered in GenBank

TABLE III

Common probe (Com-1705)* for Fungi

| Species | | GenBank name | Com-1205<br>ACGGGGAAACTCACCAGG |
|---|---|---|---|
| I. Fungi | | | |
| *Pneumocystis carinii* | | PMC16SRR1 | ──────────────── |
| *Cryptococcus neoformans* | | CPCDA | ──────────────── |
| *Coccidiodes immitis* | | COIDA | ──────────────── |
| *Blastomyces dermatitidis* | | BLODA | ──────────────── |
| *Aspergillus* | *fumagatus* | ASNDA | ──────────────── |
| | *fumigatus* | ASNRR5SS | ──────────────── |
| | *fumigatus* | ASNRRSSB | ──────────────── |
| *Candida* | *albicans* | YSASRSUA | ──────────────── |
| | *albicans* | YSAL16S | ──────────────── |
| | *lusitaniae* | YSASRRNAA | ──────────────── |
| | *lusitaniae* | YSASRSUE | ──────────────── |
| | *kefyr* | YSASRSUB | ──────────────── |
| | *krusei* | YSASRRNAC | ──────────────── |
| | *krusei* | YSASRSUD | ──────────────── |
| | *tropicalis* | YSASRRNAB | ──────────────── |
| | *tropicalis* | YSASRSUG | ──────────────── |
| | *viswanathii* | YSASRSUH | ──────────────── |
| | *parapsilosis* | YSASRSUF | ──────────────── |
| | *guilliermondii* | YSASRSUC | ──────────────── |
| | *glabrata* | YS5CRRNAS | ──────────────── |

*Com-1205 is identical among 42 different rRNAs registered in GenBank

TABLE IV

Common probe (Com-1544)* for Fungi

| Species | | GenBank name | Com-1544<br>TCGTGCTGGGGATAGAGC |
|---|---|---|---|
| I. Fungi | | | |
| *Pneumocystis carinii* | | PMC16SRR1 | ──────────────── |
| *Cryptococcus neoformans* | | CPCDA | ──────────────── |
| *Coccidiodes immitis* | | COIDA | ──────────────── |
| *Blastomyces dermatitidis* | | BLODA | ──────────────── |
| *Aspergillus* | *fumagatus* | ASNDA | ──────────────── |
| | *fumigatus* | ASNRR5SS | ──────────────── |
| | *fumigatus* | ASNRRSSB | ──────────────── |
| *Candida* | *albicans* | YSASRSUA | ──────────────── |

TABLE IV-continued

Common probe (Com-1544)* for Fungi

| Species | | GenBank name | Com-1544 TCGTGCTGGGGATAGAGC |
|---|---|---|---|
| | albicans | YSAL16S | ------------------ |
| | lusitaniae | YSASRRNAA | ------------------ |
| | lusitaniae | YSASRSUE | ------------------ |
| | kefyr | YSASRSUB | ------------------ |
| | krusei | YSASRRNAC | ------------------ |
| | krusei | YSASRSUD | |
| | tropicalis | YSASRRNAB | ------------------ |
| | tropicalis | YSASRSUG | ------------------ |
| | viswanathii | YSASRSUH | ------------------ |
| | parapsilosis | YSASRSUF | ------------------ |
| | guilliermondii | YSASRSUC | ------------------ |
| | glabrata | YS5CRRNAS | ------------------ |

*Com-392 is identical among 40 different rRNAs registered in GenBank

TABLE V

Probes for *Pneumocystis carinii* (Cari-685)

| Species | GenBank name | Cari-685 GCGCAACTGATCCTTCCC |
|---|---|---|
| I. Fungi | | |
| Pneumocystis carinii | PMC16SRR1 | ------------------ |
| Cryptococcus neoformans | CPCDA | -T--CGGC---G-----AT |
| Coccidiodes immitis | COIDA | A-CTGGT--------G--A |
| Blastomyces dermatitidis | BLODA | A-CTGGT--------G--A |
| Aspergillus fumagatus | ASNDA | A-CTGGT--------G--A |
| fumigatus | ASNRR5SS | ----CGGC---GG---AT |
| fumigatus | ASNRRSSB | ----CGGC---GG---AT |
| Candida albicans | YSASRSUA | -------G-C---AGCTTG |
| albicans | YSAL16S | ------G-C---AGCTTG |
| lusitaniae | YSASRRNAA | -------G-C---AGCTTG |
| lusitaniae | YSASRSUE | ------G-C---AGCTTG |
| kefyr | YSASRSUB | -------G-C---AGCTTG |
| krusei | YSASRRNAC | -------G-C---AGCTTG |
| krusei | YSASRSUD | -------G-C---AGCTTG |
| tropicalis | YSASRRNAB | -------G-C---AGCTTG |
| tropicalis | YSASRSUG | ------G-C---AGCTTG |
| viswanathii | YSASRSUH | ------G-C---AGCTTG |
| parapsilosis | YSASRSUF | ------G-C---AGCTTG |
| guilliermondii | YSASRSUC | -------G-C---AGCTTG |
| glabrata | YS5CRRNAS | ------G-C---AGCTTG |
| II. Highest homologous sequence in GenBank | | |
| Human TAN-1 | HUMTAN1 | --------A-C-------- |
| Abccelsyn xylium | ABCCELSYN | -A-G-------------- |
| Human mRNA neuron | HUMNSEMRNA | CTC-C------------- |

TABLE VI

Probes for Pneumocystis Carinii (Carl-1056)

| Species | GenBank name | Cari-1056 GGCGATGTTTTTTTCTTGACTCG |
|---|---|---|
| I. Fungi | | |
| Pneumocystis carinii | PMC16SRR1 | ----------------------- |
| Cryptococcus neoformans | CPCDA | --------C--CA----AAATA--T |
| Coccidiodes immitis | COIDA | --------G--CA----AAATT--T |
| Blastomyces dermatitidis | BLODA | --------G--CA----AAATT--T |
| Aspergillus fumagatus | ASNDA | ----G-----C-A-GA-----C-- |
| fumigatus | ASNRR5SS | ----G-----C-A-GA-----C-- |

TABLE VI-continued

Probes for Pneumocystis Carinii (Cari-1056)

| Species | GenBank name | Cari-1056 GGCGATGTTTTTTCTTGACTCG |
|---|---|---|
| fumigatus | ASNRRSSB | ----G-----C-A-GA----C-- |
| Candida albicans | YSASRSUA | -TT-T----C----A-----G-A |
| albicans | YSAL16S | -TT-T----C----A-----G-A |
| lusitaniae | YSASRRNAA | ----GC---CA---AG----G-- |
| lusitaniae | YSASRSUE | ----GC---CA---AG----G-- |
| kefyr | YSASRSUB | -------G--CA---AAATTTCT |
| krusei | YSASRRNAC | ---CG-T---AG-C----GAGTG |
| krusei | YSASRSUD | TATTT----NG-----A-GACCA |
| tropicalis | YSASRRNAB | -TT-T----C----A-----G-A |
| tropicalis | YSASRSUG | -TT-T----C----A-----G-A |
| viswanathii | YSASRSUH | -TT-T----C----A-----G-A |
| parapsilosis | YSASRSUF | -TT-T----C----A-----G-A |
| guilliemondii | YSASRSUC | --T-T----C-K--T-----G-A |
| glabrata | YS5CRRNAS | --T-G----------AG----C-A |
| II. Highest homologous sequence in GenBank | | |
| Tobacco chloroplast | TOBCPTGRG | C-A-CC----------------- |
| Aureobasidium pullulans | AURRR16S | ----------A-CA-T-------- |
| N. tabacum | TOBCOCG | C-A-CC----------------- |

TABLE VII

Probes for Aspergillus (Asp-693)

| Species | GenBank name | Asp-693 CTTCTGGGGAACCTCATGG |
|---|---|---|
| I. Fungi | | |
| Pneumocystis carinii | PMC16SRR1 | AACAC------A-----CCA |
| Cryptococcus neoformans | CPCDA | AACAC------A-----CCA |
| Coccidiodes immitis | COIDA | --------------CT---- |
| Blastomyces dermatitidis | BLODA | ---C-----A-G--C----- |
| Aspergillus fumagatus | ASNDA | -------------------- |
| fumigatus | ASNRR5SS | -------------------- |
| fumigatus | ASNRRSSB | -------------------- |
| Candida albicans | YSASRSUA | AAAGG---C--------TC |
| albicans | YSAL16S | AACAC------A-----CCA |
| lusitaniae | YSASRRNAA | AA---T-----A---CGTC |
| lusitaniae | YSASRSUE | AA---T-----A---CGTC |
| kefyr | YSASRSUB | -------CT-----GTACT |
| krusei | YSASRRNAC | AACAC------A-----CCA |
| krusei | YSASRSUD | --------CT-S-----GG-C |
| tropicalis | YSASRRNAB | --------CT-G---TT---- |
| tropicalis | YSASRSUG | --------CT-G---TT---- |
| viswanathii | YSASRSUH | --------CT-G---TT---- |
| parapsilosis | YSASRSUF | AACAC------A-----CCA |
| guilliemondii | YSASRSUC | --------CT-----ATTC-C |
| glabrata | YS5CRRNAS | --------CT-----C---A-T |
| II. Highest homologous sequence in GenBank | | |
| Penniclium notatum sub | PNNDA | -------------------- |
| Human HLA-B-AT3 | HUMBAT3A | ----------------GC-A- |
| Rat olfactory protein | RATOLFPRON | ---C--------------CA |

TABLE VIII

Probes for Aspergillus (Asp-1046)

| Species | GenBank name | Asp-1046 GGCGGTGTTTCTATGATGACC |
|---|---|---|
| I. Fungi | | |
| Pneumocystis carinii | PMC16SRR1 | ----A-----T-T-CT----T |
| Cryptococcus neoformans | CPCDA | TTGTTG-------G---CG-- |
| Coccidiodes immitis | COIDA | ACGT---G------TT--TTG |

TABLE VIII-continued

Probes for Aspergillus (Asp-1046)

| Species | GenBank name | Asp-1046 GGCGGTGTTTCTATGATGACC |
|---|---|---|
| *Blastomyces dermatitidis* | BLODA | -A---G---CT----------- |
| *Aspergillus fumagatus* | ASNDA | --------------------- |
| *fumigatus* | ASNRR5SS | --------------------- |
| *fumigatus* | ASNRRSSB | --------------------- |
| *Candida albicans* | YSASRSUA | CCTTCG-GC---T------TT |
| *albicans* | YSAL16S | CCTTCG-GC---T------TT |
| *lusitaniae* | YSASRRNAA | -----C---CA-T-AG----G |
| *lusitaniae* | YSASRSUE | -----C---CA-T-AG----G |
| *kefyr* | YSASRSUB | --T-------T-C-T------ |
| *krusei* | YSASRRNAC | -A----C-AC-----G-A-G- |
| *krusei* | YSASRSUD | -A----C-AC-----G-A-G- |
| *tropicalis* | YSASRRNAB | TCTTCG-AC---T------TT |
| *tropicalis* | YSASRSUG | TCTTCG-AC---T------TT |
| *viswanathii* | YSASRSUH | CCTTCG-GC---T------TT |
| *parapsilosis* | YSASRSUF | ----A--G---AT-C-AATTT |
| *guilliermondii* | YSASRSUC | TCTTTGAGC---T------TT |
| *glabrata* | YS5CRRNAS | --T-------T-T-AG----- |
| II. Highest homologous sequence in GenBank | | |
| *Nanochlorum eucaryotum* | NANRRN18S | -CG-------T-T-------- |
| *Moraxella sp.* MspI | MBOMSPI | TCTA-------A--------T |
| *E. coli* cvaA,B operon | ECOCVAB | -T--------G-G------TG |

TABLE IX

Probes for Blastomyces (Blast-694)

| Species | GenBank name | Blast-694 TCCTGGGAAGCCCCATG |
|---|---|---|
| I. Fungi | | |
| *Pneumocystis carinii* | PMC16SRR1 | GT---T--T----TTA- |
| *Cryptococcus neoformans* | CPCDA | -G---AA-------GAC |
| *Coccidiodes immitis* | COIDA | -T-----G-A---T--- |
| *Blastomyces dermatitidis* | BLODA | ----------------- |
| *Aspergillus fumagatus* | ASNDA | -T-----G-A--T---- |
| *fumigatus* | ASNRR5SS | -T-----G-A--T---- |
| *fumigatus* | ASNRRSSB | -T-----G-A--T---- |
| *Candida albicans* | YSASRSUA | -T-----T----ATT-A |
| *albicans* | YSAL16S | GT---T--T----TTA- |
| *lusitaniae* | YSASRRNAA | GT---T--T----TTA- |
| *lusitaniae* | YSASRSUE | GT---T--T----TTA- |
| *kefyr* | YSASRSUB | GT---T--T----TTA- |
| *krusei* | YSASRRNAC | GT---T--T----TTA- |
| *krusei* | YSASRSUD | GT---T--T----TTA- |
| *tropicalis* | YSASRRNAB | GT---T--T----TTA- |
| *tropicalis* | YSASRSUG | GT---T--T----TTA- |
| *viswanathii* | YSASRSUH | GT---T--T----TTA- |
| *parapsilosis* | YSASRSUF | GT---T--T----TTA- |
| *guilliermondii* | YSASRSUC | GT---T--T----TTA- |
| *glabrata* | YS5CRRNAS | G------T----GGTCC |
| II. Highest homologous sequence in GenBank | | |
| Avian influenza | FLAHA5 | ----------A------ |
| Mouse perlecan | MUSPERPA | -------C--G------ |
| Mouse basement membrane | MUSPGCBMA | -------C--G------ |

TABLE X

Probes for Blastomyces (Blast-1046)

| Species | GenBank name | Blast-1046<br>GACGGGGTTCTTATGATGACC |
|---|---|---|
| I. Fungi | | |
| *Pneumocystis carinii* | PMC16SRR1 | CG-----C-------GAGG---T |
| *Cryptococcus neoformans* | CPCDA | -GT-AAA------GAT-----G |
| *Coccidiodes immitis* | COIDA | ------CAA---TGA--A--- |
| *Blastomyces dermatitidis* | BLODA | -------------------- |
| *Aspergillus fumagatus* | ASNDA | -G---T---TC---------- |
| *fumigatus* | ASNRR5SS | -G---T---TC---------- |
| *fumigatus* | ASNRRSSB | -G---T---TC---------- |
| *Candida albicans* | YSASRSUA | -TT-TT------T-AT----G |
| *albicans* | YSAL16S | -TT-TT------T-AT----G |
| *lusitaniae* | YSASRRNAA | -G---C-----A-T-AG----G |
| *lusitaniae* | YSASRSUE | -G---C----A-T-AG----G |
| *kefyr* | YSASRSUB | -GT--T---T--C-T------ |
| *krusei* | YSASRRNAC | -----TC-A-C----G-A-G- |
| *krusei* | YSASRSUD | -----TC-A-C----G-A-G- |
| *tropicalis* | YSASRRNAB | -TT-TT------T-AT----G |
| *tropicalis* | YSASRSUG | -TT-TT------T-AT----G |
| *viswanathii* | YSASRSUH | -TT-TT------T-AT----G |
| *parapsilosis* | YSASRSUF | -TT-TT------T-AT----G |
| *guilliermondii* | YSASRSUC | -GT-TT-----KT-TT----G |
| *glabrata* | YS5CRRNAS | -GT--T---T--T-AG----- |
| II. Highest homologous sequence in GenBank | | |
| Rat ITPR2 Type2inositol | RATITPR2R | ----------CC--CT------ |
| Canine mRNA | DOGSRPR | CTGCTAA-------------- |
| Mitochondrion Oenothera | OBEMTNAD12 | C-GTCTT-------------- |

30

TABLE XI

Probes for Candida (Cand-513)

| Species | GenBank name | Cand-513<br>GAGTACAATGTAAATACCTTAACGAG |
|---|---|---|
| I. Fungi | | |
| *Pneumocystis carinii* | PMC16SRR1 | ----------T--G-------------- |
| *Cryptococcus neoformans* | CPCDA | ----------T------C---------- |
| *Coccidiodes immitis* | COIDA | ----------T------C---------- |
| *Blastomyces dermatitidis* | BLODA | ----------C------C---------- |
| *Aspergillus fumagatus* | ASNDA | ----------C------C---------- |
| *fumigatus* | ASNRR5SS | ----------C------C---------- |
| *fumigatus* | ASNRRSSB | ----------C------C---------- |
| *Candida albicans* | YSASRSUA | -------------------------- |
| *albicans* | YSAL16S | -------------------------- |
| *lusitaniae* | YSASRRNAA | -------------------------- |
| *lusitaniae* | YSASRSUE | -------------------------- |
| *kefyr* | YSASRSUB | -------------------------- |
| *krusei* | YSASRRNAC | -------------------------- |
| *krusei* | YSASRSUD | -------------------------- |
| *tropicalis* | YSASRRNAB | -------------------------- |
| *tropicalis* | YSASRSUG | -------------------------- |
| *viswanathii* | YSASRSUH | -------------------------- |
| *parapsilosis* | YSASRSUF | -------------------------- |
| *guilliermondii* | YSASRSUC | -------------------------- |
| *glabrata* | YS5CRRNAS | -------------------------- |
| II. Highest homologous sequence in GenBank | | |
| Yeast 18S rRNA | YSCRNA5 | -------------------------- |
| Yeast (*S. cerevisiae*) | YSCRGEA | -------------------------- |
| *Kluyveromyces lactis* | YSK17SRRNA | -------------------------- |
| *Torulaspora delbrueckii* | TOUSRSR | -------------------------- |
| *T. glabrata* rRNA | YSLSRSUA | -------------------------- |
| *H. polymorphA* rRNA | HASSRSUA | -------------------------- |
| *S. pombe* rRNA | YSPRRNASS | -------------------------- |

TABLE XII

Probes for Candida (Cand-701)

| Species | GenBank name | Cand-701<br>GGTAGCCATTTATGGCGAACC |
|---|---|---|
| I. Fungi | | |
| *Pneumocystis carinii* | PMC16SRR1 | TTA------GC---T-T--GT |
| *Cryptococcus neoformans* | CPCDA | TTCG---C-C-----T---T- |
| *Coccidiodes immitis* | COIDA | TTA------GC---T-T--GT |
| *Blastomyces dermatitidis* | BLODA | TTA------GC---T-T--GT |
| *Aspergillus fumagatus* | ASNDA | ATA---A------ACG-TGAA |
| *fumigatus* | ASNRR5SS | ATA---A------ACG-TGAA |
| *fumigatus* | ASNRRSSB | ATA---A------ACG-TGAA |
| *Candida albicans* | YSASRSUA | --------------------- |
| *albicans* | YSAL16S | --------------------- |
| *lusitaniae* | YSASRRNAA | TTA------GC---T-T--GT |
| *lusitaniae* | YSASRSUE | -C------TNG-C------CG-N |
| *kefyr* | YSASRSUB | -C-----NC--GC---TTN--T |
| *krusei* | YSASRRNAC | C--TTT----A--CAA----G |
| *krusei* | YSASRSUD | TTA------GC---T-T--GT |
| *tropicalis* | YSASRRNAB | -C-----    --T--------- |
| *tropicalis* | YSASRSUG | -C-----    --T--------- |
| *viswanathii* | YSASRSUH | -C-----    --T--------- |
| *parapsilosis* | YSASRSUF | -C-----   ---T--------- |
| *guilliermondii* | YSASRSUC | ---CCG-C---T------GTA |
| *glabrata* | YS5CRRNAS | ATA---A------ACA-TGAA |
| II. Highest homologous sequence in GenBank | | |
| *S. enterica* | STYRFB | -------G---------CGCTT |
| *Clostridium pasteurianum* | CLONIFH5 | ------T---------AA--GG |
| *C. pasteurianum* nifH | CLONIFH | ------T---------AA--GG |
| *C. pasteurianum* nifH | CLONIFHL | ------T---------AA--GG |

TABLE XIII

Probes for Coccidiodes (Cocc-659)

| Species | GenBank name | Cocc-659<br>CTTCGCGGCGTGCACTG |
|---|---|---|
| I. Fungi | | |
| *Pneumocystis carinii* | PMC16SRR1 | --------ATC---TG- |
| *Cryptococcus neoformans* | CPCDA | -C--A---A-------- |
| *Coccidiodes immitis* | COIDA | ----------------- |
| *Blastomyces dermatitidis* | BLODA | -C--A-C---------- |
| *Aspergillus fumagatus* | ASNDA | -C--AT---C-T----- |
| *fumigatus* | ASNRR5SS | -C--AT---C-T----- |
| *fumigatus* | ASNRRSSB | -C--AT---C-T----- |
| *Candida albicans* | YSASRSUA | GCA----CGC-A----- |
| *albicans* | YSAL16S | GCA----CGC-A----- |
| *lusitaniae* | YSASRRNAA | -GCTTA----A------ |
| *lusitaniae* | YSASRSUE | TNGTCT----C--N--T |
| *kefyr* | YSASRSUB | GCA----CGC-A----- |
| *krusei* | YSASRRNAC | GCA----CGC-A----- |
| *krusei* | YSASRSUD | GCA----CGC-A----- |
| *tropicalis* | YSASRRNAB | GCA----CGC-A----- |
| *tropicalis* | YSASRSUG | GCA----CGC-A----- |
| *viswanathii* | YSASRSUH | GCA----CGC-A----- |
| *parapsilosis* | YSASRSUF | GCA----CGC-A----- |
| *guilliermondii* | YSASRSUC | ---TTT----A-T---- |
| *glabrata* | YS5CRRNAS | ---G------AA-CAG- |
| II. Highest homologous sequence in GenBank | | |
| Rabbit progest. recep. | RABPRG1 | ------A---------G- |
| *Streptomyces lividans* 66 | STMTRNGM | ------C---------GA |
| Human mRNA cysteine | HUMCYSTCR | G-GT-------------- |

TABLE XIV

Probes for Coccidiodes (Cocc-1050)

| Species | GenBank name | Cocco-1050<br>GGCAACTTTGAATAACCCGTTC |
|---|---|---|
| I. Fungi | | |
| *Pneumocystis carinii* | PMC16SRR1 | TTACTAC---G------GTGGT |
| *Cryptococcus neoformans* | CPCDA | CTGCC-----T-C-CA---CC-C |
| *coccidiodes immitis* | COIDA | ----------------------- |
| *Blastomyces dermatitidis* | BLODA | --GTT----ATG--G-------- |
| *Aspergillus fumagatus* | ASNDA | CTGCC-----T-C-CA---CC- |
| *fumigatus* | ASNRR5SS | TT----G-G----GC-TA--AG |
| *fumigatus* | ASNRRSSB | TT----G-G----GC-TA--AG |
| *Candida albicans* | YSASRSUA | TTACTAC---G------GTGGT |
| *albicans* | YSAL16S | TTACTAC---G------GTGGT |
| *lusitaniae* | YSASRRNAA | T-TT--------G---ATGAGAG |
| *lusitaniae* | YSASRSUE | T-TT--------G---ATGAGAG |
| *kefyr* | YSASRSUB | TTTT---------A--ATTAGAG |
| *krusei* | YSASRRNAC | ----------CCCATGGGGCCGA |
| *krusei* | YSASRSUD | ----------CCCATGGGGCCGA |
| *tropicalis* | YSASRRNAB | TTACTAC---G------GTGGT |
| *tropicalis* | YSASRSUG | TTACTAC---G------GTGGT |
| *viswanathii* | YSASRSUH | TTACTAC---G------GTGGT |
| *parapsilosis* | YSASRSUF | TTACTAC---G------GTGGT |
| *guilliermondii* | YSASRSUC | TTACTAC---G------GTGGT |
| *glabrata* | YS5CRRNAS | TTTT---------A--ATTAGAG |
| II. Highest homologous sequence in GenBank | | |
| *Genome bacteriophage T7* | PT7DOT7 | --ACTTC---------------- |
| *Bacteriophage T7,comple.* | PT7CG | --ACTTC---------------- |
| *Staphylococcus aureus* | STATOXA | ------------C------TCGA |

TABLE XV

Probes for Cryptococcus (Cryp-691)

| Species | GenBank name | Cryp-691<br>GTGGTCCTGTATGCTCTTTACT |
|---|---|---|
| I. Fungi | | |
| *Pneumocystis carinii* | PMC16SRR1 | -----GG--C---GC-G--CT- |
| *Cryptococcus neoformans* | CPCDA | ---------------------- |
| *Coccidiodes immitis* | COIDA | C-------G-CTG-AC-----C-- |
| *Blastomyces dermatitidis* | BLODA | C-------G-CCG-AC-----C-- |
| *Aspergillus fumagatus* | ASNDA | C-------G-CTG-AC-----C-- |
| *fumigatus* | ASNRR5SS | CA----TGTG----C---AGA- |
| *fumigatus* | ASNRRSSB | CA----TGTG----C---AGA- |
| *Candida albicans* | YSASRSUA | -----GG--C---GC-G--CT- |
| *albicans* | YSAL16S | -----GG--C---GC-G--CT- |
| *lusitaniae* | YSASRRNAA | -----GG--C---GC-G--CT- |
| *lusitaniae* | YSASRSUE | CA----TGTG----C---AGAC |
| *kefyr* | YSASRSUB | ----NNG--C---GC-G--CT- |
| *krusei* | YSASRRNAC | -----GG--C---GC-G--TT- |
| *krusei* | YSASRSUD | CA----TGTG----C---AGAC |
| *tropicalis* | YSASRRNAB | -----GG--C---GC-G--CT- |
| *tropicalis* | YSASRSUG | ------NG--C---GC-G--CT- |
| *viswanathii* | YSASRSUH | -----GG--C---GC-G--CT- |
| *parapsilosis* | YSASRSUF | -----NG--C---GC-G--CT- |
| *guilliermondii* | YSASRSUC | TAAAAAA-CA---------GAG |
| *glabrata* | YS5CRRNAS | -----GG--C---GC-G--CT- |
| II. Highest homologous sequence in GenBank | | |
| Rat α tropomyosin | RATTMA3 | T--------T----------CGT- |
| Human ribonucl/angio | HUMRAJ | C----------C-ACA------ |
| Human ribonucl/angio inh | HUMRAI | C----------C-ACA------ |

TABLE XVI

Probes for Cryptococcus (Cryp-1042)

| Species | GenBank name | Cryp-1042<br>CACGTCAATCTCTGACTGGG |
|---|---|---|
| I. Fungi | | |
| *Pneumocystis carinii* | PMC16SRR1 | TT-T-G-T---A--GG---T |
| *Cryptococcus neoformans* | CPCDA | -------------------- |
| *Coccidiodes immitis* | COIDA | GG-----G-A-TC-G---TC |
| *Blastomyces dermatitidis* | BLODA | CG-----G-A-TC-G---TC |
| *Aspergillus fumagatus* | ASNDA | -G--CGCTA-A-----A--- |
| *fumigatus* | ASNRR5SS | -G--CGCTA-A-----A--- |
| *fumigatus* | ASNRRSSB | -G--CGCTA-A-----A--- |
| *Candida albicans* | YSASRSUA | GGG-G---C---ATT----A |
| *albicans* | YSAL16S | --TTCA---T----C-CTAT |
| *lusitaniae* | YSASRRNAA | --TTCA---T----C-CTAT |
| *lusitaniae* | YSASRSUE | --TTCA---T----C-CTAT |
| *kefyr* | YSASRSUB | A-AA-----G---TCGGACT |
| *krusei* | YSASRRNAC | TG----A--G-C-C----TC- |
| *krusei* | YSASRSUD | -T---G--A---C-T-GT-C |
| *tropicalis* | YSASRRNAB | A-AA-----G---TCGGACT |
| *tropicalis* | YSASRSUG | -TN-----A--TG-N-ATTT |
| *viswanathii* | YSASRSUH | A-A---NNNGGGNNCNN--- |
| *parapsilosis* | YSASRSUF | --TTCA---T----C-CTAT |
| *guilliermondii* | YSASRSUC | --TTCA---T----C-CTAT |
| *glabrata* | YS5CRRNAS | GTT---C-CT---T-GA--- |
| II. Highest homologous sequence in GenBank | | |
| Rat α-1-acid gly.pro. | RATAGPA1H | T-TTA---------------T |
| Rat α-1-acid gly(sp-daw) | RATAGPA1G | T-TTA---------------T |
| *S. pneumoniae* malX malM | STRMALMXP | T-ACC------A-------- |

TABLE XVII

Jun-commmon sense primer (S943-2, SEQ ID NO:728).

| Locus | Pos | SEQ ID NO: | Sequences (5'-3')<br>CCGCTGTCCCCCATCGACATGG |
|---|---|---|---|
| Human | | | |
| B: humjunca | 1189 | 408 | ---G-----------A------ |
| C: humjuna | 1981 | 409 | --C------------------- |
| D: humjundr | 943 | 410 | ---T-----G------------ |
| Mouse | | | |
| B: musjunba | 1079 | 411 | --TG-----------A------ |
| C: musjunc | 1344 | 412 | --C--------T---------- |
| C: muscjun | 1646 | 413 | --C--------T---------- |
| C: musjun | 1084 | 414 | --C--------T---------- |
| D: musjund | 927 | 415 | --------G------------- |
| D: musjunda | 782 | 416 | --------G------------- |
| D: musjundr | 793 | 417 | --------G------------- |
| Rat | | | |
| C: atjunap1 | 1082 | 418 | --CT------------------ |
| C: ratrjg9 | 2984 | 419 | --CT------------------ |
| Chicken | | | |
| C: chkjun | 1470 | 420 | --C--------T--T------- |
| Quail | | | |
| C: quljun | 1186 | 421 | --C--------T--T------- |
| Drosophila | | | |
| C: drojun | 1038 | 422 | A-CG-TAAT-----T------- |
| Highest matched sequences in EMBL | | | |
| SDNAM2G | Yeast NAM2 gene | 423 | ----------A-A------GAAT |
| PRK2TRFB | Plasmid PK2 trfb ope | 424 | GT--------------GC-T- |
| DMSYT | *D. melanogaster* synap | 425 | -------G-A----UC------ |

TABLE XVIII

Jun-common antisense primer (AS1132-2, SEQ ID NO:729).

| Locus | Pos | SEQ ID NO: | Sequences (5'–3')<br>CCGCTGTCCCCATCGACATGG |
|---|---|---|---|
| Human | | | |
| B: humjunca | 1378 | 426 | --------G------G------ |
| C: humjuna | 2170 | 427 | --------T-------------- |
| D: humjundr | 1132 | 428 | ----------------G--C--- |
| Mouse | | | |
| B: musjunba | 1268 | 429 | --T-------------G--C--- |
| C: musjunc | 1835 | 430 | --------T---------C--- |
| C: muscjun | 1273 | 431 | --------T---------C--- |
| C: musjun | 1533 | 432 | --------T---------C--- |
| D: musjund | 982 | 433 | ------------GC-G------ |
| D: musjunda | 1116 | 434 | ----------------G------ |
| D: musjundr | 971 | 435 | ----------------G------ |
| Rat | | | |
| C: atjunap1 | 1271 | 436 | --------T-------------- |
| C: ratrjg9 | 3173 | 437 | --------T-------------- |
| Chicken | | | |
| C: chkjun | 1659 | 438 | -----A--T---------C--- |
| Quail | | | |
| C: quljun | 1375 | 439 | -----A--T---------C--- |
| Drosophila | | | |
| C: drojun | 1227 | 440 | ---A----------GC-C--C--- |
| Highest matched sequences in EMBL | | | |
| HSATFA | Human mRNA for ATF-a | 441 | C-------G----A-C------- |
| ECDCM | E. coli dom gene | 442 | AA----------------ACCA |
| ECDCMA | E. coli dom | 443 | AA----------------ACCA |
| OCIGKCI | Rabbit Ig germkine k | 444 | --------G---------G-CGA |
| OCIG05 | Rabbit Ig k2 L chain | 445 | --------G---------G-CGA |
| OCKIB4 | Rabbit Ig kappa L | 446 | --------G---------G-CGA |
| OCIGKCG | Rabbit Ig kappa2 J-C | 447 | --------G---------G-CGA |
| OCIGKC02 | Rabbit Ig kappa1 J-C | 448 | --------G---------G-CGA |

TABLE XIX

Jun-B specific probe (B-1258, SEQ ID NO:730).

| GenBank | SEQ ID NO: | B1258(5'–3')<br>CTGGCGGCCACCAAGTG |
|---|---|---|
| Human | | |
| B: HUMJUNCA | 449 | ------------------ |
| C: HUMJUNA | 450 | A-C--T---T-------- |
| D: HUMJUNDR | 451 | A------------TCCAA |
| Mouse | | |
| B: MUSJUNBA | 452 | ------------------ |
| C: MUSJUNC | 453 | A-T---C----T-------- |
| MUSCJUN | 454 | A-T--C---T-------- |
| MUSJUN | 455 | A-T--C---T-------- |
| D: MUSJUND | 456 | -----C-------CCCG- |
| MUSJUNDA | 457 | ------T-----GCCA- |
| MUSJUNDR | 458 | ------T-----GCCA- |
| Rat | | |
| C: RATRJG9 | 459 | ------T-----GCCAA |
| RATJUNAP | 460 | A-C--T---T-------- |
| Chicken | | |
| C: CHKJUN | 461 | -C-------G-----CCC |
| Quail | | |
| C: QULJUN | 462 | GGC------AG-----TG- |
| Drosophila | | |
| C: DROJUN | 463 | G-----T--AT-------- |

TABLE XIX-continued

Jun-B specific probe (B-1258, SEQ ID NO:730).

| GenBank | | SEQ ID NO: | B1258(5'-3')<br>CTGGCGGCCACCAAGTG |
|---|---|---|---|
| Homologous sequences in GenBank | | | |
| J04695 | FIG. 2. Nucleo. | 464 | G--------A------G |
| M27884 | FIG. 2. Nucleo. | 465 | ---------A------GC |
| HUMCNPG2 | green cone photo. | 466 | --------------T-AA |
| HUMCNPR2 | green cone photo. | 467 | --------------T-AA |
| HUMPIGMF2 | colour-blind pho. | 468 | --------------T-AA |

TABLE XX c-jun specific probe (C2147).

| Subtype | GenBank name | SEQ ID NO: | C2147.DNA<br>CCACGGCCAACATGCTC |
|---|---|---|---|
| Human | | | |
| B: | HUMJUNCA | 469 | -G---A---C---CAGC |
| C: | HUMJUNA | 470 | ----------------- |
| D: | HUMJUNDR | 471 | -------G-G-C-----G |
| Mouse | | | |
| B: | MUSJUNBA | 472 | -G-------C---CAGC |
| C: | MUSJUN | 473 | ----------------- |
|  | MUSCJUN | 474 | ----------------- |
|  | MUSJUNC | 475 | ----------------- |
| D: | MUSJUND | 476 | ----C-----G-C-----G |
|  | MUSJUNDR | 477 | ----C-----G-C-----G |
|  | MUSJUNDA | 478 | ----C-----G-C-----G |
| Rat | | | |
| C: | RATJUNAP | 479 | ----------------- |
|  | RATRJG9 | 480 | ----C------------ |
| Chicken | | | |
| C: | CHKJUN | 481 | ----------------- |
| Quail | | | |
| C: | QULJUN | 482 | ----T------------ |
| Drosophila | | | |
| C: | DROJUN | 483 | CCTACA--------ACC |
| Homologous sequences in GenBank | | | |
| MXBPALPA | L. enzymogenes | 484 | --------------CG-- |
| MXBPALP | L. enzymogenes | 485 | --------------CG-- |

TABLE XXI

Human jun-D specific probe (HUMD965)

| Subtype | GenBank name | SEQ ID NO: | HUMD965<br>ACACGCAGGAGCGCATC |
|---|---|---|---|
| Human | | | |
| B: | HUMJUNCA | 486 | GG-A--T---------- |
| C: | HUMJUNA | 487 | -GT-C--------G--- |
| D: | HUMJUNDR | 488 | ----------------- |
| Mouse | | | |
| B: | MUSJUNBA | 489 | -AGAC------------ |
| C: | MUSJUNC | 490 | -GT-T--------G--- |
|  | MUSCJUN | 491 | -GT-T--------G--- |
|  | MUSJUN | 492 | GT-T--------G---- |
| D: | MUSJUND | 493 | -------A--A------ |
|  | MUSJUNDA | 494 | -------A--A------ |

TABLE XXI-continued

Human jun-D specific probe (HUMD965)

| Subtype | GenBank name | SEQ ID NO: | HUMD965<br>ACACGCAGGAGCGCATC |
|---|---|---|---|
| | MUSJUNDR | 495 | --------A--A------ |
| Rat | | | |
| C: | RATJUNAP | 496 | -GT-T--------G--- |
| | RATRJG9 | 497 | -GT-T--------G--- |
| Chicken | | | |
| C: | CHKJUN | 498 | -GT--------A-A--- |
| Quail | | | |
| C: | QULJUN | 499 | -GT--------A-A--- |
| Drosophila | | | |
| C: | DROJUN | 500 | G--A--T---------- |
| Homologous sequences in GenBank | | | |
| CELPOLII | *C. elegans* RNA | 501 | --------------A-AA |
| ECOPRIAY | *E. coli* primo. | 502 | -ACA-------------- |
| SINOCK82 | Ockelbo 82 g. | 503 | C-------------TGC |
| TRPPROC | Treponema pa. | 504 | G-------------TGC |
| ECOCYSJIHA | *E. coli* NADPH- | 505 | ------T--------G-G |

TABLE XXII

Mouse jun-D specific probe (MUSD1063).

| Subtype | GenBank name | SEQ ID NO: | MUSD1063.DNA<br>CCCTCAAAAGCCAGAACACCG |
|---|---|---|---|
| Human | | | |
| B: | HUMJUNCA | 506 | -G------GGC-G------G-G- |
| C: | HUMJUNA | 507 | AA--GC-C-------------GC |
| D: | HUMJUNDR | 508 | -------G--T---------G- |
| Mouse | | | |
| B: | MUSJUNBA | 509 | TA---TCC-----TCTG-----C |
| C: | MUSJUNC | 510 | AA--GC-T-------------GC |
| | MUSJUN | 511 | AA--GC-T-------------GC |
| | MUSCJUN | 512 | AA--GC-T-------------GC |
| D: | MUSJUNDA | 513 | ---------------------- |
| | MUSJUNDR | 514 | ---------------------- |
| | MUSJUND | 515 | ---------------------- |
| Rat | | | |
| C: | RATRJG9 | 516 | G-----GCC---GC-C----TT |
| | RATJUNAP | 517 | G-----GCC---GC-C----TT |
| Chicken | | | |
| C: | CHKJUN | 518 | A---G-GG-A-A-----G--- |
| Quail | | | |
| C: | QULJUN | 519 | ---C--G-T-----TG--G-A |
| Drosophila | | | |
| C: | DROJUN | 520 | A------GGA---TGTGGCGC |
| Homologous sequences in GenBank | | | |
| M27221 | FIG. 3. | 521 | TG-------T--T-------- |
| DROAMY | *D. erecta* | 522 | G-------G-A--T-------- |
| DROAMYQ | *D. erecta* | 523 | G-------G-A--T-------- |
| HUMIGCMUDE | Immunoglob. | 524 | A--C--------------GTT |

TABLE XXIII

G protein common primer (G2-S)

G2-S
SEQ ID NO: AGCACCATTGTGAAGCAGATGA

Human

| | | | |
|---|---|---|---|
| Gi-1 | HUMGNBPAI | 525 | --T--A---------------- |
| Gi-2 | HUMGIAA | 526 | --------C--C---------- |
| Gi-3 | HUMGIAB | 527 | --------------A------- |
| Gs | HUMGNPAS | 528 | ---------------------- |
| Go | HUMGOAQ01 | 529 | ---------------------- |

Rat

| | | | |
|---|---|---|---|
| Gi-1 | RATBPGTPB | 530 | ------A--------------- |
| Gi-2 | RATBPGTPA | 531 | --------C--C---------- |
| Gi-3 | RATBPGTP | 532 | --T--T---------------- |
| Gs | RATBPGTPD | 533 | ---------------------- |
| Go | RATBPGTPC | 534 | ---------------------- |
| Gx | RATGXA | 535 | --------C--C---------- |

Highest matched sequences in GenBank

| | | | |
|---|---|---|---|
| HUMADECYC | adenyl cyclase | 536 | ---------------------- |
| RATACOA1 | acyl-coA oxidase | 537 | GC------G------A------ |
| HUMTGASE | transglutaminase | 538 | CT---------------CC-AC |

TABLE XXIV

G protein common primer (G4-AS, SEQ ID NO:731).

G4-AS
SEQ ID NO: TGTTTGATGTGGGAGGCCAGAG

Human

| | | | |
|---|---|---|---|
| Gi-1 | HUMGNBPAI | 539 | ------------------T----- |
| Gi-2 | HLTMGIAA | 540 | --------------T--T---C-- |
| Gi-3 | HUMGIAB | 541 | ------------A--T------A-- |
| Gs | HUMGNPAS | 542 | --------C------T------C- |
| Go | HUMGOAQ01 | 543 | -------C--C-----------C- |

Rat

| | | | |
|---|---|---|---|
| Gi-1 | RATBPGTPB | 544 | --------C---------------- |
| Gi-2 | RATBPGTPA | 545 | --------------T--T---C- |
| Gi-3 | RATBPGTP | 546 | ----------A--T-----A-- |
| Gs | RATBPGTPD | 547 | ----C--------C------C- |
| Go | RATBPGTPC | 548 | --------C--T--G------C- |
| Gx | RATGXA | 549 | --G-G-----------G----- |

Highest matched sequences in GenBank

| | | | |
|---|---|---|---|
| HUMLDLRRL | LDL-receptor | 550 | CTGA---------------TACT |
| MUSHEPGFA | hepatocyte growth | 551 | GAG-G--------T--A------ |
| HUMKEREP | epidermal keratin | 552 | AG------AT---GG-------- |

TABLE XXV

Gi-1 protein specific, human-rat common primer (Gi-1)

Gi-1
SEQ ID NO: GATGTTCTCAGAACTAGAGTGAAAAC

Human

| | | | |
|---|---|---|---|
| Gi-1 | HUMGNBPAI | 553 | -------------------------- |
| Gi-2 | HUMGIAA | 554 | TT----------CT-CCCCTGTCCCCT |
| Gi-3 | HUMGIAB | 555 | --------TC-G--G---------G-- |
| Gs | HUMGNPAS | 556 | AC---G-C---T---TCCTG--C--G |
| Go | HUMGOAQ01 | 557 | --CA-C---C----C--G--C----- |

Rat

| | | | |
|---|---|---|---|
| Gi-1 | PATBPGTPB | 558 | -------------------------- |
| Gi-2 | RATBPGTPA | 559 | -----G--GC-G--CC-T-----G-- |

TABLE XXV-continued

Gi-1 protein specific, human-rat common primer (Gi-1)

|  |  | SEQ ID NO: | Gi-1<br>GATGTTCTCAGAACTAGAGTGAAAAC |
|---|---|---|---|
| Gi-3 | RATBPGTP | 560 | --------TC-G--G--------G-- |
| Gs | RATBPGTPD | 561 | A-GCACAATTA-TTA---------CG |
| Go | RATBPGTPC | 562 | --CA-C---C-----C--G--C----- |
| Gx | RATGXA | 563 | TCA----GAG--C----A-CC----CA |

TABLE XXVI

Gi-2 protein specific, human-rat common primer (Gi-2)

|  |  | SEQ ID NO: | Gi-2<br>GCAACCTGCAGATCGACTTTG |
|---|---|---|---|
| Human | | | |
| Gi-1 | HUMGNBPAI | 564 | -G-GGT--A----A-------- |
| Gi-2 | HUTMGIAA | 565 | ---------------------- |
| Gi-3 | HUMGIAB | 566 | -ACGG--AA----T-------- |
| Gs | HUMGNPAS | 567 | AGT----A--T---T----G-- |
| Go | HUMGOAQ01 | 568 | CTTCT-------G-TG-----C |
| Rat | | | |
| Gi-1 | RATBPGTPB | 569 | -G-GAT--A-A---------- |
| Gi-2 | RATBPGTPA | 570 | ---------------------- |
| Gi-3 | RATBPGTP | 571 | AA----G------T-T-TT---- |
| Gs | RATBPGTPD | 572 | AGT----A--T--------G-- |
| Go | RATBPGTPC | 573 | ATTCT-------A-TG----C |
| Gx | RATGXA | 574 | -T---A-C---T-T-T----C- |

TABLE XXVII

Gi-3 protein specific, human-rat common primer (Gi-3)

|  |  | SEQ ID NO: | Gi-3<br>TCTTCGGACGAGAGTGAAGAC |
|---|---|---|---|
| Human | | | |
| Gi-1 | HUMGNBPAI | 575 | ----CA-A--T---------A-- |
| Gi-2 | HUMGIAA | 576 | G--A-----CC-C--A----- |
| Gi-3 | HUMGIAB | 577 | ---------------------- |
| Gs | HUMGNPAS | 578 | GGGAAATCGA---T---G--- |
| Go | HUMGOAQ01 | 579 | ---C----GA---CGTG-A-- |
| Rat | | | |
| Gi-1 | RATBPGTPB | 580 | ----CA-A--T---------A-- |
| Gi-2 | RATBPGTPA | 581 | G--G-----CC-T--------- |
| Gi-3 | RATBPGTP | 582 | ---------------------- |
| Gs | RATBPGTPD | 583 | TTCCT----A---T---T-TG |
| Go | RATBPGTPC | 584 | CGCAT----G--C-C----CCA |
| Gx | RATGXA | 585 | AAC----G-A----CACCAT- |

TABLE XXVIII

Gs Protein specific, human-rat common primer (Gs, SEQ ID NO:732)

|  |  | SEQ ID NO: | Gs<br>AATTCTATGAGCATGCCAAGGC |
|---|---|---|---|
| Human | | | |
| Gi-1 | HUMGNBPAI | 586 | GGGCGG----T---C-----CT |
| Gi-2 | HUMGIAA | 587 | ---ATG-----GCA----GCTA |
| Gi-3 | HUMGIAB | 588 | C-G----ACTA---T-----CTC |
| Gs | HUMGNPAS | | |

TABLE XXIX

Go Protein specific, human-rat common primer (Go)

|  |  | SEQ ID NO: | Go<br>CTGCTTTCTGCCATGATGCG |
|---|---|---|---|
| Human | | | |
| Gi-1 | HUMGNBPAI | 589 | GAC------TAA---TGACA |
| Gi-2 | HUMGIAA | 590 | ---TGA---C-A-G-C---- |
| Gi-3 | HUMGIAB | 591 | ----A----AGA-CTTCACA |
| Gs | HUMGNPAS | 592 | TCAACGA------G---CATC |
| Go | HUMGOAQ01 | 593 | -------------------- |
| Rat | | | |
| Gi-1 | RATBPGTPB | 594 | ---A----CCA-G-T---TT |
| Gi-2 | RATBPGTPA | 595 | T-----GA-CC---GCG---- |
| Gi-3 | RATBPGTP | 596 | ------G---T----TG-CAC |
| Gs | RATBPGTPD | 597 | ------G---AG-A-G-C-T |
| Go | RATBPGTPC | 598 | -------------------- |
| Gx | RATGXA | 599 | -A---C-T----C---CTG- |

TABLE XXX

Human-rodent common jun-B specific probes.

| | Name in GenBank | B-504 (5'-3') CACGACTACAAACTCCTGAAAC | Seq. ID No: | B-739 (5'-3') GGACAGTACTTTTACCCCCG | Seq ID No: | Size (bp) |
|---|---|---|---|---|---|---|
| Mouse | | | | | | |
| jun-B | MUSJUNBA | ---------------------- | 600 | -------------------- | 607 | 251 |
| c-JUN | MUSCJUN | A-AT--A-T-----AT-----A | 601 | ACC----T---G-G----AA | 608 | |
| jun-D | MUSJUND | T----G-C--C-T-----TTCC | 602 | ACG----T-C-C-----GAA | 609 | |
| Human | | | | | | |
| jun-B | HUMJUNCA | ---------------------- | 603 | -------------------- | 610 | 251 |
| C-jun | HUMJUNA | AGTA--CC---GA--------- | 604 | ----A--C-GCGG------AC | 611 | |
| jun-D | HUMJUNDR | T----G-C--C-T-----TTTG | 605 | TC-----T-C-C------AA | 612 | |
| GenBank | | | | | | |
| | MUSMETI | -------T---CG-------GTA | 606 | | | |
| | RATMYHCD2 | | | ------C-------AT---A | 613 | |

*: Size of PCR products using B-504 and B-739 as primers.
**: The highest matched sequences in GenBank (release 68.0) next to the jun genes.

TABLE XXXI

Human-rodent common c-jun specific probes.

| | Name in GenBank | C-2101 (5'-3') GAGGAAAAAGTGAAAACCTTGAAAGC | Seq. ID No: | C-2219 (5'-3') GCCAACTCATGCTAACGCAG | Seq. ID No: | Size (bp) |
|---|---|---|---|---|---|---|
| Mouse | | | | | | |
| jun-B | MUSJUNBA | -----C--G-----G--AC-C--G-- | 614 | -----GT-GC-----GG-GTC | 621 | |
| c-JUN | MUSCJUN | -------------------------- | 615 | -------------------- | 622 | 138 |
| jun-D | MUSJUND | -----G-----C--G---C-C---AG | 616 | T----A-GCC--A-G----A | 623 | |
| Human | | | | | | |
| jun-B | HUMJUNCA | -----C--G-----G--GC-C--G-- | 617 | -----G-C-CC-AG-----GC | 624 | |
| C-jun | HUMJUNA | -------------------------- | 618 | -------------------- | 625 | 138 |
| jun-D | HUMJUNDR | --A--G---------G---C-C--GAG | 619 | T----G-GCC--A-G----A | 626 | |
| GenBank | | | | | | |
| | HUMGASTA | A-A-------AA-----A---A----- | 620 | | | |
| | MUSOCT22 | | | C------------G---GGC | 627 | |

*: Size of PCR products using C-2101 and C-2219 as primers.
**: The highest matched sequences in GenBank (release 68.0) next to the jun genes.

TABLE XXXII

Human-rodent common jun-D specific probes.

| | Name in GenBank | D-916 (5'-3') GACGTGCCGAGCTTCGG | Seq. ID No: | D-1153 (5'-3') AAAGTCCTCAGCCACGTCAAC | Seq. ID No: | Size (bp) |
|---|---|---|---|---|---|---|
| Mouse | | | | | | |
| jun-B | MUSJUNBA | CTG-G-------ACT-- | 628 | --G----A-G-C---T----G- | 635 | |
| c-JUN | MUSCJUN | T-A------AG---AGAC | 629 | ------A-G-A------T--- | 636 | 258 |
| jun-D | MUSJUND | ----------------- | 630 | -------------------- | 637 | |
| Human | | | | | | |
| jun-B | HUMJUNCA | C---C-----CC-----C | 631 | --G----A-G-C--------G- | 638 | |
| C-jun | HUMJUNA | T-A---TT-----CG-- | 632 | ------A-G-A------T--- | 638 | |
| jun-D | HUMJUNDR | ----------------- | 633 | -------------------- | 640 | 258 |
| GenBank | | | | | | |
| | HUMTRKR | ------TG--------- | 634 | | | |
| | HUMBSSL | | | ---A----------A--CTG | 641 | |

*: Size of PCR products using D-916 and D-1153 as primers.
**: The highest matched sequences in GenBank (release 68.0) next to the jun genes.

TABLE XXXIII

Human-rodent common Gs specific probes.

| | Name in GenBank | Gs-246 (5'-3') GCCAACAAAAAGATCGAGAAGC | Seq.ID No: | Gs-824 (5'-3') GGACAAAGTCAACTTCCACATG | Seq. ID No: | Size (bp) |
|---|---|---|---|---|---|---|
| Rat | | | | | | |
| Gs | RATBPGTPD | ---------------------- | 642 | ---------------------- | 652 | 600 |
| Gi-1 | RATBPGTPB | CG--G---G-T------CCGCA | 643 | ------G-CGGC-G-GG-GCGC | 653 | |
| Gi-2 | RATBPGTPA | CAA-GG------CA-A------ | 644 | A-------C-C--C-G-T---T | 654 | |
| Gi-3 | RATBPGTP | TGAGGA-----T--A------T | 645 | -TCAGG---A-TA-------GC | 655 | |
| Go | RATBPGTPC | TTTGG-G-G-----TA-----T | 646 | CCGAGG--CGGCGA-G------ | 656 | |
| Mouse | | | | | | |
| Gs-1 | MUSGS | ---------------------- | 647 | ---------------------- | 657 | 555 |
| Gs-2 | MUSGTPAMU | ---------------------- | 648 | ---------------------- | 658 | 600 |
| Human | | | | | | |
| Gs-1 | HUMGSA1R | ---------------------- | 649 | ---------------------- | 659 | 558 |
| Gs-2 | HUMGSA2R | ---------------------- | 650 | ---------------------- | 660 | 600 |
| GenBank | | | | | | |
| | HUMMBP2 | A-----A--C-------A------ | 651 | | | |
| | RATAFPM | | | A-------T---T--------A- | 661 | |

*: Size of PCR products using Gs-246 and Gs-824 as primers.
**: The highest matched sequences in GenBank (release 68.0) next to the Gs protein DNAs.

TABLE XXXIV

Human-rodent common Gi-1 specific probes.

| | Name in GenBank | Gi1-735 (5'-3') GATGTTCTCAGAACTAGAGTGAAAAC | Seq. ID No: | Gi1-1131 (5'-3') TGTCAGTTTGAAGACCTCAATAAAAG | Seq. ID No: | Size (bp) |
|---|---|---|---|---|---|---|
| Rat | | | | | | |
| Gs | RATBPGTPD | A-GCACAATTA-TTA---------CG | 662 | AACAGAAA-A-----AA-A---G---T | 669 | |
| Gi-1 | RATBPGTPB | -------------------------- | 663 | -------------------------- | 670 | 422 |
| Gi-2 | RATBPGTPA | -----G--GC-G--CC-T-----G-- | 664 | A-CA-------G-----G-------C- | 671 | |
| Gi-3 | RATBPGTP | --------TC-G--G--------G-- | 665 | --C-----------T--G--CCG---- | 672 | |
| Go | RATBPGTPC | --CA-C---C----C--G--C----- | 666 | ACA---------AG-AAA--CCGCTC | 673 | |
| Human | | | | | | |
| Gs-1 | HUMGNBPA | -------------------------- | 667 | -------------------------- | 674 | 422 |
| GenBank | | | | | | |
| | HUMCPH192 | C---C---G--C---G----A-----G | 668 | | | |
| | MUSGBPA | | | A-C---CC--T--C------------- | 675 | |

*: Size of PCR products using Gi1-735 and Gi1-1131 as primers.
**: The highest matched sequences in GenBank (release 68.0) next to the Gs protein DNAs.

TABLE XXXV

Human-rodent common Gi-2 specific probes.

| | Name in GenBank | Gi2-742 (5'-3') AAGATGTTTGATGTGGGTGGTC | Seq. ID No: | Gi2-1102 (5'-3') AAGGAGATCTACACGCACTTCA | Seq. ID No: | Size (bp) |
|---|---|---|---|---|---|---|
| Rat | | | | | | |
| Gs | RATBPGTPD | G-C-A-A---------ATCAAG- | 676 | ---C--G------CG-GC-ACGC | 684 | |
| Gi-1 | RATBPGTPB | --A--------C-----A--C- | 677 | -----A--T-----C------- | 685 | |
| Gi-2 | RATBPGTPA | ---------------------- | 678 | ---------------------- | 686 | 382 |
| Gi-3 | RATBPGTP | --A-----------A-----C- | 679 | ------G--------T-----T- | 687 | |
| Go | RATBPGTPC | -G-C--------C--T--G--C- | 680 | CTA-------G---C-CTCA-C | 688 | |
| Mouse | | | | | | |
| Gs-2 | MUSGI | ---------------------- | 681 | ---------------------- | 689 | 382 |
| Human | | | | | | |
| Gs-2 | HUMGIR | ---------------------- | 682 | ---------------------- | 690 | 382 |

TABLE XXXV-continued

Human-rodent common Gi-2 specific probes.

| Name in GenBank | Gi2-742 (5'-3') AAGATGTTTGATGTGGGTGGTC | Seq. ID No: | Gi2-1102 (5'-3') AAGGAGATCTACACGCACTTCA | Seq. ID No: | Size (bp) |
|---|---|---|---|---|---|
| GenBank | | | | | |
| HUMCMPF | -----------C-------TGG | | | | |
| MUSHSP84A | | | -------A-----A-A-G---T | | 691 |

\*: Size of PCR products using G1i2-742 and Gi2-1102 as primers.
\*\*: The highest matched sequences in GenBank (release 68.0) next to the Gs protein DNAs.
Rat G$_{i-2}$ was shown to be specifically amplified when PCR was performed with G$_{i-2}$ and SEQ ID NO:678 and SEQ ID NO:686 as PCR primers.

TABLE XXXVI

Human-rodent common Gi-3 specific probes.

| | Name in GenBank | Gi3-407 (5'-3') TTGTTTTAGCTGGCAGTGCTGA | Seq. ID No: | Gi3-730 (5'-3') GAGGGAGTGACAGCAATTATCT | Seq. ID No: | Size (bp) |
|---|---|---|---|---|---|---|
| Rat | | | | | | |
| Gs | RATBPGTPD | CC-GAAGT-GATC--------TC | 692 | A-T-AT-----T--C--C---- | 699 | |
| Gi-1 | RATBPGTPB | A-----GA------GGC-CTA-T | 693 | --A--C-----T--C--C---- | 700 | |
| Gi-2 | RATBPGTPA | CCTACAC---A--AT------C | 694 | -----T--C--G--C--C---- | 701 | |
| Gi-3 | RATBPGTP | ---------------------- | 695 | ---------------------- | 702 | 345 |
| Go | RATBPGTPC | CG-------T--AGTC-TTAC- | | TC------AT----TCAACGAC | 703 | |
| Human | | | | | | |
| Gi-3 | HUMGTPBP | ---------------------- | 697 | ---------------------- | 704 | 345 |
| GenBank | | | | | | |
| | HUMAPOB | G-----C--A-----T-----C | 698 | | | |
| | HUMINSR02 | | | C---------G---AC---T--- | 705 | |

\*: Size of PCR products using Gi3-407 and Gi3-730 as primers.
\*\*: The highest matched sequences in GenBank (release 68.0) next to the Gs protein DNAs.
Rat G$_{i-3}$ was shown to be specifically amplified when PCR was performed with G$_{i-2}$ and SEQ ID NO:697 and SEQ ID NO:704 as PCR primers.

TABLE XXXVII

Human-rodent common Go specific probes.

| | Name in GenBank | Go-1224 (5'-3') AGGACATCCTCCGAACCAG | Seq. ID No: | Go-1397 (5'-3') TATGACCAGGTGCTCCACG | Seq. ID No: | Size (bp) |
|---|---|---|---|---|---|---|
| Rat | | | | | | |
| Gs | RATBPGTPD | --------AAAAAC-A-CT | 706 | AG--------AC---G-TTC | 717 | |
| Gi-1 | RATBPGTPB | G--G-CG------GG---- | 707 | -------T---T--TGCT- | 718 | |
| Gi-2 | RATBPGTPA | CCAT-------TTCCT--A | 708 | -TCTGTT-------GG-GA | 719 | |
| Gi-3 | RATBPGTP | G-CCA-AGA-------GGA | 709 | A--------TA-T-AATTT | 720 | |
| Go | RATBPGTPC | ------------------- | 710 | ------------------- | 721 | 192 |
| Mouse | | | | | | |
| Go-A | MUSGOASA | ------------------- | 711 | ------------------- | 722 | 192 |
| Go-B | MUSGOASB | ------------------- | 712 | ------------------- | 723 | 192 |
| Hamster | | | | | | |
| Go-1 | HAMHITAO1 | ------------------- | 713 | ------------------- | 724 | 192 |
| Go-2 | HAMHITAO2 | ------------------- | | ------------------- | 725 | 192 |
| Human | | | | | | |
| Go | HUMGOA1(2) | ------------------- | 715 | ------------------- | 726 | 192 |

TABLE XXXVII-continued

Human-rodent common Go specific probes.

| Name in GenBank | Go-1224 (5'-3') AGGACATCCTCCGAACCAG | Seq. ID No: | Go-1397 (5'-3') TATGACCAGGTGCTCCACG | Seq. ID No: | Size (bp) |
|---|---|---|---|---|---|
| GenBank | | | | | |
| MUSPC3AA | G------T--TC------ | 716 | | | |
| RATACACA | | | ---------------A-GT | 727 | |

*: Size of PCR products using Go-1224 and Go-1397 as primers.
**: The highest matched sequences in GenBank (release 68.0) next to the Gs protein DNAs.

---

What is claimed is:

1. A method of identifying probes and thereafter detecting the presence of a particular organism, infectious agent, or biological component of a cell or organism in a sample derived from biological material that contains polynucleotides, by detecting an analyte polynucleotide in said sample that is indicative of the presence of said organism, infectious agent, or biological component, said method comprising the step of:

(a) identifying a first polynucleotide probe having a nucleotide sequence complementary to a first nucleotide sequence contained in an analyte polynucleotide specific to a particular organism, infectious agent, or biological component, said first polynucleotide probe having a melting temperature ($T_m$) within a preselected range with said analyte polynucleotide at a selected sodium and formamide concentration, by a method comprising:

(i) retrieving from a database a plurality of user-selected gene sequences including a gene sequence from said organism, infectious agent, or biological component, and inputting said sequences into a computer system for calculating $T_m$;

(ii) calculating the $T_m$'s of a plurality of candidate probes having nucleotide sequences derived from the gene sequence from said organism, infectious agent, or biological component, at the selected sodium and formamide concentration with said gene sequence from said organism, infectious agent, or biological component, using said computer system;

(iii) calculating the $T_m$'s of said plurality of candidate probes having nucleotide sequences at the selected sodium and formamide concentration with each of said user-selected gene sequences other than that of said gene sequence from said organism, infectious agent, or biological component; and (iv) identifying said first polynucleotide probe as the candidate probe which has a $T_m$ with said analyte polynucleotide within the preselected range at the selected sodium and formamide concentration, and that has the lowest $T_m$ overall with the other user-selected gene sequences;

(b) immobilizing said first polynucleotide probe to a solid support;

(c) hybridizing said analyte polynucleotide in said sample to said first nucleotide sequence of said first polynucleotide probe, if said analyte polynucleotide is present in said sample;

(d) identifying a second polynucleotide probe having a nucleotide sequence complementary to a second nucleotide sequence contained in said analyte polynucleotide, said second polynucleotide probe being different from said first nucleotide sequence, said second polynucleotide probe having a $T_m$ with said analyte polynucleotide at a selected sodium and formamide concentration, said $T_m$ being approximately the same or lower than the $T_m$ of said first polynucleotide probe;

(e) hybridizing said second polynucleotide probe to said second sequence of said analyte polynucleotide hybridized to said first polynucleotide probe; and (f) determining the presence of said particular organism, infectious agent, or biological component in said sample by detecting the presence of said second polynucleotide probe on said solid support.

2. A method according to claim 1, wherein said second nucleotide sequence is common to a plurality of different organisms, infectious agents, or biological components.

3. The method of claim 2, wherein said first polynucleotide probe has a $T_m$ within the range of from approximately 48° C. to approximately 60° C.

4. The method of claim 2, wherein a label is attached to said second polynucleotide probe, and wherein the determining step comprises detecting the presence of said label.

5. The method of claim 4, wherein said label is selected from the group consisting of a radionuclide, an enzyme, an enzyme substrate, a specific binding moiety, an binding partner for a specific binding moiety, biotin, avidin, a nucleic acid stain, and a fluorescent material.

6. The method of claim 5, wherein said label is a nucleic acid stain selected from the group consisting of ethidium bromide, yoyo-1, and toro-1.

7. The method of claim 4, wherein said label can be measured by light emitted therefrom, and wherein step (f) comprises measuring the amount of light emitted by said label.

8. The method of claim 7, wherein the step of measuring the amount of light emitted by said label comprises:

recording the amount of light on film; and measuring the exposure of the film using a densitometer.

9. The method of claim 7, wherein said label comprises alkaline phosphatase, and wherein step (f) of claim 1 comprises adding ATTOPHOS and measuring the fluorescense emitted using a fluorimeter.

10. The method of claim 2, wherein said solid support comprises a microtiter plate having a plurality of wells.

11. The method of claim 2, wherein said first polynucleotide probe comprises DNA.

12. The method of claim 2, wherein said first and second polynucleotide probes comprise DNA.

13. The method of claim 2, additionally comprising the step of washing said solid support after hybridizing said analyte polynucleotide in said sample to said first polynucleotide probe so that substantially all of said biological sample not annealed to said first polynucleotide probe is removed from said solid support.

14. The method of claim 2, additionally comprising the step of washing said solid support after hybridizing said second polynucleotide probe with said analyte polynucleotide in said sample which is hybridized to said first polynucleotide probe so that substantially all of said second polynucleotide probe not hybridized with said analyte polynucleotide is removed from said solid support.

15. The method of claim 2, wherein the polynucleotide hybridized to said first polynucleotide probe is selected from the group consisting of mRNA, rRNA, and genomic DNA.

16. The method of claim 1, wherein said melting temperature is determined by the formula;

$$Tm=81.5-16.6(\log[Na])-0.63\%(\text{formamide})+0.41(\%/(G+C))-600/N,$$

wherein Log[Na] is the log function of the sodium concentration, 0.63% (formamide) is the concentration of formamide, %(G+C) is the percentage of matched GC base pairs, and N is the probe length.

17. A kit for identifying the presence of an organism, infectious agent, or biological component of a cell or organism in a biological sample, comprising:

a microtiter plate having a plurality of wells, to which at least two different polynucleotide probes are immobilized, each polynucleotide probe being immobilized to a different well, each polynucleotide probe being complementary to or homologous to a first nucleotide sequence in an analyte polynucleotide specific to a different organism, infectious agent, or biological component to be detected, each polynucleotide probe having approximately the same $T_m$ within the range of from approximately 48° C. to approximately 60° C., each polynucleotide probe being identified by a method comprising:

(i) retrieving from a database a plurality of user-selected gene sequences including a gene sequence from said organism, infectious agent, or biological component, and inputting said sequences into a computer system for calculating $T_m$;

(ii) calculating the $T_m$'s of a plurality of candidate probes having nucleotide sequences derived from the gene sequence from said organism, infectious agent, or biological component, at the selected sodium and formamide concentration with said gene sequence from said organism, infectious agent, or biological component, using said computer system;

(iii) calculating the $T_m$'s of said plurality of candidate probes having nucleotide sequences at the selected sodium and formamide concentration with each of said user-selected gene sequences other than that of said gene sequence from said organism, infectious agent, or biological component; and (iv) identifying each of said polynucleotide probes as the candidate probe which has a $T_m$ with said analyte polynucleotide within the preselected range at the selected sodium and formamide concentration, and that has the lowest $T_m$ overall with the other user-selected gene sequences; and a common polynucleotide probe complementary to or homologous to a second nucleotide sequence in said analyte polynucleotide of said organism, infectious agent, or biological component, said common polynucleotide probe being complementary to polynucleotide contained in a plurality of different organisms, infectious agents, or biological components, said common polynucleotide probe having about the same or lower $T_m$ than each specific polynucleotide probe.

18. The kit of claim 17, additionally comprising at least one of the following: dNTP's, a reverse transcriptase, a polymerase, and a buffer appropriate for addition of dNTP's to a primer using a reverse transcriptase or polymerase.

19. The kit of claim 17, additionally comprising a buffer appropriate for the hybridization of said probes and polynucleotides, said polynucleotides being selected from the group consisting of mRNA, rRNA, and genomic DNA.

20. The kit of claim 17, wherein said second polynucleotide probe bears a label.

21. The kit of claim 20, wherein said label is selected from the group consisting of a radionuclide, an enzyme, an enzyme substrate, a specific binding moiety, an binding partner for a specific binding moiety, biotin, avidin, a nucleic acid stain, and a flouresecent material.

22. The kit of claim 17, wherein said specific polynucleotide probe comprises a first specific primer which is complementary or homologous to a sequence specific to a particular organism, infectious agent, or biological component, said kit additionally comprising a second specific polynucleotide primer which is complementary or homologous to a different sequence specific to said organism, infectious agent, or biological component.

23. The kit of claim 17, including a DNA polymerase that has significant polymerase activity at temperatures above 50° C.

24. The method of claim 10, wherein each of said wells has a first polynucleotide probe covalently immobilized thereon.

25. A method of identifying probes and thereafter detecting the presence of an organism, infectious agent, or biological component of a cell or organism in a sample derived from biological material that contains polynucleotides, by detecting an analyte polynucleotide in said sample that is indicative of the presence of said organism, infectious agent, or biological component, said method comprising the steps of:

(a) immobilizing a first polynucleotide probe to a solid support, said first polynucleotide probe having a nucleotide sequence complementary to a first nucleotide sequence contained in an analyte polynucleotide, common to a plurality of different organisms, infectious agents, or biological components, said first polynucleotide probe having a $T_m$ within a preselected range between approximately 48° C. and approximately 60° C. with said analyte polynucleotide at a selected sodium and formamide concentration;

(b) identifying a second polynucleotide probe having a label thereon, wherein the nucleotide sequence of said second polynucleotide probe is complementary to a second nucleotide sequence contained in said analyte polynucleotide, specific to an organism, infectious agent, or biological component, and has approximately the same $T_m$ as said first polynucleotide probe so that said first and second polynucleotide probes can hybridize to said analyte polynucleotide under the same conditions, said identification being conducted, by a method comprising:

(i) retrieving from a database a plurality of user-selected gene sequences including the gene sequence of said organism, infectious agent, or biological component, and inputting said sequences into a computer system for calculating $T_m$;

(ii) calculating the $T_m$'s of a plurality of candidate probes having nucleotide sequences derived from the gene sequence from said organism, infectious agent, or biological component, at the selected sodium and formamide concentration with said gene sequence from said organism, infectious agent, or biological component, using said computer system;

(iii) calculating the $T_m$'s of said plurality of candidate probes having nucleotide sequences at the selected sodium and formamide concentration with each of said user-selected gene sequences other than that of said gene sequence from said organism, infectious agent, or biological component; and (iv) identifying said second polynucleotide probe as the candidate probe which has a $T_m$ within the preselected range with said analyte polynucleotide and has the lowest $T_m$ overall with the other user-selected gene sequences;

(c) contacting the polynucleotides present in said sample with said first polynucleotide probe and said second polynucleotide probe having a label thereon with said polynucleotides present in said sample, whereby said first nucleotide sequence contained in said analyte polynucleotide hybridizes to said first polynucleotide probe, and said second polynucleotide probe hybridizes to said second nucleotide sequence contained in said analyte polynucleotide, if said analyte polynucleotide is present in said sample; and (d) determining the presence of said organism, infectious agent, or biological component in said sample by detecting the presence of said label on said second polynucleotide probe if hybridized to said analyte polynucleotide.

26. The method of claim 25, wherein said solid support is a microtiter plate having a plurality of wells, each of said wells having a specific polynucleotide probe covalently immobilized thereon.

27. The method of claim 25, additionally comprising the step of:

washing said solid support after hybridizing said first and second polynucleotide probes so that substantially all of said second polynucleotide probe not annealed to said analyte polynucleotide is removed from said solid support.

28. The method of claim 1, wherein step (a) further comprises determining the hybridization strengths between said user-selected gene sequences and said candidate polynucleotide sequences by the calculated $T_m$'s in steps (a)(ii) and (iii), and identifying said first polynucleotide probe as the candidate probe in step (a)(iv) by numbers of hybridizations or false hybridizations to said user-selected gene sequences calculated by said hybridization strengths.

29. The method of claim 1, wherein said candidate probes in step (a) are selected at positions along said analyte polynucleotide, based on a nucleation threshold that places a minimum value on the number of base pairs at any nucleation site, selected by the user, in addition to said preselected $T_m$ range.

30. The method of claim 1, wherein said preselected $T_m$ range is specified by a minimum $T_m$ with said analyte polynucleotide.

31. The method of claim 1, wherein said second polynucleotide probe is identified by a method comprising the steps of:

calculating the $T_m$'s of a plurality of candidate probes at the selected sodium and formamide concentration with said analyte polynucleotide at every possible hybridization point; and identifying said second polynucleotide probe as the candidate probe which has a $T_m$ within the preselected range with the nucleotide sequence complementary to the second nucleotide sequence of said analyte polynucleotide other than the first nucleotide sequence of said analyte polynucleotide and has the lowest $T_m$ with the nucleotide sequence complementary to said first polynucleotide probe.

32. The method of claim 31, wherein said candidate probes are selected at positions along said analyte polynucleotide, based on a nucleation threshold that places a minimum value on the number of base pairs at any nucleation site, selected by the user, in addition to said preselected $T_m$ range.

33. The method of claim 31, wherein a preselected $T_m$ range for said second polynucleotide probe is specified by a minimum $T_m$ with said analyte polynucleotide.

34. The method of claim 31, wherein said melting temperature is determined by the formula;

$$Tm=81.5-16.6(\log[Na])-0.63\%(formamide)+0.41(\%(G+C))-600/N,$$

wherein Log[Na] is the log function of the sodium concentration, 0.63% (formamide) is the concentration of formamide, %(G+C) is the percentage of matched GC base pairs, and N is the probe length.

35. The method of claim 10, wherein said first probe is immobilized to said microtiter plate via its 5' end.

36. The method of claim 10, wherein step (a) further comprises identifying in the same way at least one different first polynucleotide probe, each different first polynucleotide probe having a nucleotide sequence complementary to a first nucleotide sequence contained in a different analyte polynucleotide, specific to a particular organism, infectious agent, or biological component, each different first polynucleotide probe having a $T_m$ with said analyte polynucleotide at a selected sodium and formamide concentration, said $T_m$ being about the same as that of any other first polynucleotide probe so that each first polynucleotide probe can be hybridized to the corresponding analyte polynucleotide under the same conditions; step (b) further comprises immobilizing each first polynucleotide probe to a different well of said microtiter plate having a plurality of wells; in step (c), hybridization is conducted in such a way that each analyte polynucleotide in said sample is hybridized with each first polynucleotide probe, if said analyte polynucleotide is present in said sample, under the same conditions, whereby plural types of organisms, infectious agents, or biological components are simultaneously detected.

37. A method of identifying probes and thereafter detecting the presence of a particular polynucleotide in a sample, said method comprising the step of:

(a) identifying a first polynucleotide probe having a nucleotide sequence complementary to a first nucleotide sequence contained in said particular polynucleotide, said first polynucleotide probe having a melting temperature ($T_m$) within a preselected range with said particular polynucleotide at a selected sodium and formamide concentration, by a method comprising:

(i) retrieving from a database a plurality of user-selected gene sequences including the gene sequence of said organism, infectious agent, or biological component, and inputting said sequences into a computer system for calculating $T_m$;

(ii) calculating the $T_m$'s of a plurality of candidate probes having nucleotide sequences derived from the gene sequence from said organism, infectious agent, or biological component, at the selected sodium and formamide concentration with said gene sequence form said organism, infectious agent, or biological component, using said computer system;

(iii) calculating the $T_m$'s of said plurality of candidate probes having nucleotide sequences at the selected sodium and formamide concentration with each of said user-selected gene sequence other than that of said gene sequence from said organism, infectious agent, or biological component; and (iv) identifying said first polynucleotide probe as the candidate probe which has a $T_m$ within the preselected range with said particular polynucleotide indicative of the presence of said organism, infectious agent, or biological component, and that has the lowest $T_m$ overall with the other user-selected gene sequences;

(b) immobilizing said first polynucleotide probe to a solid support;

(c) hybridizing said particular polynucleotide in said sample to said first nucleotide sequence of said first polynucleotide probe, if said particular polynucleotide is present in said sample;

(d) identifying a second polynucleotide probe having a nucleotide sequence complementary to a second nucleotide sequence contained in said particular polynucleotide, different from said first nucleotide sequence, and having a $T_m$ with said particular polynucleotide at a selected sodium and formamide concentration, said $T_m$ being approximately the same or lower than the $T_m$ of said first polynucleotide probe;

(e) hybridizing said second polynucleotide probe to said second sequence of said particular polynucleotide hybridized to said first polynucleotide probe; and (f) determining the presence of said particular polynucleotide in said sample by detecting the presence of said second polynucleotide probe on said solid support.

* * * * *

UNITED STATES PATENT AND TRADEMARK OFFICE
CERTIFICATE OF CORRECTION

PATENT NO. : 5,639,612
DATED : June 17, 1997
INVENTOR(S) : Masato Mitsuhashi, et. al.

It is certified that error appears in the above-identified patent and that said Letters Patent is hereby corrected as shown below:

On the title page: Item [73] Assignee, add --Hitachi Chemical Research Center, Inc., Irvine, California, U.S.A.-- as a second Assignee.

Signed and Sealed this

Tenth Day of February, 1998

Attest:

BRUCE LEHMAN

Attesting Officer        Commissioner of Patents and Trademarks

SEQUENCE LISTING ( 1 ) GENERAL INFORMATION:

( i i i ) NUMBER OF SEQUENCES: 726

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Pneumocystis carinii ( v i i ) IMMEDIATE SOURCE:
        ( B ) CLONE: PMC16SRR1

( x i ) SEQUENCE DESCRIPTION: SEQ ID NO:1:

GAGGGAGCCT GAGAAACG                          18

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Cryptococcus neoformans ( v i i ) IMMEDIATE SOURCE:
        ( B ) CLONE: CPCDA ( x i ) SEQUENCE DESCRIPTION: SEQ ID NO:2:

GAGGGAGCCT GAGAAACG                          18

( 2 ) INFORMATION FOR SEQ ID NO:3:

( i ) SEQUENCE CHARACTERISTICS:
        ( A ) LENGTH: 18 base pairs
        ( B ) TYPE: nucleic acid (C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
  (A) ORGANISM: Coccidiodes immitis (vii) IMMEDIATE SOURCE:
  (B) CLONE: COIDA (xi) SEQUENCE DESCRIPTION: SEQ ID NO:3:

GAGGGAGCCT GAGAAACG    18

(2) INFORMATION FOR SEQ ID NO:4:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: cDNA to rRNA (iii) HYPOTHETICAL: NO (iv) ANTI-SENSE: NO (vi) ORIGINAL SOURCE:
  (A) ORGANISM: Blastomyces dermatitidis (vii) IMMEDIATE SOURCE:
  (B) CLONE: BLODA (xi) SEQUENCE DESCRIPTION: SEQ ID NO:4:

GAGGGAGCCT GAGAAACG    18

(2) INFORMATION FOR SEQ ID NO:5:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: cDNA to rRNA (iii) HYPOTHETICAL: NO (iv) ANTI-SENSE: NO (vi) ORIGINAL SOURCE:
  (A) ORGANISM: Aspergillus fumagatus (vii) IMMEDIATE SOURCE:
  (B) CLONE: ASNDA (xi) SEQUENCE DESCRIPTION: SEQ ID NO:5:

GAGGGAGCCT GAGAAACG    18

(2) INFORMATION FOR SEQ ID NO:6:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Aspergillus fumigatus ( v i i ) IMMEDIATE SOURCE:
    ( B ) CLONE: ASNRR5SS ( x i ) SEQUENCE DESCRIPTION: SEQ ID NO:6:

GAGGGAGCCT GAGAAACG  18

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRRSSB ( x i ) SEQUENCE DESCRIPTION: SEQ ID NO:7:

GAGGGAGCCT GAGAAACG  18

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida albicans ( v i i ) IMMEDIATE SOURCE:
        ( B ) CLONE: YSASRSUA ( x i ) SEQUENCE DESCRIPTION: SEQ ID NO:8:

GAGGGAGCCT GAGAAACG  18

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Candidi albicans (vii) IMMEDIATE SOURCE:
(B) CLONE: YSAL16S (xi) SEQUENCE DESCRIPTION: SEQ ID NO:9:

GAGGGAGCCT GAGAAACG                                                                                      18

(2) INFORMATION FOR SEQ ID NO:10:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida lusitaniae (vii) IMMEDIATE SOURCE:
(B) CLONE: YSASRRNAA (xi) SEQUENCE DESCRIPTION: SEQ ID NO:10:

GAGGGAGCCT GAGAAACG                                                                                      18

(2) INFORMATION FOR SEQ ID NO:11:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida lusitaniae (vii) IMMEDIATE SOURCE:
(B) CLONE: YSASRSUE (xi) SEQUENCE DESCRIPTION: SEQ ID NO:11:

GAGGGAGCCT GAGAAACG                                                                                      18

(2) INFORMATION FOR SEQ ID NO:12:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida kefyr (vii) IMMEDIATE SOURCE:
(B) CLONE: YSASRSUB ( x i ) SEQUENCE DESCRIPTION: SEQ ID NO:12:

GAGGGAGCCT GAGAAACG 18

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRRNAC ( x i ) SEQUENCE DESCRIPTION: SEQ ID NO:13:

GAGGGAGCCT GAGAAACG 18

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRSUD ( x i ) SEQUENCE DESCRIPTION: SEQ ID NO:14:

GAGGGAGCCT GAGAAACG 18

( 2 ) INFORMATION FOR SEQ ID NO:15:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRRNAB ( x i ) SEQUENCE DESCRIPTION: SEQ ID NO:15:

GAGGGAGCCT GAGAAACG 18

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRSUG ( x i ) SEQUENCE DESCRIPTION: SEQ ID NO:16:

GAGGGAGCCT GAGAAACG        18

( 2 ) INFORMATION FOR SEQ ID NO:17:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida viswanathii ( v i i ) IMMEDIATE SOURCE:
        ( B ) CLONE: YSASRSUH ( x i ) SEQUENCE DESCRIPTION: SEQ ID NO:17:

GAGGGAGCCT GAGAAACG        18

( 2 ) INFORMATION FOR SEQ ID NO:18:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida parapsilosis ( v i i ) IMMEDIATE SOURCE:
        ( B ) CLONE: YSASRSUF ( x i ) SEQUENCE DESCRIPTION: SEQ ID NO:18:

GAGGGAGCCT GAGAAACG        18

( 2 ) INFORMATION FOR SEQ ID NO:19:

( i ) SEQUENCE CHARACTERISTICS:
        ( A ) LENGTH: 18 base pairs
        ( B ) TYPE: nucleic acid ( C ) STRANDEDNESS: single
         ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
         ( A ) ORGANISM: Candida guilliermondii ( v i i ) IMMEDIATE SOURCE:
         ( B ) CLONE: YSASRSUC ( x i ) SEQUENCE DESCRIPTION: SEQ ID NO:19:

GAGGGAGCCT GAGAAACG                                                                  18

( 2 ) INFORMATION FOR SEQ ID NO:20:

( i ) SEQUENCE CHARACTERISTICS:
         ( A ) LENGTH: 18 base pairs
         ( B ) TYPE: nucleic acid
         ( C ) STRANDEDNESS: single
         ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
         ( A ) ORGANISM: Candida glabrata ( v i i ) IMMEDIATE SOURCE:
         ( B ) CLONE: YS5CRRNAS ( x i ) SEQUENCE DESCRIPTION: SEQ ID NO:20:

GAGGGAGCCT GAGAAACG                                                                  18

( 2 ) INFORMATION FOR SEQ ID NO:21:

( i ) SEQUENCE CHARACTERISTICS:
         ( A ) LENGTH: 18 base pairs
         ( B ) TYPE: nucleic acid
         ( C ) STRANDEDNESS: single
         ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
         ( A ) ORGANISM: Pneumocystis carinii ( v i i ) IMMEDIATE SOURCE:
         ( B ) CLONE: PMC16SRR1

( x i ) SEQUENCE DESCRIPTION: SEQ ID NO:21:

TCCAAGGAAG GCAGCAGG                                                                  18

( 2 ) INFORMATION FOR SEQ ID NO:22:

( i ) SEQUENCE CHARACTERISTICS:
         ( A ) LENGTH: 18 base pairs
         ( B ) TYPE: nucleic acid
         ( C ) STRANDEDNESS: single
         ( D ) TOPOLOGY: linear ( i i ) MOLECULE TYPE: cDNA to rRNA (iii) HYPOTHETICAL: NO (iv) ANTI-SENSE: NO (vi) ORIGINAL SOURCE:
    (A) ORGANISM: Cryptococcus neoformans (vii) IMMEDIATE SOURCE:
    (B) CLONE: CPCDA (xi) SEQUENCE DESCRIPTION: SEQ ID NO:22:

TCCAAGGAAG GCAGCAGG    18

(2) INFORMATION FOR SEQ ID NO:23:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Coccidiodes immitis (vii) IMMEDIATE SOURCE:
    (B) CLONE: COIDA (xi) SEQUENCE DESCRIPTION: SEQ ID NO:23:

TCCAAGGAAG GCAGCAGG    18

(2) INFORMATION FOR SEQ ID NO:24:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Blastomyces dermatitidis (vii) IMMEDIATE SOURCE:
    (B) CLONE: BLODA (xi) SEQUENCE DESCRIPTION: SEQ ID NO:24:

TCCAAGGAAG GCAGCAGG    18

(2) INFORMATION FOR SEQ ID NO:25:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:

(A) ORGANISM: Aspergillus fumagatus (vii) IMMEDIATE SOURCE:
            (B) CLONE: ASNDA (xi) SEQUENCE DESCRIPTION: SEQ ID NO:25:

TCCAAGGAAG GCAGCAGG                                                                                  18

(2) INFORMATION FOR SEQ ID NO:26:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA to rRNA (iii) HYPOTHETICAL: NO (iv) ANTI-SENSE: NO (vi) ORIGINAL SOURCE:
            (A) ORGANISM: Aspergillus fumigatus (vii) IMMEDIATE SOURCE:
            (B) CLONE: ASNRR5SS (xi) SEQUENCE DESCRIPTION: SEQ ID NO:26:

TCCAAGGAAG GCAGCAGG                                                                                  18

(2) INFORMATION FOR SEQ ID NO:27:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA to rRNA (iii) HYPOTHETICAL: NO (iv) ANTI-SENSE: NO (vi) ORIGINAL SOURCE:
            (A) ORGANISM: Aspergillus fumigatus (vii) IMMEDIATE SOURCE:
            (B) CLONE: ASNRRSSB (xi) SEQUENCE DESCRIPTION: SEQ ID NO:27:

TCCAAGGAAG GCAGCAGG                                                                                  18

(2) INFORMATION FOR SEQ ID NO:28:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA to rRNA (iii) HYPOTHETICAL: NO (iv) ANTI-SENSE: NO (vi) ORIGINAL SOURCE:
            (A) ORGANISM: Candida albicans (vii) IMMEDIATE SOURCE:
            (B) CLONE: YSASRSUA ( x i ) SEQUENCE DESCRIPTION: SEQ ID NO:28:

TCCAAGGAAG GCAGCAGG  18

( 2 ) INFORMATION FOR SEQ ID NO:29:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candidi albicans ( v i i ) IMMEDIATE SOURCE:
        ( B ) CLONE: YSAL16S ( x i ) SEQUENCE DESCRIPTION: SEQ ID NO:29:

TCCAAGGAAG GCAGCAGG  18

( 2 ) INFORMATION FOR SEQ ID NO:30:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRRNAA ( x i ) SEQUENCE DESCRIPTION: SEQ ID NO:30:

TCCAAGGAAG GCAGCAGG  18

( 2 ) INFORMATION FOR SEQ ID NO:31:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRSUE ( x i ) SEQUENCE DESCRIPTION: SEQ ID NO:31:

TCCAAGGAAG GCAGCAGG  18

( 2 ) INFORMATION FOR SEQ ID NO:32:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida kefyr ( v i i ) IMMEDIATE SOURCE:
        ( B ) CLONE: YSASRSUB ( x i ) SEQUENCE DESCRIPTION: SEQ ID NO:32:

TCCAAGGAAG GCAGCAGG                                                   18

( 2 ) INFORMATION FOR SEQ ID NO:33:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRRNAC ( x i ) SEQUENCE DESCRIPTION: SEQ ID NO:33:

TCCAAGGAAG GCAGCAGG                                                   18

( 2 ) INFORMATION FOR SEQ ID NO:34:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRSUD ( x i ) SEQUENCE DESCRIPTION: SEQ ID NO:34:

TCCAAGGAAG GCAGCAGG                                                   18

( 2 ) INFORMATION FOR SEQ ID NO:35:

( i ) SEQUENCE CHARACTERISTICS:
        ( A ) LENGTH: 18 base pairs
        ( B ) TYPE: nucleic acid ( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
 ( A ) ORGANISM: Candida tropicalis ( v i i ) IMMEDIATE SOURCE:
 ( B ) CLONE: YSASRRNAB ( x i ) SEQUENCE DESCRIPTION: SEQ ID NO:35:

TCCAAGGAAG GCAGCAGG    18

( 2 ) INFORMATION FOR SEQ ID NO:36:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
  ( A ) ORGANISM: Candida tropicalis ( v i i ) IMMEDIATE SOURCE:
  ( B ) CLONE: YSASRSUG ( x i ) SEQUENCE DESCRIPTION: SEQ ID NO:36:

TCCAAGGAAG GCAGCAGG    18

( 2 ) INFORMATION FOR SEQ ID NO:37:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
  ( A ) ORGANISM: Candida viswanathii ( v i i ) IMMEDIATE SOURCE:
  ( B ) CLONE: YSASRSUH ( x i ) SEQUENCE DESCRIPTION: SEQ ID NO:37:

TCCAAGGAAG GCAGCAGG    18

( 2 ) INFORMATION FOR SEQ ID NO:38:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida parapsilosis ( v i i ) IMMEDIATE SOURCE:
    ( B ) CLONE: YSASRSUF ( x i ) SEQUENCE DESCRIPTION: SEQ ID NO:38:

TCCAAGGAAG GCAGCAGG 18

( 2 ) INFORMATION FOR SEQ ID NO:39:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida guilliermondii ( v i i ) IMMEDIATE SOURCE:
        ( B ) CLONE: YSASRSUC ( x i ) SEQUENCE DESCRIPTION: SEQ ID NO:39:

TCCAAGGAAG GCAGCAGG 18

( 2 ) INFORMATION FOR SEQ ID NO:40:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida glabrata ( v i i ) IMMEDIATE SOURCE:
        ( B ) CLONE: YS5CRRNAS ( x i ) SEQUENCE DESCRIPTION: SEQ ID NO:40:

TCCAAGGAAG GCAGCAGG 18

( 2 ) INFORMATION FOR SEQ ID NO:41:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Pneumocystis carinii (vii) IMMEDIATE SOURCE:
 (B) CLONE: PMC16SRR1

(xi) SEQUENCE DESCRIPTION: SEQ ID NO:41:

ACGGGGAAAC TCACCAGG 18

(2) INFORMATION FOR SEQ ID NO:42:

(i) SEQUENCE CHARACTERISTICS:
 (A) LENGTH: 18 base pairs
 (B) TYPE: nucleic acid
 (C) STRANDEDNESS: single
 (D) TOPOLOGY: linear (ii) MOLECULE TYPE: cDNA to rRNA (iii) HYPOTHETICAL: NO (iv) ANTI-SENSE: NO (vi) ORIGINAL SOURCE:
 (A) ORGANISM: Cryptococcus neoformans (vii) IMMEDIATE SOURCE:
 (B) CLONE: CPCDA (xi) SEQUENCE DESCRIPTION: SEQ ID NO:42:

ACGGGGAAAC TCACCAGG 18

(2) INFORMATION FOR SEQ ID NO:43:

(i) SEQUENCE CHARACTERISTICS:
 (A) LENGTH: 18 base pairs
 (B) TYPE: nucleic acid
 (C) STRANDEDNESS: single
 (D) TOPOLOGY: linear (ii) MOLECULE TYPE: cDNA to rRNA (iii) HYPOTHETICAL: NO (iv) ANTI-SENSE: NO (vi) ORIGINAL SOURCE:
 (A) ORGANISM: Coccidiodes immitis (vii) IMMEDIATE SOURCE:
 (B) CLONE: COIDA (xi) SEQUENCE DESCRIPTION: SEQ ID NO:43:

ACGGGGAAAC TCACCAGG 18

(2) INFORMATION FOR SEQ ID NO:44:

(i) SEQUENCE CHARACTERISTICS:
 (A) LENGTH: 18 base pairs
 (B) TYPE: nucleic acid
 (C) STRANDEDNESS: single
 (D) TOPOLOGY: linear (ii) MOLECULE TYPE: cDNA to rRNA (iii) HYPOTHETICAL: NO (iv) ANTI-SENSE: NO (vi) ORIGINAL SOURCE:
 (A) ORGANISM: Blastomyces dermatitidis (vii) IMMEDIATE SOURCE:
 (B) CLONE: BLODA (x i) SEQUENCE DESCRIPTION: SEQ ID NO:44:

ACGGGGAAAC TCACCAGG 18

(2) INFORMATION FOR SEQ ID NO:45:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Aspergillus fumagatus (v i i) IMMEDIATE SOURCE:
        (B) CLONE: ASNDA (x i) SEQUENCE DESCRIPTION: SEQ ID NO:45:

ACGGGGAAAC TCACCAGG 18

(2) INFORMATION FOR SEQ ID NO:46:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Aspergillus fumigatus (v i i) IMMEDIATE SOURCE:
        (B) CLONE: ASNRR5SS (x i) SEQUENCE DESCRIPTION: SEQ ID NO:46:

ACGGGGAAAC TCACCAGG 18

(2) INFORMATION FOR SEQ ID NO:47:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Aspergillus fumigatus (v i i) IMMEDIATE SOURCE:
        (B) CLONE: ASNRRSSB (x i) SEQUENCE DESCRIPTION: SEQ ID NO:47:

ACGGGGAAAC TCACCAGG 18

( 2 ) INFORMATION FOR SEQ ID NO:48:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida albicans ( v i i ) IMMEDIATE SOURCE:
        ( B ) CLONE: YSASRSUA ( x i ) SEQUENCE DESCRIPTION: SEQ ID NO:48:

ACGGGGAAAC TCACCAGG                                  18

( 2 ) INFORMATION FOR SEQ ID NO:49:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candidi albicans ( v i i ) IMMEDIATE SOURCE:
        ( B ) CLONE: YSAL16S ( x i ) SEQUENCE DESCRIPTION: SEQ ID NO:49:

ACGGGGAAAC TCACCAGG                                  18

( 2 ) INFORMATION FOR SEQ ID NO:50:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRRNAA ( x i ) SEQUENCE DESCRIPTION: SEQ ID NO:50:

ACGGGGAAAC TCACCAGG                                  18

( 2 ) INFORMATION FOR SEQ ID NO:51:

( i ) SEQUENCE CHARACTERISTICS:
        ( A ) LENGTH: 18 base pairs
        ( B ) TYPE: nucleic acid ( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida lusitaniae ( v i i ) IMMEDIATE SOURCE:
    ( B ) CLONE: YSASRSUE ( x i ) SEQUENCE DESCRIPTION: SEQ ID NO:51:

ACGGGGAAAC TCACCAGG     18

( 2 ) INFORMATION FOR SEQ ID NO:52:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida kefyr ( v i i ) IMMEDIATE SOURCE:
        ( B ) CLONE: YSASRSUB ( x i ) SEQUENCE DESCRIPTION: SEQ ID NO:52:

ACGGGGAAAC TCACCAGG     18

( 2 ) INFORMATION FOR SEQ ID NO:53:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRRNAC ( x i ) SEQUENCE DESCRIPTION: SEQ ID NO:53:

ACGGGGAAAC TCACCAGG     18

( 2 ) INFORMATION FOR SEQ ID NO:54:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
  ( A ) ORGANISM: Candida krusei ( v i i ) IMMEDIATE SOURCE:
  ( B ) CLONE: YSASRSUD ( x i ) SEQUENCE DESCRIPTION: SEQ ID NO:54:

ACGGGGAAAC TCACCAGG 18

( 2 ) INFORMATION FOR SEQ ID NO:55:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida tropicalis ( v i i ) IMMEDIATE SOURCE:
    ( B ) CLONE: YSASRRNAB ( x i ) SEQUENCE DESCRIPTION: SEQ ID NO:55:

ACGGGGAAAC TCACCAGG 18

( 2 ) INFORMATION FOR SEQ ID NO:56:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida tropicalis ( v i i ) IMMEDIATE SOURCE:
    ( B ) CLONE: YSASRSUG ( x i ) SEQUENCE DESCRIPTION: SEQ ID NO:56:

ACGGGGAAAC TCACCAGG 18

( 2 ) INFORMATION FOR SEQ ID NO:57:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Candida viswanathii (vii) IMMEDIATE SOURCE:
    (B) CLONE: YSASRSUH (xi) SEQUENCE DESCRIPTION: SEQ ID NO:57:

ACGGGGAAAC TCACCAGG                                                                                      18

(2) INFORMATION FOR SEQ ID NO:58:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Candida parapsilosis (vii) IMMEDIATE SOURCE:
        (B) CLONE: YSASRSUF (xi) SEQUENCE DESCRIPTION: SEQ ID NO:58:

ACGGGGAAAC TCACCAGG                                                                                      18

(2) INFORMATION FOR SEQ ID NO:59:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Candida guilliermondii (vii) IMMEDIATE SOURCE:
        (B) CLONE: YSASRSUC (xi) SEQUENCE DESCRIPTION: SEQ ID NO:59:

ACGGGGAAAC TCACCAGG                                                                                      18

(2) INFORMATION FOR SEQ ID NO:60:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Candida glabrata (vii) IMMEDIATE SOURCE:
        (B) CLONE: YS5CRRNAS ( x i ) SEQUENCE DESCRIPTION: SEQ ID NO:60:

ACGGGGAAAC TCACCAGG 18

( 2 ) INFORMATION FOR SEQ ID NO:61:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Pneumocystis carinii ( v i i ) IMMEDIATE SOURCE:
        ( B ) CLONE: PMC16SRR1

( x i ) SEQUENCE DESCRIPTION: SEQ ID NO:61:

TCGTGCTGGG GATAGAGC 18

( 2 ) INFORMATION FOR SEQ ID NO:62:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Cryptococcus neoformans ( v i i ) IMMEDIATE SOURCE:
        ( B ) CLONE: CPCDA ( x i ) SEQUENCE DESCRIPTION: SEQ ID NO:62:

TCGTGCTGGG GATAGAGC 18

( 2 ) INFORMATION FOR SEQ ID NO:63:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Coccidiodes immitis ( v i i ) IMMEDIATE SOURCE:
        ( B ) CLONE: COIDA ( x i ) SEQUENCE DESCRIPTION: SEQ ID NO:63:

TCGTGCTGGG GATAGAGC 18

( 2 ) INFORMATION FOR SEQ ID NO:64:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
      ( A ) ORGANISM: Blastomyces dermatitidis ( v i i ) IMMEDIATE SOURCE:
      ( B ) CLONE: BLODA ( x i ) SEQUENCE DESCRIPTION: SEQ ID NO:64:

TCGTGCTGGG GATAGAGC                                                                 18

( 2 ) INFORMATION FOR SEQ ID NO:65:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
      ( A ) ORGANISM: Aspergillus fumagatus ( v i i ) IMMEDIATE SOURCE:
      ( B ) CLONE: ASNDA ( x i ) SEQUENCE DESCRIPTION: SEQ ID NO:65:

TCGTGCTGGG GATAGAGC                                                                 18

( 2 ) INFORMATION FOR SEQ ID NO:66:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
      ( A ) ORGANISM: Aspergillus fumigatus ( v i i ) IMMEDIATE SOURCE:
      ( B ) CLONE: ASNRR5SS ( x i ) SEQUENCE DESCRIPTION: SEQ ID NO:66:

TCGTGCTGGG GATAGAGC                                                                 18

( 2 ) INFORMATION FOR SEQ ID NO:67:

( i ) SEQUENCE CHARACTERISTICS:
      ( A ) LENGTH: 18 base pairs
      ( B ) TYPE: nucleic acid ( C ) STRANDEDNESS: single
          ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
          ( A ) ORGANISM: Aspergillus fumigatus ( v i i ) IMMEDIATE SOURCE:
          ( B ) CLONE: ASNRRSSB ( x i ) SEQUENCE DESCRIPTION: SEQ ID NO:67:

TCGTGCTGGG GATAGAGC                                                                                          18

( 2 ) INFORMATION FOR SEQ ID NO:68:

( i ) SEQUENCE CHARACTERISTICS:
          ( A ) LENGTH: 18 base pairs
          ( B ) TYPE: nucleic acid
          ( C ) STRANDEDNESS: single
          ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
          ( A ) ORGANISM: Candida albicans ( v i i ) IMMEDIATE SOURCE:
          ( B ) CLONE: YSASRSUA ( x i ) SEQUENCE DESCRIPTION: SEQ ID NO:68:

TCGTGCTGGG GATAGAGC                                                                                          18

( 2 ) INFORMATION FOR SEQ ID NO:69:

( i ) SEQUENCE CHARACTERISTICS:
          ( A ) LENGTH: 18 base pairs
          ( B ) TYPE: nucleic acid
          ( C ) STRANDEDNESS: single
          ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
          ( A ) ORGANISM: Candidi albicans ( v i i ) IMMEDIATE SOURCE:
          ( B ) CLONE: YSAL16S ( x i ) SEQUENCE DESCRIPTION: SEQ ID NO:69:

TCGTGCTGGG GATAGAGC                                                                                          18

( 2 ) INFORMATION FOR SEQ ID NO:70:

( i ) SEQUENCE CHARACTERISTICS:
          ( A ) LENGTH: 18 base pairs
          ( B ) TYPE: nucleic acid
          ( C ) STRANDEDNESS: single
          ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
               ( A ) ORGANISM: Candida lusitaniae ( v i i ) IMMEDIATE SOURCE:
               ( B ) CLONE: YSASRRNAA ( x i ) SEQUENCE DESCRIPTION: SEQ ID NO:70:

TCGTGCTGGG GATAGAGC 18

( 2 ) INFORMATION FOR SEQ ID NO:71:

( i ) SEQUENCE CHARACTERISTICS:
               ( A ) LENGTH: 18 base pairs
               ( B ) TYPE: nucleic acid
               ( C ) STRANDEDNESS: single
               ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
               ( A ) ORGANISM: Candida lusitaniae ( v i i ) IMMEDIATE SOURCE:
               ( B ) CLONE: YSASRSUE ( x i ) SEQUENCE DESCRIPTION: SEQ ID NO:71:

TCGTGCTGGG GATAGAGC 18

( 2 ) INFORMATION FOR SEQ ID NO:72:

( i ) SEQUENCE CHARACTERISTICS:
               ( A ) LENGTH: 18 base pairs
               ( B ) TYPE: nucleic acid
               ( C ) STRANDEDNESS: single
               ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
               ( A ) ORGANISM: Candida kefyr ( v i i ) IMMEDIATE SOURCE:
               ( B ) CLONE: YSASRSUB ( x i ) SEQUENCE DESCRIPTION: SEQ ID NO:72:

TCGTGCTGGG GATAGAGC 18

( 2 ) INFORMATION FOR SEQ ID NO:73:

( i ) SEQUENCE CHARACTERISTICS:
               ( A ) LENGTH: 18 base pairs
               ( B ) TYPE: nucleic acid
               ( C ) STRANDEDNESS: single
               ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Candida krusei (vii) IMMEDIATE SOURCE:
(B) CLONE: YSASRRNAC (xi) SEQUENCE DESCRIPTION: SEQ ID NO:73:

TCGTGCTGGG GATAGAGC  18

(2) INFORMATION FOR SEQ ID NO:74:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida krusei (vii) IMMEDIATE SOURCE:
(B) CLONE: YSASRSUD (xi) SEQUENCE DESCRIPTION: SEQ ID NO:74:

TCGTGCTGGG GATAGAGC  18

(2) INFORMATION FOR SEQ ID NO:75:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida tropicalis (vii) IMMEDIATE SOURCE:
(B) CLONE: YSASRRNAB (xi) SEQUENCE DESCRIPTION: SEQ ID NO:75:

TCGTGCTGGG GATAGAGC  18

(2) INFORMATION FOR SEQ ID NO:76:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida tropicalis (vii) IMMEDIATE SOURCE:
(B) CLONE: YSASRSUG ( x i ) SEQUENCE DESCRIPTION: SEQ ID NO:76:

TCGTGCTGGG GATAGAGC　　　　　　　　　　　　　　　　　　　　　　　　　　　18

( 2 ) INFORMATION FOR SEQ ID NO:77:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida viswanathii ( v i i ) IMMEDIATE SOURCE:
        ( B ) CLONE: YSASRSUH ( x i ) SEQUENCE DESCRIPTION: SEQ ID NO:77:

TCGTGCTGGG GATAGAGC　　　　　　　　　　　　　　　　　　　　　　　　　　　18

( 2 ) INFORMATION FOR SEQ ID NO:78:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida parapsilosis ( v i i ) IMMEDIATE SOURCE:
        ( B ) CLONE: YSASRSUF ( x i ) SEQUENCE DESCRIPTION: SEQ ID NO:78:

TCGTGCTGGG GATAGAGC　　　　　　　　　　　　　　　　　　　　　　　　　　　18

( 2 ) INFORMATION FOR SEQ ID NO:79:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida guilliermondii ( v i i ) IMMEDIATE SOURCE:
        ( B ) CLONE: YSASRSUC ( x i ) SEQUENCE DESCRIPTION: SEQ ID NO:79:

TCGTGCTGGG GATAGAGC　　　　　　　　　　　　　　　　　　　　　　　　　　　18

( 2 ) INFORMATION FOR SEQ ID NO:80:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida glabrata ( v i i ) IMMEDIATE SOURCE:
        ( B ) CLONE: YS5CRRNAS ( x i ) SEQUENCE DESCRIPTION: SEQ ID NO:80:

TCGTGCTGGG GATAGAGC         18

( 2 ) INFORMATION FOR SEQ ID NO:81:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Pneumocystis carinii ( v i i ) IMMEDIATE SOURCE:
        ( B ) CLONE: PMC16SRR1

( x i ) SEQUENCE DESCRIPTION: SEQ ID NO:81:

GCGCAACTGA TCCTTCCC         18

( 2 ) INFORMATION FOR SEQ ID NO:82:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Cryptococcus neoformans ( v i i ) IMMEDIATE SOURCE:
        ( B ) CLONE: CPCDA ( x i ) SEQUENCE DESCRIPTION: SEQ ID NO:82:

GTGCCGGCGA TGCTTCAT         18

( 2 ) INFORMATION FOR SEQ ID NO:83:

( i ) SEQUENCE CHARACTERISTICS:
        ( A ) LENGTH: 18 base pairs
        ( B ) TYPE: nucleic acid (C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
 (A) ORGANISM: Coccidiodes immitis (vii) IMMEDIATE SOURCE:
 (B) CLONE: COIDA (xi) SEQUENCE DESCRIPTION: SEQ ID NO:83:

ACCTGGTTGA TCCTGCCA 18

(2) INFORMATION FOR SEQ ID NO:84:

(i) SEQUENCE CHARACTERISTICS:
 (A) LENGTH: 18 base pairs
 (B) TYPE: nucleic acid
 (C) STRANDEDNESS: single
 (D) TOPOLOGY: linear (ii) MOLECULE TYPE: cDNA to rRNA (iii) HYPOTHETICAL: NO (iv) ANTI-SENSE: NO (vi) ORIGINAL SOURCE:
 (A) ORGANISM: Blastomyces dermatitidis (vii) IMMEDIATE SOURCE:
 (B) CLONE: BLODA (xi) SEQUENCE DESCRIPTION: SEQ ID NO:84:

ACCTGGTTGA TCCTGCCA 18

(2) INFORMATION FOR SEQ ID NO:85:

(i) SEQUENCE CHARACTERISTICS:
 (A) LENGTH: 18 base pairs
 (B) TYPE: nucleic acid
 (C) STRANDEDNESS: single
 (D) TOPOLOGY: linear (ii) MOLECULE TYPE: cDNA to rRNA (iii) HYPOTHETICAL: NO (iv) ANTI-SENSE: NO (vi) ORIGINAL SOURCE:
 (A) ORGANISM: Aspergillus fumagatus (vii) IMMEDIATE SOURCE:
 (B) CLONE: ASNDA (xi) SEQUENCE DESCRIPTION: SEQ ID NO:85:

ACCTGGTTGA TCCTGCCA 18

(2) INFORMATION FOR SEQ ID NO:86:

(i) SEQUENCE CHARACTERISTICS:
 (A) LENGTH: 18 base pairs
 (B) TYPE: nucleic acid
 (C) STRANDEDNESS: single
 (D) TOPOLOGY: linear (ii) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Aspergillus fumigatus ( v i i ) IMMEDIATE SOURCE:
    ( B ) CLONE: ASNRR5SS ( x i ) SEQUENCE DESCRIPTION: SEQ ID NO:86:

GCGCCGGCGA TGGTTCAT                                                                  18

( 2 ) INFORMATION FOR SEQ ID NO:87:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRRSSB ( x i ) SEQUENCE DESCRIPTION: SEQ ID NO:87:

GCGCCGGCGA TGGTTCAT                                                                  18

( 2 ) INFORMATION FOR SEQ ID NO:88:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida albicans ( v i i ) IMMEDIATE SOURCE:
        ( B ) CLONE: YSASRSUA ( x i ) SEQUENCE DESCRIPTION: SEQ ID NO:88:

GCGCAAGTCA TCAGCTTG                                                             18

( 2 ) INFORMATION FOR SEQ ID NO:89:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Candida albicans (vii) IMMEDIATE SOURCE:
    (B) CLONE: YSAL16S (xi) SEQUENCE DESCRIPTION: SEQ ID NO:89:

GCGCAAGTCA TCAGCTTG　　　　　　　　　　　　　　　　　　　　　　　　　　　　18

(2) INFORMATION FOR SEQ ID NO:90:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Candida lusitaniae (vii) IMMEDIATE SOURCE:
        (B) CLONE: YSASRRNAA (xi) SEQUENCE DESCRIPTION: SEQ ID NO:90:

GCGCAAGTCA TCAGCTTG　　　　　　　　　　　　　　　　　　　　　　　　　　　　18

(2) INFORMATION FOR SEQ ID NO:91:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Candida lusitaniae (vii) IMMEDIATE SOURCE:
        (B) CLONE: YSASRSUE (xi) SEQUENCE DESCRIPTION: SEQ ID NO:91:

GCGCAAGTCA TCAGCTTG　　　　　　　　　　　　　　　　　　　　　　　　　　　　18

(2) INFORMATION FOR SEQ ID NO:92:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Candida kefyr (vii) IMMEDIATE SOURCE:
        (B) CLONE: YSASRSUB 5,639,612

153

154

-continued ( x i ) SEQUENCE DESCRIPTION: SEQ ID NO:92:

GCGCAAGTCA TCAGCTTG								18

( 2 ) INFORMATION FOR SEQ ID NO:93:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRRNAC ( x i ) SEQUENCE DESCRIPTION: SEQ ID NO:93:

GCGCAAGTCA TCAGCTTG								18

( 2 ) INFORMATION FOR SEQ ID NO:94:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRSUD ( x i ) SEQUENCE DESCRIPTION: SEQ ID NO:94:

GCGCAAGTCA TCAGCTTG								18

( 2 ) INFORMATION FOR SEQ ID NO:95:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRRNAB ( x i ) SEQUENCE DESCRIPTION: SEQ ID NO:95:

GCGCAAGTCA TCAGCTTG								18

(2) INFORMATION FOR SEQ ID NO:96:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida tropicalis (vii) IMMEDIATE SOURCE:
    (B) CLONE: YSASRSUG (xi) SEQUENCE DESCRIPTION: SEQ ID NO:96:

GCGCAAGTCA TCAGCTTG                                         18

(2) INFORMATION FOR SEQ ID NO:97:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida viswanathii (vii) IMMEDIATE SOURCE:
    (B) CLONE: YSASRSUH (xi) SEQUENCE DESCRIPTION: SEQ ID NO:97:

GCGCAAGTCA TCAGCTTG                                         18

(2) INFORMATION FOR SEQ ID NO:98:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida parapsilosis (vii) IMMEDIATE SOURCE:
    (B) CLONE: YSASRSUF (xi) SEQUENCE DESCRIPTION: SEQ ID NO:98:

GCGCAAGTCA TCAGCTTG                                         18

(2) INFORMATION FOR SEQ ID NO:99:

(i) SEQUENCE CHARACTERISTICS:
    (A) LENGTH: 18 base pairs
    (B) TYPE: nucleic acid (C) STRANDEDNESS: single
            (D) TOPOLOGY: linear (ii) MOLECULE TYPE: cDNA to rRNA (iii) HYPOTHETICAL: NO (iv) ANTI-SENSE: NO (vi) ORIGINAL SOURCE:
            (A) ORGANISM: Candida guilliermondii (vii) IMMEDIATE SOURCE:
            (B) CLONE: YSASRSUC (xi) SEQUENCE DESCRIPTION: SEQ ID NO:99:

GCGCAAGTCA TCAGCTTG                                                                                    18

(2) INFORMATION FOR SEQ ID NO:100:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA to rRNA (iii) HYPOTHETICAL: NO (iv) ANTI-SENSE: NO (vi) ORIGINAL SOURCE:
            (A) ORGANISM: Candida glabrata (vii) IMMEDIATE SOURCE:
            (B) CLONE: YS5CRRNAS (xi) SEQUENCE DESCRIPTION: SEQ ID NO:100:

GCGCAAGTCA TCAGCTTG                                                                                    18

(2) INFORMATION FOR SEQ ID NO:101:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA to rRNA (iii) HYPOTHETICAL: NO (iv) ANTI-SENSE: NO (vi) ORIGINAL SOURCE:
            (A) ORGANISM: Human TAN-1

(vii) IMMEDIATE SOURCE:
            (B) CLONE: HUMTAN1

(xi) SEQUENCE DESCRIPTION: SEQ ID NO:101:

GCGCAACAGC TCCTTCCC                                                                                    18

(2) INFORMATION FOR SEQ ID NO:102:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA to rRNA (  i i i ) HYPOTHETICAL: NO (  i v ) ANTI-SENSE: NO (  v i ) ORIGINAL SOURCE:
     ( A ) ORGANISM: Abccelsyn xylium (  v i i ) IMMEDIATE SOURCE:
     ( B ) CLONE: ABCCELSYN (  x i ) SEQUENCE DESCRIPTION: SEQ ID NO:102:

GAGGAACTGA TCCTTCCC 18

( 2 ) INFORMATION FOR SEQ ID NO:103:

( i ) SEQUENCE CHARACTERISTICS:
       ( A ) LENGTH: 18 base pairs
       ( B ) TYPE: nucleic acid
       ( C ) STRANDEDNESS: single
       ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
       ( A ) ORGANISM: Human mRNA neuron ( v i i ) IMMEDIATE SOURCE:
       ( B ) CLONE: HUMNSEMRNA ( x i ) SEQUENCE DESCRIPTION: SEQ ID NO:103:

CTCCCACTGA TCCTTCCC 18

( 2 ) INFORMATION FOR SEQ ID NO:104:

( i ) SEQUENCE CHARACTERISTICS:
       ( A ) LENGTH: 23 base pairs
       ( B ) TYPE: nucleic acid
       ( C ) STRANDEDNESS: single
       ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
       ( A ) ORGANISM: Pneumocystis carinii ( v i i ) IMMEDIATE SOURCE:
       ( B ) CLONE: PMC16SRR1

( x i ) SEQUENCE DESCRIPTION: SEQ ID NO:104:

GGCGATGTTT TTTTCTTGAC TCG 23

( 2 ) INFORMATION FOR SEQ ID NO:105:

( i ) SEQUENCE CHARACTERISTICS:
       ( A ) LENGTH: 23 base pairs
       ( B ) TYPE: nucleic acid
       ( C ) STRANDEDNESS: single
       ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Cryptococcus neoformans (vii) IMMEDIATE SOURCE:
        (B) CLONE: CPCDA (xi) SEQUENCE DESCRIPTION: SEQ ID NO:105:

GGCGATGCTT CATTCAAATA TCT                    23

(2) INFORMATION FOR SEQ ID NO:106:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Coccidiodes immitis (vii) IMMEDIATE SOURCE:
        (B) CLONE: COIDA (xi) SEQUENCE DESCRIPTION: SEQ ID NO:106:

GGCGATGGTT CATTCAAATT TCT                    23

(2) INFORMATION FOR SEQ ID NO:107:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Blastomyces dermatitidis (vii) IMMEDIATE SOURCE:
        (B) CLONE: BLODA (xi) SEQUENCE DESCRIPTION: SEQ ID NO:107:

GGCGATGGTT CATTCAAATT TCT                    23

(2) INFORMATION FOR SEQ ID NO:108:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Aspergillus fumagatus (vii) IMMEDIATE SOURCE:
        (B) CLONE: ASNDA ( x i ) SEQUENCE DESCRIPTION: SEQ ID NO:108:

GGCGGTGTTT CTATGATGAC CCG 23

( 2 ) INFORMATION FOR SEQ ID NO:109:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRR5SS ( x i ) SEQUENCE DESCRIPTION: SEQ ID NO:109:

GGCGGTGTTT CTATGATGAC CCG 23

( 2 ) INFORMATION FOR SEQ ID NO:110:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRRSSB ( x i ) SEQUENCE DESCRIPTION: SEQ ID NO:110:

GGCGGTGTTT CTATGATGAC CCG 23

( 2 ) INFORMATION FOR SEQ ID NO:111:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida albicans ( v i i ) IMMEDIATE SOURCE:
        ( B ) CLONE: YSASRSUA ( x i ) SEQUENCE DESCRIPTION: SEQ ID NO:111:

GTTGTTGTTC TTTTATTGAC GCA 23

( 2 ) INFORMATION FOR SEQ ID NO:112:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candidi albicans ( v i i ) IMMEDIATE SOURCE:
        ( B ) CLONE: YSAL16S ( x i ) SEQUENCE DESCRIPTION: SEQ ID NO:112:

GTTGTTGTTC TTTTATTGAC GCA                                                                                      2 3

( 2 ) INFORMATION FOR SEQ ID NO:113:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRRNAA ( x i ) SEQUENCE DESCRIPTION: SEQ ID NO:113:

GGCGGCGTTC ATTTAGTGAC GCG                                                                                      2 3

( 2 ) INFORMATION FOR SEQ ID NO:114:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRSUE ( x i ) SEQUENCE DESCRIPTION: SEQ ID NO:114:

GGCGGCGTTC ATTTAGTGAC GCG                                                                                      2 3

( 2 ) INFORMATION FOR SEQ ID NO:115:

( i ) SEQUENCE CHARACTERISTICS:
        ( A ) LENGTH: 23 base pairs
        ( B ) TYPE: nucleic acid ( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
( A ) ORGANISM: Candida kefyr ( v i i ) IMMEDIATE SOURCE:
( B ) CLONE: YSASRSUB ( x i ) SEQUENCE DESCRIPTION: SEQ ID NO:115:

GGCGATGGTT CATTCAAATT TCT   23

( 2 ) INFORMATION FOR SEQ ID NO:116:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
( A ) ORGANISM: Candida krusei ( v i i ) IMMEDIATE SOURCE:
( B ) CLONE: YSASRRNAC ( x i ) SEQUENCE DESCRIPTION: SEQ ID NO:116:

GGCCGTTTTT AGTCCTTGGA GTG   23

( 2 ) INFORMATION FOR SEQ ID NO:117:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
( A ) ORGANISM: Candida krusei ( v i i ) IMMEDIATE SOURCE:
( B ) CLONE: YSASRSUD ( x i ) SEQUENCE DESCRIPTION: SEQ ID NO:117:

TATTTTGTTN GTTTCTAGGA CCA   23

( 2 ) INFORMATION FOR SEQ ID NO:118:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida tropicalis ( v i i ) IMMEDIATE SOURCE:
    ( B ) CLONE: YSASRRNAB ( x i ) SEQUENCE DESCRIPTION: SEQ ID NO:118:

GTTGTTGTTC TTTTATTGAC GCA    23

( 2 ) INFORMATION FOR SEQ ID NO:119:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRSUG ( x i ) SEQUENCE DESCRIPTION: SEQ ID NO:119:

GTTGTTGTTC TTTTATTGAC GCA    23

( 2 ) INFORMATION FOR SEQ ID NO:120:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida viswanathii ( v i i ) IMMEDIATE SOURCE:
        ( B ) CLONE: YSASRSUH ( x i ) SEQUENCE DESCRIPTION: SEQ ID NO:120:

GTTGTTGTTC TTTTATTGAC GCA    23

( 2 ) INFORMATION FOR SEQ ID NO:121:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

( A ) ORGANISM: Candida parapsilosis ( v i i ) IMMEDIATE SOURCE:
                    ( B ) CLONE: YSASRSUF ( x i ) SEQUENCE DESCRIPTION: SEQ ID NO:121:

GTTGTTGTTC TTTTATTGAC GCA                                                        23

( 2 ) INFORMATION FOR SEQ ID NO:122:

( i ) SEQUENCE CHARACTERISTICS:
                    ( A ) LENGTH: 23 base pairs
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Candida guilliermondii ( v i i ) IMMEDIATE SOURCE:
                    ( B ) CLONE: YSASRSUC ( x i ) SEQUENCE DESCRIPTION: SEQ ID NO:122:

GGTGTTGTTC TKTTTTGAC GCA                                                         23

( 2 ) INFORMATION FOR SEQ ID NO:123:

( i ) SEQUENCE CHARACTERISTICS:
                    ( A ) LENGTH: 23 base pairs
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Candida glabrata ( v i i ) IMMEDIATE SOURCE:
                    ( B ) CLONE: YS5CRRNAS ( x i ) SEQUENCE DESCRIPTION: SEQ ID NO:123:

GGTGGTGTTT TTTTAGTGAC CCA                                                        23

( 2 ) INFORMATION FOR SEQ ID NO:124:

( i ) SEQUENCE CHARACTERISTICS:
                    ( A ) LENGTH: 23 base pairs
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Tobacco chloroplast ( v i i ) IMMEDIATE SOURCE:
                    ( B ) CLONE: TOBCPTGRG ( x i ) SEQUENCE DESCRIPTION: SEQ ID NO:124:

CGAGCCGTTT TTTTCTTGAC TCG                 23

( 2 ) INFORMATION FOR SEQ ID NO:125:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aureobasidium pullulans ( v i i ) IMMEDIATE SOURCE:
        ( B ) CLONE: AURRR16S ( x i ) SEQUENCE DESCRIPTION: SEQ ID NO:125:

GGCGATGTTA TCATTTTGAC TCG                 23

( 2 ) INFORMATION FOR SEQ ID NO:126:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: N. Tabacum ( v i i ) IMMEDIATE SOURCE:
        ( B ) CLONE: TOBCOCG ( x i ) SEQUENCE DESCRIPTION: SEQ ID NO:126:

CGAGCCGTTT TTTTCTTGAC TCG                 23

( 2 ) INFORMATION FOR SEQ ID NO:127:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Pneumocystis carinii ( v i i ) IMMEDIATE SOURCE:
        ( B ) CLONE: PMC16SRR1

( x i ) SEQUENCE DESCRIPTION: SEQ ID NO:127:

AACACGGGGA AACTCACCA                      19

( 2 ) INFORMATION FOR SEQ ID NO:128:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Cryptococcus neoformans ( v i i ) IMMEDIATE SOURCE:
        ( B ) CLONE: CPCDA ( x i ) SEQUENCE DESCRIPTION: SEQ ID NO:128:

AACACGGGGA AACTCACCA                                                        19

( 2 ) INFORMATION FOR SEQ ID NO:129:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Coccidiodes immitis ( v i i ) IMMEDIATE SOURCE:
        ( B ) CLONE: COIDA ( x i ) SEQUENCE DESCRIPTION: SEQ ID NO:129:

CTTCTGGGGA ACCCTATGG                                                        19

( 2 ) INFORMATION FOR SEQ ID NO:130:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Blastomyces dermatitidis ( v i i ) IMMEDIATE SOURCE:
        ( B ) CLONE: BLODA ( x i ) SEQUENCE DESCRIPTION: SEQ ID NO:130:

CTCCTGGGAA GCCCCATGG                                                        19

( 2 ) INFORMATION FOR SEQ ID NO:131:

( i ) SEQUENCE CHARACTERISTICS:
        ( A ) LENGTH: 19 base pairs
        ( B ) TYPE: nucleic acid (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Aspergillus fumagatus (vii) IMMEDIATE SOURCE:
        (B) CLONE: ASNDA (xi) SEQUENCE DESCRIPTION: SEQ ID NO:131:

CTTCTGGGGA ACCTCATGG 19

(2) INFORMATION FOR SEQ ID NO:132:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Aspergillus fumigatus (vii) IMMEDIATE SOURCE:
        (B) CLONE: ASNRR5SS (xi) SEQUENCE DESCRIPTION: SEQ ID NO:132:

CTTCTGGGGA ACCTCATGG 19

(2) INFORMATION FOR SEQ ID NO:133:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Aspergillus fumigatus (vii) IMMEDIATE SOURCE:
        (B) CLONE: ASNRRSSB (xi) SEQUENCE DESCRIPTION: SEQ ID NO:133:

CTTCTGGGGA ACCTCATGG 19

(2) INFORMATION FOR SEQ ID NO:134:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida albicans (vii) IMMEDIATE SOURCE:
    (B) CLONE: YSASRSUA (xi) SEQUENCE DESCRIPTION: SEQ ID NO:134:

AAAGGGGCA ACCTCATTC      19

(2) INFORMATION FOR SEQ ID NO:135:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Candidi albicans (vii) IMMEDIATE SOURCE:
        (B) CLONE: YSAL16S (xi) SEQUENCE DESCRIPTION: SEQ ID NO:135:

AACACGGGA AACTCACCA      19

(2) INFORMATION FOR SEQ ID NO:136:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Candida lusitaniae (vii) IMMEDIATE SOURCE:
        (B) CLONE: YSASRRNAA (xi) SEQUENCE DESCRIPTION: SEQ ID NO:136:

AATCTTGGGA AACTCCGTC      19

(2) INFORMATION FOR SEQ ID NO:137:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:

(A) ORGANISM: Candida lusitaniae (vii) IMMEDIATE SOURCE:
(B) CLONE: YSASRSUE (xi) SEQUENCE DESCRIPTION: SEQ ID NO:137:

AATCTTGGGA AACTCCGTC 19

(2) INFORMATION FOR SEQ ID NO:138:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida kefyr (vii) IMMEDIATE SOURCE:
(B) CLONE: YSASRSUB (xi) SEQUENCE DESCRIPTION: SEQ ID NO:138:

CTTCTGGCTA ACCTGTACT 19

(2) INFORMATION FOR SEQ ID NO:139:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida krusei (vii) IMMEDIATE SOURCE:
(B) CLONE: YSASRRNAC (xi) SEQUENCE DESCRIPTION: SEQ ID NO:139:

AACACGGGGA AACTCACCA 19

(2) INFORMATION FOR SEQ ID NO:140:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida krusei (vii) IMMEDIATE SOURCE:
(B) CLONE: YSASRSUD ( x i ) SEQUENCE DESCRIPTION: SEQ ID NO:140:

CTTCTGGCTA SCCTCGGGC                                                19

( 2 ) INFORMATION FOR SEQ ID NO:141:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRRNAB ( x i ) SEQUENCE DESCRIPTION: SEQ ID NO:141:

CTTCTGGCTA GCCTTTTGG                                                19

( 2 ) INFORMATION FOR SEQ ID NO:142:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRSUG ( x i ) SEQUENCE DESCRIPTION: SEQ ID NO:142:

CTTCTGGCTA GCCTTTTGG                                                19

( 2 ) INFORMATION FOR SEQ ID NO:143:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida viswanathii ( v i i ) IMMEDIATE SOURCE:
        ( B ) CLONE: YSASRSUH ( x i ) SEQUENCE DESCRIPTION: SEQ ID NO:143:

CTTCTGGCTA GCCTTTTGG                                                19

( 2 ) INFORMATION FOR SEQ ID NO:144:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida parapsilosis ( v i i ) IMMEDIATE SOURCE:
        ( B ) CLONE: YSASRSUF ( x i ) SEQUENCE DESCRIPTION: SEQ ID NO:144:

AACACGGGGA AACTCACCA     19

( 2 ) INFORMATION FOR SEQ ID NO:145:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida guilliermondii ( v i i ) IMMEDIATE SOURCE:
        ( B ) CLONE: YSASRSUC ( x i ) SEQUENCE DESCRIPTION: SEQ ID NO:145:

CTTCTGGCTA ACCATTCGC     19

( 2 ) INFORMATION FOR SEQ ID NO:146:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida glabrata ( v i i ) IMMEDIATE SOURCE:
        ( B ) CLONE: YS5CRRNAS ( x i ) SEQUENCE DESCRIPTION: SEQ ID NO:146:

CTTCTGGCTA ACCCCAAGT     19

( 2 ) INFORMATION FOR SEQ ID NO:147:

( i ) SEQUENCE CHARACTERISTICS:
        ( A ) LENGTH: 19 base pairs
        ( B ) TYPE: nucleic acid ( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Penniclium notatum sub ( v i i ) IMMEDIATE SOURCE:
    ( B ) CLONE: PNNDA ( x i ) SEQUENCE DESCRIPTION: SEQ ID NO:147:

CTTCTGGCTA ACCTCATGG　　　　　　　　　　　　　　　　　　　　　　　　　19

( 2 ) INFORMATION FOR SEQ ID NO:148:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Human HLA-B-AT3

( v i i ) IMMEDIATE SOURCE:
        ( B ) CLONE: HUMBAT3A ( x i ) SEQUENCE DESCRIPTION: SEQ ID NO:148:

CTTCTGGCTA ACCTGCTAG　　　　　　　　　　　　　　　　　　　　　　　　　19

( 2 ) INFORMATION FOR SEQ ID NO:149:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Rat Olfactory protein ( v i i ) IMMEDIATE SOURCE:
        ( B ) CLONE: RATOLFPRON ( x i ) SEQUENCE DESCRIPTION: SEQ ID NO:149:

CTCCTGGCTA ACCTCATCA　　　　　　　　　　　　　　　　　　　　　　　　　19

( 2 ) INFORMATION FOR SEQ ID NO:150:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Pneumocystis carinii ( v i i ) IMMEDIATE SOURCE:
    ( B ) CLONE: PMC16SRR1

( x i ) SEQUENCE DESCRIPTION: SEQ ID NO:150:

```
GGCGATGTTT TTTTCTTGAG T                                              21
```

( 2 ) INFORMATION FOR SEQ ID NO:151:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Cryptococcus neoformans ( v i i ) IMMEDIATE SOURCE:
        ( B ) CLONE: CPCDA ( x i ) SEQUENCE DESCRIPTION: SEQ ID NO:151:

```
TTGTTGGTTT CTAGGATCGC C                                              21
```

( 2 ) INFORMATION FOR SEQ ID NO:152:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Coccidiodes immitis ( v i i ) IMMEDIATE SOURCE:
        ( B ) CLONE: COIDA ( x i ) SEQUENCE DESCRIPTION: SEQ ID NO:152:

```
ACGTGTGGTT CTATTTGTT G                                               21
```

( 2 ) INFORMATION FOR SEQ ID NO:153:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Blastomyces dermatitidis (vii) IMMEDIATE SOURCE:
        (B) CLONE: BLODA (xi) SEQUENCE DESCRIPTION: SEQ ID NO:153:

GACGGGGTTC TTATGATGAC C                                              21

(2) INFORMATION FOR SEQ ID NO:154:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Aspergillus fumagatus (vii) IMMEDIATE SOURCE:
        (B) CLONE: ASNDA (xi) SEQUENCE DESCRIPTION: SEQ ID NO:154:

GGCGGTGTTT CTATGATGAC C                                              21

(2) INFORMATION FOR SEQ ID NO:155:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Aspergillus fumigatus (vii) IMMEDIATE SOURCE:
        (B) CLONE: ASNRR5SS (xi) SEQUENCE DESCRIPTION: SEQ ID NO:155:

GGCGGTGTTT CTATGATGAC C                                              21

(2) INFORMATION FOR SEQ ID NO:156:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Aspergillus fumigatus (vii) IMMEDIATE SOURCE:
        (B) CLONE: ASNRRSSB ( x i ) SEQUENCE DESCRIPTION: SEQ ID NO:156:

GGCGGTGTTT CTATGATGAC C                    21

( 2 ) INFORMATION FOR SEQ ID NO:157:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida albicans ( v i i ) IMMEDIATE SOURCE:
        ( B ) CLONE: YSASRSUA ( x i ) SEQUENCE DESCRIPTION: SEQ ID NO:157:

CCTTCGGGCT CTTTGATGAT T                    21

( 2 ) INFORMATION FOR SEQ ID NO:158:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candidi albicans ( v i i ) IMMEDIATE SOURCE:
        ( B ) CLONE: YSAL16S ( x i ) SEQUENCE DESCRIPTION: SEQ ID NO:158:

CCTTCGGGCT CTTTGATGAT T                    21

( 2 ) INFORMATION FOR SEQ ID NO:159:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRRNAA ( x i ) SEQUENCE DESCRIPTION: SEQ ID NO:159:

GGCGGCGTTC ATTTAGTGAC G                    21

( 2 ) INFORMATION FOR SEQ ID NO:160:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRSUE ( x i ) SEQUENCE DESCRIPTION: SEQ ID NO:160:

GGCGGCGTTC ATTTAGTGAC G        21

( 2 ) INFORMATION FOR SEQ ID NO:161:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida kefyr ( v i i ) IMMEDIATE SOURCE:
        ( B ) CLONE: YSASRSUB ( x i ) SEQUENCE DESCRIPTION: SEQ ID NO:161:

GGTGGTGTTT TTCTTATGAC C        21

( 2 ) INFORMATION FOR SEQ ID NO:162:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRRNAC ( x i ) SEQUENCE DESCRIPTION: SEQ ID NO:162:

GACGGTCTAC CTATGGTAAG C        21

( 2 ) INFORMATION FOR SEQ ID NO:163:

( i ) SEQUENCE CHARACTERISTICS:
        ( A ) LENGTH: 21 base pairs
        ( B ) TYPE: nucleic acid (C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
  (A) ORGANISM: Candida krusei (vii) IMMEDIATE SOURCE:
  (B) CLONE: YSASRSUD (xi) SEQUENCE DESCRIPTION: SEQ ID NO:163:

GACGGTCTAC CTATGGTAAG C                               21

(2) INFORMATION FOR SEQ ID NO:164:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida tropicalis (vii) IMMEDIATE SOURCE:
    (B) CLONE: YSASRRNAB (xi) SEQUENCE DESCRIPTION: SEQ ID NO:164:

TCTTCGGACT CTTTGATGAT T                               21

(2) INFORMATION FOR SEQ ID NO:165:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida tropicalis (vii) IMMEDIATE SOURCE:
    (B) CLONE: YSASRSUG (xi) SEQUENCE DESCRIPTION: SEQ ID NO:165:

TCTTCGGACT CTTTGATGAT T                               21

(2) INFORMATION FOR SEQ ID NO:166:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida viswanathii ( v i i ) IMMEDIATE SOURCE:
    ( B ) CLONE: YSASRSUH ( x i ) SEQUENCE DESCRIPTION: SEQ ID NO:166:

CCTTCGGGCT CTTTGATGAT T    21

( 2 ) INFORMATION FOR SEQ ID NO:167:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida parapsilosis ( v i i ) IMMEDIATE SOURCE:
        ( B ) CLONE: YSASRSUF ( x i ) SEQUENCE DESCRIPTION: SEQ ID NO:167:

GGCGATGGTT CATTCAAATT T    21

( 2 ) INFORMATION FOR SEQ ID NO:168:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida guilliermondii ( v i i ) IMMEDIATE SOURCE:
        ( B ) CLONE: YSASRSUC ( x i ) SEQUENCE DESCRIPTION: SEQ ID NO:168:

TCTTTGAGCT CTTTGATGAT T    21

( 2 ) INFORMATION FOR SEQ ID NO:169:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Candida glabrata (vii) IMMEDIATE SOURCE:
    (B) CLONE: YS5CRRNAS (xi) SEQUENCE DESCRIPTION: SEQ ID NO:169:

GGTGGTGTTT TTTTAGTGAC C    21

(2) INFORMATION FOR SEQ ID NO:170:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Nanochlorum eucaryotum (vii) IMMEDIATE SOURCE:
    (B) CLONE: NANRRN18S (xi) SEQUENCE DESCRIPTION: SEQ ID NO:170:

GCGGGTGTTT TTTGATGAC C    21

(2) INFORMATION FOR SEQ ID NO:171:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Moraxella sp. MspI (vii) IMMEDIATE SOURCE:
    (B) CLONE: MBOMSPI (xi) SEQUENCE DESCRIPTION: SEQ ID NO:171:

TCTAGTGTTT CAATGATGAC T    21

(2) INFORMATION FOR SEQ ID NO:172:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: E. Coli cvaA,B operon (vii) IMMEDIATE SOURCE:
    (B) CLONE: ECOCVAB ( x i ) SEQUENCE DESCRIPTION: SEQ ID NO:172:

GTCGGTGTTT GTGTGATGAT G  21

( 2 ) INFORMATION FOR SEQ ID NO:173:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Pneumocystis carinii ( v i i ) IMMEDIATE SOURCE:
    ( B ) CLONE: PMC16SRR1

( x i ) SEQUENCE DESCRIPTION: SEQ ID NO:173:

GTCTGTGATG CCCTTAG  17

( 2 ) INFORMATION FOR SEQ ID NO:174:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Cryptococcus neoformans ( v i i ) IMMEDIATE SOURCE:
    ( B ) CLONE: CPCDA ( x i ) SEQUENCE DESCRIPTION: SEQ ID NO:174:

TGCTGAAAAG CCCCGAC  17

( 2 ) INFORMATION FOR SEQ ID NO:175:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Coccidiodes immitis ( v i i ) IMMEDIATE SOURCE:
    ( B ) CLONE: COIDA ( x i ) SEQUENCE DESCRIPTION: SEQ ID NO:175:

TTCTGGGGAA CCCTAGT  17

( 2 ) INFORMATION FOR SEQ ID NO:176:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Blastomyces dermatitidis ( v i i ) IMMEDIATE SOURCE:
        ( B ) CLONE: BLODA ( x i ) SEQUENCE DESCRIPTION: SEQ ID NO:176:

TCCTGGGAAG CCCCATG                                17

( 2 ) INFORMATION FOR SEQ ID NO:177:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumagatus ( v i i ) IMMEDIATE SOURCE:
        ( B ) CLONE: ASNDA ( x i ) SEQUENCE DESCRIPTION: SEQ ID NO:177:

TTCTGGGGAA CCTCATG                                17

( 2 ) INFORMATION FOR SEQ ID NO:178:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRR5SS ( x i ) SEQUENCE DESCRIPTION: SEQ ID NO:178:

TTCTGGGGAA CCTCATG                                17

( 2 ) INFORMATION FOR SEQ ID NO:179:

( i ) SEQUENCE CHARACTERISTICS:
        ( A ) LENGTH: 17 base pairs
        ( B ) TYPE: nucleic acid ( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Aspergillus fumigatus ( v i i ) IMMEDIATE SOURCE:
    ( B ) CLONE: ASNRRSSB ( x i ) SEQUENCE DESCRIPTION: SEQ ID NO:179:

TTCTGGGGAA CCTCATG                    17

( 2 ) INFORMATION FOR SEQ ID NO:180:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida albicans ( v i i ) IMMEDIATE SOURCE:
        ( B ) CLONE: YSASRSUA ( x i ) SEQUENCE DESCRIPTION: SEQ ID NO:180:

TTCTGGGTAG CCATTTA                    17

( 2 ) INFORMATION FOR SEQ ID NO:181:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candidi albicans ( v i i ) IMMEDIATE SOURCE:
        ( B ) CLONE: YSAL16S ( x i ) SEQUENCE DESCRIPTION: SEQ ID NO:181:

GTCTGTGATG CCCTTAG                    17

( 2 ) INFORMATION FOR SEQ ID NO:182:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to rRNA (iii) HYPOTHETICAL: NO (iv) ANTI-SENSE: NO (vi) ORIGINAL SOURCE:
 (A) ORGANISM: Candida lusitaniae (vii) IMMEDIATE SOURCE:
 (B) CLONE: YSASRRNAA (xi) SEQUENCE DESCRIPTION: SEQ ID NO:182:

GTCTGTGATG CCCTTAG 17

(2) INFORMATION FOR SEQ ID NO:183:

(i) SEQUENCE CHARACTERISTICS:
 (A) LENGTH: 17 base pairs
 (B) TYPE: nucleic acid
 (C) STRANDEDNESS: single
 (D) TOPOLOGY: linear (ii) MOLECULE TYPE: cDNA to rRNA (iii) HYPOTHETICAL: NO (iv) ANTI-SENSE: NO (vi) ORIGINAL SOURCE:
 (A) ORGANISM: Candida lusitaniae (vii) IMMEDIATE SOURCE:
 (B) CLONE: YSASRSUE (xi) SEQUENCE DESCRIPTION: SEQ ID NO:183:

GTCTGTGATG CCCTTAG 17

(2) INFORMATION FOR SEQ ID NO:184:

(i) SEQUENCE CHARACTERISTICS:
 (A) LENGTH: 17 base pairs
 (B) TYPE: nucleic acid
 (C) STRANDEDNESS: single
 (D) TOPOLOGY: linear (ii) MOLECULE TYPE: cDNA to rRNA (iii) HYPOTHETICAL: NO (iv) ANTI-SENSE: NO (vi) ORIGINAL SOURCE:
 (A) ORGANISM: Candida kefyr (vii) IMMEDIATE SOURCE:
 (B) CLONE: YSASRSUB (xi) SEQUENCE DESCRIPTION: SEQ ID NO:184:

GTCTGTGATG CCCTTAG 17

(2) INFORMATION FOR SEQ ID NO:185:

(i) SEQUENCE CHARACTERISTICS:
 (A) LENGTH: 17 base pairs
 (B) TYPE: nucleic acid
 (C) STRANDEDNESS: single
 (D) TOPOLOGY: linear (ii) MOLECULE TYPE: cDNA to rRNA (iii) HYPOTHETICAL: NO (iv) ANTI-SENSE: NO (vi) ORIGINAL SOURCE:

(A) ORGANISM: Candida krusei (vii) IMMEDIATE SOURCE:
    (B) CLONE: YSASRRNAC (xi) SEQUENCE DESCRIPTION: SEQ ID NO:185:

GTCTGTGATG CCCTTAG                                                                    17

(2) INFORMATION FOR SEQ ID NO:186:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Candida krusei (vii) IMMEDIATE SOURCE:
        (B) CLONE: YSASRSUD (xi) SEQUENCE DESCRIPTION: SEQ ID NO:186:

GTCTGTGATG CCCTTAG                                                                    17

(2) INFORMATION FOR SEQ ID NO:187:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Candida tropicalis (vii) IMMEDIATE SOURCE:
        (B) CLONE: YSASRRNAB (xi) SEQUENCE DESCRIPTION: SEQ ID NO:187:

GTCTGTGATG CCCTTAG                                                                    17

(2) INFORMATION FOR SEQ ID NO:188:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Candida tropicalis (vii) IMMEDIATE SOURCE:
        (B) CLONE: YSASRSUG ( x i ) SEQUENCE DESCRIPTION: SEQ ID NO:188:

GTCTGTGATG CCCTTAG                                                                                      17

( 2 ) INFORMATION FOR SEQ ID NO:189:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida viswanathii ( v i i ) IMMEDIATE SOURCE:
        ( B ) CLONE: YSASRSUH ( x i ) SEQUENCE DESCRIPTION: SEQ ID NO:189:

GTCTGTGATG CCCTTAG                                                                                      17

( 2 ) INFORMATION FOR SEQ ID NO:190:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida parapsilosis ( v i i ) IMMEDIATE SOURCE:
        ( B ) CLONE: YSASRSUF ( x i ) SEQUENCE DESCRIPTION: SEQ ID NO:190:

GTCTGTGATG CCCTTAG                                                                                      17

( 2 ) INFORMATION FOR SEQ ID NO:191:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida guilliermondii ( v i i ) IMMEDIATE SOURCE:
        ( B ) CLONE: YSASRSUC ( x i ) SEQUENCE DESCRIPTION: SEQ ID NO:191:

GTCTGTGATG CCCTTAG                                                                                      17

( 2 ) INFORMATION FOR SEQ ID NO:192:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida glabrata ( v i i ) IMMEDIATE SOURCE:
    ( B ) CLONE: YS5CRRNAS ( x i ) SEQUENCE DESCRIPTION: SEQ ID NO:192:

GCCTGGGTAG CCGGTCC              17

( 2 ) INFORMATION FOR SEQ ID NO:193:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Avian influenza ( v i i ) IMMEDIATE SOURCE:
    ( B ) CLONE: FLAHA5

( x i ) SEQUENCE DESCRIPTION: SEQ ID NO:193:

TCCTGGGAAA CCCCATG              17

( 2 ) INFORMATION FOR SEQ ID NO:194:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Mouse perlecan ( v i i ) IMMEDIATE SOURCE:
    ( B ) CLONE: MUSPERPA ( x i ) SEQUENCE DESCRIPTION: SEQ ID NO:194:

TCCTGGGCAG GCCCATG              17

( 2 ) INFORMATION FOR SEQ ID NO:195:

( i ) SEQUENCE CHARACTERISTICS:
    ( A ) LENGTH: 17 base pairs
    ( B ) TYPE: nucleic acid (C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Mouse basement membrane (vii) IMMEDIATE SOURCE:
    (B) CLONE: MUSPGCBMA (xi) SEQUENCE DESCRIPTION: SEQ ID NO:195:

```
TCCTGGGCAG GCCCATG                                              17
```

(2) INFORMATION FOR SEQ ID NO:196:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Pneumocystis carinii (vii) IMMEDIATE SOURCE:
    (B) CLONE: PMC16SRR1

(xi) SEQUENCE DESCRIPTION: SEQ ID NO:196:

```
CGCGGGCTTC TTAGAGGGAC T                                         21
```

(2) INFORMATION FOR SEQ ID NO:197:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Cryptococcus neoformans (vii) IMMEDIATE SOURCE:
    (B) CLONE: CPCDA (xi) SEQUENCE DESCRIPTION: SEQ ID NO:197:

```
GGTGAAATTC TTAGATTGAC G                                         21
```

(2) INFORMATION FOR SEQ ID NO:198:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Coccidiodes immitis (vii) IMMEDIATE SOURCE:
    (B) CLONE: COIDA (xi) SEQUENCE DESCRIPTION: SEQ ID NO:198:

GACGGGCAAC TTTGAATAAC C         21

(2) INFORMATION FOR SEQ ID NO:199:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: cDNA to rRNA (iii) HYPOTHETICAL: NO (iv) ANTI-SENSE: NO (vi) ORIGINAL SOURCE:
       (A) ORGANISM: Blastomyces dermatitidis (vii) IMMEDIATE SOURCE:
       (B) CLONE: BLODA (xi) SEQUENCE DESCRIPTION: SEQ ID NO:199:

GACGGGGTTC TTATGATGAC C         21

(2) INFORMATION FOR SEQ ID NO:200:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: cDNA to rRNA (iii) HYPOTHETICAL: NO (iv) ANTI-SENSE: NO (vi) ORIGINAL SOURCE:
       (A) ORGANISM: Aspergillus fumagatus (vii) IMMEDIATE SOURCE:
       (B) CLONE: ASNDA (xi) SEQUENCE DESCRIPTION: SEQ ID NO:200:

GGCGGTGTTT CTATGATGAC C         21

(2) INFORMATION FOR SEQ ID NO:201:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: cDNA to rRNA (iii) HYPOTHETICAL: NO (iv) ANTI-SENSE: NO (vi) ORIGINAL SOURCE:

(A) ORGANISM: Aspergillus fumigatus (vii) IMMEDIATE SOURCE:
    (B) CLONE: ASNRR5SS (xi) SEQUENCE DESCRIPTION: SEQ ID NO:201:

GGCGGTGTTT CTATGATGAC C     21

(2) INFORMATION FOR SEQ ID NO:202:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Aspergillus fumigatus (vii) IMMEDIATE SOURCE:
    (B) CLONE: ASNRRSSB (xi) SEQUENCE DESCRIPTION: SEQ ID NO:202:

GGCGGTGTTT CTATGATGAC C     21

(2) INFORMATION FOR SEQ ID NO:203:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida albicans (vii) IMMEDIATE SOURCE:
    (B) CLONE: YSASRSUA (xi) SEQUENCE DESCRIPTION: SEQ ID NO:203:

GTTGTTGTTC TTTTATTGAC G     21

(2) INFORMATION FOR SEQ ID NO:204:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candidi albicans (vii) IMMEDIATE SOURCE:
    (B) CLONE: YSAL16S ( x i ) SEQUENCE DESCRIPTION: SEQ ID NO:204:

GTTGTTGTTC TTTTATTGAC G 21

( 2 ) INFORMATION FOR SEQ ID NO:205:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRRNAA ( x i ) SEQUENCE DESCRIPTION: SEQ ID NO:205:

GGCGGCGTTC ATTTAGTGAC G 21

( 2 ) INFORMATION FOR SEQ ID NO:206:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRSUE ( x i ) SEQUENCE DESCRIPTION: SEQ ID NO:206:

GGCGGCGTTC ATTTAGTGAC G 21

( 2 ) INFORMATION FOR SEQ ID NO:207:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida kefyr ( v i i ) IMMEDIATE SOURCE:
        ( B ) CLONE: YSASRSUB ( x i ) SEQUENCE DESCRIPTION: SEQ ID NO:207:

GGTGGTGTTT TTCTTATGAC C 21

( 2 ) INFORMATION FOR SEQ ID NO:208:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRRNAC ( x i ) SEQUENCE DESCRIPTION: SEQ ID NO:208:

GACGGTCTAC CTATGGTAAG C     21

( 2 ) INFORMATION FOR SEQ ID NO:209:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRSUD ( x i ) SEQUENCE DESCRIPTION: SEQ ID NO:209:

GACGGTCTAC CTATGGTAAG C     21

( 2 ) INFORMATION FOR SEQ ID NO:210:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRRNAB ( x i ) SEQUENCE DESCRIPTION: SEQ ID NO:210:

GTTGTTGTTC TTTATTGAC G     21

( 2 ) INFORMATION FOR SEQ ID NO:211:

( i ) SEQUENCE CHARACTERISTICS:
        ( A ) LENGTH: 21 base pairs
        ( B ) TYPE: nucleic acid ( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
  ( A ) ORGANISM: Candida tropicalis ( v i i ) IMMEDIATE SOURCE:
  ( B ) CLONE: YSASRSUG ( x i ) SEQUENCE DESCRIPTION: SEQ ID NO:211:

GTTGTTGTTC TTTTATTGAC G    21

( 2 ) INFORMATION FOR SEQ ID NO:212:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida viswanathii ( v i i ) IMMEDIATE SOURCE:
    ( B ) CLONE: YSASRSUH ( x i ) SEQUENCE DESCRIPTION: SEQ ID NO:212:

GTTGTTGTTC TTTTATTGAC G    21

( 2 ) INFORMATION FOR SEQ ID NO:213:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida parapsilosis ( v i i ) IMMEDIATE SOURCE:
    ( B ) CLONE: YSASRSUF ( x i ) SEQUENCE DESCRIPTION: SEQ ID NO:213:

GTTGTTGTTC TTTTATTGAC G    21

( 2 ) INFORMATION FOR SEQ ID NO:214:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida guilliermondii ( v i i ) IMMEDIATE SOURCE:
    ( B ) CLONE: YSASRSUC ( x i ) SEQUENCE DESCRIPTION: SEQ ID NO:214:

GGTGTTGTTC TKTTTTTGAC G          21

( 2 ) INFORMATION FOR SEQ ID NO:215:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida glabrata ( v i i ) IMMEDIATE SOURCE:
        ( B ) CLONE: YS5CRRNAS ( x i ) SEQUENCE DESCRIPTION: SEQ ID NO:215:

GGTGGTGTTT TTTTAGTGAC C          21

( 2 ) INFORMATION FOR SEQ ID NO:216:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Rat ITPR2 Type 2 inositol ( v i i ) IMMEDIATE SOURCE:
        ( B ) CLONE: RATITPR2R ( x i ) SEQUENCE DESCRIPTION: SEQ ID NO:216:

GACGGGGTTC CCACTATGAC C          21

( 2 ) INFORMATION FOR SEQ ID NO:217:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Canine mRNA (vii) IMMEDIATE SOURCE:
 (B) CLONE: DOGSRPR (xi) SEQUENCE DESCRIPTION: SEQ ID NO:217:

CTGCTAATTC TTATGATGAC C  21

(2) INFORMATION FOR SEQ ID NO:218:

(i) SEQUENCE CHARACTERISTICS:
 (A) LENGTH: 21 base pairs
 (B) TYPE: nucleic acid
 (C) STRANDEDNESS: single
 (D) TOPOLOGY: linear (ii) MOLECULE TYPE: cDNA to rRNA (iii) HYPOTHETICAL: NO (iv) ANTI-SENSE: NO (vi) ORIGINAL SOURCE:
 (A) ORGANISM: Mitochondrion Oenothera (vii) IMMEDIATE SOURCE:
 (B) CLONE: OBEMTNAD12

(xi) SEQUENCE DESCRIPTION: SEQ ID NO:218:

CAGTCTTTTC TTATGATGAC C  21

(2) INFORMATION FOR SEQ ID NO:219:

(i) SEQUENCE CHARACTERISTICS:
 (A) LENGTH: 18 base pairs
 (B) TYPE: nucleic acid
 (C) STRANDEDNESS: single
 (D) TOPOLOGY: linear (ii) MOLECULE TYPE: cDNA to rRNA (iii) HYPOTHETICAL: NO (iv) ANTI-SENSE: NO (vi) ORIGINAL SOURCE:
 (A) ORGANISM: Pneumocystis carinii (vii) IMMEDIATE SOURCE:
 (B) CLONE: PMC16SRR1

(xi) SEQUENCE DESCRIPTION: SEQ ID NO:219:

TTTCTGGANA AGTTGATC  18

(2) INFORMATION FOR SEQ ID NO:220:

(i) SEQUENCE CHARACTERISTICS:
 (A) LENGTH: 18 base pairs
 (B) TYPE: nucleic acid
 (C) STRANDEDNESS: single
 (D) TOPOLOGY: linear (ii) MOLECULE TYPE: cDNA to rRNA (iii) HYPOTHETICAL: NO (iv) ANTI-SENSE: NO (vi) ORIGINAL SOURCE:
 (A) ORGANISM: Cryptococcus neoformans (vii) IMMEDIATE SOURCE:
 (B) CLONE: CPCDA ( x i ) SEQUENCE DESCRIPTION: SEQ ID NO:220:

TGTCTGAGNC CAGCGAGT                                                                                       18

( 2 ) INFORMATION FOR SEQ ID NO:221:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Coccidiodes immitis ( v i i ) IMMEDIATE SOURCE:
        ( B ) CLONE: COIDA ( x i ) SEQUENCE DESCRIPTION: SEQ ID NO:221:

GGTCTGGCNT CAGGGAGG                                                                                       18

( 2 ) INFORMATION FOR SEQ ID NO:222:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Blastomyces dermatitidis ( v i i ) IMMEDIATE SOURCE:
        ( B ) CLONE: BLODA ( x i ) SEQUENCE DESCRIPTION: SEQ ID NO:222:

GCTCTGGTNC CGGCCGGA                                                                                       18

( 2 ) INFORMATION FOR SEQ ID NO:223:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumagatus ( v i i ) IMMEDIATE SOURCE:
        ( B ) CLONE: ASNDA ( x i ) SEQUENCE DESCRIPTION: SEQ ID NO:223:

GGTCTGGCNT CAGGGGAG                                                                                       18

( 2 ) INFORMATION FOR SEQ ID NO:224:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRR5SS ( x i ) SEQUENCE DESCRIPTION: SEQ ID NO:224:

GGTCTGGCNT CAGGGGAG     18

( 2 ) INFORMATION FOR SEQ ID NO:225:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRRSSB ( x i ) SEQUENCE DESCRIPTION: SEQ ID NO:225:

GGTCTGGCNT CAGGGGAG     18

( 2 ) INFORMATION FOR SEQ ID NO:226:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida albicans ( v i i ) IMMEDIATE SOURCE:
        ( B ) CLONE: YSASRSUA ( x i ) SEQUENCE DESCRIPTION: SEQ ID NO:226:

GTTCTGGACC CAGCCGAG     18

( 2 ) INFORMATION FOR SEQ ID NO:227:

( i ) SEQUENCE CHARACTERISTICS:
        ( A ) LENGTH: 18 base pairs
        ( B ) TYPE: nucleic acid

```
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Candidi albicans ( v i i ) IMMEDIATE SOURCE:
            ( B ) CLONE: YSAL16S ( x i ) SEQUENCE DESCRIPTION: SEQ ID NO:227:

GTTCTGGANC CAGCCGAG                                                                    18

( 2 ) INFORMATION FOR SEQ ID NO:228:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Candida lusitaniae ( v i i ) IMMEDIATE SOURCE:
            ( B ) CLONE: YSASRRNAA ( x i ) SEQUENCE DESCRIPTION: SEQ ID NO:228:

GATTTGTCNT AAGCCGAG                                                                    18

( 2 ) INFORMATION FOR SEQ ID NO:229:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Candida lusitaniae ( v i i ) IMMEDIATE SOURCE:
            ( B ) CLONE: YSASRSUE ( x i ) SEQUENCE DESCRIPTION: SEQ ID NO:229:

GATTTGTCNT AAGCCGAG                                                                    18

( 2 ) INFORMATION FOR SEQ ID NO:230:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: cDNA to rRNA
```

( i i i ) HYPOTHETICAL: NO ( i v ) ANTI-SENSE: NO ( v i ) ORIGINAL SOURCE:
    ( A ) ORGANISM: Candida kefyr ( v i i ) IMMEDIATE SOURCE:
    ( B ) CLONE: YSASRSUB ( x i ) SEQUENCE DESCRIPTION: SEQ ID NO:230:

TGTCGGAGNC CAGCGAGT 18

( 2 ) INFORMATION FOR SEQ ID NO:231:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRRNAC ( x i ) SEQUENCE DESCRIPTION: SEQ ID NO:231:

GCTCTGTTNG CGGCCGGG 18

( 2 ) INFORMATION FOR SEQ ID NO:232:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRSUD ( x i ) SEQUENCE DESCRIPTION: SEQ ID NO:232:

GCTCTGTTNG CGGCCGGG 18

( 2 ) INFORMATION FOR SEQ ID NO:233:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

( A ) ORGANISM: Candida tropicalis ( v i i ) IMMEDIATE SOURCE:
                    ( B ) CLONE: YSASRRNAB ( x i ) SEQUENCE DESCRIPTION: SEQ ID NO:233:

GTTCTGGACC CAACCGAG                                                                              18

( 2 ) INFORMATION FOR SEQ ID NO:234:

( i ) SEQUENCE CHARACTERISTICS:
                    ( A ) LENGTH: 18 base pairs
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v ) ORIGINAL SOURCE:
                    ( A ) ORGANISM: Candida tropicalis ( v i i ) IMMEDIATE SOURCE:
                    ( B ) CLONE: YSASRSUG ( x i ) SEQUENCE DESCRIPTION: SEQ ID NO:234:

GTTCTGGACC CAACCGAG                                                                              18

( 2 ) INFORMATION FOR SEQ ID NO:235:

( i ) SEQUENCE CHARACTERISTICS:
                    ( A ) LENGTH: 18 base pairs
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v ) ORIGINAL SOURCE:
                    ( A ) ORGANISM: Candida viswanathii ( v i i ) IMMEDIATE SOURCE:
                    ( B ) CLONE: YSASRSUH ( x i ) SEQUENCE DESCRIPTION: SEQ ID NO:235:

GTTCTGGACC CAACCGAG                                                                              18

( 2 ) INFORMATION FOR SEQ ID NO:236:

( i ) SEQUENCE CHARACTERISTICS:
                    ( A ) LENGTH: 18 base pairs
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v ) ORIGINAL SOURCE:
                    ( A ) ORGANISM: Candida parapsilosis ( v i i ) IMMEDIATE SOURCE:
                    ( B ) CLONE: YSASRSUF ( x i ) SEQUENCE DESCRIPTION: SEQ ID NO:236:

GTTCTGGACC CAGCCGAG                          18

( 2 ) INFORMATION FOR SEQ ID NO:237:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida guilliermondii ( v i i ) IMMEDIATE SOURCE:
        ( B ) CLONE: YSASRSUC ( x i ) SEQUENCE DESCRIPTION: SEQ ID NO:237:

GTTCTGGACC CAACCGAG                          18

( 2 ) INFORMATION FOR SEQ ID NO:238:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida glabrata ( v i i ) IMMEDIATE SOURCE:
        ( B ) CLONE: YS5CRRNAS ( x i ) SEQUENCE DESCRIPTION: SEQ ID NO:238:

GTTCTGGANA TGCACCCG                          18

( 2 ) INFORMATION FOR SEQ ID NO:239:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: A. vinelandii major nif ( v i i ) IMMEDIATE SOURCE:
        ( B ) CLONE: AVINIFC ( x i ) SEQUENCE DESCRIPTION: SEQ ID NO:239:

GTTCTGGANC CAGCCAGG                          18

( 2 ) INFORMATION FOR SEQ ID NO:240:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Mouse MHC II A beta ( v i i ) IMMEDIATE SOURCE:
        ( B ) CLONE: MUSMHABMO8

( x i ) SEQUENCE DESCRIPTION: SEQ ID NO:240:

GTTCTGGANC CAGCCAGC         18

( 2 ) INFORMATION FOR SEQ ID NO:241:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Human DRB1 transplant ( v i i ) IMMEDIATE SOURCE:
        ( B ) CLONE: HUMDRB1L ( x i ) SEQUENCE DESCRIPTION: SEQ ID NO:241:

GTTCTGGANA CAGCCGGA         18

( 2 ) INFORMATION FOR SEQ ID NO:242:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Pneumocystis carinii ( v i i ) IMMEDIATE SOURCE:
        ( B ) CLONE: PMC16SRR1

( x i ) SEQUENCE DESCRIPTION: SEQ ID NO:242:

TAGTATTCAA TTGTCNAGAG GTG         23

( 2 ) INFORMATION FOR SEQ ID NO:243:

( i ) SEQUENCE CHARACTERISTICS:
        ( A ) LENGTH: 23 base pairs
        ( B ) TYPE: nucleic acid ( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Cryptococcus neoformans ( v i i ) IMMEDIATE SOURCE:
    ( B ) CLONE: CPCDA ( x i ) SEQUENCE DESCRIPTION: SEQ ID NO:243:

GTTAATTCCG ATAACGAACG AGA 23

( 2 ) INFORMATION FOR SEQ ID NO:244:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Coccidiodes immitis ( v i i ) IMMEDIATE SOURCE:
        ( B ) CLONE: COIDA ( x i ) SEQUENCE DESCRIPTION: SEQ ID NO:244:

TAGTATTCGG CTGTCNAGAG GTG 23

( 2 ) INFORMATION FOR SEQ ID NO:245:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Blastomyces dermatitidis ( v i i ) IMMEDIATE SOURCE:
        ( B ) CLONE: BLODA ( x i ) SEQUENCE DESCRIPTION: SEQ ID NO:245:

TAGTATTCGG CTGTCNAGAG GTG 23

( 2 ) INFORMATION FOR SEQ ID NO:246:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA to rRNA (iii) HYPOTHETICAL: NO (iv) ANTI-SENSE: NO (vi) ORIGINAL SOURCE:
    (A) ORGANISM: Aspergillus fumagatus (vii) IMMEDIATE SOURCE:
    (B) CLONE: ASNDA (xi) SEQUENCE DESCRIPTION: SEQ ID NO:246:

TAGTATTCAG CTGTCNAGAG GTG    23

(2) INFORMATION FOR SEQ ID NO:247:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Aspergillus fumigatus (vii) IMMEDIATE SOURCE:
        (B) CLONE: ASNRR5SS (xi) SEQUENCE DESCRIPTION: SEQ ID NO:247:

TAGTATTCAG CTGTCNAGAG GTG    23

(2) INFORMATION FOR SEQ ID NO:248:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Aspergillus fumigatus (vii) IMMEDIATE SOURCE:
        (B) CLONE: ASNRRSSB (xi) SEQUENCE DESCRIPTION: SEQ ID NO:248:

TAGTATTCAG CTGTCNAGAG GTG    23

(2) INFORMATION FOR SEQ ID NO:249:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:

( A ) ORGANISM: Candida albicans ( v i i ) IMMEDIATE SOURCE:
                    ( B ) CLONE: YSASRSUA ( x i ) SEQUENCE DESCRIPTION: SEQ ID NO:249:

TAGTATTCAG TTGTCNAGAG GTG                                                                         2 3

( 2 ) INFORMATION FOR SEQ ID NO:250:

( i ) SEQUENCE CHARACTERISTICS:
                    ( A ) LENGTH: 23 base pairs
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Candidi albicans ( v i i ) IMMEDIATE SOURCE:
                    ( B ) CLONE: YSAL16S ( x i ) SEQUENCE DESCRIPTION: SEQ ID NO:250:

TAGTATTCAG ATGTCGAGAA GTG                                                                         2 3

( 2 ) INFORMATION FOR SEQ ID NO:251:

( i ) SEQUENCE CHARACTERISTICS:
                    ( A ) LENGTH: 23 base pairs
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Candida lusitaniae ( v i i ) IMMEDIATE SOURCE:
                    ( B ) CLONE: YSASRRNAA ( x i ) SEQUENCE DESCRIPTION: SEQ ID NO:251:

TAGTATTCAG TTGTCNAGAG GTG                                                                         2 3

( 2 ) INFORMATION FOR SEQ ID NO:252:

( i ) SEQUENCE CHARACTERISTICS:
                    ( A ) LENGTH: 23 base pairs
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Candida lusitaniae ( v i i ) IMMEDIATE SOURCE:
                    ( B ) CLONE: YSASRSUE -continued ( x i ) SEQUENCE DESCRIPTION: SEQ ID NO:252:

TAGTATTCAG TTGTCNAGAG GTG 23

( 2 ) INFORMATION FOR SEQ ID NO:253:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida kefyr ( v i i ) IMMEDIATE SOURCE:
        ( B ) CLONE: YSASRSUB ( x i ) SEQUENCE DESCRIPTION: SEQ ID NO:253:

TAGTATTCAA TTGTCNAGAG GTG 23

( 2 ) INFORMATION FOR SEQ ID NO:254:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRRNAC ( x i ) SEQUENCE DESCRIPTION: SEQ ID NO:254:

TAGTATTCAG TCGTCNAGAG GTG 23

( 2 ) INFORMATION FOR SEQ ID NO:255:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRSUD ( x i ) SEQUENCE DESCRIPTION: SEQ ID NO:255:

TAGTATTCAG TCGTCNAGAG GTG 23

( 2 ) INFORMATION FOR SEQ ID NO:256:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida tropicalis ( v i i ) IMMEDIATE SOURCE:
    ( B ) CLONE: YSASRRNAB ( x i ) SEQUENCE DESCRIPTION: SEQ ID NO:256:

TAGTATTCAG TTGTCNAGAG GTG                 23

( 2 ) INFORMATION FOR SEQ ID NO:257:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida tropicalis ( v i i ) IMMEDIATE SOURCE:
    ( B ) CLONE: YSASRSUG ( x i ) SEQUENCE DESCRIPTION: SEQ ID NO:257:

TAGTATTCAG TTGTCNAGAG GTG                 23

( 2 ) INFORMATION FOR SEQ ID NO:258:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida viswanathii ( v i i ) IMMEDIATE SOURCE:
    ( B ) CLONE: YSASRSUH ( x i ) SEQUENCE DESCRIPTION: SEQ ID NO:258:

TAGTATTCAG TTGTCNAGAG GTG                 23

( 2 ) INFORMATION FOR SEQ ID NO:259:

( i ) SEQUENCE CHARACTERISTICS:
    ( A ) LENGTH: 23 base pairs
    ( B ) TYPE: nucleic acid (C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
 (A) ORGANISM: Candida parapsilosis (vii) IMMEDIATE SOURCE:
 (B) CLONE: YSASRSUF (xi) SEQUENCE DESCRIPTION: SEQ ID NO:259:

TAGTATTCAG TAGTCNAGAG GTG 23

(2) INFORMATION FOR SEQ ID NO:260:

(i) SEQUENCE CHARACTERISTICS:
 (A) LENGTH: 23 base pairs
 (B) TYPE: nucleic acid
 (C) STRANDEDNESS: single
 (D) TOPOLOGY: linear (ii) MOLECULE TYPE: cDNA to rRNA (iii) HYPOTHETICAL: NO (iv) ANTI-SENSE: NO (vi) ORIGINAL SOURCE:
 (A) ORGANISM: Candida guilliermondii (vii) IMMEDIATE SOURCE:
 (B) CLONE: YSASRSUC (xi) SEQUENCE DESCRIPTION: SEQ ID NO:260:

TAGTATTCAG TTGTCNAGAG GTG 23

(2) INFORMATION FOR SEQ ID NO:261:

(i) SEQUENCE CHARACTERISTICS:
 (A) LENGTH: 23 base pairs
 (B) TYPE: nucleic acid
 (C) STRANDEDNESS: single
 (D) TOPOLOGY: linear (ii) MOLECULE TYPE: cDNA to rRNA (iii) HYPOTHETICAL: NO (iv) ANTI-SENSE: NO (vi) ORIGINAL SOURCE:
 (A) ORGANISM: Candida glabrata (vii) IMMEDIATE SOURCE:
 (B) CLONE: YS5CRRNAS (xi) SEQUENCE DESCRIPTION: SEQ ID NO:261:

TAGTATTCAA TTGTCNAGAG GTG 23

(2) INFORMATION FOR SEQ ID NO:262:

(i) SEQUENCE CHARACTERISTICS:
 (A) LENGTH: 23 base pairs
 (B) TYPE: nucleic acid
 (C) STRANDEDNESS: single
 (D) TOPOLOGY: linear (ii) MOLECULE TYPE: cDNA to rRNA ( i i i ) HYPOTHETICAL: NO ( i v ) ANTI-SENSE: NO ( v i ) ORIGINAL SOURCE:
  ( A ) ORGANISM: Vesicular stomatitis ( v i i ) IMMEDIATE SOURCE:
  ( B ) CLONE: VSVGPNJAD ( x i ) SEQUENCE DESCRIPTION: SEQ ID NO:262:

TTGATATCAG ATGTCGAAAG GAT    23

( 2 ) INFORMATION FOR SEQ ID NO:263:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Vesicular stomatis ( v i i ) IMMEDIATE SOURCE:
    ( B ) CLONE: VSVGPNJAC ( x i ) SEQUENCE DESCRIPTION: SEQ ID NO:263:

TTGATATCAG ATGTCGAAAG GAT    23

( 2 ) INFORMATION FOR SEQ ID NO:264:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Human glutatione S- tra.

( v i i ) IMMEDIATE SOURCE:
    ( B ) CLONE: HUMGSTPIA ( x i ) SEQUENCE DESCRIPTION: SEQ ID NO:264:

TTTTATTCAG AAGTAGAAAG GGA    23

( 2 ) INFORMATION FOR SEQ ID NO:265:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Pneumocystis carinii (vii) IMMEDIATE SOURCE:
    (B) CLONE: PMC16SRR1

(xi) SEQUENCE DESCRIPTION: SEQ ID NO:265:

CTTCGCGGAT CGCATGG    17

(2) INFORMATION FOR SEQ ID NO:266:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Cryptococcus neoformans (vii) IMMEDIATE SOURCE:
    (B) CLONE: CPCDA (xi) SEQUENCE DESCRIPTION: SEQ ID NO:266:

CCTCACGGAG TGCACTG    17

(2) INFORMATION FOR SEQ ID NO:267:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Coccidiodes immitis (vii) IMMEDIATE SOURCE:
    (B) CLONE: COIDA (xi) SEQUENCE DESCRIPTION: SEQ ID NO:267:

CTTCGCGGCG TGCACTG    17

(2) INFORMATION FOR SEQ ID NO:268:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Blastomyces dermatitidis (vii) IMMEDIATE SOURCE:
    (B) CLONE: BLODA ( x i ) SEQUENCE DESCRIPTION: SEQ ID NO:268:

CCTCACCGCG TGCACTG 17

( 2 ) INFORMATION FOR SEQ ID NO:269:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumagatus ( v i i ) IMMEDIATE SOURCE:
        ( B ) CLONE: ASNDA ( x i ) SEQUENCE DESCRIPTION: SEQ ID NO:269:

CCTCATGGCC TTCACTG 17

( 2 ) INFORMATION FOR SEQ ID NO:270:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRR5SS ( x i ) SEQUENCE DESCRIPTION: SEQ ID NO:270:

CCTCATGGCC TTCACTG 17

( 2 ) INFORMATION FOR SEQ ID NO:271:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRRSSB ( x i ) SEQUENCE DESCRIPTION: SEQ ID NO:271:

CCTCATGGCC TTCACTG 17

( 2 ) INFORMATION FOR SEQ ID NO:272:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida albicans ( v i i ) IMMEDIATE SOURCE:
        ( B ) CLONE: YSASRSUA ( x i ) SEQUENCE DESCRIPTION: SEQ ID NO:272:

GCACGCGCGC TACACTG                                        17

( 2 ) INFORMATION FOR SEQ ID NO:273:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candidi albicans ( v i i ) IMMEDIATE SOURCE:
        ( B ) CLONE: YSAL16S ( x i ) SEQUENCE DESCRIPTION: SEQ ID NO:273:

GCACGCGCGC TACACTG                                        17

( 2 ) INFORMATION FOR SEQ ID NO:274:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRRNAA ( x i ) SEQUENCE DESCRIPTION: SEQ ID NO:274:

CGCTTAGGCG AGCACTG                                        17

( 2 ) INFORMATION FOR SEQ ID NO:275:

( i ) SEQUENCE CHARACTERISTICS:
        ( A ) LENGTH: 17 base pairs
        ( B ) TYPE: nucleic acid ( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
( A ) ORGANISM: Candida lusitaniae ( v i i ) IMMEDIATE SOURCE:
( B ) CLONE: YSASRSUE ( x i ) SEQUENCE DESCRIPTION: SEQ ID NO:275:

TNGTCTGGCG CGCNCTT 17

( 2 ) INFORMATION FOR SEQ ID NO:276:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
( A ) ORGANISM: Candida kefyr ( v i i ) IMMEDIATE SOURCE:
( B ) CLONE: YSASRSUB ( x i ) SEQUENCE DESCRIPTION: SEQ ID NO:276:

GCACGCGCGC TACACTG 17

( 2 ) INFORMATION FOR SEQ ID NO:277:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
( A ) ORGANISM: Candida krusei ( v i i ) IMMEDIATE SOURCE:
( B ) CLONE: YSASRRNAC ( x i ) SEQUENCE DESCRIPTION: SEQ ID NO:277:

GCACGCGCGC TACACTG 17

( 2 ) INFORMATION FOR SEQ ID NO:278:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida krusei ( v i i ) IMMEDIATE SOURCE:
    ( B ) CLONE: YSASRSUD ( x i ) SEQUENCE DESCRIPTION: SEQ ID NO:278:

GCACGCGCGC TACACTG     17

( 2 ) INFORMATION FOR SEQ ID NO:279:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida tropicalis ( v i i ) IMMEDIATE SOURCE:
    ( B ) CLONE: YSASRRNAB ( x i ) SEQUENCE DESCRIPTION: SEQ ID NO:279:

GCACGCGCGC TACACTG     17

( 2 ) INFORMATION FOR SEQ ID NO:280:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida tropicalis ( v i i ) IMMEDIATE SOURCE:
    ( B ) CLONE: YSASRSUG ( x i ) SEQUENCE DESCRIPTION: SEQ ID NO:280:

GCACGCGCGC TACACTG     17

( 2 ) INFORMATION FOR SEQ ID NO:281:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Candida viswanathii (vii) IMMEDIATE SOURCE:
    (B) CLONE: YSASRSUH (xi) SEQUENCE DESCRIPTION: SEQ ID NO:281:

GCACGCGCGC TACACTG      17

(2) INFORMATION FOR SEQ ID NO:282:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida parapsilosis (vii) IMMEDIATE SOURCE:
    (B) CLONE: YSASRSUF (xi) SEQUENCE DESCRIPTION: SEQ ID NO:282:

GCACGCGCGC TACACTG      17

(2) INFORMATION FOR SEQ ID NO:283:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida guilliermondii (vii) IMMEDIATE SOURCE:
    (B) CLONE: YSASRSUC (xi) SEQUENCE DESCRIPTION: SEQ ID NO:283:

CTTTTGGCG AGTACTG      17

(2) INFORMATION FOR SEQ ID NO:284:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida glabrata (vii) IMMEDIATE SOURCE:
    (B) CLONE: YS5CRRNAS ( x i ) SEQUENCE DESCRIPTION: SEQ ID NO:284:

CTTGGCGGCG AACCAGG                                                                                               17

( 2 ) INFORMATION FOR SEQ ID NO:285:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Rabbit progest. recept ( v i i ) IMMEDIATE SOURCE:
        ( B ) CLONE: RABPRG1

( x i ) SEQUENCE DESCRIPTION: SEQ ID NO:285:

CTTCGCAGCG TGCACGG                                                                                               17

( 2 ) INFORMATION FOR SEQ ID NO:286:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Streptomyces lividans 66

( v i i ) IMMEDIATE SOURCE:
        ( B ) CLONE: STMTRNGM ( x i ) SEQUENCE DESCRIPTION: SEQ ID NO:286:

CTTCGCCGCG TGCACGA                                                                                               17

( 2 ) INFORMATION FOR SEQ ID NO:287:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Human mRNA cysteine ( v i i ) IMMEDIATE SOURCE:
        ( B ) CLONE: HUMCYSTCR ( x i ) SEQUENCE DESCRIPTION: SEQ ID NO:287:

GTGTGCGGCG TGCACTG                                                                                               17

( 2 ) INFORMATION FOR SEQ ID NO:288:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
      ( A ) ORGANISM: Pneumocystis carinii ( v i i ) IMMEDIATE SOURCE:
      ( B ) CLONE: PMC16SRR1

( x i ) SEQUENCE DESCRIPTION: SEQ ID NO:288:

TTACTACTTG GATAACCGTG GT                                                    22

( 2 ) INFORMATION FOR SEQ ID NO:289:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
      ( A ) ORGANISM: Cryptococcus neoformans ( v i i ) IMMEDIATE SOURCE:
      ( B ) CLONE: CPCDA ( x i ) SEQUENCE DESCRIPTION: SEQ ID NO:289:

CTGCCCTTTG TACACACCGC CC                                                    22

( 2 ) INFORMATION FOR SEQ ID NO:290:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
      ( A ) ORGANISM: Coccidiodes immitis ( v i i ) IMMEDIATE SOURCE:
      ( B ) CLONE: COIDA ( x i ) SEQUENCE DESCRIPTION: SEQ ID NO:290:

GGCAACTTTG AATAACCCGT TC                                                    22

( 2 ) INFORMATION FOR SEQ ID NO:291:

( i ) SEQUENCE CHARACTERISTICS:
      ( A ) LENGTH: 22 base pairs
      ( B ) TYPE: nucleic acid ( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
( A ) ORGANISM: Blastomyces dermatitidis ( v i i ) IMMEDIATE SOURCE:
( B ) CLONE: BLODA ( x i ) SEQUENCE DESCRIPTION: SEQ ID NO:291:

GGGTTCTTAT GATGACCCGT TC 22

( 2 ) INFORMATION FOR SEQ ID NO:292:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
( A ) ORGANISM: Aspergillus fumagatus ( v i i ) IMMEDIATE SOURCE:
( B ) CLONE: ASNDA ( x i ) SEQUENCE DESCRIPTION: SEQ ID NO:292:

CTGCCCTTTG TACACACCGC CC 22

( 2 ) INFORMATION FOR SEQ ID NO:293:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
( A ) ORGANISM: Aspergillus fumigatus ( v i i ) IMMEDIATE SOURCE:
( B ) CLONE: ASNRR5SS ( x i ) SEQUENCE DESCRIPTION: SEQ ID NO:293:

TTCAACGTGG AATGCCTAGT AG 22

( 2 ) INFORMATION FOR SEQ ID NO:294:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
  ( A ) ORGANISM: Aspergillus fumigatus ( v i i ) IMMEDIATE SOURCE:
  ( B ) CLONE: ASNRRSSB ( x i ) SEQUENCE DESCRIPTION: SEQ ID NO:294:

TTCAACGTGG AATGCCTAGT AG 22

( 2 ) INFORMATION FOR SEQ ID NO:295:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida albicans ( v i i ) IMMEDIATE SOURCE:
    ( B ) CLONE: YSASRSUA ( x i ) SEQUENCE DESCRIPTION: SEQ ID NO:295:

TTACTACTTG GATAACCGTG GT 22

( 2 ) INFORMATION FOR SEQ ID NO:296:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candidi albicans ( v i i ) IMMEDIATE SOURCE:
    ( B ) CLONE: YSAL16S ( x i ) SEQUENCE DESCRIPTION: SEQ ID NO:296:

TTACTACTTG GATAACCGTG GT 22

( 2 ) INFORMATION FOR SEQ ID NO:297:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Candida lusitaniae (vii) IMMEDIATE SOURCE:
(B) CLONE: YSASRRNAA (xi) SEQUENCE DESCRIPTION: SEQ ID NO:297:

TGTTACTTTG AGTAAATGAG AG    22

(2) INFORMATION FOR SEQ ID NO:298:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida lusitaniae (vii) IMMEDIATE SOURCE:
(B) CLONE: YSASRSUE (xi) SEQUENCE DESCRIPTION: SEQ ID NO:298:

TGTTACTTTG AGTAAATGAG AG    22

(2) INFORMATION FOR SEQ ID NO:299:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida kefyr (vii) IMMEDIATE SOURCE:
(B) CLONE: YSASRSUB (xi) SEQUENCE DESCRIPTION: SEQ ID NO:299:

TTTTACTTTG AAAAAATTAG AG    22

(2) INFORMATION FOR SEQ ID NO:300:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida krusei (vii) IMMEDIATE SOURCE:
(B) CLONE: YSASRRNAC ( x i ) SEQUENCE DESCRIPTION: SEQ ID NO:300:

GGCAACTTTC CCATGGGGCC GA                                    22

( 2 ) INFORMATION FOR SEQ ID NO:301:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRSUD ( x i ) SEQUENCE DESCRIPTION: SEQ ID NO:301:

GGCAACTTTC CCATGGGGCC GA                                    22

( 2 ) INFORMATION FOR SEQ ID NO:302:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRRNAB ( x i ) SEQUENCE DESCRIPTION: SEQ ID NO:302:

TTACTACTTG GATAACCGTG GT                                    22

( 2 ) INFORMATION FOR SEQ ID NO:303:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRSUG ( x i ) SEQUENCE DESCRIPTION: SEQ ID NO:303:

TTACTACTTG GATAACCGTG GT                                    22

( 2 ) INFORMATION FOR SEQ ID NO:304:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida viswanathii ( v i i ) IMMEDIATE SOURCE:
        ( B ) CLONE: YSASRSUH ( x i ) SEQUENCE DESCRIPTION: SEQ ID NO:304:

TTACTACTTG GATAACCGTG GT        22

( 2 ) INFORMATION FOR SEQ ID NO:305:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida parapsilosis ( v i i ) IMMEDIATE SOURCE:
        ( B ) CLONE: YSASRSUF ( x i ) SEQUENCE DESCRIPTION: SEQ ID NO:305:

TTACTACTTG GATAACCGTG GT        22

( 2 ) INFORMATION FOR SEQ ID NO:306:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida guilliermondii ( v i i ) IMMEDIATE SOURCE:
        ( B ) CLONE: YSASRSUC ( x i ) SEQUENCE DESCRIPTION: SEQ ID NO:306:

TTACTACTTG GATAACCGTG GT        22

( 2 ) INFORMATION FOR SEQ ID NO:307:

( i ) SEQUENCE CHARACTERISTICS:
        ( A ) LENGTH: 22 base pairs
        ( B ) TYPE: nucleic acid ( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
( A ) ORGANISM: Candida glabrata ( v i i ) IMMEDIATE SOURCE:
( B ) CLONE: YS5CRRNAS ( x i ) SEQUENCE DESCRIPTION: SEQ ID NO:307:

TTTACTTTG AAAAAATTAG AG          22

( 2 ) INFORMATION FOR SEQ ID NO:308:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
( A ) ORGANISM: Genome bacteriophage T7

( v i i ) IMMEDIATE SOURCE:
( B ) CLONE: PT7DOT7

( x i ) SEQUENCE DESCRIPTION: SEQ ID NO:308:

GGACTTCTTG AATAACCCGT TC          22

( 2 ) INFORMATION FOR SEQ ID NO:309:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
( A ) ORGANISM: Bacteriophage T7, comple.

( v i i ) IMMEDIATE SOURCE:
( B ) CLONE: PT7CG ( x i ) SEQUENCE DESCRIPTION: SEQ ID NO:309:

GGACTTCTTG AATAACCCGT TC          22

( 2 ) INFORMATION FOR SEQ ID NO:310:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: cDNA to rRNA (i i i) HYPOTHETICAL: NO (i v) ANTI-SENSE: NO (v i) ORIGINAL SOURCE:
    (A) ORGANISM: Staphylococcus aureus (v i i) IMMEDIATE SOURCE:
    (B) CLONE: STATOXA (x i) SEQUENCE DESCRIPTION: SEQ ID NO:310:

GGCAACTTTG ACTAACCCTC GA                                      22

(2) INFORMATION FOR SEQ ID NO:311:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Pneumocystis carinii (v i i) IMMEDIATE SOURCE:
        (B) CLONE: PMC16SRR1

(x i) SEQUENCE DESCRIPTION: SEQ ID NO:311:

GTGGTGGTGC ATGGCCGTTC TT                                      22

(2) INFORMATION FOR SEQ ID NO:312:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Cryptococcus neoformans (v i i) IMMEDIATE SOURCE:
        (B) CLONE: CPCDA (x i) SEQUENCE DESCRIPTION: SEQ ID NO:312:

GTGGTCCTGT ATGCTCTTTA CT                                      22

(2) INFORMATION FOR SEQ ID NO:313:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:

(A) ORGANISM: Coccidiodes immitis (vii) IMMEDIATE SOURCE:
  (B) CLONE: COIDA (xi) SEQUENCE DESCRIPTION: SEQ ID NO:313:

CTGGTCCGGC CGGACCTTTC CT 22

(2) INFORMATION FOR SEQ ID NO:314:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Blastomyces dermatitidis (vii) IMMEDIATE SOURCE:
    (B) CLONE: BLODA (xi) SEQUENCE DESCRIPTION: SEQ ID NO:314:

CTGGTCCGGC TGGACCTTTC CT 22

(2) INFORMATION FOR SEQ ID NO:315:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Aspergillus fumagatus (vii) IMMEDIATE SOURCE:
    (B) CLONE: ASNDA (xi) SEQUENCE DESCRIPTION: SEQ ID NO:315:

CTGCCCTTTG TACACACCGC CC 22

(2) INFORMATION FOR SEQ ID NO:316:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Aspergillus fumigatus (vii) IMMEDIATE SOURCE:
    (B) CLONE: ASNRR5SS ( x i ) SEQUENCE DESCRIPTION: SEQ ID NO:316:

CAGGTCTGTG ATGCCCTTAG AT 22

( 2 ) INFORMATION FOR SEQ ID NO:317:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRRSSB ( x i ) SEQUENCE DESCRIPTION: SEQ ID NO:317:

CAGGTCTGTG ATGCCCTTAG AT 22

( 2 ) INFORMATION FOR SEQ ID NO:318:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida albicans ( v i i ) IMMEDIATE SOURCE:
        ( B ) CLONE: YSASRSUA ( x i ) SEQUENCE DESCRIPTION: SEQ ID NO:318:

GTGGTGGTGC ATGGCCGTTC TT 22

( 2 ) INFORMATION FOR SEQ ID NO:319:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candidi albicans ( v i i ) IMMEDIATE SOURCE:
        ( B ) CLONE: YSAL16S ( x i ) SEQUENCE DESCRIPTION: SEQ ID NO:319:

GTGGTGGTGC ATGGCCGTTC TT 22

( 2 ) INFORMATION FOR SEQ ID NO:320:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida lusitaniae ( v i i ) IMMEDIATE SOURCE:
    ( B ) CLONE: YSASRRNAA ( x i ) SEQUENCE DESCRIPTION: SEQ ID NO:320:

```
GTGGTGGTGC ATGGCCGTTC TT                                            22
```

( 2 ) INFORMATION FOR SEQ ID NO:321:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida lusitaniae ( v i i ) IMMEDIATE SOURCE:
    ( B ) CLONE: YSASRSUE ( x i ) SEQUENCE DESCRIPTION: SEQ ID NO:321:

```
CAGGTCTGTG ATGCCCTTAG AC                                            22
```

( 2 ) INFORMATION FOR SEQ ID NO:322:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida kefyr ( v i i ) IMMEDIATE SOURCE:
    ( B ) CLONE: YSASRSUB ( x i ) SEQUENCE DESCRIPTION: SEQ ID NO:322:

```
GTGGNNGTGC ATGGCCGTTC TT                                            22
```

( 2 ) INFORMATION FOR SEQ ID NO:323:

( i ) SEQUENCE CHARACTERISTICS:
    ( A ) LENGTH: 22 base pairs
    ( B ) TYPE: nucleic acid (C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida krusei (vii) IMMEDIATE SOURCE:
    (B) CLONE: YSASRRNAC (xi) SEQUENCE DESCRIPTION: SEQ ID NO:323:

```
GTGGTGGTGC ATGGCCGTTT TT                                    22
```

(2) INFORMATION FOR SEQ ID NO:324:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Candida krusei (vii) IMMEDIATE SOURCE:
        (B) CLONE: YSASRSUD (xi) SEQUENCE DESCRIPTION: SEQ ID NO:324:

```
CAGGTCTGTG ATGCCCTTAG AC                                    22
```

(2) INFORMATION FOR SEQ ID NO:325:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Candida tropicalis (vii) IMMEDIATE SOURCE:
        (B) CLONE: YSASRRNAB (xi) SEQUENCE DESCRIPTION: SEQ ID NO:325:

```
GTGGTGGTGC ATGGCCGTTC TT                                    22
```

(2) INFORMATION FOR SEQ ID NO:326:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA to rRNA (i i i) HYPOTHETICAL: NO (i v) ANTI-SENSE: NO (v i) ORIGINAL SOURCE:
    (A) ORGANISM: Candida tropicalis (v i i) IMMEDIATE SOURCE:
    (B) CLONE: YSASRSUG (x i) SEQUENCE DESCRIPTION: SEQ ID NO:326:

GTGGTNGTGC ATGGCCGTTC TT      22

(2) INFORMATION FOR SEQ ID NO:327:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Candida viswanathii (v i i) IMMEDIATE SOURCE:
        (B) CLONE: YSASRSUH (x i) SEQUENCE DESCRIPTION: SEQ ID NO:327:

GTGGTGGTGC ATGGCCGTTC TT      22

(2) INFORMATION FOR SEQ ID NO:328:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Candida parapsilosis (v i i) IMMEDIATE SOURCE:
        (B) CLONE: YSASRSUF (x i) SEQUENCE DESCRIPTION: SEQ ID NO:328:

GTGGTNGTGC ATGGCCGTTC TT      22

(2) INFORMATION FOR SEQ ID NO:329:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:

(A) ORGANISM: Candida guilliermondii (vii) IMMEDIATE SOURCE:
    (B) CLONE: YSASRSUC (xi) SEQUENCE DESCRIPTION: SEQ ID NO:329:

TAAAAAATCA ATGCTCTTTG AG    22

(2) INFORMATION FOR SEQ ID NO:330:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Candida glabrata (vii) IMMEDIATE SOURCE:
        (B) CLONE: YS5CRRNAS (xi) SEQUENCE DESCRIPTION: SEQ ID NO:330:

GTGGTGGTGC ATGGCCGTTC TT    22

(2) INFORMATION FOR SEQ ID NO:331:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Rat alpha tropomyosin (vii) IMMEDIATE SOURCE:
        (B) CLONE: RATTMA3

(xi) SEQUENCE DESCRIPTION: SEQ ID NO:331:

TTGGTCCTTT ATGCTCTTCG TT    22

(2) INFORMATION FOR SEQ ID NO:332:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Human ribonucl/angio (vii) IMMEDIATE SOURCE:
        (B) CLONE: HUMRAJ ( x i ) SEQUENCE DESCRIPTION: SEQ ID NO:332:

CTGGTCCTGT ACGACATTA CT 22

( 2 ) INFORMATION FOR SEQ ID NO:333:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Human ribonucl/angio inh ( v i i ) IMMEDIATE SOURCE:
    ( B ) CLONE: HUMRAI ( x i ) SEQUENCE DESCRIPTION: SEQ ID NO:333:

CTGGTCCTGT ACGACATTA CT 22

( 2 ) INFORMATION FOR SEQ ID NO:334:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Pneumocystis carinii ( v i i ) IMMEDIATE SOURCE:
    ( B ) CLONE: PMC16SRR1

( x i ) SEQUENCE DESCRIPTION: SEQ ID NO:334:

TTCTTGATTC TATGGGTGGT 20

( 2 ) INFORMATION FOR SEQ ID NO:335:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Cryptococcus neoformans ( v i i ) IMMEDIATE SOURCE:
    ( B ) CLONE: CPCDA ( x i ) SEQUENCE DESCRIPTION: SEQ ID NO:335:

CACGTCAATC TCTGACTGGT 20

( 2 ) INFORMATION FOR SEQ ID NO:336:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Coccidiodes immitis ( v i i ) IMMEDIATE SOURCE:
        ( B ) CLONE: COIDA ( x i ) SEQUENCE DESCRIPTION: SEQ ID NO:336:

GGCGTCAGTA TTCGGCTGTC        20

( 2 ) INFORMATION FOR SEQ ID NO:337:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Blastomyces dermatitidis ( v i i ) IMMEDIATE SOURCE:
        ( B ) CLONE: BLODA ( x i ) SEQUENCE DESCRIPTION: SEQ ID NO:337:

GGCGTCAGTA TTCGGCTGTC        20

( 2 ) INFORMATION FOR SEQ ID NO:338:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumagatus ( v i i ) IMMEDIATE SOURCE:
        ( B ) CLONE: ASNDA ( x i ) SEQUENCE DESCRIPTION: SEQ ID NO:338:

CGCGCGCTAC ACTGACAGGT        20

( 2 ) INFORMATION FOR SEQ ID NO:339:

( i ) SEQUENCE CHARACTERISTICS:
        ( A ) LENGTH: 20 base pairs
        ( B ) TYPE: nucleic acid ( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Aspergillus fumigatus ( v i i ) IMMEDIATE SOURCE:
    ( B ) CLONE: ASNRR5SS ( x i ) SEQUENCE DESCRIPTION: SEQ ID NO:339:

CGCGCGCTAC ACTGACAGGT     20

( 2 ) INFORMATION FOR SEQ ID NO:340:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Aspergillus fumigatus ( v i i ) IMMEDIATE SOURCE:
    ( B ) CLONE: ASNRRSSB ( x i ) SEQUENCE DESCRIPTION: SEQ ID NO:340:

CGCGCGCTAC ACTGACAGGT     20

( 2 ) INFORMATION FOR SEQ ID NO:341:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida albicans ( v i i ) IMMEDIATE SOURCE:
    ( B ) CLONE: YSASRSUA ( x i ) SEQUENCE DESCRIPTION: SEQ ID NO:341:

GGGGGCAACC TCATTCTGGA     20

( 2 ) INFORMATION FOR SEQ ID NO:342:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candidi albicans ( v i i ) IMMEDIATE SOURCE:
    ( B ) CLONE: YSAL16S ( x i ) SEQUENCE DESCRIPTION: SEQ ID NO:342:

CATTCAAATT TCTGCCCTAT 20

( 2 ) INFORMATION FOR SEQ ID NO:343:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRRNAA ( x i ) SEQUENCE DESCRIPTION: SEQ ID NO:343:

CATTCAAATT TCTGCCCTAT 20

( 2 ) INFORMATION FOR SEQ ID NO:344:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRSUE ( x i ) SEQUENCE DESCRIPTION: SEQ ID NO:344:

CATTCAAATT TCTGCCCTAT 20

( 2 ) INFORMATION FOR SEQ ID NO:345:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Candida kefyr (vii) IMMEDIATE SOURCE:
    (B) CLONE: YSASRSUB (xi) SEQUENCE DESCRIPTION: SEQ ID NO:345:

AAAATCAATG TCTTCGGACT 20

(2) INFORMATION FOR SEQ ID NO:346:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida krusei (vii) IMMEDIATE SOURCE:
    (B) CLONE: YSASRRNAC (xi) SEQUENCE DESCRIPTION: SEQ ID NO:346:

TGCGTAAAGC CCCGACTTCT 20

(2) INFORMATION FOR SEQ ID NO:347:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida krusei (vii) IMMEDIATE SOURCE:
    (B) CLONE: YSASRSUD (xi) SEQUENCE DESCRIPTION: SEQ ID NO:347:

CTCGTGAAAC TCCGTCGTGC 20

(2) INFORMATION FOR SEQ ID NO:348:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida tropicalis (vii) IMMEDIATE SOURCE:
    (B) CLONE: YSASRRNAB ( x i ) SEQUENCE DESCRIPTION: SEQ ID NO:348:

AAAATCAATG TCTTCGGACT    20

( 2 ) INFORMATION FOR SEQ ID NO:349:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRSUG ( x i ) SEQUENCE DESCRIPTION: SEQ ID NO:349:

CTNGTCAAAC TTGGNCATTT    20

( 2 ) INFORMATION FOR SEQ ID NO:350:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida viswanathii ( v i i ) IMMEDIATE SOURCE:
        ( B ) CLONE: YSASRSUH ( x i ) SEQUENCE DESCRIPTION: SEQ ID NO:350:

AAAGTCNNNG GGNNCNNGGT    20

( 2 ) INFORMATION FOR SEQ ID NO:351:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida parapsilosis ( v i i ) IMMEDIATE SOURCE:
        ( B ) CLONE: YSASRSUF ( x i ) SEQUENCE DESCRIPTION: SEQ ID NO:351:

CATTCAAATT TCTGCCCTAT    20

( 2 ) INFORMATION FOR SEQ ID NO:352:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida guilliermondii ( v i i ) IMMEDIATE SOURCE:
        ( B ) CLONE: YSASRSUC ( x i ) SEQUENCE DESCRIPTION: SEQ ID NO:352:

CATTCAAATT TCTGCCCTAT                                              20

( 2 ) INFORMATION FOR SEQ ID NO:353:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida glabrata ( v i i ) IMMEDIATE SOURCE:
        ( B ) CLONE: YS5CRRNAS ( x i ) SEQUENCE DESCRIPTION: SEQ ID NO:353:

GTTGTCCACT TCTTAGAGGT                                              20

( 2 ) INFORMATION FOR SEQ ID NO:354:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Rat alpha-1-acid gly. pro.

( v i i ) IMMEDIATE SOURCE:
        ( B ) CLONE: RATAGPA1H ( x i ) SEQUENCE DESCRIPTION: SEQ ID NO:354:

TATTACAATC TCTGACTGGT                                              20

( 2 ) INFORMATION FOR SEQ ID NO:355:

( i ) SEQUENCE CHARACTERISTICS:
        ( A ) LENGTH: 20 base pairs
        ( B ) TYPE: nucleic acid ( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
 ( A ) ORGANISM: Rat alpha-1-acid gly(sp-daw)

( v i i ) IMMEDIATE SOURCE:
 ( B ) CLONE: RATAGPA1G ( x i ) SEQUENCE DESCRIPTION: SEQ ID NO:355:

TATTACAATC TCTGACTGGT 20

( 2 ) INFORMATION FOR SEQ ID NO:356:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
  ( A ) ORGANISM: S. pneumoniae malX malM ( v i i ) IMMEDIATE SOURCE:
  ( B ) CLONE: STRMALMXP ( x i ) SEQUENCE DESCRIPTION: SEQ ID NO:356:

TAACCCAATC TATGACTGGT 20

( 2 ) INFORMATION FOR SEQ ID NO:357:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
  ( A ) ORGANISM: Pneumocystis carinii ( v i i ) IMMEDIATE SOURCE:
  ( B ) CLONE: PMC16SRR1

( x i ) SEQUENCE DESCRIPTION: SEQ ID NO:357:

GAGTACAATT TAGATACCTT AACGAG 26

( 2 ) INFORMATION FOR SEQ ID NO:358:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( i i ) MOLECULE TYPE: cDNA to rRNA (iii) HYPOTHETICAL: NO (iv) ANTI-SENSE: NO (vi) ORIGINAL SOURCE:
  (A) ORGANISM: Cryptococcus neoformans (vii) IMMEDIATE SOURCE:
  (B) CLONE: CPCDA (xi) SEQUENCE DESCRIPTION: SEQ ID NO:358:

GAGTACAATT TAAATCCCTT AACGAG  26

(2) INFORMATION FOR SEQ ID NO:359:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Coccidiodes immitis (vii) IMMEDIATE SOURCE:
    (B) CLONE: COIDA (xi) SEQUENCE DESCRIPTION: SEQ ID NO:359:

GAGTACAATT TAAATCCCTT AACGAG  26

(2) INFORMATION FOR SEQ ID NO:360:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Blastomyces dermatitidis (vii) IMMEDIATE SOURCE:
    (B) CLONE: BLODA (xi) SEQUENCE DESCRIPTION: SEQ ID NO:360:

GAGTACAATC TAAATCCCTT AACGAG  26

(2) INFORMATION FOR SEQ ID NO:361:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:

(A) ORGANISM: Aspergillus fumagatus (vii) IMMEDIATE SOURCE:
(B) CLONE: ASNDA (xi) SEQUENCE DESCRIPTION: SEQ ID NO:361:

GAGTACAATC TAAATCCCTT AACGAG 26

(2) INFORMATION FOR SEQ ID NO:362:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Aspergillus fumigatus (vii) IMMEDIATE SOURCE:
(B) CLONE: ASNRR5SS (xi) SEQUENCE DESCRIPTION: SEQ ID NO:362:

GAGTACAATC TAAATCCCTT AACGAG 26

(2) INFORMATION FOR SEQ ID NO:363:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Aspergillus fumigatus (vii) IMMEDIATE SOURCE:
(B) CLONE: ASNRRSSB (xi) SEQUENCE DESCRIPTION: SEQ ID NO:363:

GAGTACAATC TAAATCCCTT AACGAG 26

(2) INFORMATION FOR SEQ ID NO:364:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida albicans (vii) IMMEDIATE SOURCE:
(B) CLONE: YSASRSUA ( x i ) SEQUENCE DESCRIPTION: SEQ ID NO:364:

GAGTACAATG TAAATACCTT AACGAG 26

( 2 ) INFORMATION FOR SEQ ID NO:365:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candidi albicans ( v i i ) IMMEDIATE SOURCE:
        ( B ) CLONE: YSAL16S ( x i ) SEQUENCE DESCRIPTION: SEQ ID NO:365:

GAGTACAATG TAAATACCTT AACGAG 26

( 2 ) INFORMATION FOR SEQ ID NO:366:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRRNAA ( x i ) SEQUENCE DESCRIPTION: SEQ ID NO:366:

GAGTACAATG TAAATACCTT AACGAG 26

( 2 ) INFORMATION FOR SEQ ID NO:367:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRSUE ( x i ) SEQUENCE DESCRIPTION: SEQ ID NO:367:

GAGTACAATG TAAATACCTT AACGAG 26

( 2 ) INFORMATION FOR SEQ ID NO:368:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida kefyr ( v i i ) IMMEDIATE SOURCE:
        ( B ) CLONE: YSASRSUB ( x i ) SEQUENCE DESCRIPTION: SEQ ID NO:368:

GAGTACAATG TAAATACCTT AACGAG     26

( 2 ) INFORMATION FOR SEQ ID NO:369:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRRNAC ( x i ) SEQUENCE DESCRIPTION: SEQ ID NO:369:

GAGTACAATG TAAATACCTT AACGAG     26

( 2 ) INFORMATION FOR SEQ ID NO:370:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRSUD ( x i ) SEQUENCE DESCRIPTION: SEQ ID NO:370:

GAGTACAATG TAAATACCTT AACGAG     26

( 2 ) INFORMATION FOR SEQ ID NO:371:

( i ) SEQUENCE CHARACTERISTICS:
        ( A ) LENGTH: 26 base pairs
        ( B ) TYPE: nucleic acid ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Candida tropicalis ( v i i ) IMMEDIATE SOURCE:
            ( B ) CLONE: YSASRRNAB ( x i ) SEQUENCE DESCRIPTION: SEQ ID NO:371:

GAGTACAATG TAAATACCTT AACGAG                    26

( 2 ) INFORMATION FOR SEQ ID NO:372:

( i ) SEQUENCE CHARACTERISTICS:
            ( A ) LENGTH: 26 base pairs
            ( B ) TYPE: nucleic acid
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Candida tropicalis ( v i i ) IMMEDIATE SOURCE:
            ( B ) CLONE: YSASRSUG ( x i ) SEQUENCE DESCRIPTION: SEQ ID NO:372:

GAGTACAATG TAAATACCTT AACGAG                    26

( 2 ) INFORMATION FOR SEQ ID NO:373:

( i ) SEQUENCE CHARACTERISTICS:
            ( A ) LENGTH: 26 base pairs
            ( B ) TYPE: nucleic acid
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Candida viswanathii ( v i i ) IMMEDIATE SOURCE:
            ( B ) CLONE: YSASRSUH ( x i ) SEQUENCE DESCRIPTION: SEQ ID NO:373:

GAGTACAATG TAAATACCTT AACGAG                    26

( 2 ) INFORMATION FOR SEQ ID NO:374:

( i ) SEQUENCE CHARACTERISTICS:
            ( A ) LENGTH: 26 base pairs
            ( B ) TYPE: nucleic acid
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida parapsilosis ( v i i ) IMMEDIATE SOURCE:
    ( B ) CLONE: YSASRSUF ( x i ) SEQUENCE DESCRIPTION: SEQ ID NO:374:

GAGTACAATG TAAATACCTT AACGAG    26

( 2 ) INFORMATION FOR SEQ ID NO:375:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida guilliermondii ( v i i ) IMMEDIATE SOURCE:
        ( B ) CLONE: YSASRSUC ( x i ) SEQUENCE DESCRIPTION: SEQ ID NO:375:

GAGTACAATG TAAATACCTT AACGAG    26

( 2 ) INFORMATION FOR SEQ ID NO:376:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida glabrata ( v i i ) IMMEDIATE SOURCE:
        ( B ) CLONE: YS5CRRNAS ( x i ) SEQUENCE DESCRIPTION: SEQ ID NO:376:

GAGTACAATG TAAATACCTT AACGAG    26

( 2 ) INFORMATION FOR SEQ ID NO:377:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Yeast 18s RNA (vii) IMMEDIATE SOURCE:
                (B) CLONE: YSCRNA5

(xi) SEQUENCE DESCRIPTION: SEQ ID NO:377:

GAGTACAATG TAAATACCTT AACGAG                                                          26

(2) INFORMATION FOR SEQ ID NO:378:

(i) SEQUENCE CHARACTERISTICS:
                (A) LENGTH: 26 base pairs
                (B) TYPE: nucleic acid
                (C) STRANDEDNESS: single
                (D) TOPOLOGY: linear (ii) MOLECULE TYPE: cDNA to rRNA (iii) HYPOTHETICAL: NO (iv) ANTI-SENSE: NO (vi) ORIGINAL SOURCE:
                (A) ORGANISM: Yeast (S. cerevisiae)

(vii) IMMEDIATE SOURCE:
                (B) CLONE: TSCRGEA (xi) SEQUENCE DESCRIPTION: SEQ ID NO:378:

GAGTACAATG TAAATACCTT AACGAG                                                          26

(2) INFORMATION FOR SEQ ID NO:379:

(i) SEQUENCE CHARACTERISTICS:
                (A) LENGTH: 26 base pairs
                (B) TYPE: nucleic acid
                (C) STRANDEDNESS: single
                (D) TOPOLOGY: linear (ii) MOLECULE TYPE: cDNA to rRNA (iii) HYPOTHETICAL: NO (iv) ANTI-SENSE: NO (vi) ORIGINAL SOURCE:
                (A) ORGANISM: Kluyveromyces lactis (vii) IMMEDIATE SOURCE:
                (B) CLONE: YSK17SRRNA (xi) SEQUENCE DESCRIPTION: SEQ ID NO:379:

GAGTACAATG TAAATACCTT AACGAG                                                          26

(2) INFORMATION FOR SEQ ID NO:380:

(i) SEQUENCE CHARACTERISTICS:
                (A) LENGTH: 26 base pairs
                (B) TYPE: nucleic acid
                (C) STRANDEDNESS: single
                (D) TOPOLOGY: linear (ii) MOLECULE TYPE: cDNA to rRNA (iii) HYPOTHETICAL: NO (iv) ANTI-SENSE: NO (vi) ORIGINAL SOURCE: Torulaspora delbrueckii
                (A) ORGANISM:

(vii) IMMEDIATE SOURCE:
                (B) CLONE: TOUSRSR ( x i ) SEQUENCE DESCRIPTION: SEQ ID NO:380:

GAGTACAATG TAAATACCTT AACGAG  26

( 2 ) INFORMATION FOR SEQ ID NO:381:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: T. glabrata rRNA ( v i i ) IMMEDIATE SOURCE:
        ( B ) CLONE: YSLSRSUA ( x i ) SEQUENCE DESCRIPTION: SEQ ID NO:381:

GAGTACAATG TAAATACCTT AACGAG  26

( 2 ) INFORMATION FOR SEQ ID NO:382:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: H. polymorpha rRNA ( v i i ) IMMEDIATE SOURCE:
        ( B ) CLONE: HASSRSUA ( x i ) SEQUENCE DESCRIPTION: SEQ ID NO:382:

GAGTACAATG TAAATACCTT AACGAG  26

( 2 ) INFORMATION FOR SEQ ID NO:383:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: S. pombe rRNA ( v i i ) IMMEDIATE SOURCE:
        ( B ) CLONE: YSPRRNASS ( x i ) SEQUENCE DESCRIPTION: SEQ ID NO:383:

GAGTACAATG TAAATACCTT AACGAG  26

( 2 ) INFORMATION FOR SEQ ID NO:384:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Pneumocystis carinii ( v i i ) IMMEDIATE SOURCE:
    ( B ) CLONE: PMC16SRR1

( x i ) SEQUENCE DESCRIPTION: SEQ ID NO:384:

TTAAGCCATG CATGTCTAAG T                    21

( 2 ) INFORMATION FOR SEQ ID NO:385:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Cryptococcus neoformans ( v i i ) IMMEDIATE SOURCE:
    ( B ) CLONE: CPCDA ( x i ) SEQUENCE DESCRIPTION: SEQ ID NO:385:

TTCGGCCCTC TATGGTGAAT C                    21

( 2 ) INFORMATION FOR SEQ ID NO:386:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Coccidiodes immitis ( v i i ) IMMEDIATE SOURCE:
    ( B ) CLONE: COIDA ( x i ) SEQUENCE DESCRIPTION: SEQ ID NO:386:

TTAAGCCATG CATGTCTAAG T                    21

( 2 ) INFORMATION FOR SEQ ID NO:387:

( i ) SEQUENCE CHARACTERISTICS:
    ( A ) LENGTH: 21 base pairs
    ( B ) TYPE: nucleic acid ( C ) STRANDEDNESS: single
                ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                ( A ) ORGANISM: Blastomyces dermatitidis ( v i i ) IMMEDIATE SOURCE:
                ( B ) CLONE: BLODA ( x i ) SEQUENCE DESCRIPTION: SEQ ID NO:387:

TTAAGCCATG CATGTCTAAG T                                            21

( 2 ) INFORMATION FOR SEQ ID NO:388:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                ( A ) ORGANISM: Aspergillus fumagatus ( v i i ) IMMEDIATE SOURCE:
                ( B ) CLONE: ASNDA ( x i ) SEQUENCE DESCRIPTION: SEQ ID NO:388:

ATAAGCAATT TATACGGTGA A                                            21

( 2 ) INFORMATION FOR SEQ ID NO:389:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                ( A ) ORGANISM: Aspergillus fumigatus ( v i i ) IMMEDIATE SOURCE:
                ( B ) CLONE: ASNRR5SS ( x i ) SEQUENCE DESCRIPTION: SEQ ID NO:389:

ATAAGCAATT TATACGGTGA A                                            21

( 2 ) INFORMATION FOR SEQ ID NO:390:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
   ( A ) ORGANISM: Aspergillus fumigatus ( v i i ) IMMEDIATE SOURCE:
   ( B ) CLONE: ASNRRSSB ( x i ) SEQUENCE DESCRIPTION: SEQ ID NO:390:

ATAAGCAATT TATACGGTGA A                                     21

( 2 ) INFORMATION FOR SEQ ID NO:391:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
      ( A ) ORGANISM: Candida albicans ( v i i ) IMMEDIATE SOURCE:
      ( B ) CLONE: YSASRSUA ( x i ) SEQUENCE DESCRIPTION: SEQ ID NO:391:

GGTAGCCATT TATGGCGAAC C                                     21

( 2 ) INFORMATION FOR SEQ ID NO:392:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
      ( A ) ORGANISM: Candidi albicans ( v i i ) IMMEDIATE SOURCE:
      ( B ) CLONE: YSAL16S ( x i ) SEQUENCE DESCRIPTION: SEQ ID NO:392:

GGTAGCCATT TATGGCGAAC C                                     21

( 2 ) INFORMATION FOR SEQ ID NO:393:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Candida lusitaniae (vii) IMMEDIATE SOURCE:
(B) CLONE: YSASRRNAA (xi) SEQUENCE DESCRIPTION: SEQ ID NO:393:

TTAAGCCATG CATGTCTAAG T 21

(2) INFORMATION FOR SEQ ID NO:394:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida lusitaniae (vii) IMMEDIATE SOURCE:
(B) CLONE: YSASRSUE (xi) SEQUENCE DESCRIPTION: SEQ ID NO:394:

GCTAGCCTNG TCTGGCGCGC N 21

(2) INFORMATION FOR SEQ ID NO:395:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida kefyr (vii) IMMEDIATE SOURCE:
(B) CLONE: YSASRSUB (xi) SEQUENCE DESCRIPTION: SEQ ID NO:395:

GCTAGCNCTT GCTGGTTNAC T 21

(2) INFORMATION FOR SEQ ID NO:396:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida krusei (vii) IMMEDIATE SOURCE:
(B) CLONE: YSASRRNAC ( x i ) SEQUENCE DESCRIPTION: SEQ ID NO:396:

CGTTTTCATT AATCAAGAAC G 21

( 2 ) INFORMATION FOR SEQ ID NO:397:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRSUD ( x i ) SEQUENCE DESCRIPTION: SEQ ID NO:397:

TTAAGCCATG CATGTCTAAG T 21

( 2 ) INFORMATION FOR SEQ ID NO:398:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRRNAB ( x i ) SEQUENCE DESCRIPTION: SEQ ID NO:398:

GCTAGCCTTT TGGCGAACC 19

( 2 ) INFORMATION FOR SEQ ID NO:399:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRSUG ( x i ) SEQUENCE DESCRIPTION: SEQ ID NO:399:

GCTAGCCTTT TGGCGAACC 19

( 2 ) INFORMATION FOR SEQ ID NO:400:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida viswanathii ( v i i ) IMMEDIATE SOURCE:
        ( B ) CLONE: YSASRSUH ( x i ) SEQUENCE DESCRIPTION: SEQ ID NO:400:

GCTAGCCTTT TGGCGAACC       19

( 2 ) INFORMATION FOR SEQ ID NO:401:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida parapsilosis ( v i i ) IMMEDIATE SOURCE:
        ( B ) CLONE: YSASRSUF ( x i ) SEQUENCE DESCRIPTION: SEQ ID NO:401:

GCTAGCCTTT TTGGCGAACC       20

( 2 ) INFORMATION FOR SEQ ID NO:402:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida guilliermondii ( v i i ) IMMEDIATE SOURCE:
        ( B ) CLONE: YSASRSUC ( x i ) SEQUENCE DESCRIPTION: SEQ ID NO:402:

GGTCCGCCTT TTTGGCGAGT A       21

( 2 ) INFORMATION FOR SEQ ID NO:403:

( i ) SEQUENCE CHARACTERISTICS:
        ( A ) LENGTH: 21 base pairs
        ( B ) TYPE: nucleic acid ( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
( A ) ORGANISM: Candida glabrata ( v i i ) IMMEDIATE SOURCE:
( B ) CLONE: YS5CRRNAS ( x i ) SEQUENCE DESCRIPTION: SEQ ID NO:403:

ATAAGCAATT TATACAGTGA A    21

( 2 ) INFORMATION FOR SEQ ID NO:404:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
( A ) ORGANISM: S. enterica ( v i i ) IMMEDIATE SOURCE:
( B ) CLONE: STYRFB ( x i ) SEQUENCE DESCRIPTION: SEQ ID NO:404:

GGTAGCCGTT TATGGCCGCT T    21

( 2 ) INFORMATION FOR SEQ ID NO:405:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
( A ) ORGANISM: Cloistridium pasteurianum ( v i i ) IMMEDIATE SOURCE:
( B ) CLONE: CLONIFH5

( x i ) SEQUENCE DESCRIPTION: SEQ ID NO:405:

GGTAGCTATT TATGGAAAAG G    21

( 2 ) INFORMATION FOR SEQ ID NO:406:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
  ( A ) ORGANISM: C. pasteurianum nifH ( v i i ) IMMEDIATE SOURCE:
  ( B ) CLONE: CLONIFH ( x i ) SEQUENCE DESCRIPTION: SEQ ID NO:406:

GGTAGCTATT TATGGAAAAG G    21

( 2 ) INFORMATION FOR SEQ ID NO:407:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: C. pasteurianum nifH ( v i i ) IMMEDIATE SOURCE:
    ( B ) CLONE: CLONIFH1

( x i ) SEQUENCE DESCRIPTION: SEQ ID NO:407:

GGTAGCTATT TATGGAAAAG G    21

( 2 ) INFORMATION FOR SEQ ID NO:408:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:408:

CCGGTGTCCC CCATCAACAT GG    22

( 2 ) INFORMATION FOR SEQ ID NO:409:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:409:

CCCCTGTCCC CCATCGACAT GG    22

( 2 ) INFORMATION FOR SEQ ID NO:410:

( i ) SEQUENCE CHARACTERISTICS:
              ( A ) LENGTH: 22 base pairs
              ( B ) TYPE: nucleic acid
              ( C ) STRANDEDNESS: double
              ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:410:

CCGTTGTCGC CCATCGACAT GG                     22

( 2 ) INFORMATION FOR SEQ ID NO:411:

( i ) SEQUENCE CHARACTERISTICS:
              ( A ) LENGTH: 22 base pairs
              ( B ) TYPE: nucleic acid
              ( C ) STRANDEDNESS: double
              ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:411:

CCTGTGTCCC CCATCAACAT GG                     22

( 2 ) INFORMATION FOR SEQ ID NO:412:

( i ) SEQUENCE CHARACTERISTICS:
              ( A ) LENGTH: 22 base pairs
              ( B ) TYPE: nucleic acid
              ( C ) STRANDEDNESS: double
              ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:412:

CCCCTGTCCC CTATCGACAT GG                     22

( 2 ) INFORMATION FOR SEQ ID NO:413:

( i ) SEQUENCE CHARACTERISTICS:
              ( A ) LENGTH: 22 base pairs
              ( B ) TYPE: nucleic acid
              ( C ) STRANDEDNESS: double
              ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:413:

CCCCTGTCCC CTATCGACAT GG                     22

( 2 ) INFORMATION FOR SEQ ID NO:414:

( i ) SEQUENCE CHARACTERISTICS:
              ( A ) LENGTH: 22 base pairs
              ( B ) TYPE: nucleic acid
              ( C ) STRANDEDNESS: double (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:414:

CCCCTGTCCC CTATCGACAT GG 22

(2) INFORMATION FOR SEQ ID NO:415:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:415:

CCGCTGTCGC CCATCGACAT GG 22

(2) INFORMATION FOR SEQ ID NO:416:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:416:

CCGCTGTCGC CCATCGACAT GG 22

(2) INFORMATION FOR SEQ ID NO:417:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:417:

CCGCTGTCGC CCATCGACAT GG 22

(2) INFORMATION FOR SEQ ID NO:418:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:418:

CCCTTGTCCC CCATCGACAT GG 22

( 2 ) INFORMATION FOR SEQ ID NO:419:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:419:

CCCTTGTCCC CCATCGACAT GG 22

( 2 ) INFORMATION FOR SEQ ID NO:420:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:420:

CCCCTGTCCC CTATTGACAT GG 22

( 2 ) INFORMATION FOR SEQ ID NO:421:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:421:

CCCCTGTCCC CTATTGACAT GG 22

( 2 ) INFORMATION FOR SEQ ID NO:422:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:422:

ACCGTTAATC CCATTGACAT GG 22

( 2 ) INFORMATION FOR SEQ ID NO:423:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:423:

CCGCTGTCCA CAATCGACGA AT 22

( 2 ) INFORMATION FOR SEQ ID NO:424:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:424:

GTGCTGTCCC CCATCGAGCT TG 22

( 2 ) INFORMATION FOR SEQ ID NO:425:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:425:

CCGCTGTGCA CCATCACAT GG 22

( 2 ) INFORMATION FOR SEQ ID NO:426:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:426:

CCGCTGTCGC CCATCGACAT GG 22

( 2 ) INFORMATION FOR SEQ ID NO:427:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:427:

CCGCTGTCTC CCATCGACAT GG    22

( 2 ) INFORMATION FOR SEQ ID NO:428:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:428:

CCGCTGTCCC CCATCGACCT GG    22

( 2 ) INFORMATION FOR SEQ ID NO:429:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:429:

CCTCTGTCCC CCATCGACCT GG    22

( 2 ) INFORMATION FOR SEQ ID NO:430:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:430:

CCGCTGTCTC CCATCGACCT GG    22

( 2 ) INFORMATION FOR SEQ ID NO:431:

( i ) SEQUENCE CHARACTERISTICS:

(A) LENGTH: 22 base pairs
            (B) TYPE: nucleic acid
            (C) STRANDEDNESS: double
            (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:431:

CCGCTGTCTC CCATCGACCT GG                                                        22

(2) INFORMATION FOR SEQ ID NO:432:

(i) SEQUENCE CHARACTERISTICS:
            (A) LENGTH: 22 base pairs
            (B) TYPE: nucleic acid
            (C) STRANDEDNESS: double
            (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:432:

CCGCTGTCTC CCATCGACCT GG                                                        22

(2) INFORMATION FOR SEQ ID NO:433:

(i) SEQUENCE CHARACTERISTICS:
            (A) LENGTH: 22 base pairs
            (B) TYPE: nucleic acid
            (C) STRANDEDNESS: double
            (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:433:

CCGCTGTCCC CCGCCGACAT GG                                                        22

(2) INFORMATION FOR SEQ ID NO:434:

(i) SEQUENCE CHARACTERISTICS:
            (A) LENGTH: 22 base pairs
            (B) TYPE: nucleic acid
            (C) STRANDEDNESS: double
            (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:434:

CCGCTGTCCC CCATCGACAT GG                                                        22

(2) INFORMATION FOR SEQ ID NO:435:

(i) SEQUENCE CHARACTERISTICS:
            (A) LENGTH: 22 base pairs
            (B) TYPE: nucleic acid
            (C) STRANDEDNESS: double
            (D) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:435:

CCGCTGTCCC CCATCGACAT GG　　　　　　　　　　　　　　　　　　　　　　　22

( 2 ) INFORMATION FOR SEQ ID NO:436:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:436:

CCGCTGTCTC CCATCGACAT GG　　　　　　　　　　　　　　　　　　　　　　　22

( 2 ) INFORMATION FOR SEQ ID NO:437:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:437:

CCGCTGTCTC CCATCGACAT GG　　　　　　　　　　　　　　　　　　　　　　　22

( 2 ) INFORMATION FOR SEQ ID NO:438:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:438:

CCGCTATCTC CCATCGACCT GG　　　　　　　　　　　　　　　　　　　　　　　22

( 2 ) INFORMATION FOR SEQ ID NO:439:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO (i v) ANTI-SENSE: NO (x i) SEQUENCE DESCRIPTION: SEQ ID NO:439:

CCGCTATCTC CCATCGACCT GG                                                22

(2) INFORMATION FOR SEQ ID NO:440:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:440:

CCACTGTCCC CCGCCCACCT GG                                                22

(2) INFORMATION FOR SEQ ID NO:441:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:441:

CCGCTGTCGC CCATCGACAT GG                                                22

(2) INFORMATION FOR SEQ ID NO:442:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:442:

AAGCTGTCCC CCATCGACAC CA                                                22

(2) INFORMATION FOR SEQ ID NO:443:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:443:

AAGCTGTCCC CCATCGACAC CA                                            22

(2) INFORMATION FOR SEQ ID NO:444:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:444:

CCGCTGTCGC CCATCGAGAC GA                                            22

(2) INFORMATION FOR SEQ ID NO:445:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:445:

CCGCTGTCGC CCATCGAGAC GA                                            22

(2) INFORMATION FOR SEQ ID NO:446:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:446:

CCGCTGTCGC CCATCGAGAC GA                                            22

(2) INFORMATION FOR SEQ ID NO:447:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:447:

CCGCTGTCGC CCATCGAGAC GA                                            22

( 2 ) INFORMATION FOR SEQ ID NO:448:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:448:

CCGCTGTCGC CCATCGAGAC GA 22

( 2 ) INFORMATION FOR SEQ ID NO:449:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:449:

CTGGCGGCCA CCAAGTG 17

( 2 ) INFORMATION FOR SEQ ID NO:450:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:450:

ATCGCTGCCT CCAAGTG 17

( 2 ) INFORMATION FOR SEQ ID NO:451:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:451:

ATGGCGGCCA CCTCCAA 17

( 2 ) INFORMATION FOR SEQ ID NO:452:

( i ) SEQUENCE CHARACTERISTICS:
        ( A ) LENGTH: 17 base pairs (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:452:

CTGGCGGCCA CCAAGTG  17

(2) INFORMATION FOR SEQ ID NO:453:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:453:

ATTGCCGCCT CCAAGTG  17

(2) INFORMATION FOR SEQ ID NO:454:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:454:

ATTGCCGCCT CCAAGTG  17

(2) INFORMATION FOR SEQ ID NO:455:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:455:

ATTGCCGCCT CCAAGTG  17

(2) INFORMATION FOR SEQ ID NO:456:

(i) SEQUENCE CHARACTERISTICS:
        (A) LENGTH: 17 base pairs
        (B) TYPE: nucleic acid
        (C) STRANDEDNESS: double
        (D) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:456:

CTGGCCGCCA CCCCCGG 17

( 2 ) INFORMATION FOR SEQ ID NO:457:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:457:

CTGGCGTCCA CCGCCAG 17

( 2 ) INFORMATION FOR SEQ ID NO:458:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:458:

CTGGCGTCCA CCGCCAG 17

( 2 ) INFORMATION FOR SEQ ID NO:459:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:459:

CTGGCGTCCA CCGCCAA 17

( 2 ) INFORMATION FOR SEQ ID NO:460:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO -continued ( i v ) ANTI-SENSE: NO ( x i ) SEQUENCE DESCRIPTION: SEQ ID NO:460:

ATCGCTGCCT CCAAGTG 17

( 2 ) INFORMATION FOR SEQ ID NO:461:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:461:

CCGGCGGCGA CCAACCC 17

( 2 ) INFORMATION FOR SEQ ID NO:462:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:462:

GGCGCGGCAG CCAATGG 17

( 2 ) INFORMATION FOR SEQ ID NO:463:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:463:

GTGGCTGCAT CCAAGTG 17

( 2 ) INFORMATION FOR SEQ ID NO:464:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:464:

```
GTGGCGGCCA CCAAGTG                                                                17
```

( 2 ) INFORMATION FOR SEQ ID NO:465:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:465:

```
CTGGCGGCAA CCAAGGC                                                                17
```

( 2 ) INFORMATION FOR SEQ ID NO:466:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:466:

```
CTGGCGGCCA CCATGAA                                                                17
```

( 2 ) INFORMATION FOR SEQ ID NO:467:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:467:

```
CTGGCGGCCA CCATGAA                                                                17
```

( 2 ) INFORMATION FOR SEQ ID NO:468:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:468:

```
CTGGCGGCCA CCATGAA                                                                17
```

( 2 ) INFORMATION FOR SEQ ID NO:469:

( i ) SEQUENCE CHARACTERISTICS:
    ( A ) LENGTH: 17 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:469:

CGACGACCAC CATCAGC      17

( 2 ) INFORMATION FOR SEQ ID NO:470:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:470:

CCACGGCCAA CATGCTC      17

( 2 ) INFORMATION FOR SEQ ID NO:471:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:471:

CCACGGCGAG CCTGCTG      17

( 2 ) INFORMATION FOR SEQ ID NO:472:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:472:

CGACGGCCAC CATCAGC      17

( 2 ) INFORMATION FOR SEQ ID NO:473:

( i ) SEQUENCE CHARACTERISTICS:
        ( A ) LENGTH: 17 base pairs
        ( B ) TYPE: nucleic acid (C) STRANDEDNESS: double
            (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:473:

CCACGGCCAA CATGCTC 17

(2) INFORMATION FOR SEQ ID NO:474:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:474:

CCACGGCCAA CATGCTC 17

(2) INFORMATION FOR SEQ ID NO:475:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:475:

CCACGGCCAA CATGCTC 17

(2) INFORMATION FOR SEQ ID NO:476:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:476:

CCACCGCCAG CCTGCTG 17

(2) INFORMATION FOR SEQ ID NO:477:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (i i) MOLECULE TYPE: cDNA to mRNA (iii) HYPOTHETICAL: NO (iv) ANTI-SENSE: NO (xi) SEQUENCE DESCRIPTION: SEQ ID NO:477:

CCACCGCCAG CCTGCTG 17

(2) INFORMATION FOR SEQ ID NO:478:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:478:

CCACCGCCAG CCTGCTG 17

(2) INFORMATION FOR SEQ ID NO:479:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:479:

CCACGGCCAA CATGCTC 17

(2) INFORMATION FOR SEQ ID NO:480:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:480:

CCACCGCCAA CATGCTC 17

(2) INFORMATION FOR SEQ ID NO:481:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO ( x i ) SEQUENCE DESCRIPTION: SEQ ID NO:481:

CCACGGCCAA CATGCTC 17

( 2 ) INFORMATION FOR SEQ ID NO:482:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:482:

CCACTGCCAA CATGCTC 17

( 2 ) INFORMATION FOR SEQ ID NO:483:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:483:

CCTACACCAA CATGACC 17

( 2 ) INFORMATION FOR SEQ ID NO:484:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:484:

CCACGGCCAA CATCGTC 17

( 2 ) INFORMATION FOR SEQ ID NO:485:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:485:

CCACGGCCAA CATCGTC 17

( 2 ) INFORMATION FOR SEQ ID NO:486:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:486:

GGAAGCTGGA GCGCATC        17

( 2 ) INFORMATION FOR SEQ ID NO:487:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:487:

AGTCCCAGGA GCGGATC        17

( 2 ) INFORMATION FOR SEQ ID NO:488:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:488:

ACACGCAGGA GCGCATC        17

( 2 ) INFORMATION FOR SEQ ID NO:489:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:489:

AAGACCAGGA GCGCATC        17

( 2 ) INFORMATION FOR SEQ ID NO:490:

( i ) SEQUENCE CHARACTERISTICS:
 ( A ) LENGTH: 17 base pairs
 ( B ) TYPE: nucleic acid
 ( C ) STRANDEDNESS: double
 ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:490:

AGTCTCAGGA GCGGATC    17

( 2 ) INFORMATION FOR SEQ ID NO:491:

( i ) SEQUENCE CHARACTERISTICS:
  ( A ) LENGTH: 17 base pairs
  ( B ) TYPE: nucleic acid
  ( C ) STRANDEDNESS: double
  ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:491:

AGTCTCAGGA GCGGATC    17

( 2 ) INFORMATION FOR SEQ ID NO:492:

( i ) SEQUENCE CHARACTERISTICS:
  ( A ) LENGTH: 17 base pairs
  ( B ) TYPE: nucleic acid
  ( C ) STRANDEDNESS: double
  ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:492:

AGTCTCAGGA GCGGATC    17

( 2 ) INFORMATION FOR SEQ ID NO:493:

( i ) SEQUENCE CHARACTERISTICS:
  ( A ) LENGTH: 17 base pairs
  ( B ) TYPE: nucleic acid
  ( C ) STRANDEDNESS: double
  ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:493:

ACACGCAAGA ACGCATC    17

( 2 ) INFORMATION FOR SEQ ID NO:494:

( i ) SEQUENCE CHARACTERISTICS:
  ( A ) LENGTH: 17 base pairs
  ( B ) TYPE: nucleic acid
  ( C ) STRANDEDNESS: double (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:494:

ACACGCAAGA ACGCATC 17

(2) INFORMATION FOR SEQ ID NO:495:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:495:

ACACGCAAGA ACGCATC 17

(2) INFORMATION FOR SEQ ID NO:496:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:496:

AGTCTCAGGA GCGGATC 17

(2) INFORMATION FOR SEQ ID NO:497:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:497:

AGTCTCAGGA GCGGATC 17

(2) INFORMATION FOR SEQ ID NO:498:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (i i) MOLECULE TYPE: cDNA to mRNA (iii) HYPOTHETICAL: NO (iv) ANTI-SENSE: NO (xi) SEQUENCE DESCRIPTION: SEQ ID NO:498:

AGTCGCAGGA GAGAATC                                                                                              17

(2) INFORMATION FOR SEQ ID NO:499:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:499:

AGTCGCAGGA GAGAATC                                                                                              17

(2) INFORMATION FOR SEQ ID NO:500:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:500:

GCAAGCTGGA GCGCATC                                                                                              17

(2) INFORMATION FOR SEQ ID NO:501:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:501:

ACACGCAGGA GCGAAAA                                                                                              17

(2) INFORMATION FOR SEQ ID NO:502:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO ( x i ) SEQUENCE DESCRIPTION: SEQ ID NO:502:

AACAGCAGGA GCGCATC							17

( 2 ) INFORMATION FOR SEQ ID NO:503:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:503:

CCACGCAGGA GCGCTGC							17

( 2 ) INFORMATION FOR SEQ ID NO:504:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:504:

GCACGCAGGA GCGCTGC							17

( 2 ) INFORMATION FOR SEQ ID NO:505:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:505:

ACACGCTGGA GCGCGTG							17

( 2 ) INFORMATION FOR SEQ ID NO:506:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:506:

CGCTCAAGGC CGAGAACGCG G							21

( 2 ) INFORMATION FOR SEQ ID NO:507:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:507:

AACTGCACAG CCAGAACACG C         21

( 2 ) INFORMATION FOR SEQ ID NO:508:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:508:

CCCTCAAGAG TCAGAACACG G         21

( 2 ) INFORMATION FOR SEQ ID NO:509:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:509:

TACTCTCCAG CCTCTGCACC C         21

( 2 ) INFORMATION FOR SEQ ID NO:510:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:510:

AACTGCATAG CCAGAACACG C         21

( 2 ) INFORMATION FOR SEQ ID NO:511:

( i ) SEQUENCE CHARACTERISTICS:

(A) LENGTH: 21 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:511:

AACTGCATAG CCAGAACACG C    21

(2) INFORMATION FOR SEQ ID NO:512:

(i) SEQUENCE CHARACTERISTICS:
(A) LENGTH: 21 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:512:

AACTGCATAG CCAGAACACG C    21

(2) INFORMATION FOR SEQ ID NO:513:

(i) SEQUENCE CHARACTERISTICS:
(A) LENGTH: 21 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:513:

CCCTCAAAAG CCAGAACACC G    21

(2) INFORMATION FOR SEQ ID NO:514:

(i) SEQUENCE CHARACTERISTICS:
(A) LENGTH: 21 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:514:

CCCTCAAAAG CCAGAACACC G    21

(2) INFORMATION FOR SEQ ID NO:515:

(i) SEQUENCE CHARACTERISTICS:
(A) LENGTH: 21 base pairs
(B) TYPE: nucleic acid
(C) STRANDEDNESS: double
(D) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:515:

CCCTCAAAAG CCAGAACACC G 21

( 2 ) INFORMATION FOR SEQ ID NO:516:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:516:

GCCTCAGCCG CCGCACCACT T 21

( 2 ) INFORMATION FOR SEQ ID NO:517:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:517:

GCCTCAGCCG CCGCACCACT T 21

( 2 ) INFORMATION FOR SEQ ID NO:518:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:518:

ACCTGAGGAA CAAGAACGCC G 21

( 2 ) INFORMATION FOR SEQ ID NO:519:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:519:

CCCCCAGATG CCAGTGCAGC A        21

( 2 ) INFORMATION FOR SEQ ID NO:520:

( i ) SEQUENCE CHARACTERISTICS:
                ( A ) LENGTH: 21 base pairs
                ( B ) TYPE: nucleic acid
                ( C ) STRANDEDNESS: double
                ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:520:

ACCTCAAGGA CCATGTGGCG C        21

( 2 ) INFORMATION FOR SEQ ID NO:521:

( i ) SEQUENCE CHARACTERISTICS:
                ( A ) LENGTH: 21 base pairs
                ( B ) TYPE: nucleic acid
                ( C ) STRANDEDNESS: double
                ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:521:

TGCTCAAAAT CCTGAACACC G        21

( 2 ) INFORMATION FOR SEQ ID NO:522:

( i ) SEQUENCE CHARACTERISTICS:
                ( A ) LENGTH: 21 base pairs
                ( B ) TYPE: nucleic acid
                ( C ) STRANDEDNESS: double
                ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:522:

GCCTCAAGAA CCTGAACACC G        21

( 2 ) INFORMATION FOR SEQ ID NO:523:

( i ) SEQUENCE CHARACTERISTICS:
                ( A ) LENGTH: 21 base pairs
                ( B ) TYPE: nucleic acid
                ( C ) STRANDEDNESS: double
                ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:523:

GCCTCAAGAA CCTGAACACC G                                                    21

( 2 ) INFORMATION FOR SEQ ID NO:524:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:524:

ACCCCAAAAG CCAGAACAGT T                                                    21

( 2 ) INFORMATION FOR SEQ ID NO:525:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:525:

AGTACAATTG TGAAGCAGAT GA                                                   22

( 2 ) INFORMATION FOR SEQ ID NO:526:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:526:

AGCACCATCG TCAAGCAGAT GA                                                   22

( 2 ) INFORMATION FOR SEQ ID NO:527:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:527:

AGCACCATTG TGAAACAGAT GA                                                   22

( 2 ) INFORMATION FOR SEQ ID NO:528:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:528:

AGCACCATTG TGAAGCAGAT GA        22

( 2 ) INFORMATION FOR SEQ ID NO:529:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:529:

AGCACCATTG TGAAGCAGAT GA        22

( 2 ) INFORMATION FOR SEQ ID NO:530:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:530:

AGCACAATTG TGAAGCAGAT GA        22

( 2 ) INFORMATION FOR SEQ ID NO:531:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:531:

AGCACCATCG TCAAGCAGAT GA        22

( 2 ) INFORMATION FOR SEQ ID NO:532:

( i ) SEQUENCE CHARACTERISTICS:
        ( A ) LENGTH: 22 base pairs ( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:532:

AGTACTATTG TGAAGCAGAT GA 22

( 2 ) INFORMATION FOR SEQ ID NO:533:

( i ) SEQUENCE CHARACTERISTICS:
( A ) LENGTH: 22 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:533:

AGCACCATTG TGAAGCAGAT GA 22

( 2 ) INFORMATION FOR SEQ ID NO:534:

( i ) SEQUENCE CHARACTERISTICS:
( A ) LENGTH: 22 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:534:

AGCACCATTG TGAAGCAGAT GA 22

( 2 ) INFORMATION FOR SEQ ID NO:535:

( i ) SEQUENCE CHARACTERISTICS:
( A ) LENGTH: 22 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:535:

AGCACCATCG TCAAGCAGAT GA 22

( 2 ) INFORMATION FOR SEQ ID NO:536:

( i ) SEQUENCE CHARACTERISTICS:
( A ) LENGTH: 22 base pairs
( B ) TYPE: nucleic acid
( C ) STRANDEDNESS: double
( D ) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:536:

AGCACCATTG TGAAGCAGAT GA    22

(2) INFORMATION FOR SEQ ID NO:537:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:537:

GCCACCATGG TGAAGAAGAT GA    22

(2) INFORMATION FOR SEQ ID NO:538:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:538:

CTCACCATTG TGAAGCACCT AC    22

(2) INFORMATION FOR SEQ ID NO:539:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:539:

TGTTTGATGT GGGAGGTCAG AG    22

(2) INFORMATION FOR SEQ ID NO:540:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (i i) MOLECULE TYPE: cDNA to mRNA (i i i) HYPOTHETICAL: NO (iv) ANTI-SENSE: NO (xi) SEQUENCE DESCRIPTION: SEQ ID NO:540:

TGTTTGATGT GGGTGGTCAG CG					22

(2) INFORMATION FOR SEQ ID NO:541:

(i) SEQUENCE CHARACTERISTICS:
      (A) LENGTH: 22 base pairs
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:541:

TGTTTGATGT AGGTGGCCAA AG					22

(2) INFORMATION FOR SEQ ID NO:542:

(i) SEQUENCE CHARACTERISTICS:
      (A) LENGTH: 22 base pairs
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:542:

TGTTTGACGT GGGTGGCCAG CG					22

(2) INFORMATION FOR SEQ ID NO:543:

(i) SEQUENCE CHARACTERISTICS:
      (A) LENGTH: 22 base pairs
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:543:

TGTTTGACGT CGGAGGCCAG CG					22

(2) INFORMATION FOR SEQ ID NO:544:

(i) SEQUENCE CHARACTERISTICS:
      (A) LENGTH: 22 base pairs
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:544:

```
TGTTTGACGT GGGAGGCCAG AG                                              22
```

( 2 ) INFORMATION FOR SEQ ID NO:545:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:545:

```
TGTTTGATGT GGGTGGTCAG CG                                              22
```

( 2 ) INFORMATION FOR SEQ ID NO:546:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:546:

```
TGTTTGATGT AGGTGGCCAA AG                                              22
```

( 2 ) INFORMATION FOR SEQ ID NO:547:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:547:

```
TGTTCGATGT GGGCGGCCAG CG                                              22
```

( 2 ) INFORMATION FOR SEQ ID NO:548:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:548:

```
TGTTTGACGT TGGGGGCCAG CG                                              22
```

( 2 ) INFORMATION FOR SEQ ID NO:549:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:549:

TGGTGGATGT GGGAGGGCAG AG 22

( 2 ) INFORMATION FOR SEQ ID NO:550:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:550:

CTGATGATGT GGGAGGCCTA CT 22

( 2 ) INFORMATION FOR SEQ ID NO:551:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:551:

GAGTGGATGT GGTAGACCAG AG 22

( 2 ) INFORMATION FOR SEQ ID NO:552:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:552:

AGTTTGATAT GGGGGGCCAG AG 22

( 2 ) INFORMATION FOR SEQ ID NO:553:

( i ) SEQUENCE CHARACTERISTICS:
    ( A ) LENGTH: 26
    ( B ) TYPE: nucleic acid (C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:553:

GATGTTCTCA GAACTAGAGT GAAAAC 26

(2) INFORMATION FOR SEQ ID NO:554:

(i) SEQUENCE CHARACTERISTICS:
(A) LENGTH: 26
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:554:

TTTGTTCTCA GCTCCCCCTG TCCCCT 26

(2) INFORMATION FOR SEQ ID NO:555:

(i) SEQUENCE CHARACTERISTICS:
(A) LENGTH: 26
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:555:

GATGTTCTTC GGACGAGAGT GAAGAC 26

(2) INFORMATION FOR SEQ ID NO:556:

(i) SEQUENCE CHARACTERISTICS:
(A) LENGTH: 26
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:556:

ACTGTGCCCA GTACTTCCTG GACAAG 26

(2) INFORMATION FOR SEQ ID NO:557:

(i) SEQUENCE CHARACTERISTICS:
(A) LENGTH: 26
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:557:

GACATCCTCC GAACCAGGGT CAAAAC          26

(2) INFORMATION FOR SEQ ID NO:558:

(i) SEQUENCE CHARACTERISTICS:
  (A) LENGTH: 26
  (B) TYPE: nucleic acid
  (C) STRANDEDNESS: double
  (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:558:

GATGTTCTCA GAACTAGAGT GAAAAC          26

(2) INFORMATION FOR SEQ ID NO:559:

(i) SEQUENCE CHARACTERISTICS:
  (A) LENGTH: 26
  (B) TYPE: nucleic acid
  (C) STRANDEDNESS: double
  (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:559:

GATGTGCTGC GGACCCGTGT GAAGAC          26

(2) INFORMATION FOR SEQ ID NO:560:

(i) SEQUENCE CHARACTERISTICS:
  (A) LENGTH: 26
  (B) TYPE: nucleic acid
  (C) STRANDEDNESS: double
  (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:560:

GATGTTCTTC GGACGAGAGT GAAGAC          26

(2) INFORMATION FOR SEQ ID NO:561:

(i) SEQUENCE CHARACTERISTICS:
  (A) LENGTH: 26
  (B) TYPE: nucleic acid
  (C) STRANDEDNESS: double
  (D) TOPOLOGY: linear (ii) MOLECULE TYPE: cDNA to mRNA (iii) HYPOTHETICAL: NO (iv) ANTI-SENSE: NO ( x i ) SEQUENCE DESCRIPTION: SEQ ID NO:561:

AAGCACAATT AATTAAGAGT GAAACG 26

( 2 ) INFORMATION FOR SEQ ID NO:562:

( i ) SEQUENCE CHARACTERISTICS:
        ( A ) LENGTH: 26
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:562:

GACATCCTCC GAACCAGGGT CAAAAC 26

( 2 ) INFORMATION FOR SEQ ID NO:563:

( i ) SEQUENCE CHARACTERISTICS:
        ( A ) LENGTH: 26
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:563:

TCAGTTCGAG GACCTAAACC GAAACA 26

( 2 ) INFORMATION FOR SEQ ID NO:564:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:564:

GGAGGTTGAA GATAGACTTT G 21

( 2 ) INFORMATION FOR SEQ ID NO:565:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:565:

GCAACCTGCA GATCGACTTT G 21

( 2 ) INFORMATION FOR SEQ ID NO:566:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:566:

GACGGCTAAA GATTGACTTT G       21

( 2 ) INFORMATION FOR SEQ ID NO:567:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:567:

AGTACCAGCT GATTGACTGT G       21

( 2 ) INFORMATION FOR SEQ ID NO:568:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:568:

CTTCTCTGCA GAGCTGCTTT C       21

( 2 ) INFORMATION FOR SEQ ID NO:569:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:569:

GGAGATTGAA AATCGACTTT G       21

( 2 ) INFORMATION FOR SEQ ID NO:570:

( i ) SEQUENCE CHARACTERISTICS:
  ( A ) LENGTH: 21 base pairs
  ( B ) TYPE: nucleic acid
  ( C ) STRANDEDNESS: double
  ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:570:

GCAACCTGCA GATCGACTTT G　　　　　　　　　　　　　　21

( 2 ) INFORMATION FOR SEQ ID NO:571:

( i ) SEQUENCE CHARACTERISTICS:
  ( A ) LENGTH: 21 base pairs
  ( B ) TYPE: nucleic acid
  ( C ) STRANDEDNESS: double
  ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:571:

AAAACGTGCA GTTTGTTTTT G　　　　　　　　　　　　　　21

( 2 ) INFORMATION FOR SEQ ID NO:572:

( i ) SEQUENCE CHARACTERISTICS:
  ( A ) LENGTH: 21 base pairs
  ( B ) TYPE: nucleic acid
  ( C ) STRANDEDNESS: double
  ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:572:

AGTACCAGCT GATCGACTGT G　　　　　　　　　　　　　　21

( 2 ) INFORMATION FOR SEQ ID NO:573:

( i ) SEQUENCE CHARACTERISTICS:
  ( A ) LENGTH: 21 base pairs
  ( B ) TYPE: nucleic acid
  ( C ) STRANDEDNESS: double
  ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:573:

ATTCTCTGCA GAACTGCTTT C　　　　　　　　　　　　　　21

( 2 ) INFORMATION FOR SEQ ID NO:574:

( i ) SEQUENCE CHARACTERISTICS:
  ( A ) LENGTH: 21 base pairs
  ( B ) TYPE: nucleic acid
  ( C ) STRANDEDNESS: double (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:574:

GTAACATCCA GTTTGTCTTC G 21

(2) INFORMATION FOR SEQ ID NO:575:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:575:

TCTCAGAACT AGAGTGAAAA C 21

(2) INFORMATION FOR SEQ ID NO:576:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:576:

GCTACGGACC CGCGTAAAGA C 21

(2) INFORMATION FOR SEQ ID NO:577:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:577:

TCTTCGGACG AGAGTGAAGA C 21

(2) INFORMATION FOR SEQ ID NO:578:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:578:

GGGAAATCGA AGATTGAGGA C    21

(2) INFORMATION FOR SEQ ID NO:579:

(i) SEQUENCE CHARACTERISTICS:
(A) LENGTH: 21 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:579:

TCTCCGGAGA AGACGTGAAA C    21

(2) INFORMATION FOR SEQ ID NO:580:

(i) SEQUENCE CHARACTERISTICS:
(A) LENGTH: 21 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:580:

TCTCAGAACT AGAGTGAAAA C    21

(2) INFORMATION FOR SEQ ID NO:581:

(i) SEQUENCE CHARACTERISTICS:
(A) LENGTH: 21 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:581:

GCTGCGGACC CGTGTGAAGA C    21

(2) INFORMATION FOR SEQ ID NO:582:

(i) SEQUENCE CHARACTERISTICS:
(A) LENGTH: 21 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO ( x i ) SEQUENCE DESCRIPTION: SEQ ID NO:582:

TCTTCGGACG AGAGTGAAGA C                                                                  2 1

( 2 ) INFORMATION FOR SEQ ID NO:583:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:583:

TTCCTGGACA AGATTGATGT G                                                                  2 1

( 2 ) INFORMATION FOR SEQ ID NO:584:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:584:

CGCATGGAGG ACACTGAACC A                                                                  2 1

( 2 ) INFORMATION FOR SEQ ID NO:585:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:585:

AACTCGGGCA AGAGCACCAT C                                                                  2 1

( 2 ) INFORMATION FOR SEQ ID NO:586:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:586:

GGGCGGATGA TCATCCCAAG CT                                                                 2 2

( 2 ) INFORMATION FOR SEQ ID NO:587:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:587:

AATATGATGA GGCAGCCAGC TA        22

( 2 ) INFORMATION FOR SEQ ID NO:588:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:588:

CAGTCTAACT ACATTCCAAC TC        22

( 2 ) INFORMATION FOR SEQ ID NO:589:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:589:

GACCTTTCTT AAATGTGACA        20

( 2 ) INFORMATION FOR SEQ ID NO:590:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:590:

CTGTGATCTC CAAGGCTGCG        20

( 2 ) INFORMATION FOR SEQ ID NO:591:

( i ) SEQUENCE CHARACTERISTICS:

( A ) LENGTH: 20 base pairs
                    ( B ) TYPE: nucleic acid
                    ( C ) STRANDEDNESS: double
                    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:591:

CTGCATTCTA GAACTTCACA                    20

( 2 ) INFORMATION FOR SEQ ID NO:592:

( i ) SEQUENCE CHARACTERISTICS:
                    ( A ) LENGTH: 20 base pairs
                    ( B ) TYPE: nucleic acid
                    ( C ) STRANDEDNESS: double
                    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:592:

TCAACGACTG CCGTGACATC                    20

( 2 ) INFORMATION FOR SEQ ID NO:593:

( i ) SEQUENCE CHARACTERISTICS:
                    ( A ) LENGTH: 20 base pairs
                    ( B ) TYPE: nucleic acid
                    ( C ) STRANDEDNESS: double
                    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:593:

CTGCTTTCTG CCATGATGCG                    20

( 2 ) INFORMATION FOR SEQ ID NO:594:

( i ) SEQUENCE CHARACTERISTICS:
                    ( A ) LENGTH: 20 base pairs
                    ( B ) TYPE: nucleic acid
                    ( C ) STRANDEDNESS: double
                    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:594:

CTGATTTCCC ACGTTATGTT                    20

( 2 ) INFORMATION FOR SEQ ID NO:595:

( i ) SEQUENCE CHARACTERISTICS:
                    ( A ) LENGTH: 20 base pairs
                    ( B ) TYPE: nucleic acid
                    ( C ) STRANDEDNESS: double
                    ( D ) TOPOLOGY: linear -continued ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:595:

TTGCTGACCC CCAGCGTGCG　　　　　　　　　　　　　　　　　　　　　　　　　20

( 2 ) INFORMATION FOR SEQ ID NO:596:

( i ) SEQUENCE CHARACTERISTICS:
          ( A ) LENGTH: 20 base pairs
          ( B ) TYPE: nucleic acid
          ( C ) STRANDEDNESS: double
          ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:596:

CTGCTTGCTG TCATTGTCAC　　　　　　　　　　　　　　　　　　　　　　　　　20

( 2 ) INFORMATION FOR SEQ ID NO:597:

( i ) SEQUENCE CHARACTERISTICS:
          ( A ) LENGTH: 20 base pairs
          ( B ) TYPE: nucleic acid
          ( C ) STRANDEDNESS: double
          ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:597:

CTGCTTGCTG AGAAGGTCCT　　　　　　　　　　　　　　　　　　　　　　　　　20

( 2 ) INFORMATION FOR SEQ ID NO:598:

( i ) SEQUENCE CHARACTERISTICS:
          ( A ) LENGTH: 20 base pairs
          ( B ) TYPE: nucleic acid
          ( C ) STRANDEDNESS: double
          ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:598:

CTGCTTTCTG CCATGATGCG　　　　　　　　　　　　　　　　　　　　　　　　　20

( 2 ) INFORMATION FOR SEQ ID NO:599:

( i ) SEQUENCE CHARACTERISTICS:
          ( A ) LENGTH: 20 base pairs
          ( B ) TYPE: nucleic acid
          ( C ) STRANDEDNESS: double
          ( D ) TOPOLOGY: linear ( i i ) MOLECULE TYPE: cDNA to mRNA ( i i i ) HYPOTHETICAL: NO

5,639,612

441  442

-continued ( i v ) ANTI-SENSE: NO ( x i ) SEQUENCE DESCRIPTION: SEQ ID NO:599:

CAGCTCTTTG CCCTGACTGG                                              20

( 2 ) INFORMATION FOR SEQ ID NO:600:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:600:

CACGACTAGA AACTCCTGAA AC                                         22

( 2 ) INFORMATION FOR SEQ ID NO:601:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:601:

AAATACAATA AACTATTGAA AA                                         22

( 2 ) INFORMATION FOR SEQ ID NO:602:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:602:

TACGAGTCCA CATTCCTGTT CC                                         22

( 2 ) INFORMATION FOR SEQ ID NO:603:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:603:

CACGACTACA AACTCCTGAA AC    22

( 2 ) INFORMATION FOR SEQ ID NO:604:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:604:

AGTAACCCCA AGATCCTGAA AC    22

( 2 ) INFORMATION FOR SEQ ID NO:605:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:605:

TACGAGTCCA CATTCCTGTT TG    22

( 2 ) INFORMATION FOR SEQ ID NO:606:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:606:

CACGACTTCA ACGTCCTGAG TA    22

( 2 ) INFORMATION FOR SEQ ID NO:607:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:607:

GGACAGTACT TTTACCCCCG    20

( 2 ) INFORMATION FOR SEQ ID NO:608:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:608:

ACCCAGTTCT TGTGCCCCAA     20

( 2 ) INFORMATION FOR SEQ ID NO:609:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:609:

ACGCAGTTCC TCTACCCGAA     20

( 2 ) INFORMATION FOR SEQ ID NO:610:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:610:

GGACAGTACT TTTACCCCCG     20

( 2 ) INFORMATION FOR SEQ ID NO:611:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:611:

GGAAAGCAGC GGTACCCCAC     20

( 2 ) INFORMATION FOR SEQ ID NO:612:

( i ) SEQUENCE CHARACTERISTICS:
        ( A ) LENGTH: 20 base pairs (B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:612:

TCACAGTTCC TCTACCCCAA                        20

(2) INFORMATION FOR SEQ ID NO:613:

(i) SEQUENCE CHARACTERISTICS:
(A) LENGTH: 20 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:613:

GGACAGCTCT TTTAATCCCA                        20

(2) INFORMATION FOR SEQ ID NO:614:

(i) SEQUENCE CHARACTERISTICS:
(A) LENGTH: 26 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:614:

GAGGACAAGG TGAAGACACT CAAGGC                 26

(2) INFORMATION FOR SEQ ID NO:615:

(i) SEQUENCE CHARACTERISTICS:
(A) LENGTH: 26 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:615:

GAGGAAAAAG TGAAAACCTT GAAAGC                 26

(2) INFORMATION FOR SEQ ID NO:616:

(i) SEQUENCE CHARACTERISTICS:
(A) LENGTH: 26 base pairs
(B) TYPE: nucleic acid
(C) STRANDEDNESS: double
(D) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:616:

GAGGAGAAGG TCAAGACCCT CAAAAG      26

( 2 ) INFORMATION FOR SEQ ID NO:617:

( i ) SEQUENCE CHARACTERISTICS:
                ( A ) LENGTH: 26 base pairs
                ( B ) TYPE: nucleic acid
                ( C ) STRANDEDNESS: double
                ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:617:

GAGGACAAGG TGAAGACGCT CAAGGC      26

( 2 ) INFORMATION FOR SEQ ID NO:618:

( i ) SEQUENCE CHARACTERISTICS:
                ( A ) LENGTH: 26 base pairs
                ( B ) TYPE: nucleic acid
                ( C ) STRANDEDNESS: double
                ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:618:

GAGGAAAAAG TGAAAACCTT GAAAGC      26

( 2 ) INFORMATION FOR SEQ ID NO:619:

( i ) SEQUENCE CHARACTERISTICS:
                ( A ) LENGTH: 26 base pairs
                ( B ) TYPE: nucleic acid
                ( C ) STRANDEDNESS: double
                ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:619:

GAAGAGAAAG TGAAGACCCT CAAGAG      26

( 2 ) INFORMATION FOR SEQ ID NO:620:

( i ) SEQUENCE CHARACTERISTICS:
                ( A ) LENGTH: 26 base pairs
                ( B ) TYPE: nucleic acid
                ( C ) STRANDEDNESS: double
                ( D ) TOPOLOGY: linear ( i i ) MOLECULE TYPE: cDNA to mRNA ( i i i ) HYPOTHETICAL: NO (i v) ANTI-SENSE: NO (x i) SEQUENCE DESCRIPTION: SEQ ID NO:620:

AAAGAAAAAA AGAAAAACTT AAAAGC 26

(2) INFORMATION FOR SEQ ID NO:621:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:621:

GCCAGTTGCT GCTAGGGGTC 20

(2) INFORMATION FOR SEQ ID NO:622:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:622:

GCCAACTCAT GCTAACGCAG 20

(2) INFORMATION FOR SEQ ID NO:623:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:623:

TCCAAATGCC GCAAGCGCAA 20

(2) INFORMATION FOR SEQ ID NO:624:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:624:

```
GCCAGCCCCC GAGAACGCGC                                                                                   20
```

(2) INFORMATION FOR SEQ ID NO:625:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:625:

```
GCCAACTCAT GCTAACGCAG                                                                                   20
```

(2) INFORMATION FOR SEQ ID NO:626:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:626:

```
TCCAAGTGCC GCAAGCGCAA                                                                                   20
```

(2) INFORMATION FOR SEQ ID NO:627:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:627:

```
CCCAACTCAT GCTGACGGGC                                                                                   20
```

(2) INFORMATION FOR SEQ ID NO:628:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:628:

```
CTGGGGCCGA GCACTGG                                                                                      17
```

(2) INFORMATION FOR SEQ ID NO:629:

( i ) SEQUENCE CHARACTERISTICS:
    ( A ) LENGTH: 17 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:629:

TAAGTGCCAG GCTAGAC 17

( 2 ) INFORMATION FOR SEQ ID NO:630:

( i ) SEQUENCE CHARACTERISTICS:
    ( A ) LENGTH: 17 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:630:

GACGTGCCGA GCTTCGG 17

( 2 ) INFORMATION FOR SEQ ID NO:631:

( i ) SEQUENCE CHARACTERISTICS:
    ( A ) LENGTH: 17 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:631:

CACGCGCCGC CCTTCGC 17

( 2 ) INFORMATION FOR SEQ ID NO:632:

( i ) SEQUENCE CHARACTERISTICS:
    ( A ) LENGTH: 17 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:632:

TAAGTGTTGA GCTCGGG 17

( 2 ) INFORMATION FOR SEQ ID NO:633:

( i ) SEQUENCE CHARACTERISTICS:
    ( A ) LENGTH: 17 base pairs
    ( B ) TYPE: nucleic acid (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:633:

GACGTGCCGA GCTTCGG                                                                                          17

(2) INFORMATION FOR SEQ ID NO:634:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:634:

GACGTGTGGA GCTTCGG                                                                                          17

(2) INFORMATION FOR SEQ ID NO:635:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:635:

AAGGTCATGA CCCATGTCAG C                                                                                     21

(2) INFORMATION FOR SEQ ID NO:636:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:636:

AAAGTCATGA ACCACGTTAA C                                                                                     21

(2) INFORMATION FOR SEQ ID NO:637:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:637:

AAAGTCCTCA GCCACGTCAA C    21

( 2 ) INFORMATION FOR SEQ ID NO:638:

( i ) SEQUENCE CHARACTERISTICS:
                ( A ) LENGTH: 21 base pairs
                ( B ) TYPE: nucleic acid
                ( C ) STRANDEDNESS: double
                ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:638:

AAGGTCATGA CCCACGTCAG C    21

( 2 ) INFORMATION FOR SEQ ID NO:639:

( i ) SEQUENCE CHARACTERISTICS:
                ( A ) LENGTH: 21 base pairs
                ( B ) TYPE: nucleic acid
                ( C ) STRANDEDNESS: double
                ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:639:

AAAGTGATGA ACCACGTTAA C    21

( 2 ) INFORMATION FOR SEQ ID NO:640:

( i ) SEQUENCE CHARACTERISTICS:
                ( A ) LENGTH: 21 base pairs
                ( B ) TYPE: nucleic acid
                ( C ) STRANDEDNESS: double
                ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:640:

AAAGTCCTCA GCCACGTCAA C    21

( 2 ) INFORMATION FOR SEQ ID NO:641:

( i ) SEQUENCE CHARACTERISTICS:
                ( A ) LENGTH: 21 base pairs
                ( B ) TYPE: nucleic acid
                ( C ) STRANDEDNESS: double
                ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:641:

AAAATCCTCA GCCACATCCT G 21

( 2 ) INFORMATION FOR SEQ ID NO:642:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:642:

GCCAACAAAA AGATCGAGAA GC 22

( 2 ) INFORMATION FOR SEQ ID NO:643:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:643:

CGCAGCAAGA TGATCGACCG CA 22

( 2 ) INFORMATION FOR SEQ ID NO:644:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:644:

CAAAGGAAAA AGCACAAGAA GC 22

( 2 ) INFORMATION FOR SEQ ID NO:645:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:645:

TGAGGAAAAA ATATAGAGAA GT 22

( 2 ) INFORMATION FOR SEQ ID NO:646:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:646:

TTTGGCGAGA AGATTAAGAA GT        22

( 2 ) INFORMATION FOR SEQ ID NO:647:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:647:

GCCAACAAAA AGATCGAGAA GC        22

( 2 ) INFORMATION FOR SEQ ID NO:648:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:648:

GCCAACAAAA AGATCGAGAA GC        22

( 2 ) INFORMATION FOR SEQ ID NO:649:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:649:

GCCAACAAAA AGATCGAGAA GC        22

( 2 ) INFORMATION FOR SEQ ID NO:650:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:650:

GCCAACAAAA AGATCGAGAA GC                22

( 2 ) INFORMATION FOR SEQ ID NO:651:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:651:

ACCAAAAACA AGATCAAGAA GC                22

( 2 ) INFORMATION FOR SEQ ID NO:652:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:652:

GGACAAAGTC AACTTCCACA TG                22

( 2 ) INFORMATION FOR SEQ ID NO:653:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:653:

GGACAAGGCG GCCGTGGAGC GC                22

( 2 ) INFORMATION FOR SEQ ID NO:654:

( i ) SEQUENCE CHARACTERISTICS:
    ( A ) LENGTH: 22 base pairs
    ( B ) TYPE: nucleic acid
    ( C ) STRANDEDNESS: double (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:654:

AGACAAAGCC CACCTGCTCA TT 22

(2) INFORMATION FOR SEQ ID NO:655:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:655:

GTCAGGAGTA ATATTCCACA GC 22

(2) INFORMATION FOR SEQ ID NO:656:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:656:

CCGAGGAGCG GCGATGCACA TG 22

(2) INFORMATION FOR SEQ ID NO:657:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:657:

GGACAAAGTC AACTTCCACA TG 22

(2) INFORMATION FOR SEQ ID NO:658:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:658:

GGACAAAGTC AACTTCCACA TG                                                                        22

( 2 ) INFORMATION FOR SEQ ID NO:659:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:659:

GGACAAAGTC AACTTCCACA TG                                                                        22

( 2 ) INFORMATION FOR SEQ ID NO:660:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:660:

GGACAAAGTC AACTTCCACA TG                                                                        22

( 2 ) INFORMATION FOR SEQ ID NO:661:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:661:

AGACAAATTC ATCTTCCACA AG                                                                        22

( 2 ) INFORMATION FOR SEQ ID NO:662:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:662:

AAGCACAATT AATTAAGAGT GAAACG 26

( 2 ) INFORMATION FOR SEQ ID NO:663:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:663:

GATGTTCTCA GAACTAGAGT GAAAAC 26

( 2 ) INFORMATION FOR SEQ ID NO:664:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:664:

AGTGTGCTGC GGACCCGTGT GAAGAC 26

( 2 ) INFORMATION FOR SEQ ID NO:665:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:665:

GATGTTCTTC GGACGAGAGT GAAGAC 26

( 2 ) INFORMATION FOR SEQ ID NO:666:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:666:

GACATCCTCC GAACCAGGGT CAAAAC 26

( 2 ) INFORMATION FOR SEQ ID NO:667:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:667:

GATGTTCTCA GAACTAGAGT GAAAAC      26

( 2 ) INFORMATION FOR SEQ ID NO:668:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:668:

CATGCTCTGA GCACTGGAGA GAAAAG      26

( 2 ) INFORMATION FOR SEQ ID NO:669:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:669:

AACAGAAATA AAGAAATAAA TGAAAT      26

( 2 ) INFORMATION FOR SEQ ID NO:670:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:670:

TGTCAGTTTG AAGACCTCAA TAAAAG      26

( 2 ) INFORMATION FOR SEQ ID NO:671:

( i ) SEQUENCE CHARACTERISTICS:

( A ) LENGTH: 26 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:671:

AGCAAGTTTG AGGACCTGAA TAAACG 26

( 2 ) INFORMATION FOR SEQ ID NO:672:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:672:

TGCCAGTTTG AAGATCTGAA CCGAAG 26

( 2 ) INFORMATION FOR SEQ ID NO:673:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:673:

ACACAGTTTG AAAGCAAAAA CCGCTC 26

( 2 ) INFORMATION FOR SEQ ID NO:674:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:674:

TGTCAGTTTG AAGACCTCAA TAAAAG 26

( 2 ) INFORMATION FOR SEQ ID NO:675:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:675:

AGCCAGCCTG TAGCCCTCAA TAAAAG   26

(2) INFORMATION FOR SEQ ID NO:676:

(i) SEQUENCE CHARACTERISTICS:
      (A) LENGTH: 22 base pairs
      (B) TYPE: nucleic acid
      (C) STRANDEDNESS: double
      (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:676:

GACAAGATTG ATGTGATCAA GC   22

(2) INFORMATION FOR SEQ ID NO:677:

(i) SEQUENCE CHARACTERISTICS:
      (A) LENGTH: 22 base pairs
      (B) TYPE: nucleic acid
      (C) STRANDEDNESS: double
      (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:677:

AAAATGTTTG ACGTGGGAGG CC   22

(2) INFORMATION FOR SEQ ID NO:678:

(i) SEQUENCE CHARACTERISTICS:
      (A) LENGTH: 22 base pairs
      (B) TYPE: nucleic acid
      (C) STRANDEDNESS: double
      (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:678:

AAGATGTTTG ATGTGGGTGG TC   22

(2) INFORMATION FOR SEQ ID NO:679:

(i) SEQUENCE CHARACTERISTICS:
      (A) LENGTH: 22 base pairs
      (B) TYPE: nucleic acid
      (C) STRANDEDNESS: double
      (D) TOPOLOGY: linear (i i) MOLECULE TYPE: cDNA to mRNA (i i i) HYPOTHETICAL: NO ( i v ) ANTI-SENSE: NO ( x i ) SEQUENCE DESCRIPTION: SEQ ID NO:679:

AAAGTGTTTG ATGTAGGTGG CC   22

( 2 ) INFORMATION FOR SEQ ID NO:680:

( i ) SEQUENCE CHARACTERISTICS:
                ( A ) LENGTH: 22 base pairs
                ( B ) TYPE: nucleic acid
                ( C ) STRANDEDNESS: double
                ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:680:

AGGCTGTTTG ACGTTGGGGG CC   22

( 2 ) INFORMATION FOR SEQ ID NO:681:

( i ) SEQUENCE CHARACTERISTICS:
                ( A ) LENGTH: 22 base pairs
                ( B ) TYPE: nucleic acid
                ( C ) STRANDEDNESS: double
                ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:681:

AAGATGTTTG ATGTGGGTGG TC   22

( 2 ) INFORMATION FOR SEQ ID NO:682:

( i ) SEQUENCE CHARACTERISTICS:
                ( A ) LENGTH: 22 base pairs
                ( B ) TYPE: nucleic acid
                ( C ) STRANDEDNESS: double
                ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:682:

AAGATGTTTG ATGTGGGTGG TC   22

( 2 ) INFORMATION FOR SEQ ID NO:683:

( i ) SEQUENCE CHARACTERISTICS:
                ( A ) LENGTH: 22 base pairs
                ( B ) TYPE: nucleic acid
                ( C ) STRANDEDNESS: double
                ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:683:

AAGATGTTTG ACGTGGGTGT GG    22

( 2 ) INFORMATION FOR SEQ ID NO:684:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:684:

AAGCAGGTCT ACCGGGCCAC GC    22

( 2 ) INFORMATION FOR SEQ ID NO:685:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:685:

AAGGAAATTT ACACCCACTT CA    22

( 2 ) INFORMATION FOR SEQ ID NO:686:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:686:

AAGGAGATCT ACACGCACTT CA    22

( 2 ) INFORMATION FOR SEQ ID NO:687:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:687:

AAGGAGGTCT ACACTCACTT TA    22

( 2 ) INFORMATION FOR SEQ ID NO:688:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:688:

CTAGAGATCT GCACCCCTCA CC        22

( 2 ) INFORMATION FOR SEQ ID NO:689:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:689:

AAGGAGATCT ACACGCACTT CA        22

( 2 ) INFORMATION FOR SEQ ID NO:690:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:690:

AAGGAGATCT ACACGCACTT CA        22

( 2 ) INFORMATION FOR SEQ ID NO:691:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:691:

AAGGAGAACT ACAAGAAGTT CT        22

( 2 ) INFORMATION FOR SEQ ID NO:692:

( i ) SEQUENCE CHARACTERISTICS:
        ( A ) LENGTH: 22 base pairs (B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:692:

CCGGAAGTGG ATCCAGTGCT TC 22

(2) INFORMATION FOR SEQ ID NO:693:

(i) SEQUENCE CHARACTERISTICS:
(A) LENGTH: 22 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:693:

ATGTTGAAGC TGGGGCTCTA GT 22

(2) INFORMATION FOR SEQ ID NO:694:

(i) SEQUENCE CHARACTERISTICS:
(A) LENGTH: 22 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:694:

CCTACACAGC AGGATGTGCT GC 22

(2) INFORMATION FOR SEQ ID NO:695:

(i) SEQUENCE CHARACTERISTICS:
(A) LENGTH: 22 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:695:

TTGTTTTAGC TGGCAGTGCT GA 22

(2) INFORMATION FOR SEQ ID NO:696:

(i) SEQUENCE CHARACTERISTICS:
(A) LENGTH: 22 base pairs
(B) TYPE: nucleic acid
(C) STRANDEDNESS: double
(D) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:696:

CGGTTTTAGT TGAGTCTTTA CA                    22

( 2 ) INFORMATION FOR SEQ ID NO:697:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:697:

TTGTTTTAGC TGGCAGTGCT GA                    22

( 2 ) INFORMATION FOR SEQ ID NO:698:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:698:

GTGTTTCAGA TGGCATTGCT GC                    22

( 2 ) INFORMATION FOR SEQ ID NO:699:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:699:

AATGATGTGA CTGCCATCGT CT                    22

( 2 ) INFORMATION FOR SEQ ID NO:700:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:700:

GAAGGCGTGA CTGCCATCGT CT                                         22

( 2 ) INFORMATION FOR SEQ ID NO:701:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:701:

GAGGGTGTCA CGGCCATCGT CT                                         22

( 2 ) INFORMATION FOR SEQ ID NO:702:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:702:

GAGGGAGTGA CAGCAATTGT CT                                         22

( 2 ) INFORMATION FOR SEQ ID NO:703:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:703:

TCGGGAGTAT CAGCTCAACG AC                                         22

( 2 ) INFORMATION FOR SEQ ID NO:704:

( i ) SEQUENCE CHARACTERISTICS:
    ( A ) LENGTH: 22 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:704:

```
GAGGGAGTGA CAGCAATTGT CT                                                                                22
```

( 2 ) INFORMATION FOR SEQ ID NO:705:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:705:

```
CAGGGAGTGG CAGACATTTT CT                                                                                22
```

( 2 ) INFORMATION FOR SEQ ID NO:706:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:706:

```
AGGACATCAA AAACAACCT                                                                                    19
```

( 2 ) INFORMATION FOR SEQ ID NO:707:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:707:

```
GGGGCCGCCT CCGGGCCAG                                                                                    19
```

( 2 ) INFORMATION FOR SEQ ID NO:708:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:708:

```
CCATCATCCT CTTCCTCAA                                                                                    19
```

( 2 ) INFORMATION FOR SEQ ID NO:709:

( i ) SEQUENCE CHARACTERISTICS:
  ( A ) LENGTH: 19 base pairs
  ( B ) TYPE: nucleic acid
  ( C ) STRANDEDNESS: double
  ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:709:

GGCCAAAGAT CCGAACGGA                                                                 19

( 2 ) INFORMATION FOR SEQ ID NO:710:

( i ) SEQUENCE CHARACTERISTICS:
  ( A ) LENGTH: 19 base pairs
  ( B ) TYPE: nucleic acid
  ( C ) STRANDEDNESS: double
  ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:710:

AGGACATCCT CCGAACCAG                                                                 19

( 2 ) INFORMATION FOR SEQ ID NO:711:

( i ) SEQUENCE CHARACTERISTICS:
  ( A ) LENGTH: 19 base pairs
  ( B ) TYPE: nucleic acid
  ( C ) STRANDEDNESS: double
  ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:711:

AGGACATCCT CCGAACCAG                                                                 19

( 2 ) INFORMATION FOR SEQ ID NO:712:

( i ) SEQUENCE CHARACTERISTICS:
  ( A ) LENGTH: 19 base pairs
  ( B ) TYPE: nucleic acid
  ( C ) STRANDEDNESS: double
  ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:712:

AGGACATCCT CCGAACCAG                                                                 19

( 2 ) INFORMATION FOR SEQ ID NO:713:

( i ) SEQUENCE CHARACTERISTICS:
  ( A ) LENGTH: 19 base pairs
  ( B ) TYPE: nucleic acid (C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:713:

AGGACATCCT CCGAACCAG                                                                19

(2) INFORMATION FOR SEQ ID NO:714:

(i) SEQUENCE CHARACTERISTICS:
    (A) LENGTH: 19 base pairs
    (B) TYPE: nucleic acid
    (C) STRANDEDNESS: double
    (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:714:

AGGACATCCT CCGAACCAG                                                                19

(2) INFORMATION FOR SEQ ID NO:715:

(i) SEQUENCE CHARACTERISTICS:
    (A) LENGTH: 19 base pairs
    (B) TYPE: nucleic acid
    (C) STRANDEDNESS: double
    (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:715:

AGGACATCCT CCGAACCAG                                                                19

(2) INFORMATION FOR SEQ ID NO:716:

(i) SEQUENCE CHARACTERISTICS:
    (A) LENGTH: 19 base pairs
    (B) TYPE: nucleic acid
    (C) STRANDEDNESS: double
    (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:716:

GGGACATCTT CTCAACCAG                                                                19

(2) INFORMATION FOR SEQ ID NO:717:

(i) SEQUENCE CHARACTERISTICS:
    (A) LENGTH: 19 base pairs
    (B) TYPE: nucleic acid
    (C) STRANDEDNESS: double
    (D) TOPOLOGY: linear (ii) MOLECULE TYPE: cDNA to mRNA (i i i) HYPOTHETICAL: NO (i v) ANTI-SENSE: NO (x i) SEQUENCE DESCRIPTION: SEQ ID NO:717:

AGTGACCAGG ACCTGCTTC                              19

(2) INFORMATION FOR SEQ ID NO:718:

(i) SEQUENCE CHARACTERISTICS:
      (A) LENGTH: 19 base pairs
      (B) TYPE: nucleic acid
      (C) STRANDEDNESS: double
      (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:718:

TATGACCTGG TTCTTGCTG                              19

(2) INFORMATION FOR SEQ ID NO:719:

(i) SEQUENCE CHARACTERISTICS:
      (A) LENGTH: 19 base pairs
      (B) TYPE: nucleic acid
      (C) STRANDEDNESS: double
      (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:719:

TTCTGTTAGG TGCTGGAGA                              19

(2) INFORMATION FOR SEQ ID NO:720:

(i) SEQUENCE CHARACTERISTICS:
      (A) LENGTH: 19 base pairs
      (B) TYPE: nucleic acid
      (C) STRANDEDNESS: double
      (D) TOPOLOGY: linear (i i) MOLECULE TYPE: cDNA to mRNA (i i i) HYPOTHETICAL: NO (i v) ANTI-SENSE: NO (x i) SEQUENCE DESCRIPTION: SEQ ID NO:720:

AATGACCAGT AGTTAATTT                              19

(2) INFORMATION FOR SEQ ID NO:721:

(i) SEQUENCE CHARACTERISTICS:
      (A) LENGTH: 19 base pairs
      (B) TYPE: nucleic acid
      (C) STRANDEDNESS: double
      (D) TOPOLOGY: linear (i i) MOLECULE TYPE: cDNA to mRNA (i i i) HYPOTHETICAL: NO (i v) ANTI-SENSE: NO ( x i ) SEQUENCE DESCRIPTION: SEQ ID NO:721:

TATGACCAGG TGCTCCACG                    19

( 2 ) INFORMATION FOR SEQ ID NO:722:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:722:

TATGACCAGG TGCTCCACG                    19

( 2 ) INFORMATION FOR SEQ ID NO:723:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:723:

TATGACCAGG TGCTCCACG                    19

( 2 ) INFORMATION FOR SEQ ID NO:724:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:724:

TATGACCAGG TGCTCCACG                    19

( 2 ) INFORMATION FOR SEQ ID NO:725:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:725:

TATGACCAGG TGCTCCACG                    19

( 2 ) INFORMATION FOR SEQ ID NO:726:

( i ) SEQUENCE CHARACTERISTICS:
( A ) LENGTH: 19 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:726:

TATGACCAGG TGCTCCACG   1 9